(12) United States Patent
Chesworth et al.

(10) Patent No.: US 9,346,802 B2
(45) Date of Patent: May 24, 2016

(54) CARM1 INHIBITORS AND USES THEREOF

(71) Applicant: Epizyme, Inc., Cambridge, MA (US)

(72) Inventors: Richard Chesworth, Concord, MA (US); Oscar Miguel Moradei, Burlington, MA (US); Gideon Shapiro, Gainesville, FL (US); Lei Jin, Wellesley, MA (US); Robert E. Babine, Carlsbad, CA (US)

(73) Assignee: Epizyme, Inc., Cambridge, MA (US)

( * ) Notice: Subject to any disclaimer, the term of this patent is extended or adjusted under 35 U.S.C. 154(b) by 0 days.

(21) Appl. No.: 14/210,672

(22) Filed: Mar. 14, 2014

(65) Prior Publication Data

US 2014/0288067 A1    Sep. 25, 2014

Related U.S. Application Data

(60) Provisional application No. 61/794,442, filed on Mar. 15, 2013.

(51) Int. Cl.

| C07D 471/04 | (2006.01) |
|---|---|
| C07D 405/14 | (2006.01) |
| C07D 405/12 | (2006.01) |
| C07D 239/42 | (2006.01) |
| C07D 239/48 | (2006.01) |
| C07D 403/04 | (2006.01) |
| C07D 413/04 | (2006.01) |
| C07D 405/04 | (2006.01) |
| C07D 401/04 | (2006.01) |

(52) U.S. Cl.
CPC ............ *C07D 471/04* (2013.01); *C07D 239/42* (2013.01); *C07D 239/48* (2013.01); *C07D 401/04* (2013.01); *C07D 403/04* (2013.01); *C07D 405/04* (2013.01); *C07D 405/12* (2013.01); *C07D 405/14* (2013.01); *C07D 413/04* (2013.01)

(58) Field of Classification Search
None
See application file for complete search history.

(56) References Cited

U.S. PATENT DOCUMENTS

| 4,011,321 | A | 3/1977 | Coates et al. |
|---|---|---|---|
| 5,221,675 | A | 6/1993 | Chung et al. |
| 6,710,052 | B2 | 3/2004 | Pease et al. |
| 6,730,792 | B2 | 5/2004 | Evers et al. |
| 6,864,267 | B2 | 3/2005 | Bhatnagar et al. |
| 7,098,207 | B2 | 8/2006 | Niewohner et al. |
| 7,485,722 | B2 | 2/2009 | Egle et al. |
| 8,063,071 | B2 | 11/2011 | Kerns et al. |
| 8,110,579 | B2 | 2/2012 | Altenburger et al. |
| 8,338,437 | B2 | 12/2012 | Wahhab et al. |
| 8,906,900 | B2 | 12/2014 | Duncan et al. |
| 8,940,726 | B2 | 1/2015 | Duncan et al. |
| 8,952,026 | B2 | 2/2015 | Mitchell et al. |
| 8,993,555 | B2 | 3/2015 | Duncan et al. |
| 9,023,883 | B2 | 5/2015 | Kuntz et al. |
| 9,045,455 | B2 | 6/2015 | Mitchell et al. |
| 9,120,757 | B2 | 9/2015 | Chesworth et al. |

(Continued)

FOREIGN PATENT DOCUMENTS

| DE | 100 10 067 A1 | 9/2001 |
|---|---|---|
| GB | 1488330 A | 10/1977 |

(Continued)

OTHER PUBLICATIONS

International Search Report and Written Opinion for International Application No. PCT/US2014/028874 mailed May 21, 2014.
International Search Report and Written Opinion for International Application No. PCT/US2014/028463 mailed Jun. 10, 2014.
Al-Dhaheri et al., CARM1 is an important determinant of ERα-dependent breast cancer cell differentiation and proliferation in breast cancer cells. Cancer Res. Mar. 15, 2011;71(6):2118-28. doi: 10.1158/0008-5472.CAN-10-2426. Epub Jan. 31, 2011.
Copeland, Protein methyltransferase inhibitors as personalized cancer therapeutics. Drug Discovery Today. Therapeutic Strategies. 2012;9(2-3):e83-90.
Di Lorenzo et al., Castration-resistant prostate cancer: current and emerging treatment strategies. Drugs. May 28, 2010;70(8):983-1000. doi: 10.2165/10898600-000000000-00000.
El Messaoudi et al., Coactivator-associated arginine methyltransferase 1 (CARM1) is a positive regulator of the Cyclin E1 gene. Proc Natl Acad Sci U S A. Sep. 5, 2006;103(36):13351-6. Epub Aug. 28, 2006.

(Continued)

*Primary Examiner* — Michael Barker
(74) *Attorney, Agent, or Firm* — Wolf, Greenfield & Sacks, P.C.

(57) ABSTRACT

Provided herein are compounds of Formula (I):

and pharmaceutically acceptable salts thereof, and pharmaceutical compositions thereof; wherein X, $R^1$, $R^{2a}$, $R^{2b}$, $R^{2c}$, $R^{2d}$, are as defined herein, and Ring HET is a 6-membered monocyclic heteroaryl ring system of formula:

wherein $L^2$, $R^{13}$, $G_8$, $G_{10}$, $G_{11}$, and $G_{12}$ are as defined herein. Compounds of the present invention are useful for inhibiting CARM1 activity. Methods of using the compounds for treating CARM1-mediated disorders are also described.

32 Claims, No Drawings

(56) References Cited

U.S. PATENT DOCUMENTS

| | | |
|---|---|---|
| 9,133,189 B2 | 9/2015 | Chesworth et al. |
| 9,221,794 B2 | 12/2015 | Duncan et al. |
| 9,266,836 B2 | 2/2016 | Duncan et al. |
| 2003/0055244 A1 | 3/2003 | Scarborough et al. |
| 2004/0242633 A1 | 12/2004 | Evers et al. |
| 2006/0235037 A1 | 10/2006 | Purandare et al. |
| 2010/0144722 A1 | 6/2010 | Alexander et al. |
| 2011/0065681 A1 | 3/2011 | Wei et al. |
| 2011/0098268 A1 | 4/2011 | Mampreian et al. |
| 2014/0163049 A1 | 6/2014 | Duffy et al. |
| 2014/0213582 A1 | 7/2014 | Duncan et al. |
| 2014/0221310 A1 | 8/2014 | Eccles et al. |
| 2014/0228360 A1 | 8/2014 | Duncan et al. |
| 2014/0288105 A1 | 9/2014 | Chesworth et al. |
| 2014/0288124 A1 | 9/2014 | Chesworth et al. |
| 2014/0288129 A1 | 9/2014 | Mitchell et al. |
| 2014/0315961 A1 | 10/2014 | Chesworth et al. |
| 2014/0323537 A1 | 10/2014 | Chesworth et al. |
| 2015/0133427 A1 | 5/2015 | Duncan et al. |
| 2015/0252031 A1 | 9/2015 | Duncan et al. |
| 2015/0284334 A1 | 10/2015 | Kuntz et al. |
| 2015/0344433 A1 | 12/2015 | Duncan et al. |
| 2015/0344434 A1 | 12/2015 | Duncan et al. |
| 2015/0344434 A1 | 12/2015 | Duncan et al. |
| 2015/0344457 A1 | 12/2015 | Duncan et al. |
| 2015/0344463 A1 | 12/2015 | Duncan et al. |
| 2015/0361042 A1 | 12/2015 | Duncan et al. |
| 2016/0024016 A1 | 1/2016 | Chesworth et al. |
| 2016/0024017 A1 | 1/2016 | Chesworth et al. |
| 2016/0031839 A1 | 2/2016 | Chesworth et al. |
| 2016/0039767 A1 | 2/2016 | Mitchell et al. |

FOREIGN PATENT DOCUMENTS

| | | |
|---|---|---|
| GB | 1548601 A | 7/1979 |
| WO | WO 95/15952 A1 | 6/1995 |
| WO | WO 99/59959 A1 | 11/1999 |
| WO | WO 00/39101 A1 | 7/2000 |
| WO | WO 01/64653 A1 | 9/2001 |
| WO | WO 2008/104077 A1 | 9/2008 |
| WO | WO 2011/115183 A1 | 9/2011 |
| WO | WO 2012/121939 A2 | 9/2012 |
| WO | WO 2012/173689 A2 | 12/2012 |
| WO | 2014/100695 A1 | 6/2014 |
| WO | 2014/100716 A1 | 6/2014 |
| WO | 2014/100719 A2 | 6/2014 |
| WO | 2014/100730 A1 | 6/2014 |
| WO | 2014/100734 A1 | 6/2014 |
| WO | 2014/100764 A2 | 6/2014 |
| WO | 2014/144659 A1 | 9/2014 |
| WO | 2014/153090 A1 | 9/2014 |
| WO | 2014/153100 A2 | 9/2014 |
| WO | 2014/153172 A1 | 9/2014 |
| WO | 2014/153208 A1 | 9/2014 |
| WO | 2014/153214 A1 | 9/2014 |
| WO | 2014/153226 A1 | 9/2014 |
| WO | 2014/153235 A2 | 9/2014 |
| WO | WO 2014/144455 A1 | 9/2014 |
| WO | 2014/178954 A1 | 11/2014 |
| WO | 2016/022605 A1 | 2/2016 |

OTHER PUBLICATIONS

Engelmann et al., The dark side of E2F1: in transit beyond apoptosis. Cancer Res. Feb. 1, 2012;72(3):571-5. doi: 10.1158/0008-5472. CAN-11-2575.

Eymin et al., Distinct pattern of E2F1 expression in human lung tumours: E2F1 is upregulated in small cell lung carcinoma. Oncogene. Mar. 29, 2001;20(14):1678-87.

Frietze et al., CARM1 regulates estrogen-stimulated breast cancer growth through up-regulation of E2F1. Cancer Res. Jan. 1, 2008;68(1):301-6. doi: 10.1158/0008-5472.CAN-07-1983.

Hong et al., Aberrant expression of CARM1, a transcriptional coactivator of androgen receptor, in the development of prostate carcinoma and androgen-independent status. Cancer. Jul. 1, 2004;101(1):83-9.

Kim et al., Differential CARM1 expression in prostate and colorectal cancers. BMC Cancer. May 13, 2010;10:197. doi: 10.1186/1471-2407-10-197.

Majumder et al., Involvement of arginine methyltransferase CARM1 in androgen receptor function and prostate cancer cell viability. Prostate. Sep. 1, 2006;66(12):1292-301.

Ou et al., A coactivator role of CARM1 in the dysregulation of β-catenin activity in colorectal cancer cell growth and gene expression. Mol Cancer Res. May 2011;9(5):660-70. doi: 10.1158/1541-7786.MCR-10-0223. Epub Apr. 8, 2011.

Purandare et al., Pyrazole inhibitors of coactivator associated arginine methyltransferase 1 (CARM1). Bioorg Med Chem Lett. Aug. 1, 2008;18(15):4438-41. doi: 10.1016/j.bmcl.2008.06.026. Epub Jun. 12, 2008.

Teyssier et al., Protein arginine methylation in estrogen signaling and estrogen-related cancers. Trends Endocrinol Metab. Mar. 2010;21(3):181-9. doi: 10.1016/j.tem.2009.11.002. Epub Dec. 11, 2009.

Wang et al., CARM1/PRMT4 is necessary for the glycogen gene expression programme in skeletal muscle cells. Biochem J. Jun. 1, 2012;444(2):323-31. doi: 10.1042/BJ20112033.

International Search Report and Written Opinion for International Application No. PCT/US2015/050712 mailed Dec. 15, 2015.

International Search Report and Written Opinion for International Application No. PCT/US2015/050776 mailed Dec. 14, 2015.

International Search Report and Written Opinion for International Application No. PCT/US2015/050788 mailed Dec. 17, 2015.

International Search Report and Written Opinion for International Application No. PCT/US2015/050675 mailed Dec. 17, 2015.

International Search Report and Written Opinion for International Application No. PCT/US2015/050647 mailed Dec. 14, 2015.

Pubchem Submission; NIH/NCBI, Compound Identifier 90425581. Feb. 13, 2015. 9 pages.

Sack et al., Structural basis for CARM1 inhibition by indole and pyrazole inhibitors. Biochem J. Jun. 1, 2011;436(2):331-9. doi: 10.1042/BJ20102161.

Therrien et al., 1,2-Diamines as inhibitors of co-activator associated arginine methyltransferase 1 (CARM1). Bioorg Med Chem Lett. Dec. 1, 2009;19(23):6725-32. doi: 10.1016/j.bmcl.2009.09.110. Epub Oct. 2, 2009.

Wan et al., Benzo[d]imidazole inhibitors of Coactivator Associated Arginine Methyltransferase 1 (CARM1)—Hit to Lead studies. Bioorg Med Chem Lett. Sep. 1, 2009;19(17):5063-6. doi: 10.1016/j.bmcl.2009.07.040. Epub Jul. 10, 2009.

CARM1 INHIBITORS AND USES THEREOF

RELATED APPLICATIONS

The present application claims priority under 35 U.S.C. §119(e) to U.S. Provisional Patent Application, U.S. Ser. No. 61/794,442, filed Mar. 15, 2013, the entire contents of which is incorporated herein by reference.

BACKGROUND OF THE INVENTION

Epigenetic regulation of gene expression is an important biological determinant of protein production and cellular differentiation and plays a significant pathogenic role in a number of human diseases.

Epigenetic regulation involves heritable modification of genetic material without changing its nucleotide sequence. Typically, epigenetic regulation is mediated by selective and reversible modification (e.g., methylation) of DNA and proteins (e.g., histones) that control the conformational transition between transcriptionally active and inactive states of chromatin. These covalent modifications can be controlled by enzymes such as methyltransferases (e.g., CARM1 (co-activator-associated arginine methyltransferase 1; PRMT4)), many of which are associated with specific genetic alterations that can cause human disease.

Disease-associated chromatin-modifying enzymes play a role in diseases such as proliferative disorders, autoimmune disorders, muscular disorders, and neurological disorders. Thus, there is a need for the development of small molecules that are capable of inhibiting the activity of CARM1.

DETAILED DESCRIPTION OF CERTAIN EMBODIMENTS

CARM1 is an attractive target for modulation given its role in the regulation of diverse biological processes. It has now been found that compounds described herein, and pharmaceutically acceptable salts and compositions thereof, are effective as inhibitors of CARM1. Such compounds have the general Formula (I):

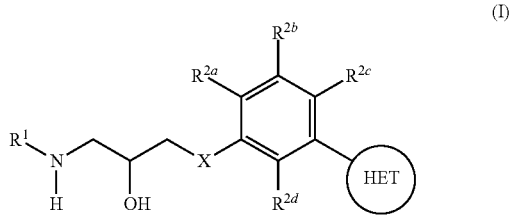

(I)

and pharmaceutically acceptable salts thereof, and pharmaceutical compositions thereof; wherein X, $R^1$, $R^{2a}$, $R^{2b}$, $R^{2c}$, $R^{2d}$, are as defined herein, and wherein Ring HET is a 6-membered monocyclic heteroaryl ring system of Formula:

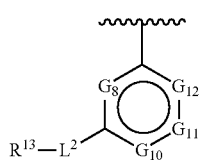

wherein $L^2$, $R^{13}$, $G_8$, $G_{10}$, $G_{11}$, and $G_{12}$ are as defined herein.

In some embodiments, pharmaceutical compositions are provided which comprise a compound described herein (e.g., a compound of Formula (I), or a pharmaceutically acceptable salt thereof) and optionally a pharmaceutically acceptable excipient.

In certain embodiments, compounds described herein inhibit activity of CARM1. In certain embodiments, methods of inhibiting CARM1 are provided which comprise contacting CARM1 with an effective amount of a compound of Formula (I), or a pharmaceutically acceptable salt thereof. The CARM1 may be purified or crude, and may be present in a cell, tissue, or a subject. Thus, such methods encompass inhibition of CARM1 activity both in vitro and in vivo. In certain embodiments, the CARM1 is wild-type CARM1. In certain embodiments, the CARM1 is overexpressed. In certain embodiments, the CARM1 is a mutant. In certain embodiments, the CARM1 is in a cell. In certain embodiments, the CARM1 is in an animal, e.g., a human. In some embodiments, the CARM1 is expressed at normal levels in a subject, but the subject would benefit from CARM1 inhibition (e.g., because the subject has one or more mutations in an CARM1 substrate that causes an increase in methylation of the substrate with normal levels of CARM1). In some embodiments, the CARM1 is in a subject known or identified as having abnormal CARM1 activity (e.g., overexpression). In some embodiments, a provided compound is selective for CARM1 over other methyltransferases. In certain embodiments, a provided compound is at least about 10-fold selective, at least about 20-fold selective, at least about 30-fold selective, at least about 40-fold selective, at least about 50-fold selective, at least about 60-fold selective, at least about 70-fold selective, at least about 80-fold selective, at least about 90-fold selective, or at least about 100-fold selective relative to one or more other methyltransferases.

In certain embodiments, methods of modulating gene expression or activity in a cell are provided which comprise contacting a cell with an effective amount of a compound of Formula (I), or a pharmaceutically acceptable salt thereof, or a pharmaceutical composition thereof. In certain embodiments, the cell in culture in vitro. In certain embodiments, cell is in an animal, e.g., a human.

In certain embodiments, methods of modulating transcription in a cell are provided which comprise contacting a cell with an effective amount of a compound of Formula (I), or a pharmaceutically acceptable salt thereof, or a pharmaceutical composition thereof. In certain embodiments, the cell in culture in vitro. In certain embodiments, the cell is in an animal, e.g., a human.

In some embodiments, methods of treating a CARM1-mediated disorder are provided which comprise administering to a subject suffering from a CARM1-mediated disorder an effective amount of a compound described herein (e.g., a compound of Formula (I), or a pharmaceutically acceptable salt thereof), or a pharmaceutical composition thereof. In certain embodiments, the CARM1-mediated disorder is a proliferative disorder. In certain embodiments, compounds described herein are useful for treating cancer. In certain embodiments, compounds described herein are useful for treating breast cancer or prostate cancer. In certain embodiments, the CARM1-mediated disorder is a metabolic disorder.

Compounds described herein are also useful for the study of CARM1 in biological and pathological phenomena, the study of intracellular signal transduction pathways mediated by CARM1, and the comparative evaluation of new CARM1 inhibitors.

This application refers to various issued patent, published patent applications, journal articles, and other publications, all of which are incorporated herein by reference.

Definitions of specific functional groups and chemical terms are described in more detail below. The chemical elements are identified in accordance with the Periodic Table of the Elements, CAS version, *Handbook of Chemistry and Physics*, 75$^{th}$ Ed., a inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, NY, 1962); and Wilen, *Tables of Resolving Agents and Optical Resolutions* p. 268 (E. L. Eliel, Ed., Univ. of Notre Dame Press, Notre Dame, Ind. 1972). The present disclosure additionally encompasses compounds described herein as individual isomers substantially free of other isomers, and alternatively, as mixtures of various isomers.

Unless otherwise stated, structures depicted herein are also meant to include compounds that differ only in the presence of one or more isotopically enriched atoms. For example, compounds having the present structures except for the replacement of hydrogen by deuterium or tritium, replacement of $^{19}$F with $^{18}$F, or the replacement of a carbon by a $^{13}$C- or $^{14}$C-enriched carbon are within the scope of the disclosure. Such compounds are useful, for example, as analytical tools or probes in biological assays.

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

"Aliphatic" refers to alkyl, alkenyl, alkynyl, and carbocyclic groups.

"Alkyl" refers to a radical of a straight-chain or branched saturated hydrocarbon group having from 1 to 20 carbon atoms ("$C_{1-20}$ alkyl"). In some embodiments, an alkyl group has 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_8$) and the like. In certain embodiments, each instance of an alkyl group is independently optionally substituted, e.g., unsubstituted (an "unsubstituted alkyl") or substituted (a "substituted alkyl") with one or more substituents. In certain embodiments, the alkyl group is unsubstituted $C_{1-10}$ alkyl (e.g., —$CH_3$). In certain embodiments, the alkyl group is substituted $C_{1-10}$ alkyl.

In some embodiments, an alkyl group is substituted with one or more halogens. "Perhaloalkyl" is a substituted alkyl group as defined herein wherein all of the hydrogen atoms are independently replaced by a halogen, e.g., fluoro, bromo, chloro, or iodo. In some embodiments, the alkyl moiety has 1 to 8 carbon atoms ("$C_{1-8}$ perhaloalkyl"). In some embodiments, the alkyl moiety has 1 to 6 carbon atoms ("$C_{1-6}$ perhaloalkyl"). In some embodiments, the alkyl moiety has 1 to 4 carbon atoms ("$C_{1-4}$ perhaloalkyl"). In some embodiments, the alkyl moiety has 1 to 3 carbon atoms ("$C_{1-3}$ perhaloalkyl"). In some embodiments, the alkyl moiety has 1 to 2 carbon atoms ("$C_{1-2}$ perhaloalkyl"). In some embodiments, all of the hydrogen atoms are replaced with fluoro. In some embodiments, all of the hydrogen atoms are replaced with chloro. Examples of perhaloalkyl groups include —$CF_3$, —$CF_2CF_3$, —$CF_2CF_2CF_3$, —$CCl_3$, —$CFCl_2$, —$CF_2Cl$, and the like.

"Alkenyl" refers to a radical of a straight-chain or branched hydrocarbon group having from 2 to 20 carbon atoms, one or more carbon-carbon double bonds (e.g., 1, 2, 3, or 4 double bonds), and optionally one or more triple bonds (e.g., 1, 2, 3, or 4 triple bonds) ("$C_{2-20}$ alkenyl"). In certain embodiments, alkenyl does not comprise triple bonds. In some embodiments, an alkenyl group has 2 to 10 carbon atoms ("$C_{2-10}$ alkenyl"). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. In certain embodiments, each instance of an alkenyl group is independently optionally substituted, e.g., unsubstituted (an "unsubstituted alkenyl") or substituted (a "substituted alkenyl") with one or more substituents. In certain embodiments, the alkenyl group is unsubstituted $C_{2-10}$ alkenyl. In certain embodiments, the alkenyl group is substituted $C_{2-10}$ alkenyl.

"Alkynyl" refers to a radical of a straight-chain or branched hydrocarbon group having from 2 to 20 carbon atoms and one or more carbon-carbon triple bonds (e.g., 1, 2, 3, or 4 triple bonds), and optionally one or more double bonds (e.g., 1, 2, 3, or 4 double bonds) ("$C_{2-20}$ alkynyl"). In certain embodiments, alkynyl does not comprise double bonds. In some embodiments, an alkynyl group has 2 to 10 carbon atoms ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. In certain embodiments, each instance of an alkynyl group is independently optionally substituted, e.g., unsubstituted (an "unsubstituted alkynyl") or substituted (a "substituted alkynyl") with one or more substituents. In certain embodiments, the alkynyl group is unsubstituted $C_{2-10}$ alkynyl. In certain embodiments, the alkynyl group is substituted $C_{2-10}$ alkynyl.

"Carbocyclyl" or "carbocyclic" refers to a radical of a non-aromatic cyclic hydrocarbon group having from 3 to 10 ring carbon atoms ("$C_{3-10}$ carbocyclyl") and zero heteroatoms in the non-aromatic ring system. In some embodiments, a carbocyclyl group has 3 to 8 ring carbon atoms ("$C_{3-8}$ carbocyclyl"). In some embodiments, a carbocyclyl group has 3 to 7 ring carbon atoms ("$C_{3-7}$ carbocyclyl"). In some embodiments, a carbocyclyl group has 3 to 6 ring carbon atoms ("$C_{3-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or contain a fused, bridged or spiro ring system such as a bicyclic system ("bicyclic carbocyclyl") or tricyclic system ("tricyclic carbocyclyl"), and can be saturated or can be partially unsaturated. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. In certain embodiments, each instance of a carbocyclyl group is independently optionally substituted, e.g., unsubstituted (an "unsubstituted carbocyclyl") or substituted (a "substituted carbocyclyl") with one or more substituents. In certain embodiments, the carbocyclyl group is unsubstituted $C_{3-10}$ carbocyclyl. In certain embodiments, the carbocyclyl group is a substituted $C_{3-10}$ carbocyclyl.

In some embodiments, "carbocyclyl" is a monocyclic, saturated carbocyclyl group having from 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). In certain embodiments, each instance of a cycloalkyl group is independently unsubstituted (an "unsubstituted cycloalkyl") or substituted (a "substituted cycloalkyl") with one or more substituents. In certain embodiments, the cycloalkyl group is unsubstituted $C_{3-10}$ cycloalkyl. In certain embodiments, the cycloalkyl group is substituted $C_{3-10}$ cycloalkyl.

"Heterocyclyl" or "heterocyclic" refers to a radical of a 3- to 10-membered non-aromatic ring system having ring carbon atoms and 1 to 4 ring heteroatoms, wherein each heteroatom is independently selected from nitrogen, oxygen, and sulfur ("3-10 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged or spiro ring system such as a bicyclic system ("bicyclic heterocyclyl") or tricyclic system ("tricyclic heterocyclyl"), and can be saturated or can be partially unsaturated. Heterocyclyl bicyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. In certain embodiments, each instance of heterocyclyl is independently optionally substituted, e.g., unsubstituted (an "unsubstituted heterocyclyl") or substituted (a "substituted heterocyclyl") with one or more substituents. In certain embodiments, the heterocyclyl group is unsubstituted 3-10 membered heterocyclyl. In certain embodiments, the heterocyclyl group is substituted 3-10 membered heterocyclyl.

In some embodiments, a heterocyclyl group is a 5-10 membered nonaromatic ring system having ring carbon atoms and 1-4 ring heteroatoms, wherein each heteroatom is independently selected from nitrogen, oxygen, and sulfur ("5-10 membered heterocyclyl"). In some embodiments, a heterocyclyl group is a 5-8 membered nonaromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has one ring heteroatom selected from nitrogen, oxygen, and sulfur.

Exemplary 3-membered heterocyclyl groups containing one heteroatom include, without limitation, azirdinyl, oxiranyl, and thiorenyl. Exemplary 4-membered heterocyclyl groups containing one heteroatom include, without limitation, azetidinyl, oxetanyl, and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, dihydropyridinyl, and thianyl. Exemplary 6-membered heterocyclyl groups containing two heteroatoms include, without limitation, piperazinyl, morpholinyl, dithianyl, and dioxanyl. Exemplary 6-membered heterocyclyl groups containing two heteroatoms include, without limitation, triazinanyl. Exemplary 7-membered heterocyclyl groups containing one heteroatom include, without limitation, azepanyl, oxepanyl and thiepanyl. Exemplary 8-membered heterocyclyl groups containing one heteroatom include, without limitation, azocanyl, oxecanyl, and thiocanyl. Exemplary 5-membered heterocyclyl groups fused to a $C_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclyl groups fused to an aryl ring (also referred to herein as a 6,6-bicyclic heterocyclic ring) include, without limitation, tetrahydroquinolinyl, tetrahydroisoquinolinyl, and the like.

"Aryl" refers to a radical of a monocyclic or polycyclic (e.g., bicyclic or tricyclic) 4n+2 aromatic ring system (e.g., having 6, 10, or 14π electrons shared in a cyclic array) having 6-14 ring carbon atoms and zero heteroatoms provided in the aromatic ring system ("$C_{6-14}$ aryl"). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. In certain embodiments, each instance of an aryl group is independently optionally substituted, e.g., unsubstituted (an "unsubstituted aryl") or substituted (a "substituted aryl") with one or more substituents. In certain embodiments, the aryl group is unsubstituted $C_{6-14}$ aryl. In certain embodiments, the aryl group is substituted $C_{6-14}$ aryl.

"Heteroaryl" refers to a radical of a 5-10 membered monocyclic or bicyclic 4n+2 aromatic ring system (e.g., having 6 or 10π electrons shared in a cyclic array) having ring carbon atoms and 1-4 ring heteroatoms provided in the aromatic ring system, wherein each heteroatom is independently selected from nitrogen, oxygen and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (arylheteroaryl) ring system. Bicyclic heteroaryl groups wherein one ring does not contain a heteroatom (e.g., indolyl, quinolinyl, carbazolyl, and the like) the point of attachment can be on either ring, e.g., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. In certain embodiments, each instance of a heteroaryl group is independently optionally substituted, e.g., unsubstituted ("unsubstituted heteroaryl") or substituted ("substituted heteroaryl") with one or more substituents. In certain embodiments, the heteroaryl group is unsubstituted 5-14 membered heteroaryl. In certain embodiments, the heteroaryl group is substituted 5-14 membered heteroaryl.

Exemplary 5-membered heteroaryl groups containing one heteroatom include, without limitation, pyrrolyl, furanyl and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl.

"Partially unsaturated" refers to a group that includes at least one double or triple bond. The term "partially unsaturated" is intended to encompass rings having multiple sites of unsaturation, but is not intended to include aromatic groups (e.g., aryl or heteroaryl groups) as herein defined. Likewise, "saturated" refers to a group that does not contain a double or triple bond, i.e., contains all single bonds.

In some embodiments, alkyl, alkenyl, alkynyl, carbocyclyl, heterocyclyl, aryl, and heteroaryl groups, as defined herein, are optionally substituted (e.g., "substituted" or "unsubstituted" alkyl, "substituted" or "unsubstituted" alkenyl, "substituted" or "unsubstituted" alkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, including any of the substituents described herein that results in the formation of a stable compound. The present disclosure contemplates any and all such combinations in order to arrive at a stable compound. For purposes of this disclosure, heteroatoms such as nitrogen may have hydrogen substituents and/or any suitable substituent as described herein which satisfy the valencies of the heteroatoms and results in the formation of a stable moiety.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$ —C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)$_2$R$^{aa}$, —OP(=O)$_2$R$^{aa}$, —P(=O)(R$^{aa}$)$_2$, —OP(=O)(R$^{aa}$)$_2$, —OP(=O)(OR$^{cc}$)$_2$, —P(=O)$_2$N(R$^{bb}$)$_2$, —OP(=O)$_2$N(R$^{bb}$)$_2$, —P(=O)(NR$^{bb}$)$_2$, —OP(=O) (NR$^{bb}$)$_2$, —NR$^{bb}$P(=O)(OR$^{cc}$)$_2$, —NR$^{bb}$P(=O)(NR$^{bb}$)$_2$, —P(R$^{cc}$)$_2$, —P(R$^{cc}$)$_3$, —OP(R$^{cc}$)$_2$, —OP(R$^{cc}$)$_3$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 R$^{dd}$ groups;

or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$;

each instance of R$^{aa}$ is, independently, selected from C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{cc}$ is, independently, selected from hydrogen, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3$$^+$X$^-$, —N(OR$^{ee}$) R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N (R$^{ff}$)$_2$, —NR$^{ff}$C(=NR$^{ff}$)N(R$^{ff}$)$_2$, —NR$^{ff}$SO$_2$R$^{ee}$, —SO$_2$ N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)$_2$R$^{ee}$, —P(=O) (R$^{ee}$)$_2$, —OP(=O)(R$^{ee}$)$_2$, —OP(=O)(OR$^{ee}$)$_2$, C$_{1-6}$ alkyl, C$_{1-6}$ perhaloalkyl, C$_{2-6}$ alkenyl, C$_{2-6}$ alkynyl, C$_{3-10}$ carbocyclyl, 3-10 membered heterocyclyl, C$_{6-10}$ aryl, 5-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups, or two geminal R$^{dd}$ substituents can be joined to form =O or =S;

each instance of R$^{ee}$ is, independently, selected from C$_{1-6}$ alkyl, C$_{1-6}$ perhaloalkyl, C$_{2-6}$ alkenyl, C$_{2-6}$ alkynyl, C$_{3-10}$ carbocyclyl, $C_{6-10}$ aryl, 3-10 membered heterocyclyl, and 3-10 membered heteroaryl, wherein each alkyl, alkenyl, alkynyl, carbocyclyl, heterocyclyl, aryl, and heteroaryl is independently substituted with 0, 1, 2, 3, 4, or 5 $R^{gg}$ groups;

each instance of $R^{ff}$ is, independently, selected from hydrogen, $C_{1-6}$ alkyl, $C_{1-6}$ perhaloalkyl, $C_{2-6}$ alkenyl, $C_{2-6}$ alkynyl, $C_{3-10}$ carbocyclyl, 3-10 membered heterocyclyl, $C_{6-10}$ aryl and 5-10 membered heteroaryl, or two $R^{ff}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{gg}$ groups; and each instance of $R^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3^+$X$^-$, —NH(C$_{1-6}$ alkyl)$_2^+$X$^-$, —NH$_2$(C$_{1-6}$ alkyl)$^+$X$^-$, —NH$_3^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$-C(=S)N(C$_{1-6}$ alkyl)$_2$, —C(=S)NH(C$_{1-6}$ alkyl), —C(=S)NH$_2$, —C(=O)S(C$_{1-6}$ alkyl), —C(=S)SC$_{1-6}$ alkyl, —SC(=S)SC$_{1-6}$ alkyl, —P(=O)$_2$(C$_{1-6}$ alkyl), —P(=O)(C$_{1-6}$ alkyl)$_2$, —OP(=O)(C$_{1-6}$ alkyl)$_2$, —OP(=O)(OC$_{1-6}$ alkyl)$_2$, C$_{1-6}$ alkyl, C$_{1-6}$ perhaloalkyl, C$_{2-6}$ alkenyl, C$_{2-6}$ alkynyl, C$_{3-10}$ carbocyclyl, C$_{6-10}$ aryl, 3-10 membered heterocyclyl, 5-10 membered heteroaryl; or two geminal $R^{gg}$ substituents can be joined to form =O or =S; wherein X$^-$ is a counterion.

A "counterion" or "anionic counterion" is a negatively charged group associated with a cationic quaternary amino group in order to maintain electronic neutrality. Exemplary counterions include halide ions (e.g., F$^-$, Cl$^-$, Br$^-$, I$^-$), NO$_3^-$, ClO$_4^-$, OH$^-$, H$_2$PO$_4^-$, HSO$_4^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), and carboxylate ions (e.g., acetate, ethanoate, propanoate, benzoate, glycerate, lactate, tartrate, glycolate, and the like).

"Halo" or "halogen" refers to fluorine (fluoro, —F), chlorine (chloro, —Cl), bromine (bromo, —Br), or iodine (iodo, —I).

"Hydroxyl" or "hydroxy" refers to the group —OH. "Substituted hydroxyl" or "substituted hydroxyl," by extension, refers to a hydroxyl group wherein the oxygen atom directly attached to the parent molecule is substituted with a group other than hydrogen, and includes groups selected from —OR$^{aa}$, —ON(R$^{bb}$)$_2$, —OC(=O)SR$^{aa}$, —OC(=O)R$^{aa}$, —OCO$_2$R$^{aa}$, —OC(=O)N(R$^{bb}$)$_2$, —OC(=NR$^{bb}$)R$^{aa}$, —OC(=NR$^{bb}$)OR$^{aa}$, —OC(=NR$^{bb}$)N(R$^{bb}$)$_2$, —OS(=O)R$^{aa}$, —OSO$_2$R$^{aa}$, —OSi(R$^{aa}$)$_3$, —OP(R$^{cc}$)$_2$, —OP(R$^{cc}$)$_3$, —OP(=O)$_2$R$^{aa}$, —OP(=O)(R$^{aa}$)$_2$, —OP(=O)(OR$^{cc}$)$_2$, —OP(=O)$_2$N(R$^{bb}$)$_2$, and —OP(=O)(NR$^{bb}$)$_2$, wherein R$^{aa}$, R$^{bb}$, and R$^{cc}$ are as defined herein.

"Thiol" or "thio" refers to the group —SH. "Substituted thiol" or "substituted thio," by extension, refers to a thiol group wherein the sulfur atom directly attached to the parent molecule is substituted with a group other than hydrogen, and includes groups selected from —SR$^{aa}$, —S=SR$^{cc}$, —SC(=S)SR$^{aa}$, —SC(=O)SR$^{aa}$, —SC(=O)OR$^{aa}$, and —SC(=O)R$^{aa}$, wherein R$^{aa}$ and R$^{cc}$ are as defined herein.

"Amino" refers to the group —NH$_2$. "Substituted amino," by extension, refers to a monosubstituted amino, a disubstituted amino, or a trisubstituted amino, as defined herein. In certain embodiments, the "substituted amino" is a monosubstituted amino or a disubstituted amino group.

"Monosubstituted amino" refers to an amino group wherein the nitrogen atom directly attached to the parent molecule is substituted with one hydrogen and one group other than hydrogen, and includes groups selected from —NH(R$^{bb}$), —NHC(=O)R$^{aa}$, —NHCO$_2$R$^{aa}$, —NHC(=O)N(R$^{bb}$)$_2$, —NHC(=NR$^{bb}$)N(R$^{bb}$)$_2$, —NHSO$_2$R$^{aa}$, —NHP(=O)(OR$^{cc}$)$_2$, and —NHP(=O)(NR$^{bb}$)$_2$, wherein R$^{aa}$, R$^{bb}$ and R$^{cc}$ are as defined herein, and wherein R$^{bb}$ of the group —NH(R$^{bb}$) is not hydrogen.

"Disubstituted amino" refers to an amino group wherein the nitrogen atom directly attached to the parent molecule is substituted with two groups other than hydrogen, and includes groups selected from —N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —NR$^{bb}$C(=NR$^{bb}$)N(R$^{bb}$)$_2$, —NR$^{bb}$SO$_2$R$^{aa}$, —NR$^{bb}$P(=O)(OR$^{cc}$)$_2$, and —NR$^{bb}$P(=O)(NR$^{bb}$)$_2$, wherein R$^{aa}$, R$^{bb}$, and R$^{cc}$ are as defined herein, with the proviso that the nitrogen atom directly attached to the parent molecule is not substituted with hydrogen.

"Trisubstituted amino" refers to an amino group wherein the nitrogen atom directly attached to the parent molecule is substituted with three groups, and includes groups selected from —N(R$^{bb}$)$_3$ and —N(R$^{bb}$)$_3^+$X$^-$, wherein R$^{bb}$ and X$^-$ are as defined herein.

"Sulfonyl" refers to a group selected from —SO$_2$N(R$^{bb}$)$_2$, —SO$_2$R$^{aa}$, and —SO$_2$OR$^{aa}$, wherein R$^{aa}$ and R$^{bb}$ are as defined herein.

"Sulfinyl" refers to the group —S(=O)R$^{aa}$, wherein R$^{aa}$ is as defined herein.

"Carbonyl" refers a group wherein the carbon directly attached to the parent molecule is sp$^2$ hybridized, and is substituted with an oxygen, nitrogen or sulfur atom, e.g., a group selected from ketones (—C(=O)R$^{aa}$), carboxylic acids (—CO$_2$H), aldehydes (—CHO), esters (—CO$_2$R$^{aa}$, —C(=O)SR$^{aa}$, —C(=S)SR$^{aa}$), amides (—C(=O)N(R$^{bb}$)$_2$, —C(=O)NR$^{bb}$SO$_2$R$^{aa}$, —C(=S)N(R$^{bb}$)$_2$), and imines (—C(=NR$^{bb}$)R$^{aa}$, —C(=NR$^{bb}$)OR$^{aa}$, —C(=NR$^{bb}$)N(R$^{bb}$)$_2$), wherein R$^{aa}$ and R$^{bb}$ are as defined herein.

Nitrogen atoms can be substituted or unsubstituted as valency permits, and include primary, secondary, tertiary, and quarternary nitrogen atoms. Exemplary nitrogen atom substitutents include, but are not limited to, hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{bb}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O(NR$^{cc}$)$_2$, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups attached to a nitrogen atom are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined above.

In certain embodiments, the substituent present on a nitrogen atom is a nitrogen protecting group (also referred to as an amino protecting group). Nitrogen protecting groups include, but are not limited to, —OH, —OR$^{aa}$, —N(R$^{cc}$)$_2$, —C(=O)R$^{aa}$, —C(=O)N(R$^{cc}$)$_2$, —CO$_2$R$^{aa}$, —SO$_2$R$^{aa}$, —C(=NR$^{cc}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, $C_{1-10}$ alkyl (e.g., aralkyl, heteroaralkyl), $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl groups, wherein each alkyl, alkenyl, alkynyl, carbocyclyl, heterocyclyl, aralkyl, aryl, and heteroaryl is independently substituted with 0, 1, 2, 3, 4, or 5 $R^{dd}$ groups, and wherein $R^{aa}$, $R^{bb}$, $R^{cc}$, and $R^{dd}$ are as defined herein. Nitrogen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

Amide nitrogen protecting groups (e.g., —C(=O)R$^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine, o-nitrobenzamide, and o-(benzoyloxymethyl)benzamide.

Carbamate nitrogen protecting groups (e.g., —C(=O)OR$^{aa}$) include, but are not limited to, methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isoborynl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, and 2,4,6-trimethylbenzyl carbamate.

Sulfonamide nitrogen protecting groups (e.g., —S(=O)$_2$R$^{aa}$) include, but are not limited to, p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

In certain embodiments, the substituent present on an oxygen atom is an oxygen protecting group (also referred to as a hydroxyl protecting group). Oxygen protecting groups include, but are not limited to, —$R^{aa}$, —$N(R^{bb})_2$, —$C(=O)SR^{aa}$, —$C(=O)R^{aa}$, —$CO_2R^{aa}$, —$C(=O)N(R^{bb})_2$, —$C(=NR^{bb})R^{aa}$, —$C(=NR^{bb})OR^{aa}$, —$C(=NR^{bb})N(R^{bb})_2$, —$S(=O)R^{aa}$, —$SO_2R^{aa}$, —$Si(R^{aa})_3$, —$P(R^{cc})_2$, —$P(R^{cc})_3$, —$P(=O)_2R^{aa}$, —$P(=O)(R^{aa})_2$, —$P(=O)(OR^{cc})_2$, —$P(=O)_2N(R^{bb})_2$, and —$P(=O)(NR^{bb})_2$, wherein $R^{aa}$, $R^{bb}$, and $R^{cc}$ are as defined herein. Oxygen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

Exemplary oxygen protecting groups include, but are not limited to, methyl, methoxymethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodisulfuran-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), methyl carbonate, 9-fluorenylmethyl carbonate (Fmoc), ethyl carbonate, t-butyl carbonate (Boc), 2,2,2-trichloroethyl carbonate (Troc), 2-(trimethylsilyl)ethyl carbonate (TMSEC), 2-(phenylsulfonyl)ethyl carbonate (Psec), 2-(triphenylphosphonio) ethyl carbonate (Peoc), isobutyl carbonate, vinyl carbonate, allyl carbonate, p-nitrophenyl carbonate, benzyl carbonate, p-methoxybenzyl carbonate, 3,4-dimethoxybenzyl carbonate, o-nitrobenzyl carbonate, p-nitrobenzyl carbonate, S-benzyl thiocarbonate, 4-ethoxy-1-napthtyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

In certain embodiments, the substituent present on a sulfur atom is a sulfur protecting group (also referred to as a thiol protecting group). Sulfur protecting groups include, but are not limited to, —$R^{aa}$, —$N(R^{bb})_2$, —$C(=O)SR^{aa}$, —$C(=O)R^{aa}$, —$CO_2R^{aa}$, —$C(=O)N(R^{bb})_2$, —$C(=NR^{bb})R^{aa}$, —$C(=NR^{bb})OR^{aa}$, —$C(=NR^{bb})N(R^{bb})_2$, —$S(=O)R^{aa}$, —$SO_2R^{aa}$, —$Si(R^{aa})_3$, —$P(R^{cc})_2$, —$P(R^{cc})_3$, —$P(=O)_2R^{aa}$, —$P(=O)(R^{aa})_2$, —$P(=O)(OR^{cc})_2$, —$P(=O)_2N(R^{bb})_2$, and —$P(=O)(NR^{bb})_2$, wherein $R^{aa}$, $R^{bb}$, and $R^{cc}$ are as defined herein. Sulfur protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

These and other exemplary substituents are described in more detail in the Detailed Description, Examples, and claims. The present disclosure is not intended to be limited in any manner by the above exemplary listing of substituents.

"Pharmaceutically acceptable salt" refers to those salts which are, within the scope of sound medical judgment, suitable for use in contact with the tissues of humans and other animals without undue toxicity, irritation, allergic response, and the like, and are commensurate with a reasonable benefit/risk ratio. Pharmaceutically acceptable salts are well known in the art. For example, Berge et al. describe pharmaceutically acceptable salts in detail in *J. Pharmaceutical Sciences* (1977) 66:1-19. Pharmaceutically acceptable salts of the compounds describe herein include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid, or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, quaternary salts.

A "subject" to which administration is contemplated includes, but is not limited to, humans (e.g., a male or female of any age group, e.g., a pediatric subject (e.g, infant, child, adolescent) or adult subject (e.g., young adult, middle-aged adult or senior adult)) and/or other non-human animals, for example, non-human mammals (e.g., primates (e.g., cynomolgus monkeys, rhesus monkeys); commercially relevant mammals such as cattle, pigs, horses, sheep, goats, cats, and/ or dogs), birds (e.g., commercially relevant birds such as chickens, ducks, geese, and/or turkeys), rodents (e.g., rats and/or mice), reptiles, amphibians, and fish. In certain embodiments, the nonhuman animal is a mammal. The non-human animal may be a male or female at any stage of development. A nonhuman animal may be a transgenic animal.

"Condition," "disease," and "disorder" are used interchangeably herein.

"Treat," "treating" and "treatment" encompasses an action that occurs while a subject is suffering from a condition which reduces the severity of the condition or retards or slows the progression of the condition ("therapeutic treatment"). "Treat," "treating" and "treatment" also encompasses an action that occurs before a subject begins to suffer from the condition and which inhibits or reduces the severity of the condition ("prophylactic treatment").

An "effective amount" of a compound refers to an amount sufficient to elicit the desired biological response, e.g., treat the condition. As will be appreciated by those of ordinary skill in this art, the effective amount of a compound described herein may vary depending on such factors as the desired biological endpoint, the pharmacokinetics of the compound, the condition being treated, the mode of administration, and the age and health of the subject. An effective amount encompasses therapeutic and prophylactic treatment.

A "therapeutically effective amount" of a compound is an amount sufficient to provide a therapeutic benefit in the treatment of a condition or to delay or minimize one or more symptoms associated with the condition. A therapeutically effective amount of a compound means an amount of therapeutic agent, alone or in combination with other therapies, which provides a therapeutic benefit in the treatment of the condition. The term "therapeutically effective amount" can encompass an amount that improves overall therapy, reduces or avoids symptoms or causes of the condition, or enhances the therapeutic efficacy of another therapeutic agent.

A "prophylactically effective amount" of a compound is an amount sufficient to prevent a condition, or one or more symptoms associated with the condition or prevent its recurrence. A prophylactically effective amount of a compound means an amount of a therapeutic agent, alone or in combination with other agents, which provides a prophylactic benefit in the prevention of the condition. The term "prophylactically effective amount" can encompass an amount that improves overall prophylaxis or enhances the prophylactic efficacy of another prophylactic agent.

As used herein, the term "methyltransferase" represents transferase class enzymes that are able to transfer a methyl group from a donor molecule to an acceptor molecule, e.g., an amino acid residue of a protein or a nucleic base of a DNA molecule. Methyltransferases typically use a reactive methyl group bound to sulfur in S-adenosyl methionine (SAM) as the methyl donor. In some embodiments, a methyltransferase described herein is a protein methyltransferase. In some embodiments, a methyltransferase described herein is a histone methyltransferase. Histone methyltransferases (HMT) are histone-modifying enzymes, (including histone-lysine N-methyltransferase and histone-arginine N-methyltransferase), that catalyze the transfer of one or more methyl groups to lysine and arginine residues of histone proteins. In certain embodiments, a methyltransferase described herein is a histone-arginine N-methyltransferase.

As generally described above, provided herein are compounds useful as CARM1 inhibitors. In some embodiments, the present disclosure provides a compound of Formula (I):

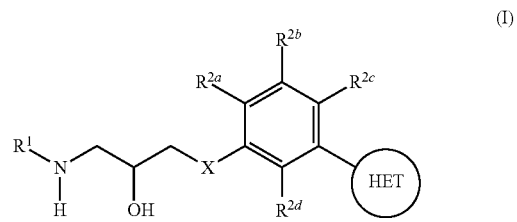

or a pharmaceutically acceptable salt thereof;

wherein:

X is —O—, —S—, or —CH$_2$—;

R$^1$ is hydrogen or optionally substituted C$_{1-4}$ aliphatic;

each of R$^{2a}$, R$^{2b}$, R$^{2c}$, and R$^{2d}$ is independently hydrogen, halogen, —CN, —NO$_2$, —C(=O)R$^{A2}$, —C(=O)OR$^{A2}$, —C(=O)N(R$^{A2}$)$_2$, —OR$^{A2}$, S—R$^{A2}$, —N(R$^{A2}$)$_2$, —S(=O)R$^{A2}$, —S(=O)$_2$R$^{A2}$, optionally substituted alkyl, optionally substituted alkenyl, optionally substituted alkynyl, optionally substituted carbocyclyl, optionally substituted heterocyclyl, wherein each instance of R$^{A2}$ is independently hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl, or two R$^{A2}$ groups attached to the same nitrogen atom are joined to form an optionally substituted heterocyclyl or optionally substituted heteroaryl ring;

Ring HET is a 6-membered monocylic heteroaryl ring system of the formula:

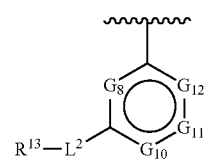

wherein:

G$_8$ is C—R$^8$ or N;

G$_{10}$ is C—R$^{10}$ or N;

$G_{11}$ is C—$R^{11}$ or N;
$G_{12}$ is C—$R^{12}$ or N;
provided at least one instance of $G_8$, $G_{10}$, $G_{11}$, or $G_{12}$ is N;
each instance of $R^8$, $R^{10}$, $R^{11}$, and $R^{12}$ is independently selected from the group consisting of hydrogen, halo, —CN, —$NO_2$, —C(=O)R', —C(=O)OR', —C(=O)N(R')$_2$, optionally substituted alkyl, and -$L^1$-$R^3$;

each instance of R' is independently hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl, or two R' groups attached to the same nitrogen are joined to form an optionally substituted heterocyclyl ring or optionally substituted heteroaryl ring;

each instance of $L^1$ and $L^2$ is independently a bond, —O—, —N($R^L$)—, —S—, —C(O)—, —C(O)O—, —C(O)S—, —C(O)N($R^L$)—, —C(O)N($R^L$)N($R^L$)—, —OC(O)—, —OC(O)N($R^L$)—, —$NR^L$C(O)—, —$NR^L$C(O)N($R^L$)—, —$NR^L$C(O)N($R^L$)N($R^L$)—, —$NR^L$C(O)O—, —SC(O)—, —C(=$NR^L$)—, —C(=$NNR^L$)—, —C(=$NOR^L$)—, —C(=$NR^L$)N($R^L$)—, —$NR^L$C(=$NR^L$)—, —C(S)—, —C(S)N($R^L$)—, —$NR^L$C(S)—, —S(O)—, —OS(O)$_2$—, —S(O)$_2$O—, —$SO_2$—, —N($R^L$)$SO_2$—, —$SO_2$N($R^L$)—, —N($R^L$)$SO_2$N($R^L$)—, an optionally substituted $C_{1-10}$ saturated or unsaturated hydrocarbon chain, wherein one or more moieties selected from the group consisting of —O—, —N($R^L$)—, —S—, —C(O)—, —C(O)O—, —C(O)S—, —C(O)N($R^L$)—, —C(O)N($R^L$)N($R^L$)—, —OC(O)—, —OC(O)N($R^L$)—, —$NR^L$C(O)—, —$NR^L$C(O)N($R^L$)—, —$NR^L$C(O)N($R^L$)N($R^L$)—, —$NR^L$C(O)O—, —SC(O)—, —C(=$NR^L$)—, —C(=$NNR^L$)—, —C(=$NOR^L$)—, —C(=$NR^L$)N($R^L$)—, —$NR^L$C(=$NR^L$)—, —C(S)—, —C(S)N($R^L$)—, —$NR^L$C(S)—, —S(O)—, —OS(O)$_2$—, —S(O)$_2$O—, —$SO_2$—, —N($R^L$)$SO_2$—, —$SO_2$N($R^L$)—, and —N($R^L$)$SO_2$N($R^L$)— is optionally and independently present between two carbon atoms of the hydrocarbon chain, and optionally and independently present at one or both ends of the hydrocarbon chain;

each $R^L$ is independently hydrogen, optionally substituted alkyl, or a nitrogen protecting group, or $R^L$ and $R^3$ taken together form an optionally substituted heterocyclyl or optionally substituted heteroaryl ring, or $R^L$ and $R^{13}$ taken together form an optionally substituted heterocyclyl or optionally substituted heteroaryl ring;

$R^3$ is hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl, provided when $R^3$ is hydrogen, then $L^1$ is not a bond; and $R^{13}$ is optionally substituted carbocyclyl, optionally substituted heterocyclyl, optionally substituted aryl, or optionally substituted heteroaryl.

It is generally understood that compounds of Formula (I), as described herein, comprises one or more asymmetric centers, and thus can exist in various isomeric forms, e.g., enantiomeric and/or diastereomeric forms. In certain embodiments, the compound of Formula (I) has the following stereochemistry (I-a) or (I-b):

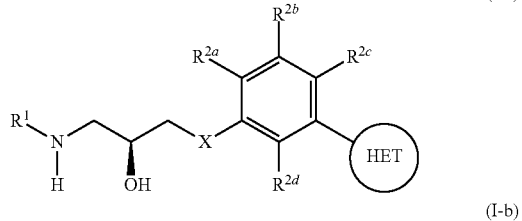

(I-a)

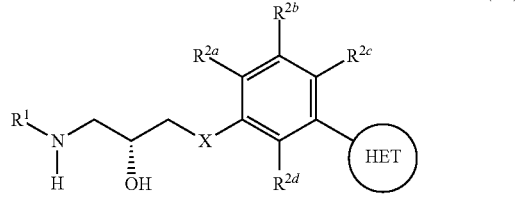

(I-b)

As generally defined herein, X is —O—, —S—, or —$CH_2$—. In certain embodiments, X is —O—. In certain embodiments, X is —S—. In certain embodiments, X is —O—.

As generally defined herein, $R^1$ is hydrogen or optionally substituted $C_{1-4}$ aliphatic. In certain embodiments, $R^1$ is hydrogen. In certain embodiments, $R^1$ is optionally substituted $C_{1-4}$ aliphatic, e.g., optionally substituted $C_1$ aliphatic, optionally substituted $C_2$ aliphatic, optionally substituted $C_3$ aliphatic, or optionally substituted $C_4$ aliphatic. It is understood that aliphatic, as used herein, encompasses alkyl, alkenyl, alkynyl, and carbocyclic groups. In certain embodiments, $R^1$ is optionally substituted $C_{1-4}$ alkyl, e.g., optionally substituted $C_{1-2}$alkyl, optionally substituted $C_{2-3}$alkyl, optionally substituted $C_{3-4}$alkyl, optionally substituted $C_1$alkyl, optionally substituted $C_2$alkyl, optionally substituted $C_3$alkyl, or optionally substituted $C_4$alkyl. Exemplary $R^1$ $C_{1-4}$ alkyl groups include, but are not limited to, methyl ($C_1$), ethyl ($C_2$), n-propyl ($C_3$), isopropyl ($C_3$), n-butyl ($C_4$), tert-butyl ($C_4$), sec-butyl ($C_4$), or iso-butyl ($C_4$), each of which may be substituted or unsubstituted. In certain embodiments, $R^1$ is optionally substituted $C_{2-4}$ alkenyl, e.g., optionally substituted $C_{2-3}$alkenyl, optionally substituted $C_{3-4}$alkenyl, optionally substituted $C_2$alkenyl, optionally substituted $C_3$alkenyl, or optionally substituted $C_4$alkenyl. In certain embodiments, $R^1$ is optionally substituted $C_{2-4}$ alkynyl, e.g., optionally substituted $C_{2-3}$alkynyl, optionally substituted $C_{3-4}$alkynyl, optionally substituted $C_2$alkynyl, optionally substituted $C_3$alkynyl, or optionally substituted $C_4$alkynyl. In certain embodiments, $R^1$ is optionally substituted $C_3$carbocyclyl, e.g., optionally substituted cyclopropyl. In certain embodiments, $R^1$ is hydrogen or an unsubstituted $C_{1-4}$ aliphatic group, e.g., for example, in certain embodiments, $R^1$ is hydrogen, methyl, ethyl, n-propyl, isopropyl, or cyclopropyl.

As generally defined herein, each of $R^{2a}$, $R^{2b}$, $R^{2c}$, and $R^{2d}$ is independently hydrogen, halo, —CN, —$NO_2$, —C(=O)$R^{A2}$, —C(=O)O$R^{A2}$, —C(=O)N($R^{A2}$)$_2$, —O$R^{A2}$, —S$R^{A2}$, —N($R^{A2}$)$_2$, —S(=O)$R^{A2}$, —S(=O)$_2R^{A2}$, optionally substituted alkyl, optionally substituted alkenyl, optionally substituted alkynyl, optionally substituted carbocyclyl, optionally substituted heterocyclyl, wherein each instance of $R^{A2}$ is independently hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl, or two $R^{A2}$ groups attached to the same nitrogen atom are joined to form an optionally substituted heterocyclyl or optionally substituted heteroaryl ring.

In certain embodiments, at least one of (e.g., one, two, three, each of) $R^{2a}$, $R^{2b}$, $R^{2c}$, and $R^{2d}$ is hydrogen. In certain embodiments, at least one of $R^{2a}$, $R^{2b}$, $R^{2c}$, and $R^{2d}$ is halo, e.g., fluoro, chloro, bromo, or iodo. In certain embodiments, at least one of $R^{2a}$, $R^{2b}$, $R^{2c}$, and $R^{2d}$ is chloro. In certain embodiments, at least one of $R^{2a}$, $R^{2b}$, $R^{2c}$, and $R^{2d}$ is —CN. In certain embodiments, at least one of $R^{2a}$, $R^{2b}$, $R^{2c}$, and $R^{2d}$ is —NO$_2$. In certain embodiments, at least one of $R^{2a}$, $R^{2b}$, $R^{2c}$, and $R^{2d}$ is —C(=O)R$^{A2}$, e.g., wherein $R^{A2}$ is hydrogen or optionally substituted alkyl (e.g., methyl). In certain embodiments, at least one of $R^{2a}$, $R^{2b}$, $R^{2c}$, and $R^{2d}$ is —C(=O)OR$^{A2}$, e.g., wherein $R^{A2}$ is hydrogen or optionally substituted alkyl (e.g., methyl). In certain embodiments, at least one of $R^{2a}$, $R^{2b}$, $R^{2c}$, and $R^{2d}$ is —C(=O)N(R$^{A2}$)$_2$, e.g., wherein each instance of $R^{A2}$ is hydrogen or optionally substituted alkyl (e.g., methyl), or two $R^{A2}$ groups attached to the same nitrogen atom are joined to form an optionally substituted heterocyclyl or optionally substituted heteroaryl ring. In certain embodiments, at least one of $R^{2a}$, $R^{2b}$, $R^{2c}$, and $R^{2d}$ is optionally substituted alkyl, e.g., optionally substituted $C_{1-4}$ alkyl, optionally substituted $C_{1-2}$alkyl, optionally substituted $C_{2-3}$alkyl, optionally substituted $C_{3-4}$alkyl, optionally substituted $C_1$alkyl, optionally substituted $C_2$alkyl, optionally substituted $C_3$alkyl, or optionally substituted $C_4$alkyl. Exemplary $R^{2a}$, $R^{2b}$, $R^{2c}$, and $R^{2d}$ $C_{1-4}$alkyl groups include, but are not limited to, methyl ($C_1$), ethyl ($C_2$), n-propyl ($C_3$), isopropyl ($C_3$), n-butyl ($C_4$), tert-butyl ($C_4$), sec-butyl ($C_4$), and iso-butyl ($C_4$), each of which may be substituted or unsubstituted. In certain embodiments, at least one of $R^{2a}$, $R^{2b}$, $R^{2c}$, and $R^{2d}$ is alkyl substituted with hydroxy or substituted hydroxy, e.g., —(CH$_2$)$_a$OH or —(CH$_2$)$_a$OCH$_3$, wherein a is 1, 2, 3, 4, 5, or 6. In certain embodiments, at least one of $R^{2a}$, $R^{2b}$, $R^{2c}$, and $R^{2d}$ is alkyl substituted with halogen (e.g., fluoro), e.g., at least one of $R^{2a}$, $R^{2b}$, $R^{2c}$, and $R^{2d}$ is —CF$_3$. In certain embodiments, at least one of $R^{2a}$, $R^{2b}$, $R^{2c}$, and $R^{2d}$ is optionally substituted alkenyl, e.g., optionally substituted $C_{2-4}$ alkenyl, optionally substituted $C_{2-3}$alkenyl, optionally substituted $C_{3-4}$alkenyl, optionally substituted $C_2$alkenyl, optionally substituted $C_3$alkenyl, or optionally substituted $C_4$alkenyl. In certain embodiments, at least one of $R^{2a}$, $R^{2b}$, $R^{2c}$, and $R^{2d}$ is optionally substituted $C_2$alkenyl or optionally substituted $C_3$alkenyl, e.g., vinyl or allyl. In certain embodiments, at least one of $R^{2a}$, $R^{2b}$, $R^{2c}$, and $R^{2d}$ is optionally substituted alkynyl, e.g., optionally substituted $C_{2-4}$ alkynyl, optionally substituted $C_{2-3}$alkynyl, optionally substituted $C_{3-4}$alkynyl, optionally substituted $C_2$alkynyl, optionally substituted $C_3$alkynyl, or optionally substituted $C_4$alkynyl. In certain embodiments, at least one of $R^{2a}$, $R^{2b}$, $R^{2c}$, and $R^{2d}$ is optionally substituted $C_2$alkynyl, e.g., acetylene. In certain embodiments, at least one of $R^{2a}$, $R^{2b}$, $R^{2c}$, and $R^{2d}$ is optionally substituted carbocyclyl, e.g., optionally substituted $C_{3-5}$carbocyclyl, optionally substituted $C_{3-4}$carbocyclyl, optionally substituted $C_{4-5}$ carbocyclyl, optionally substituted $C_3$carbocyclyl, optionally substituted $C_4$carbocyclyl, or optionally substituted $C_5$carbocyclyl. In certain embodiments, at least one of $R^{2a}$, $R^{2b}$, $R^{2c}$, and $R^{2d}$ is optionally substituted $C_3$carbocyclyl, e.g., cyclopropyl. In certain embodiments, at least one of $R^{2a}$, $R^{2b}$, $R^{2c}$, and $R^{2d}$ is optionally substituted heterocyclyl, e.g., optionally substituted 3- to 5-membered heterocyclyl, optionally substituted 3- to 4-membered heterocyclyl, optionally substituted 4- to 5-membered heterocyclyl, optionally substituted 3-membered heterocyclyl, optionally substituted 4-membered heterocyclyl, or optionally substituted 5-membered heterocyclyl. In certain embodiments, at least one of $R^{2a}$, $R^{2b}$, $R^{2c}$, and $R^{2d}$ is —OR$^{A2}$, —SR$^{A2}$, or —N(R$^{A2}$)$_2$, wherein $R^{A2}$ is as defined herein. In certain embodiments, at least one of $R^{2a}$, $R^{2b}$, $R^{2c}$, and $R^{2d}$ is —S(=O)R$^{A2}$ or —S(=O)$_2$R$^{A2}$, wherein $R^{A2}$ is as defined herein. In certain embodiments, at least one of $R^{A2}$ is hydrogen, e.g., for example, to provide at least one of $R^{2a}$, $R^{2b}$, $R^{2c}$, and $R^{2d}$ as —OH, —SH, —NH$_2$, or —NHR$^{A2}$. In certain embodiments, at least one of $R^{A2}$ is optionally substituted alkyl, e.g., optionally substituted $C_{1-4}$ alkyl, optionally substituted $C_{1-2}$alkyl, optionally substituted $C_{2-3}$alkyl, optionally substituted $C_{3-4}$alkyl, optionally substituted $C_1$alkyl, optionally substituted $C_2$alkyl, optionally substituted $C_3$alkyl, or optionally substituted $C_4$alkyl, e.g., for example, at least one of $R^{A2}$ is methyl to provide a group $R^{2a}$, $R^{2b}$, $R^{2c}$, and $R^{2d}$ of formula —OCH$_3$, —SCH$_3$, —NHCH$_3$, —N(CH$_3$)$_2$, or —NCH$_3$R$^{A2}$. In certain embodiments, at least one of $R^{A2}$ is alkyl substituted with halogen (e.g., fluoro), e.g., to provide a group $R^{2a}$, $R^{2b}$, $R^{2c}$, and $R^{2d}$ of formula —OCF$_3$, —SCF$_3$, —NHCF$_3$, —N(CF$_3$)$_2$, or —NCF$_3$R$^{A2}$. In certain embodiments, at least one of $R^{A2}$ is a group of formula —CH$_2$CH(OH)CH$_2$NHR$^1$, wherein $R^1$ is as defined herein, e.g., to provide a group $R^{2a}$, $R^{2b}$, $R^{2c}$, and $R^{2d}$ of formula —OCH$_2$CH(OH)CH$_2$NHR$^1$, —SCH$_2$CH(OH)CH$_2$NHR$^1$, —NHCH$_2$CH(OH)CH$_2$NHR$^1$, or —N(R$^{A2}$)CH$_2$CH(OH)CH$_2$NHR$^1$. In certain embodiments, at least one of $R^{A2}$ is alkyl substituted with an optionally substituted aryl (e.g., optionally substituted phenyl) or optionally substituted heteroaryl (e.g., optionally substituted pyridinyl), e.g., to provide a group $R^{2a}$, $R^{2b}$, $R^{2c}$, and $R^{2d}$ of formula —O(CH$_2$)$_a$Ar, —S(CH$_2$)$_a$Ar, —NH(CH$_2$)$_a$Ar, or —N(R$^{A2}$)(CH$_2$)$_a$Ar, wherein a is 1, 2, 3, 4, 5, or 6, and Ar is optionally substituted aryl (e.g., optionally substituted phenyl) or optionally substituted heteroaryl (e.g., optionally substituted pyridinyl). In certain embodiments, at least one of $R^{A2}$ is optionally substituted alkenyl, e.g., optionally substituted $C_{2-4}$ alkenyl, optionally substituted $C_{2-3}$alkenyl, optionally substituted $C_{3-4}$alkenyl, optionally substituted $C_2$alkenyl, optionally substituted $C_3$alkenyl, or optionally substituted $C_4$alkenyl. In certain embodiments, at least one of $R^{A2}$ is optionally substituted alkynyl, e.g., optionally substituted $C_{2-4}$ alkynyl, optionally substituted $C_{2-3}$alkynyl, optionally substituted $C_{3-4}$alkynyl, optionally substituted $C_2$alkynyl, optionally substituted $C_3$alkynyl, or optionally substituted $C_4$alkynyl. In certain embodiments, at least one of $R^{A2}$ is optionally substituted carbocyclyl, e.g., optionally substituted $C_{3-5}$carbocyclyl, optionally substituted $C_{3-4}$carbocyclyl, optionally substituted $C_{4-5}$ carbocyclyl, optionally substituted $C_3$carbocyclyl, optionally substituted $C_4$carbocyclyl, or optionally substituted $C_5$carbocyclyl. In certain embodiments, at least one of $R^{A2}$ is optionally substituted heterocyclyl, e.g., optionally substituted 3- to 5-membered heterocyclyl, optionally substituted 3- to 4-membered heterocyclyl, optionally substituted 4- to 5-membered heterocyclyl, optionally substituted 3-membered heterocyclyl, optionally substituted 4-membered heterocyclyl, or optionally substituted 5-membered heterocyclyl. In certain embodiments, at least one of $R^{A2}$ is optionally substituted aryl (e.g., optionally substituted phenyl) or optionally substituted heteroaryl (e.g., optionally substituted pyridinyl). In certain embodiments, two $R^{A2}$ groups, e.g., of —N(R$^{A2}$)$_2$, are joined to form an optionally substituted heterocyclyl or optionally substituted heteroaryl ring.

In certain embodiments, at least one of $R^{2a}$, $R^{2b}$, $R^{2c}$, and $R^{2s}$ is hydrogen. In certain embodiments, at least two of $R^{2a}$, $R^{2b}$, $R^{2c}$, and $R^{2d}$ is hydrogen. In certain embodiments, at least three of $R^{2a}$, $R^{2b}$, $R^{2c}$, and $R^{2d}$ is hydrogen. In certain embodiments, each of $R^{2a}$, $R^{2b}$, $R^{2c}$, and $R^{2d}$ are hydrogen, e.g., to provide a compound of Formula (I-c):

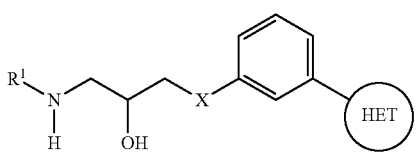
(I-c)

or a pharmaceutically acceptable salt thereof.

However, in certain embodiments, at least one of $R^{2a}$, $R^{2b}$, $R^{2c}$, and $R^{2d}$ is a non-hydrogen group. For example, in certain embodiments, $R^{2a}$ is a non-hydrogen group. In certain embodiments, $R^{2a}$ is a non-hydrogen group, and each of $R^{2b}$, $R^{2c}$, and $R^{2d}$ is hydrogen, e.g., to provide a compound of Formula (I-d):

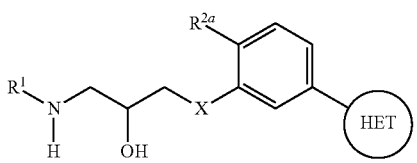
(I-d)

or a pharmaceutically acceptable salt thereof. In certain embodiments, $R^{2a}$ is a non-hydrogen group selected from the group consisting of halogen (e.g., chloro), —CN, —C(=O)$R^{A2}$, —OR$^{A2}$, —SR$^{A2}$, —N(R$^{A2}$)$_2$, optionally substituted cyclopropyl, optionally substituted C$_{1-4}$alkyl, optionally substituted C$_{2-4}$alkenyl, and optionally substituted C$_{2-4}$alkynyl, wherein R$^{A2}$ is optionally substituted alkyl.

In certain embodiments, $R^{2b}$ is a non-hydrogen group. In certain embodiments, $R^{2b}$ is a non-hydrogen group, and each of $R^{2a}$, $R^{2c}$, and $R^{2d}$ is hydrogen, e.g., to provide a compound of Formula (I-e):

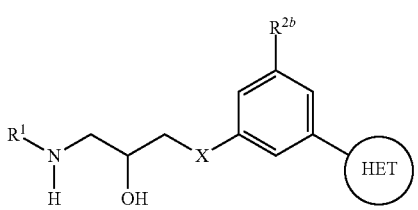
(I-e)

or a pharmaceutically acceptable salt thereof. In certain embodiments, $R^{2b}$ is a non-hydrogen group selected from the group consisting of halogen (e.g., chloro), —CN, —C(=O)$R^{A2}$, —OR$^{A2}$, —SR$^{A2}$, —N(R$^{A2}$)$_2$, optionally substituted cyclopropyl, optionally substituted C$_{1-4}$alkyl, optionally substituted C$_{2-4}$alkenyl, and optionally substituted C$_{2-4}$alkynyl, wherein R$^{A2}$ is optionally substituted alkyl.

In certain embodiments, $R^{2c}$ is a non-hydrogen group. In certain embodiments, $R^{2c}$ is a non-hydrogen group, and each of $R^{2a}$, $R^{2b}$, and $R^{2d}$ is hydrogen, e.g., to provide a compound of Formula (I-f):

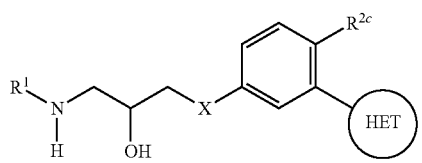
(I-f)

or a pharmaceutically acceptable salt thereof. In certain embodiments, $R^{2c}$ is a non-hydrogen group selected from the group consisting of halogen (e.g., chloro), —CN, —C(=O)$R^{A2}$, —OR$^{A2}$, —SR$^{A2}$, —N(R$^{A2}$)$_2$, optionally substituted cyclopropyl, optionally substituted C$_{1-4}$alkyl, optionally substituted C$_{2-4}$alkenyl, and optionally substituted C$_{2-4}$alkynyl, wherein R$^{A2}$ is optionally substituted alkyl.

In certain embodiments, $R^{2d}$ is a non-hydrogen group. In certain embodiments, $R^{2d}$ is a non-hydrogen group, and each of $R^{2a}$, $R^{2b}$, and $R^{2c}$ is hydrogen, e.g., to provide a compound of Formula (I-g):

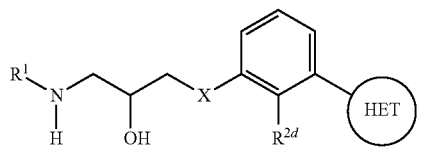
(I-g)

or a pharmaceutically acceptable salt thereof. In certain embodiments, $R^{2d}$ is a non-hydrogen group selected from the group consisting of halogen (e.g., chloro), —CN, —C(=O)$R^{A2}$, —OR$^{A2}$, —SR$^{A2}$, —N(R$^{A2}$)$_2$, optionally substituted cyclopropyl, optionally substituted C$_{1-4}$alkyl, optionally substituted C$_{2-4}$alkenyl, and optionally substituted C$_{2-4}$alkynyl, wherein R$^{A2}$ is optionally substituted alkyl.

As generally understood from the present disclosure, Ring HET is a 6-membered monocyclic heteroaryl ring system of Formula:

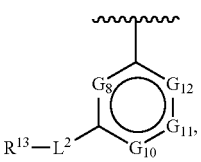

i.e., to provide a compound of Formula (I-h):

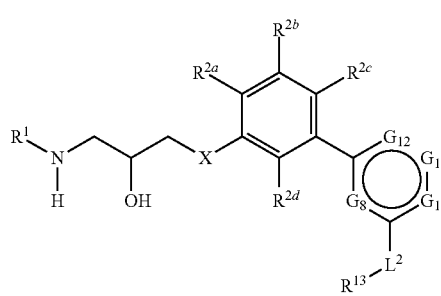
(I-h)

or pharmaceutically acceptable salt thereof, wherein at least one instance of $G_8$, $G_{10}$, $G_{11}$, or $G_{12}$ is N, e.g., at least one, two, or three instances of $G_8$, $G_{10}$, $G_{11}$, or $G_{12}$ is N. In certain embodiments, $G_8$ is N. In certain embodiments, $G_{10}$ is N. In certain embodiments, $G_{11}$ is N. In certain embodiments, $G_{12}$ is N. In certain embodiments, two instances of $G_8$, $G_{10}$, $G_{11}$, or $G_{12}$ are N. In certain embodiments, $G_8$ and $G_{10}$ are both N. In certain embodiments, $G_8$ and $G_{11}$ are both N. In certain embodiments, $G_8$ and $G_{12}$ are both N. In certain embodiments, $G_{10}$ and $G_{12}$ are both N. In certain embodiments, three instances of $G_8$, $G_{10}$, $G_{11}$, or $G_{12}$ are N. In certain embodiments, $G_8$, $G_{10}$, and $G_{12}$ are each N.

Exemplary Ring HET groups of the formula (i), (ii), or (iii), include, but are not limited to, any one of the following ring systems, wherein one, two, or three instances of $G_8$, $G_{10}$, $G_{11}$, and $G_{12}$ are N:

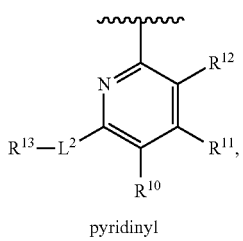
pyridinyl (i-a)

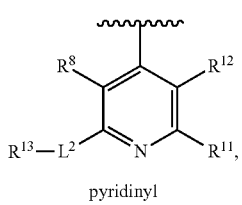
pyridinyl (i-b)

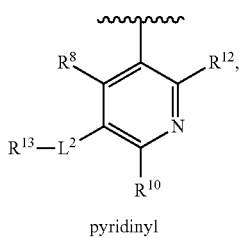
pyridinyl (i-c)

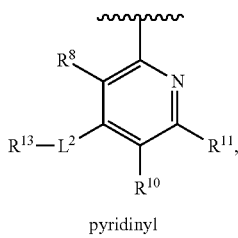
pyridinyl (i-d)

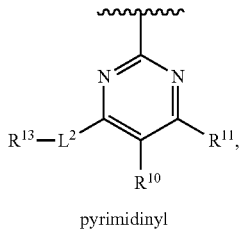
pyrimidinyl (i-e)

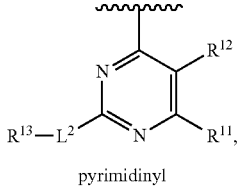
pyrimidinyl (i-f)

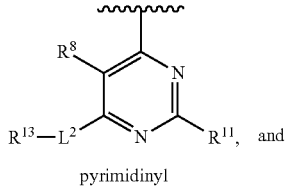
pyrimidinyl (i-g)

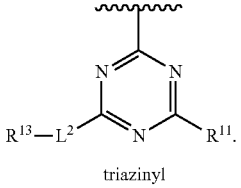
triazinyl (i-h)

Furthermore, as generally defined above, each instance of $R^8$, $R^{10}$, $R^{11}$, and $R^{12}$ is independently selected from the group consisting of hydrogen, halo, —CN, —NO$_2$, —C(=O)R', —C(=O)OR', —C(=O)N(R')$_2$, optionally substituted alkyl, or -L$^1$-R$^3$; wherein L$^1$, R$^3$, and R' are as defined herein. In certain embodiments, one of $R^8$, $R^{10}$, $R^{11}$, and $R^{12}$ is -L$^1$-R$^3$. Alternatively, neither $R^8$, $R^{10}$, $R^{11}$, and $R^{12}$ is -L$^1$-R$^3$. In certain embodiments, $R^8$ is -L$^1$-R$^3$. In certain embodiments, $R^{10}$ is -L$^1$-R$^3$. In certain embodiments, $R^{11}$ is -L$^1$-R$^3$. In certain embodiments, $R^{12}$ is -L$^1$-R$^3$. In certain embodiments, one instance of $R^8$, $R^{10}$, $R^{11}$, and $R^{12}$ is a -L$^1$-R$^3$ and the other instances (i.e., one or two instances) are a hydrogen or non-hydrogen moiety selected from the group consisting of halo, —CN, —NO$_2$, —C(=O)R', —C(=O)OR', —C(=O)N(R')$_2$, or optionally substituted alkyl. For example, in certain embodiments, at least one instance of $R^8$, $R^{10}$, $R^{11}$, and $R^{12}$ is halo, e.g., fluoro, chloro, bromo, or iodo. In certain embodiments, at least one instance of $R^8$, $R^{10}$, $R^{11}$, and $R^{12}$ is —CN. In certain embodiments, at least one instance of $R^8$, $R^{10}$, $R^{11}$, and $R^{12}$ is —NO$_2$. In certain embodiments, at least one instance of $R^8$, $R^{10}$, $R^{11}$, and $R^{12}$ is —C(=O)R', —C(=O)OR', or —C(=O)N(R')$_2$, wherein R' is as defined herein. In certain embodiments, at least one instance of $R^8$, $R^{10}$, $R^{11}$, and $R^{12}$ is optionally substituted alkyl, e.g., optionally substituted $C_{1-4}$ alkyl, optionally substituted $C_{1-2}$alkyl, optionally substituted $C_{2-3}$alkyl, optionally substituted $C_{3-4}$alkyl, optionally substituted $C_1$alkyl, optionally substituted $C_2$alkyl, optionally substituted $C_3$alkyl, or optionally substituted $C_4$alkyl. In certain embodiments, at least one instance of $R^8$, $R^{10}$, $R^{11}$, and $R^{12}$ is methyl. In certain embodiments, each instance of $R^8$, $R^{10}$, $R^{11}$, and $R^{12}$ is hydrogen. In certain embodiments, at least one instance of $R^8$, $R^{10}$, $R^{11}$, and $R^{12}$ is hydrogen or methyl.

As understood from the present disclosure, Ring HET optionally comprises a group -L$^1$-R$^3$ attached thereto. In certain embodiments, Ring HET does not comprise a group of formula -L$^1$-R$^3$ attached thereto, but in other embodiments, Ring HET does comprise a group of formula -L$^1$-R$^3$ attached thereto. In certain embodiments, -L$^1$-R$^3$ is meta to the point of attachment of Ring HET to the parent moiety. In certain embodiments, -L$^1$-R$^3$ is meta to -L$^2$-R$^{13}$. In certain embodiments, R$^3$ is an acyclic moiety selected from the group consisting of hydrogen, optionally substituted alkyl, optionally substituted alkenyl, or optionally substituted alkynyl. In certain embodiments, R$^3$ is a cyclic moiety selected from the group consisting of optionally substituted carbocyclyl, optionally substituted heterocyclyl, optionally substituted aryl, and optionally substituted heteroaryl. In certain embodiments, R$^3$ is directly attached to the Ring HET, i.e., wherein L$^1$ is a bond, provided that R$^3$ is not also hydrogen. In other embodiments, R$^3$ is indirectly attached to Ring HET, i.e., wherein L$^1$ is a linking group.

As generally defined herein, L$^1$ is a bond, —O—, —N(R$^L$)—, —S—, —C(O)—, —C(O)O—, —C(O)S—, —C(O)N(R$^L$)—, —C(O)N(R$^L$)N(R$^L$)—, —OC(O)—, —OC(O)N(R$^L$)—, —NR$^L$C(O)—, —NR$^L$C(O)N(R$^L$)—, —NR$^L$C(O)N(R$^L$)N(R$^L$)—, —NR$^L$C(O)O—, —SC(O)—, —C(=NR$^L$)—, —C(=NNR$^L$)—, —C(=NOR$^L$)—, —C(=NR$^L$)N(R$^L$)—, —NR$^L$C(=NR$^L$)—, —C(S)—, —C(S)N(R$^L$)—, —NR$^L$C(S)—, —S(O)—, —OS(O)$_2$—, —S(O)$_2$O—, —SO$_2$—, —N(R$^L$)SO$_2$—, —SO$_2$N(R$^L$)—, —N(R$^L$)SO$_2$N(R$^L$)—, or an optionally substituted C$_{1-10}$ saturated or unsaturated hydrocarbon chain, wherein one or more moieties selected from the group consisting of —O—, —N(R$^L$)—, —S—, —C(O)—, —C(O)O—, —C(O)S—, —C(O)N(R$^L$)—, —C(O)N(R$^L$)N(R$^L$)—, —OC(O), —OC(O)N(R$^L$)—, —NR$^L$C(O)—, —NR$^L$C(O)N(R$^L$)—, NR$^L$C(O)N(R$^L$)N(R$^L$)—, —NR$^L$C(O)O—, —SC(O), —C(=NR$^L$)—, —C(=NNR$^L$)—, —C(=NOR$^L$)—, C(=NR$^L$)N(R$^L$)—, —NR$^L$C(=NR$^L$)—, —C(S)—, —C(S)N(R$^L$)—, —NR$^L$C(S)—, —S(O), OS(O)$_2$—, S(O)$_2$O—, —SO$_2$—, —N(R$^L$)SO$_2$—, —SO$_2$N(R$^L$)—, and —N(R$^L$)SO$_2$N(R$^L$)— is optionally and independently present between two carbon atoms of the hydrocarbon chain, and optionally and independently present at one or both ends of the hydrocarbon chain. It is understood that the linker joining R$^3$ to Ring HET may comprise one or more of the above recited moieties in combination to form the group L$^1$.

In certain embodiments, L$^1$ is a bond. In certain embodiments, L$^1$ is a bond, and R$^3$ is optionally substituted alkyl, optionally substituted alkenyl, or optionally substituted alkynyl. In certain embodiments, L$^1$ is a bond, and R$^3$ is optionally substituted carbocyclyl, optionally substituted heterocyclyl, optionally substituted aryl, and optionally substituted heteroaryl.

In certain embodiments, L$^1$ is —O—. In certain embodiments, L$^1$ is —N(R$^L$)—. In certain embodiments, L$^1$ is —S—. In certain embodiments, L$^1$ is —C(O)—. In certain embodiments, L$^1$ is —C(O)O—. In certain embodiments, L$^1$ is —C(O)S—. In certain embodiments, L$^1$ is —C(O)N(R$^L$)—. In certain embodiments, L$^1$ is —C(O)N(R$^L$)N(R$^L$)—. In certain embodiments, L$^1$ is —OC(O)—. In certain embodiments, L$^1$ is —OC(O)N(R$^L$)—. In certain embodiments, L$^1$ is —NR$^L$C(O)—. In certain embodiments, L$^1$ is —NR$^L$C(O)N(R$^L$)—. In certain embodiments, L$^1$ is —NR$^L$C(O)N(R$^L$)N(R$^L$)—. In certain embodiments, L$^1$ is —NR$^L$C(O)O—. In certain embodiments, L$^1$ is —SC(O)—. In certain embodiments, L$^1$ is —C(=NR$^L$)—. In certain embodiments, L$^1$ is —C(=NNR$^L$)—. In certain embodiments, L$^1$ is —C(=NOR$^L$)—. In certain embodiments, L$^1$ is —C(=NR$^L$)N(R$^L$)—. In certain embodiments, L$^1$ is —NR$^L$C(=NR$^L$)—. In certain embodiments, L$^1$ is —C(S)—. In certain embodiments, L$^1$ is —C(S)N(R$^L$)—. In certain embodiments, L$^1$ is —NR$^L$C(S)—. In certain embodiments, L$^1$ is —S(O)—. In certain embodiments, L$^1$ is —OS(O)$_2$—. In certain embodiments, L$^1$ is —S(O)$_2$O—. In certain embodiments, L$^1$ is —SO$_2$. In certain embodiments, L$^1$ is —N(R$^L$)SO$_2$—. In certain embodiments, L$^1$ is —SO$_2$N(R$^L$)—. In certain embodiments, L$^1$ is —N(R$^L$)SO$_2$N(R$^L$)—.

In certain embodiments, L$^1$ is an optionally substituted C$_{1-10}$ saturated or unsaturated hydrocarbon chain, e.g., in certain embodiments, L$^1$ is an optionally substituted C$_{1-10}$ alkyl chain, L$^1$ is an optionally substituted C$_{2-10}$ alkenyl chain, or L$^1$ is an optionally substituted C$_{2-10}$ alkynyl chain. In certain embodiments, L$^1$ is an optionally substituted C$_{1-10}$ alkyl chain, e.g., an optionally substituted C$_{1-8}$ alkyl chain, optionally substituted C$_{1-6}$ alkyl chain, optionally substituted C$_{1-4}$ alkyl chain, optionally substituted C$_{1-3}$ alkyl chain, or optionally substituted C$_{1-2}$ alkyl chain. In certain embodiments, L$^1$ is an unsubstituted C$_{1-10}$ n-alkyl chain of the formula —(CH$_2$)$_x$—, wherein x is 1, 2, 3, 4, 5, 6, 7, 8, 9, or 10. In certain embodiments, L$^1$ is an optionally substituted C$_{2-10}$ alkenyl chain, e.g., an optionally substituted C$_{2-8}$ alkenyl chain, optionally substituted C$_{2-6}$ alkenyl chain, optionally substituted C$_{2-4}$ alkenyl chain, optionally substituted C$_{2-3}$ alkenyl chain, or optionally substituted C$_2$ alkenyl chain. In certain embodiments, L$^1$ is an optionally substituted C$_{2-10}$ alkynyl chain, e.g., an optionally substituted C$_{2-8}$ alkynyl chain, optionally substituted C$_{2-6}$ alkynyl chain, optionally substituted C$_{2-4}$ alkynyl chain, optionally substituted C$_{2-3}$ alkynyl chain, or optionally substituted C$_2$ alkynyl chain.

In certain embodiments, L$^1$ is an optionally substituted C$_{1-10}$ saturated or unsaturated hydrocarbon chain, wherein one or more moieties selected from the group consisting of —O—, —N(R$^L$)—, —S—, —C(O)—, —C(O)O—, —C(O)S—, —C(O)N(R$^L$)—, —C(O)N(R$^L$)N(R$^L$)—, —OC(O)—, —OC(O)N(R$^L$)—, —NR$^L$C(O)—, —NR$^L$C(O)N(R$^L$)—, —NR$^L$C(O)N(R$^L$)N(R$^L$)—, —NR$^L$C(O)O—, —SC(O)—, —C(=NR$^L$)—, —C(=NNR$^L$)—, —C(=NOR$^L$)—, —C(=NR$^L$)N(R$^L$)—, —NR$^L$C(=NR$^L$)—, —C(S)—, —C(S)N(R$^L$)—, —NR$^L$C(S)—, —S(O)—, —OS(O)$_2$—, —S(O)$_2$O—, —SO$_2$—, —N(R$^L$)SO$_2$—, —SO$_2$N(R$^L$)—, or —N(R$^L$)SO$_2$N(R$^L$)— independently present between two carbon atoms of the hydrocarbon chain, or present at one or both ends of the hydrocarbon chain. In this instance, in certain embodiments, L$^1$ is a chain of at least 2 atoms, e.g., L$^1$ is a chain comprising 1 to 10 carbon atoms (e.g., 1, 2, 3, 4, 5, 6, 7, 8, 9, or 10 carbon atoms), and 1 or more of the above recited moieties (e.g., 1, 2, 3, or more), to provide a chain of between 2 and 20 atoms, inclusive, e.g., 2, 3, 4, 5, 6, 7, 8, 9, 10, 11, 12, 13, 14, 15, 16, 17, 18, 19, or 20 chain atoms. In certain embodiments, a moiety is present between two carbon atoms of the hydrocarbon chain. In certain embodiments, a moiety is present at one end of the hydrocarbon chain. In certain embodiments, a moiety is independently present at each end of the hydrocarbon chain. In certain embodiments, L$^1$ is an optionally substituted C$_{1-10}$ alkyl chain, L$^1$ is an optionally substituted C$_{2-10}$ alkenyl chain, or L$^1$ is an optionally substituted C$_{2-10}$ alkynyl chain comprising one or more of the above recited moieties independently present between two carbon atoms of the hydrocarbon chain, or present at one or both ends of the hydrocarbon chain. In certain embodiments, L$^1$ is an optionally substituted C$_{1-10}$ alkyl chain, e.g., an optionally substituted C$_{1-8}$ alkyl chain, optionally substituted C$_{1-6}$ alkyl chain, optionally substituted C$_{1-4}$ alkyl chain, optionally substituted C$_{1-3}$ alkyl chain, or optionally substituted C$_{1-2}$ alkyl chain, comprising one or more of the above recited moieties independently present between two carbon atoms of the hydrocarbon chain, or present at one or both ends of the hydrocarbon chain. In certain embodiments, L$^1$ is an unsubstituted C$_{1-10}$ n-alkyl chain of the formula —(CH$_2$)$_x$—, wherein x is 1, 2, 3, 4, 5, 6, 7, 8, 9, or 10, comprising one or more of the above recited moieties independently present between two carbon atoms of the hydrocarbon chain, or present at one or both ends of the hydrocarbon chain. In certain embodiments, $L^1$ is an optionally substituted $C_{2-10}$ alkenyl chain, e.g., an optionally substituted $C_{2-8}$ alkenyl chain, optionally substituted $C_{2-6}$ alkenyl chain, optionally substituted $C_{2-4}$ alkenyl chain, optionally substituted $C_{2-3}$ alkenyl chain, or optionally substituted $C_2$ alkenyl chain, comprising one or more of the above recited moieties independently present between two carbon atoms of the hydrocarbon chain, or present at one or both ends of the hydrocarbon chain. In certain embodiments, $L^1$ is an optionally substituted $C_{2-10}$ alkynyl chain, e.g., an optionally substituted $C_{2-8}$ alkynyl chain, optionally substituted $C_{2-6}$ alkynyl chain, optionally substituted $C_{2-4}$ alkynyl chain, optionally substituted $C_{2-3}$ alkynyl chain, or optionally substituted $C_2$ alkynyl chain, comprising one or more of the above recited moieties independently present between two carbon atoms of the hydrocarbon chain, or present at one or both ends of the hydrocarbon chain.

As described above, in certain embodiments, $L^1$ is an unsubstituted $C_{1-10}$ n-alkyl chain of the formula $-(CH_2)_x-$, wherein x is 1, 2, 3, 4, 5, 6, 7, 8, 9, or 10, comprising one or more of the above recited moieties independently present between two carbon atoms of the hydrocarbon chain, or present at one or both ends of the hydrocarbon chain. In certain embodiments, $L^1$ is $-O-(CH_2)_x-$, $-(CH_2)_x-O-$, or $-O-(CH_2)_x-O-$. In certain embodiments, $L^1$ is $-N(R^L)-(CH_2)_x-$, $-(CH_2)_x-N(R^L)-$, $-N(R^L)-(CH_2)_x-N(R^L)-$, $-O-(CH_2)_x-N(R^L)-$, $-N(R^L)-(CH_2)_x-O-$, $-NR^L-(CH_2)_x-C(O)O-$, or $-OC(O)-(CH_2)_x-N(R^L)-$. In certain embodiments, $L^1$ is $-S-(CH_2)_x-$ or $-(CH_2)_x-S-$. In certain embodiments, $L^1$ is $-C(O)-(CH_2)_x-$ or $-(CH_2)_x-C(O)-$. In certain embodiments, $L^1$ is $-C(O)O-(CH_2)_x-$ or $-(CH_2)_x-C(O)O-$. In certain embodiments, $L^1$ is $-C(O)S-(CH_2)_x-$ or $-(CH_2)_x-C(O)S-$. In certain embodiments, $L^1$ is $-C(O)N(R^L)-(CH_2)_x-$ or $-(CH_2)_x-C(O)N(R^L)-$. In certain embodiments, $L^1$ is $-C(O)N(R^L)N(R^L)-(CH_2)_x-$ or $-(CH_2)_x-C(O)N(R^L)N(R^L)-$. In certain embodiments, $L^1$ is $-OC(O)-(CH_2)_x-$ or $-(CH_2)_x-OC(O)-$. In certain embodiments, $L^1$ is $-OC(O)N(R^L)-(CH_2)_x-$ or $-(CH_2)_x-OC(O)N(R^L)-$. In certain embodiments, $L^1$ is $-NR^LC(O)-(CH_2)_x-$ or $-(CH_2)_x-NR^LC(O)-$. In certain embodiments, $L^1$ is $-NR^LC(O)N(R^L)-(CH_2)_x-$ or $-(CH_2)_x-NR^LC(O)N(R^L)-$. In certain embodiments, $L^1$ is $-NR^LC(O)N(R^L)N(R^L)-(CH_2)_x-$ or $-(CH_2)_x-NR^LC(O)N(R^L)N(R^L)-$. In certain embodiments, $L^1$ is $-NR^LC(O)O-(CH_2)_x-$ or $-(CH_2)_x-NR^LC(O)O-$. In certain embodiments, $L^1$ is $-SC(O)-(CH_2)_x-$ or $-(CH_2)_x-SC(O)-$. In certain embodiments, $L^1$ is $-C(=NR^L)-(CH_2)_x-$ or $-(CH_2)_x-C(=NR^L)-$. In certain embodiments, $L^1$ is $-C(=NNR^L)-(CH_2)_x-$ or $-(CH_2)_x-C(=NNR^L)-$. In certain embodiments, $L^1$ is $-C(=NOR^L)-(CH_2)_x-$ or $-(CH_2)_x-C(=NOR^L)-$. In certain embodiments, $L^1$ is $-C(=NR^L)N(R^L)-(CH_2)_x-$ or $-(CH_2)_x-C(=NR^L)N(R^L)-$. In certain embodiments, $L^1$ is $-NR^LC(=NR^L)-(CH_2)_x-$ or $-(CH_2)_x-NR^LC(=NR^L)-$. In certain embodiments, $L^1$ is $-C(S)-(CH_2)_x-$ or $-(CH_2)_x-C(S)-$. In certain embodiments, $L^1$ is $-C(S)N(R^L)-(CH_2)_x-$ or $-(CH_2)_x-C(S)N(R^L)-$. In certain embodiments, $L^1$ is $-NR^LC(S)-(CH_2)_x-$ or $-(CH_2)_x-NR^LC(S)-$. In certain embodiments, $L^1$ is $-S(O)-(CH_2)_x-$ or $-(CH_2)_x-S(O)-$. In certain embodiments, $L^1$ is $-OS(O)_2-(CH_2)_x-$ or $-(CH_2)_x-OS(O)_2-$. In certain embodiments, $L^1$ is $-S(O)_2O-(CH_2)_x-$ or $-(CH_2)_x-S(O)_2O-$. In certain embodiments, $L^1$ is $-SO_2-(CH_2)_x-$ or $-(CH_2)_x-SO_2-$. In certain embodiments, $L^1$ is $-N(R^L)SO_2-(CH_2)_x-$ or $-(CH_2)_x-N(R^L)SO_2-$. In certain embodiments, $L^1$ is $-SO_2N(R^L)-(CH_2)_x-$ or $-(CH_2)_x-SO_2N(R^L)-$. In certain embodiments, $L^1$ is $-N(R^L)SO_2N(R^L)-(CH_2)_x-$ or $-(CH_2)_x-N(R^L)SO_2N(R^L)-$. In certain embodiments, $L^1$ is a bond, $-N(R^L)-$, $-NR^LC(O)O-$, $-NR^LC(O)N(R^L)-$, $-N(R^L)-$, $-N(R^L)SO_2N(R^L)-$, $-NR^L-(CH_2)_x-C(O)O-$, $-NR^L-(CH_2)_x-O-$, $-NR^LC(O)N(R^L)-$, $-NR^L-(CH_2)_x-$, $-(CH_2)_x-NR^L-$, $-NR^LC(O)O(CH_2)_x-$, $-NR^LC(O)NR^L(CH_2)_x-$, or $-NR^L(CH_2)_xNR^LC(O)-$.

In certain embodiments, $R^3$ is an acyclic moiety selected from the group consisting of hydrogen, optionally substituted alkyl, optionally substituted alkenyl, and optionally substituted alkynyl. In certain embodiments, $R^3$ is hydrogen, e.g., for example, when $L^1$ is $-N(R^L)-$ or $-NR^L-(CH_2)_x-NR^L-$. In certain embodiments, $R^3$ is optionally substituted alkyl, e.g., for example, when $L^1$ is $-NR^LC(O)O-$, $-NR^LC(O)N(R^L)-$, $-N(R^L)-$, $-N(R^L)SO_2N(R^L)-$, $-NR^L-(CH_2)_x-C(O)O-$, or $-NR^L-(CH_2)_x-O-$. In certain embodiments, $R^3$ is optionally substituted $C_{1-6}$alkyl, e.g., optionally substituted $C_{1-5}$alkyl, optionally substituted $C_{1-4}$alkyl, optionally substituted $C_{1-2}$alkyl, optionally substituted $C_{2-3}$alkyl, optionally substituted $C_{3-4}$alkyl, optionally substituted $C_1$alkyl, optionally substituted $C_2$alkyl, optionally substituted $C_3$alkyl, optionally substituted $C_4$alkyl, optionally substituted $C_5$alkyl, or optionally substituted $C_6$alkyl. Exemplary $R^3$ $C_{1-6}$alkyl groups include, but are not limited to, methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). In certain embodiments, $R^3$ is alkyl substituted with $-CN$, e.g., $-(CH_2)_yCN$, wherein y is 1, 2, 3, 4, 5, or 6. In certain embodiments, $R^3$ is alkyl substituted with hydroxy or substituted hydroxy, e.g., $-(CH_2)_yOCH_3$, wherein y is 1, 2, 3, 4, 5, or 6. In certain embodiments, $R^3$ is alkyl substituted with amino or substituted amino, e.g., $-(CH_2)_yNH_2$, wherein y is 1, 2, 3, 4, 5, or 6. In certain embodiments, $R^3$ is optionally substituted alkenyl, e.g., for example, when $L^1$ is a bond. In certain embodiments, $R^3$ is optionally substituted $C_{2-4}$ alkenyl, e.g., optionally substituted $C_{2-3}$alkenyl, optionally substituted $C_{3-4}$alkenyl, optionally substituted $C_2$alkenyl, optionally substituted $C_3$alkenyl, or optionally substituted $C_4$alkenyl. In certain embodiments, $R^3$ is optionally substituted $C_2$alkenyl or $C_3$alkenyl, e.g., optionally substituted vinyl or optionally substituted allyl. In certain embodiments, $R^3$ is optionally substituted alkynyl, e.g., for example, when $L^1$ is a bond. In certain embodiments, $R^3$ is optionally substituted $C_{2-4}$ alkynyl, e.g., optionally substituted $C_{2-3}$alkynyl, optionally substituted $C_{3-4}$alkynyl, optionally substituted $C_2$alkynyl, optionally substituted $C_3$alkynyl, or optionally substituted $C_4$alkynyl. In certain embodiments, $R^3$ is optionally substituted $C_2$alkynyl, e.g., optionally substituted acetylene.

Alternatively, in certain embodiments, $R^3$ is a cyclic moiety selected from the group consisting of optionally substituted carbocyclyl, optionally substituted heterocyclyl, optionally substituted aryl, and optionally substituted heteroaryl. It is understood that the $R^3$ cyclic moiety may be monocyclic or polycyclic (e.g., bicyclic or tricyclic). In certain embodiments, $R^3$ is a monocylic optionally substituted carbocyclyl, monocylic optionally substituted heterocyclyl, monocylic optionally substituted aryl, or monocylic optionally substituted heteroaryl. In certain embodiments, $R^3$ is a bicyclic optionally substituted carbocyclyl, bicyclic optionally substituted heterocyclyl, bicyclic optionally substituted aryl, or bicyclic optionally substituted heteroaryl.

In certain embodiments, R³ is an optionally substituted monocyclic or bicyclic carbocyclyl, e.g., an optionally substituted $C_{3-10}$ carbocyclyl, optionally substituted $C_{3-9}$ carbocyclyl, optionally substituted $C_{3-8}$ carbocyclyl, optionally substituted $C_{3-7}$ carbocyclyl, optionally substituted $C_{3-6}$ carbocyclyl, optionally substituted $C_{3-4}$ carbocyclyl, optionally substituted $C_{5-10}$ carbocyclyl, optionally substituted $C_3$ carbocyclyl, optionally substituted $C_4$ carbocyclyl, optionally substituted $C_5$ carbocyclyl, optionally substituted $C_6$ carbocyclyl, optionally substituted $C_7$ carbocyclyl, optionally substituted $C_8$ carbocyclyl, optionally substituted $C_9$ carbocyclyl, or optionally substituted $C_{10}$ carbocyclyl. In certain embodiments, R³ is an optionally substituted cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), cyclononyl ($C_9$), cyclononenyl ($C_9$), cyclodecyl ($C_{10}$), cyclodecenyl ($C_{10}$), octahydro-1H indenyl ($C_9$), decahydronaphthalenyl ($C_{10}$), or spiro[4.5]decanyl ($C_{10}$) ring.

In certain embodiments, R³ is an optionally substituted monocyclic or bicyclic heterocyclyl, e.g., an optionally substituted 3- to 10-membered heterocyclyl, 3- to 8-membered heterocyclyl, 3- to 6-membered heterocyclyl, 3- to 5-membered heterocyclyl, 3- to 4-membered heterocyclyl, 3-membered heterocyclyl, 4-membered heterocyclyl, 5-membered heterocyclyl, 6-membered heterocyclyl, 7-membered heterocyclyl, 8-membered heterocyclyl, 9-membered heterocyclyl, or 10-membered heterocyclyl. In certain embodiments, R³ is an optionally substituted azirdinyl, oxiranyl, thiorenyl, azetidinyl, oxetanyl, thietanyl, tetrahydrofuranyl, dihydrofuranyl, tetrahydrothiophenyl, dihydrothiophenyl, pyrrolidinyl, dihydropyrrolyl, pyrrolyl-2,5-dione, pyrrolidin-2-one, pyrrolyl-2,5-dione, dioxolanyl, oxasulfuranyl, disulfuranyl, oxazolidin-2-one, triazolinyl, oxadiazolinyl, thiadiazolinyl, piperidinyl, tetrahydropyranyl, dihydropyridinyl, thianyl, piperazinyl, morpholinyl, dithianyl, dioxanyl, triazinanyl, azepanyl, oxepanyl, thiepanyl, azocanyl, oxecanyl, thiocanyl, indolinyl, isoindolinyl, dihydrobenzofuranyl, dihydrobenzothienyl, benzoxazolinonyl, tetrahydroquinolinyl, tetrahydroisoquinolinyl, furo[2,3-b]furanyl, 2,3-dihydro-1,4-dioxinyl, 3-oxa-8-azabicyclo[3.2.1]octanyl, or 8-oxa-3-azabicyclo[3.2.1]octanyl ring.

In certain embodiments, R³ is an optionally substituted monocyclic or bicyclic aryl, e.g., an optionally substituted phenyl, or optionally substituted naphthyl ring.

In certain embodiments, R³ is an optionally substituted monocyclic or bicyclic heteroaryl, e.g., an optionally substituted 5- to 10-membered heteroaryl, optionally substituted 5- to 8-membered heteroaryl, optionally substituted 5- to 6-membered heteroaryl, optionally substituted 5-membered heteroaryl, or optionally substituted 6-membered heteroaryl. In certain embodiments, R³ is an optionally substituted pyrrolyl, furanyl, thiophenyl, imidazolyl, pyrazolyl, oxazolyl, isoxazolyl, thiazolyl, isothiazolyl, tetrazolyl, pyridinyl, pyridazinyl, pyrimidinyl, pyrazinyl, triazinyl, tetrazinyl, azepinyl, oxepinyl, thiepinyl, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, purinyl, naphthyridinyl, pteridinyl, quinolinyl, isoquinolinyl, cinnolinyl, quinoxalinyl, phthalazinyl, or quinazolinyl ring.

In certain embodiments, R³ is a cyclic moiety selected from the group consisting of

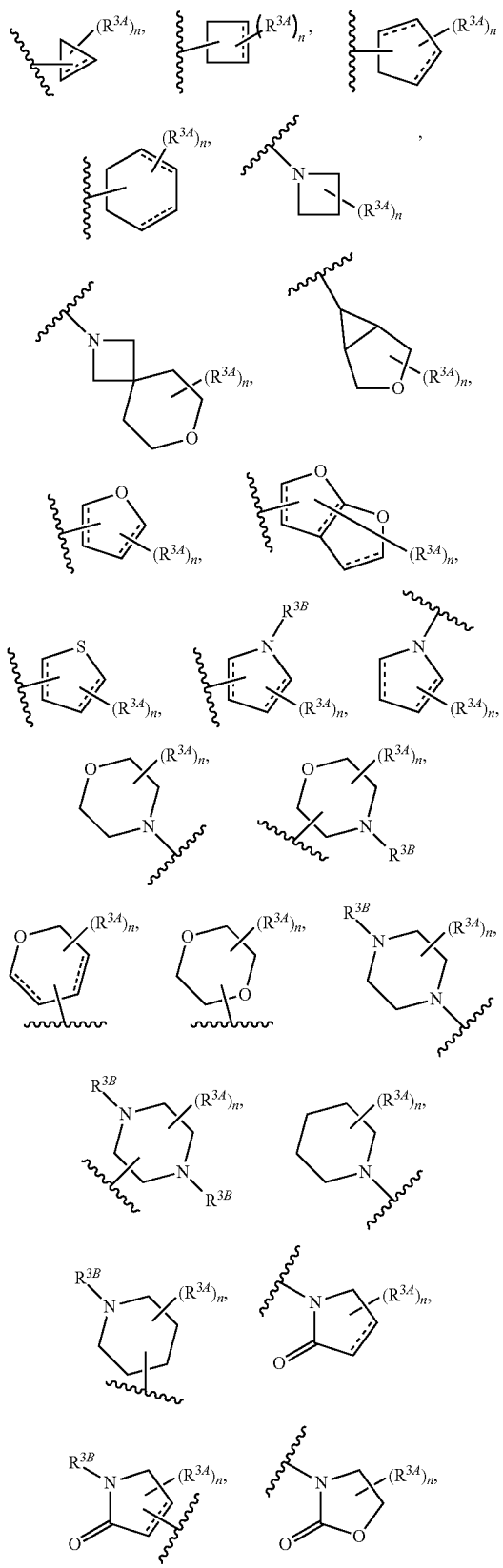

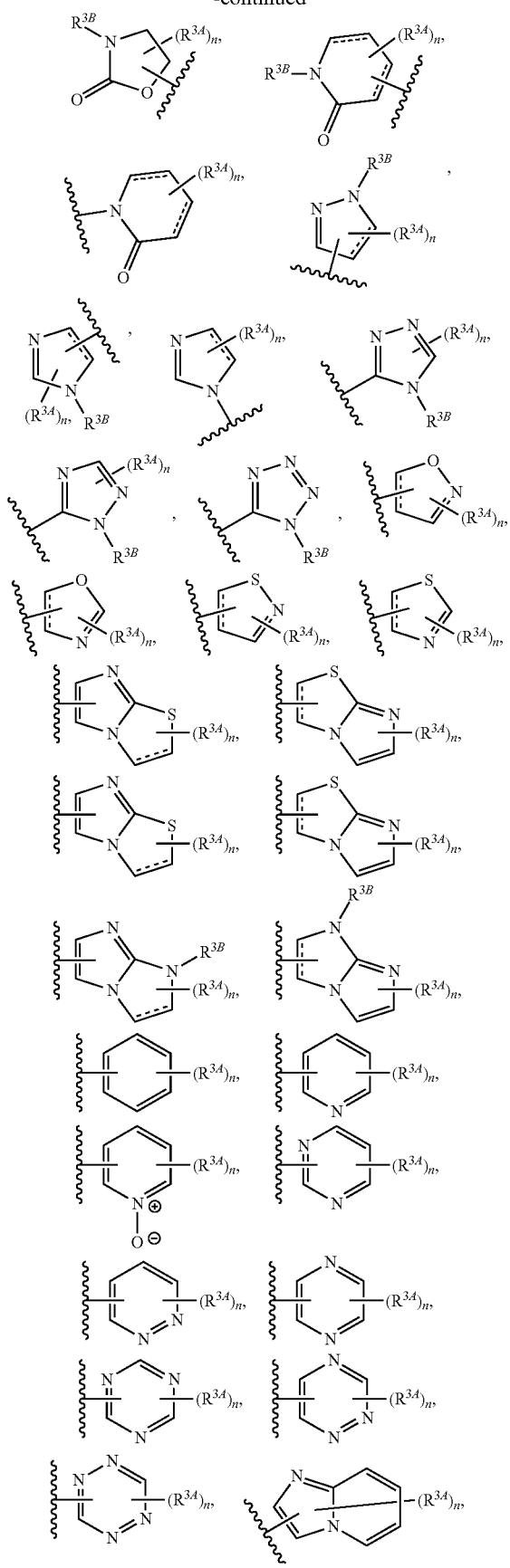
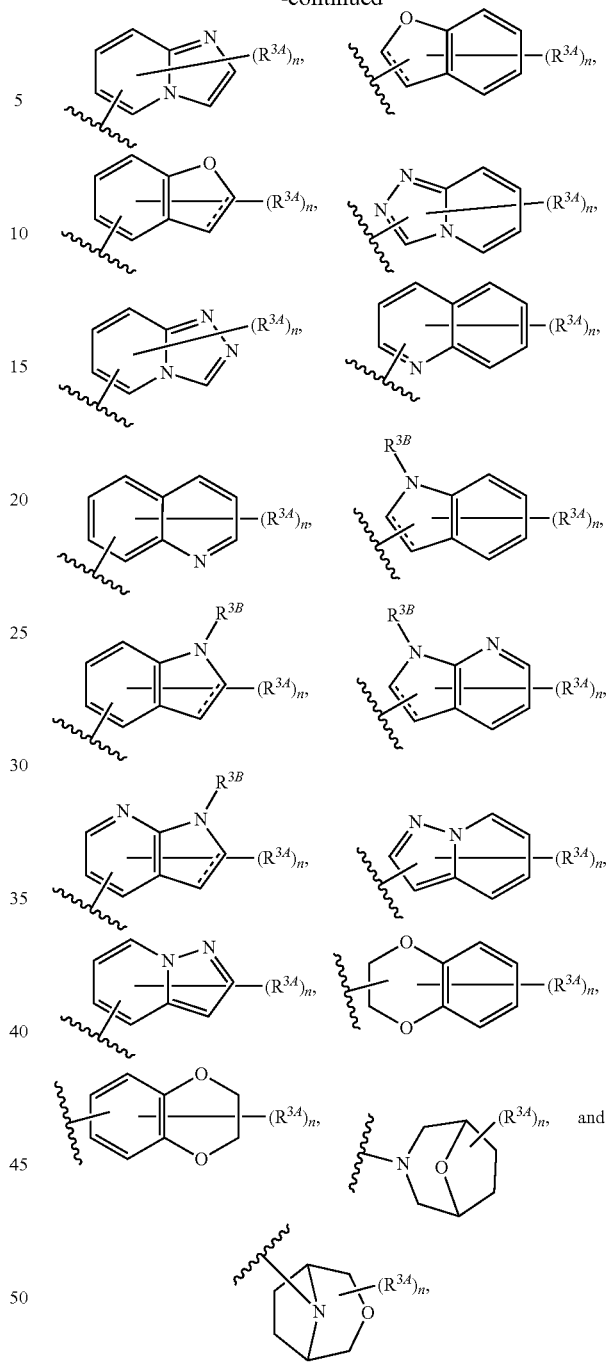

wherein:
 each instance of ⚌ independently represents a single or double bond;
 n is 0, 1, 2, or 3;
 each instance of $R^{3A}$ is independently hydroxyl, substituted hydroxyl, thiol, substituted thiol, amino, substituted amino, carbonyl, sulfonyl, sulfinyl, —CN, —NO$_2$, halogen, optionally substituted alkyl, or two $R^{3A}$ groups are joined to form an optionally substituted carbocyclic, optionally substituted heterocyclic, optionally substituted aryl, or optionally substituted heteroaryl ring, or $R^{3A}$ and $R^{3B}$ groups are joined to form an optionally substituted carbocyclic, optionally substituted heterocyclic, optionally substituted aryl, or optionally substituted heteroaryl ring; and $R^{3B}$ is hydrogen, optionally substituted alkyl, or a nitrogen protecting group.

In certain embodiments, n is 0. In certain embodiments, n is 1. In certain embodiments, n is 2. In certain embodiments, n is 3. In certain embodiments, each instance of $R^{3A}$ is independently hydroxyl, —OCH$_3$, optionally substituted C$_{1-4}$alkyl (e.g., methyl, trifluoromethyl, ethyl, propyl, isopropyl, butyl, isobutyl, secbutyl, tertbutyl), —CN, or sulfonyl (e.g., —S(O)$_2$CH$_3$).

As generally defined herein, $L^2$ is a bond, —O—, —N(R$^L$)—, —S—, —C(O)—, —C(O)O—, —C(O)S—, —C(O)N(R$^L$)—, —C(O)N(R$^L$)N(R$^L$)—, —OC(O)—, —OC(O)N(R$^L$)—, —NR$^L$C(O)—, —NR$^L$C(O)N(R$^L$)—, —NR$^L$C(O)N(R$^L$)N(R$^L$)—, —NR$^L$C(O)O—, —SC(O)—, —C(=NR$^L$)—, —C(=NNR$^L$)—, —C(=NOR$^L$)—, —C(=NR$^L$)N(R$^L$)—, —NR$^L$C(=NR$^L$)—, —C(S)—, —C(S)N(R$^L$)—, —NR$^L$C(S)—, —S(O)—, —OS(O)$_2$—, —S(O)$_2$O—, —SO$_2$—, —N(R$^L$)SO$_2$—, —SO$_2$N(R$^L$)—, —N(R$^L$)SO$_2$N(R$^L$)—, or an optionally substituted C$_{1-10}$ saturated or unsaturated hydrocarbon chain, wherein one or more moieties selected from the group consisting of —O—, —N(R$^L$)—, —S—, —C(O)—, —C(O)O—, —C(O)S—, —C(O)N(R$^L$)—, —C(O)N(R$^L$)N(R$^L$)—, —OC(O)—, —OC(O)N(R$^L$)—, —NR$^L$C(O)—, —NR$^L$C(O)N(R$^L$)—, —NR$^L$C(O)N(R$^L$)N(R$^L$)—, —NR$^L$C(O)O—, —SC(O)—, —C(=NR$^L$)—, —C(=NNR$^L$)—, —C(=NOR$^L$)—, —C(=NR$^L$)N(R$^L$)—, —NR$^L$C(=NR$^L$)—, —C(S)—, —C(S)N(R$^L$)—, —NR$^L$C(S)—, —S(O)—, —OS(O)$_2$—, —S(O)$_2$O—, —SO$_2$—, —N(R$^L$)SO$_2$—, —SO$_2$N(R$^L$)—, and —N(R$^L$)SO$_2$N(R$^L$)— is optionally and independently present between two carbon atoms of the hydrocarbon chain, and optionally and independently present at one or both ends of the hydrocarbon chain. It is understood that the linker joining $R^{13}$ to Ring HET may comprise one or more of the above recited moieties in combination to form the group $L^2$.

In certain embodiments, $L^2$ is a bond. In certain embodiments, $L^2$ is —O—. In certain embodiments, $L^2$ is —N(R$^L$)—. In certain embodiments, $L^2$ is —S—. In certain embodiments, $L^2$ is —C(O)—. In certain embodiments, $L^2$ is —C(O)O—. In certain embodiments, $L^2$ is —C(O)S—. In certain embodiments, $L^2$ is —C(O)N(R$^L$)—. In certain embodiments, $L^2$ is —C(O)N(R$^L$)N(R$^L$)—. In certain embodiments, $L^2$ is —OC(O)—. In certain embodiments, $L^2$ is —OC(O)N(R$^L$)—. In certain embodiments, $L^2$ is —NR$^L$C(O)—. In certain embodiments, $L^2$ is —NR$^L$C(O)N(R$^L$)—. In certain embodiments, $L^2$ is —NR$^L$C(O)N(R$^L$)N(R$^L$)—. In certain embodiments, $L^2$ is —NR$^L$C(O)O—. In certain embodiments, $L^2$ is —SC(O)—. In certain embodiments, $L^2$ is —C(=NR$^L$)—. In certain embodiments, $L^2$ is —C(=NNR$^L$)—. In certain embodiments, $L^2$ is —C(=NOR$^L$)—. In certain embodiments, $L^2$ is —C(=NR$^L$)N(R$^L$)—. In certain embodiments, $L^2$ is —NR$^L$C(=NR$^L$)—. In certain embodiments, $L^2$ is —C(S)—. In certain embodiments, $L^2$ is —C(S)N(R$^L$)—. In certain embodiments, $L^2$ is —NR$^L$C(S)—. In certain embodiments, $L^2$ is —S(O)—. In certain embodiments, $L^2$ is —OS(O)$_2$—. In certain embodiments, $L^2$ is —S(O)$_2$O—. In certain embodiments, $L^2$ is —SO$_2$—. In certain embodiments, $L^2$ is —N(R$^L$)SO$_2$—. In certain embodiments, $L^2$ is —SO$_2$N(R$^L$)—. In certain embodiments, $L^2$ is —N(R$^L$)SO$_2$N(R$^L$)—.

In certain embodiments, $L^2$ is an optionally substituted C$_{1-10}$ saturated or unsaturated hydrocarbon chain, e.g., in certain embodiments, $L^2$ is an optionally substituted C$_{1-10}$ alkyl chain, $L^2$ is an optionally substituted C$_{2-10}$ alkenyl chain, or $L^2$ is an optionally substituted C$_{2-10}$ alkynyl chain. In certain embodiments, $L^2$ is an optionally substituted C$_{1-10}$ alkyl chain, e.g., an optionally substituted C$_{1-8}$ alkyl chain, optionally substituted C$_{1-6}$ alkyl chain, optionally substituted C$_{1-4}$ alkyl chain, optionally substituted C$_{1-3}$ alkyl chain, or optionally substituted C$_{1-2}$ alkyl chain. In certain embodiments, $L^2$ is an unsubstituted C$_{1-10}$ n-alkyl chain of the formula —(CH$_2$)$_x$—, wherein x is 1, 2, 3, 4, 5, 6, 7, 8, 9, or 10. In certain embodiments, $L^2$ is an optionally substituted C$_{2-10}$ alkenyl chain, e.g., an optionally substituted C$_{2-8}$ alkenyl chain, optionally substituted C$_{2-6}$ alkenyl chain, optionally substituted C$_{2-4}$ alkenyl chain, optionally substituted C$_{2-3}$ alkenyl chain, or optionally substituted C$_2$ alkenyl chain. In certain embodiments, $L^2$ is an optionally substituted C$_{2-10}$ alkynyl chain, e.g., an optionally substituted C$_{2-8}$ alkynyl chain, optionally substituted C$_{2-6}$ alkynyl chain, optionally substituted C$_{2-4}$ alkynyl chain, optionally substituted C$_{2-3}$ alkynyl chain, or optionally substituted C$_2$ alkynyl chain.

In certain embodiments, $L^2$ is an optionally substituted C$_{1-10}$ saturated or unsaturated hydrocarbon chain, wherein one or more moieties selected from the group consisting of —O—, —N(R$^L$)—, —S—, —C(O)—, —C(O)O—, —C(O)S—, —C(O)N(R$^L$)—, —C(O)N(R$^L$)N(R$^L$)—, —OC(O)—, —OC(O)N(R$^L$)—, —NR$^L$C(O)—, —NR$^L$C(O)N(R$^L$)—, —NR$^L$C(O)N(R$^L$)N(R$^L$)—, —NR$^L$C(O)O—, —SC(O)—, —C(=NR$^L$)—, —C(=NNR$^L$)—, —C(=NOR$^L$)—, —C(=NR$^L$)N(R$^L$)—, —NR$^L$C(=NR$^L$)—, —C(S)—, —C(S)N(R$^L$)—, —NR$^L$C(S)—, —S(O)—, —OS(O)$_2$—, —S(O)$_2$O—, —SO$_2$—, —N(R$^L$)SO$_2$—, —SO$_2$N(R$^L$)—, or —N(R$^L$)SO$_2$N(R$^L$)— independently present between two carbon atoms of the hydrocarbon chain, or present at one or both ends of the hydrocarbon chain. In this instance, in certain embodiments, $L^2$ is a chain of at least 2 atoms, e.g., $L^2$ is a chain comprising 1 to 10 carbon atoms (e.g., 1, 2, 3, 4, 5, 6, 7, 8, 9, or 10 carbon atoms), and 1 or more of the above recited moieties (e.g., 1, 2, 3, or more), to provide a chain of between 2 and 20 atoms, inclusive, e.g., 2, 3, 4, 5, 6, 7, 8, 9, 10, 11, 12, 13, 14, 15, 16, 17, 18, 19, or 20 chain atoms. In certain embodiments, a moiety is present between two carbon atoms of the hydrocarbon chain. In certain embodiments, a moiety is present at one end of the hydrocarbon chain. In certain embodiments, a moiety is independently present at each end of the hydrocarbon chain. In certain embodiments, $L^2$ is an optionally substituted C$_{1-10}$ alkyl chain, $L^2$ is an optionally substituted C$_{2-10}$ alkenyl chain, or $L^2$ is an optionally substituted C$_{2-10}$ alkynyl chain comprising one or more of the above recited moieties independently present between two carbon atoms of the hydrocarbon chain, or present at one or both ends of the hydrocarbon chain. In certain embodiments, $L^2$ is an optionally substituted C$_{1-10}$ alkyl chain, e.g., an optionally substituted C$_{1-8}$ alkyl chain, optionally substituted C$_{1-6}$ alkyl chain, optionally substituted C$_{1-4}$ alkyl chain, optionally substituted C$_{1-3}$ alkyl chain, or optionally substituted C$_{1-2}$ alkyl chain, comprising one or more of the above recited moieties independently present between two carbon atoms of the hydrocarbon chain, or present at one or both ends of the hydrocarbon chain. In certain embodiments, $L^2$ is an unsubstituted C$_{1-10}$ n-alkyl chain of the formula —(CH$_2$)$_x$—, wherein x is 1, 2, 3, 4, 5, 6, 7, 8, 9, or 10, comprising one or more of the above recited moieties independently present between two carbon atoms of the hydrocarbon chain, or present at one or both ends of the hydrocarbon chain. In certain embodiments, $L^2$ is an optionally substituted C$_{2-10}$ alkenyl chain, e.g., an optionally substituted C$_{2-8}$ alkenyl chain, optionally substituted C$_{2-6}$ alkenyl chain, optionally substituted C$_{2-4}$ alkenyl chain, optionally substituted C$_{2-3}$ alkenyl chain, or optionally substituted C$_2$ alkenyl chain, comprising one or more of the above recited moieties independently present between two carbon atoms of the hydrocarbon chain, or present at one or both ends of the hydrocarbon chain. In certain embodiments, $L^2$ is an optionally substituted $C_{2-10}$ alkynyl chain, e.g., an optionally substituted $C_{2-8}$ alkynyl chain, optionally substituted $C_{2-6}$ alkynyl chain, optionally substituted $C_{2-4}$ alkynyl chain, optionally substituted $C_{2-3}$ alkynyl chain, or optionally substituted $C_2$ alkynyl chain, comprising one or more of the above recited moieties independently present between two carbon atoms of the hydrocarbon chain, or present at one or both ends of the hydrocarbon chain.

As described above, in certain embodiments, $L^2$ is an unsubstituted $C_{1-10}$ n-alkyl chain of the formula —$(CH_2)_x$—, wherein x is 1, 2, 3, 4, 5, 6, 7, 8, 9, or 10, comprising one or more of the above recited moieties independently present between two carbon atoms of the hydrocarbon chain, or present at one or both ends of the hydrocarbon chain. In certain embodiments, $L^2$ is —O—$(CH_2)_x$—, —$(CH_2)_x$—O—, or —O—$(CH_2)_x$—O—. In certain embodiments, $L^2$ is —N($R^L$)—$(CH_2)_x$—, —$(CH_2)_x$—N($R^L$)—, —N($R^L$)—$(CH_2)_x$—N($R^L$)—, —O—$(CH_2)_x$—N($R^L$)—, —N($R^L$)—$(CH_2)_x$—O—, —$NR^L$—$(CH_2)_x$—C(O)O—, or —OC(O)—$(CH_2)_x$—N($R^L$)—. In certain embodiments, $L^2$ is —S—$(CH_2)_x$— or —$(CH_2)_x$—S—. In certain embodiments, $L^2$ is —C(O)—$(CH_2)_x$— or —$(CH_2)_x$—C(O)—. In certain embodiments, $L^2$ is —C(O)O—$(CH_2)_x$— or —$(CH_2)_x$—C(O)O—. In certain embodiments, $L^2$ is —C(O)S—$(CH_2)_x$— or —$(CH_2)_x$—C(O)S—. In certain embodiments, $L^2$ is —C(O)N($R^L$)—$(CH_2)_x$— or —$(CH_2)_x$—C(O)N($R^L$)—. In certain embodiments, $L^2$ is —C(O)N($R^L$N($R^L$)—$(CH_2)_x$— or —$(CH_2)_x$—C(O)N($R^L$)N($R^L$)—. In certain embodiments, $L^2$ is —OC(O)—$(CH_2)_x$— or —$(CH_2)_x$—OC(O)—. In certain embodiments, $L^2$ is —OC(O)N($R^L$)—$(CH_2)_x$— or —$(CH_2)_x$—OC(O)N($R^L$)—. In certain embodiments, $L^2$ is —$NR^L$C(O)—$(CH_2)_x$— or —$(CH_2)_x$—$NR^L$C(O)—. In certain embodiments, $L^2$ is —$NR^L$C(O)N($R^L$)—$(CH_2)_x$— or —$(CH_2)_x$—$NR^L$C(O)N($R^L$)—. In certain embodiments, $L^2$ is —$NR^L$C(O)N($R^L$)N($R^L$)—$(CH_2)_x$— or —$(CH_2)_x$—$NR^L$C(O)N($R^L$)N($R^L$)—. In certain embodiments, $L^2$ is —$NR^L$C(O)O—$(CH_2)_x$— or —$(CH_2)_x$—$NR^L$C(O)O—. In certain embodiments, $L^2$ is —SC(O)—$(CH_2)_x$— or —$(CH_2)_x$—SC(O)—. In certain embodiments, $L^2$ is —C(=$NR^L$)—$(CH_2)_x$— or —$(CH_2)_x$—C(=$NR^L$)—. In certain embodiments, $L^2$ is —C(=$NNR^L$)—$(CH_2)_x$— or —$(CH_2)_x$—C(=$NNR^L$)—. In certain embodiments, $L^2$ is —C(=$NOR^L$)—$(CH_2)_x$— or —$(CH_2)_x$—C(=$NOR^L$)—. In certain embodiments, $L^2$ is —C(=$NR^L$)N($R^L$)—$(CH_2)_x$— or —$(CH_2)_x$—C(=$NR^L$)N($R^L$)—. In certain embodiments, $L^2$ is —$NR^L$C(=$NR^L$)—$(CH_2)_x$— or —$(CH_2)_x$—$NR^L$C(=$NR^L$)—. In certain embodiments, $L^2$ is —C(S)—$(CH_2)_x$— or —$(CH_2)_x$—C(S)—. In certain embodiments, $L^2$ is —C(S)N($R^L$)—$(CH_2)_x$— or —$(CH_2)_x$—C(S)N($R^L$)—. In certain embodiments, $L^2$ is —$NR^L$C(S)—$(CH_2)_x$— or —$(CH_2)_x$—$NR^L$C(S)—. In certain embodiments, $L^2$ is —S(O)—$(CH_2)_x$— or —$(CH_2)_x$—S(O)—. In certain embodiments, $L^2$ is —OS(O)$_2$—$(CH_2)_x$— or —$(CH_2)_x$—OS(O)$_2$—. In certain embodiments, $L^2$ is —S(O)$_2$O—$(CH_2)_x$— or —$(CH_2)_x$—S(O)$_2$O—. In certain embodiments, $L^2$ is —SO$_2$—$(CH_2)_x$— or —$(CH_2)_x$—SO$_2$—. In certain embodiments, $L^2$ is —N($R^L$)SO$_2$—$(CH_2)_x$— or —$(CH_2)_x$—N($R^L$)SO$_2$—. In certain embodiments, $L^2$ is —SO$_2$N($R^L$)—$(CH_2)_x$— or —$(CH_2)_x$—SO$_2$N($R^L$)—. In certain embodiments, $L^2$ is —N($R^L$)SO$_2$N($R^L$)—$(CH_2)_x$— or —$(CH_2)_x$—N($R^L$)SO$_2$N($R^L$)—. In certain embodiments, $L^2$ is a bond, —N($R^L$)—, —$NR^L$C(O)O—, —$NR^L$C(O)N($R^L$)—, —N($R^L$)—, —N($R^L$)SO$_2$N($R^L$)—, —$NR^L$—$(CH_2)_x$—C(O)O—, —$NR^L$—$(CH_2)_x$—O—, —$NR^L$C(O)N($R^L$)—, —$NR^L$—$(CH_2)_x$—, —$(CH_2)_x$—$NR^L$—, —$NR^L$C(O)O$(CH_2)_x$—, —$NR^L$C(O)N$R^L$($CH_2)_x$—, or —$NR^L$($CH_2)_x$N-$R^L$C(O)—.

As generally defined herein, $R^{13}$ attached directly (wherein $L^2$ is a bond) or indirectly (wherein $L^2$ is a linking group) to Ring HET is a cyclic moiety selected from the group consisting of optionally substituted carbocyclyl, optionally substituted heterocyclyl, optionally substituted aryl, and optionally substituted heteroaryl. It is understood that the $R^{13}$ cyclic moiety may be monocyclic or polycyclic (e.g., bicyclic or tricyclic). In certain embodiments, $R^{13}$ is a monocyclic optionally substituted carbocyclyl, monocyclic optionally substituted heterocyclyl, monocyclic optionally substituted aryl, or monocylic optionally substituted heteroaryl. In certain embodiments, $R^{13}$ is a bicyclic optionally substituted carbocyclyl, bicyclic optionally substituted heterocyclyl, bicyclic optionally substituted aryl, or bicyclic optionally substituted heteroaryl.

In certain embodiments, $R^{13}$ is an optionally substituted monocyclic or bicyclic carbocyclyl, e.g., an optionally substituted $C_{3-10}$ carbocyclyl, optionally substituted $C_{3-9}$ carbocyclyl, optionally substituted $C_{3-8}$ carbocyclyl, optionally substituted $C_{3-7}$ carbocyclyl, optionally substituted $C_{3-6}$ carbocyclyl, optionally substituted $C_{3-4}$ carbocyclyl, optionally substituted $C_{5-10}$ carbocyclyl, optionally substituted $C_3$ carbocyclyl, optionally substituted $C_4$ carbocyclyl, optionally substituted $C_5$ carbocyclyl, optionally substituted $C_6$ carbocyclyl, optionally substituted $C_7$ carbocyclyl, optionally substituted $C_8$ carbocyclyl, optionally substituted $C_9$ carbocyclyl, or optionally substituted $C_{10}$ carbocyclyl. In certain embodiments, $R^{13}$ is an optionally substituted cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), cyclononyl ($C_9$), cyclononenyl ($C_9$), cyclodecyl ($C_{10}$), cyclodecenyl ($C_{10}$), octahydro-1H indenyl ($C_9$), decahydronaphthalenyl ($C_{10}$), or spiro[4.5]decanyl ($C_{10}$) ring.

In certain embodiments, $R^{13}$ is an optionally substituted monocyclic or bicyclic heterocyclyl, e.g., an optionally substituted 3- to 10-membered heterocyclyl, 3- to 8-membered heterocyclyl, 3- to 6-membered heterocyclyl, 3- to 5-membered heterocyclyl, 3- to 4-membered heterocyclyl, 3-membered heterocyclyl, 4-membered heterocyclyl, 5-membered heterocyclyl, 6-membered heterocyclyl, 7-membered heterocyclyl, 8-membered heterocyclyl, 9-membered heterocyclyl, or 10-membered heterocyclyl. In certain embodiments, $R^3$ is an optionally substituted azirdinyl, oxiranyl, thiorenyl, azetidinyl, oxetanyl, thietanyl, tetrahydrofuranyl, dihydrofuranyl, tetrahydrothiophenyl, dihydrothiophenyl, pyrrolidinyl, dihydropyrrolyl, pyrrolidin-2-one, pyrrolyl-2,5-dione, dioxolanyl, oxasulfuranyl, disulfuranyl, oxazolidin-2-one, triazolinyl, oxadiazolinyl, thiadiazolinyl, piperidinyl, tetrahydropyranyl, dihydropyridinyl, thianyl, piperazinyl, morpholinyl, dithianyl, dioxanyl, triazinanyl, azepanyl, oxepanyl, thiepanyl, azocanyl, oxecanyl, thiocanyl, indolinyl, isoindolinyl, dihydrobenzofuranyl, dihydrobenzothienyl, benzoxazolinonyl, tetrahydroquinolinyl, tetrahydroisoquinolinyl, furo[2,3-b]furanyl, 2,3-dihydro-1,4-dioxinyl, 3-oxa-8-azabicyclo[3.2.1]octanyl, or 8-oxa-3-azabicyclo[3.2.1]octanyl ring.

In certain embodiments, $R^{13}$ is an optionally substituted monocyclic or bicyclic aryl, e.g., an optionally substituted phenyl, or optionally substituted naphthyl ring.

In certain embodiments, $R^{13}$ is an optionally substituted monocyclic or bicyclic heteroaryl, e.g., an optionally substituted 5- to 10-membered heteroaryl, optionally substituted 5- to 8-membered heteroaryl, optionally substituted 5- to 6-membered heteroaryl, optionally substituted 5-membered heteroaryl, or optionally substituted 6-membered heteroaryl. In certain embodiments, $R^{13}$ is an optionally substituted pyrrolyl, furanyl, thiophenyl, imidazolyl, pyrazolyl, oxazolyl, isoxazolyl, thiazolyl, isothiazolyl, tetrazolyl, pyridinyl, pyridazinyl, pyrimidinyl, pyrazinyl, triazinyl, tetrazinyl, azepinyl, oxepinyl, thiepinyl, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, purinyl, naphthyridinyl, pteridinyl, quinolinyl, isoquinolinyl, cinnolinyl, quinoxalinyl, phthalazinyl, or quinazolinyl ring.

In certain embodiments, $R^{13}$ is a cyclic moiety selected from the group consisting of:

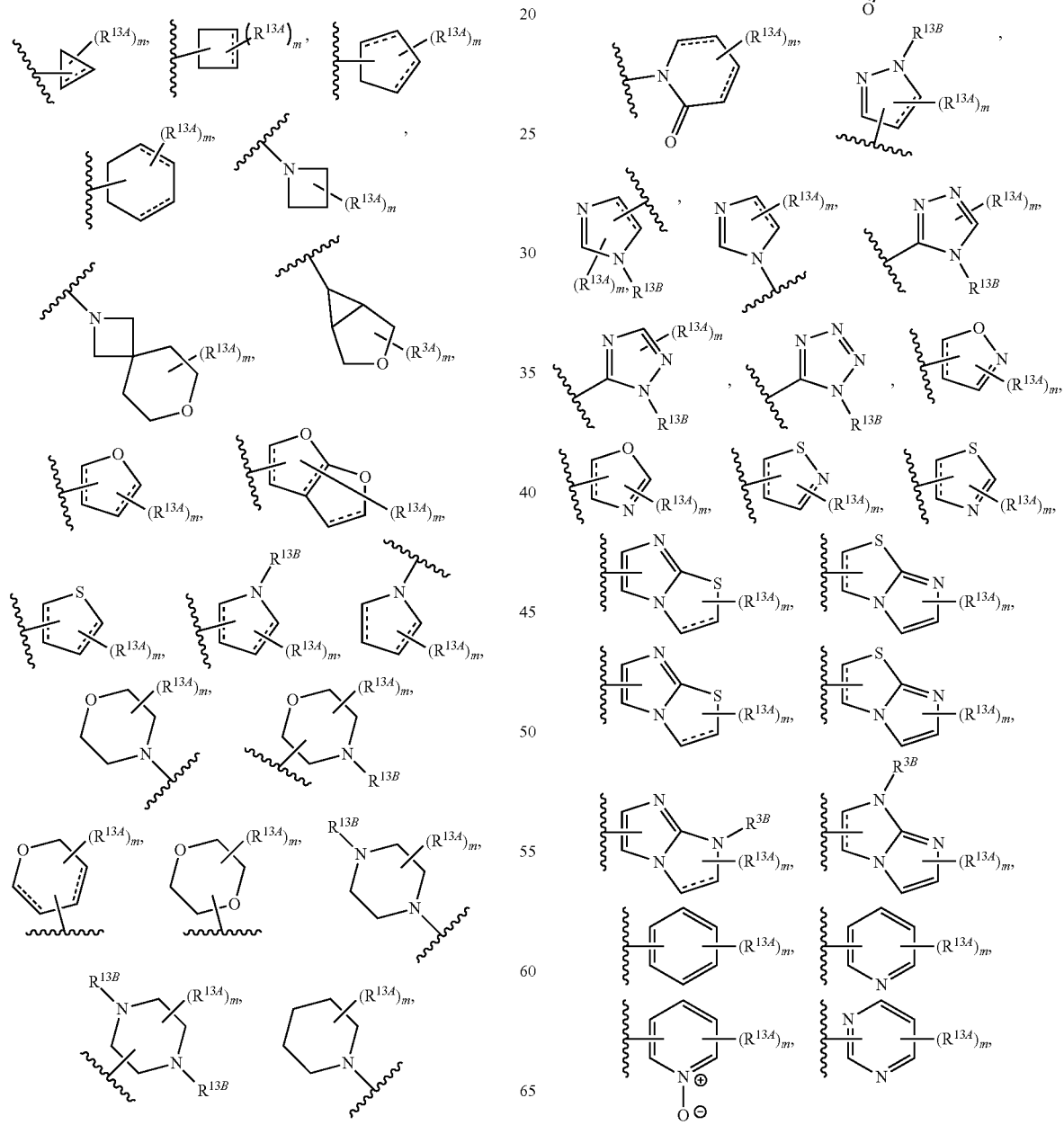

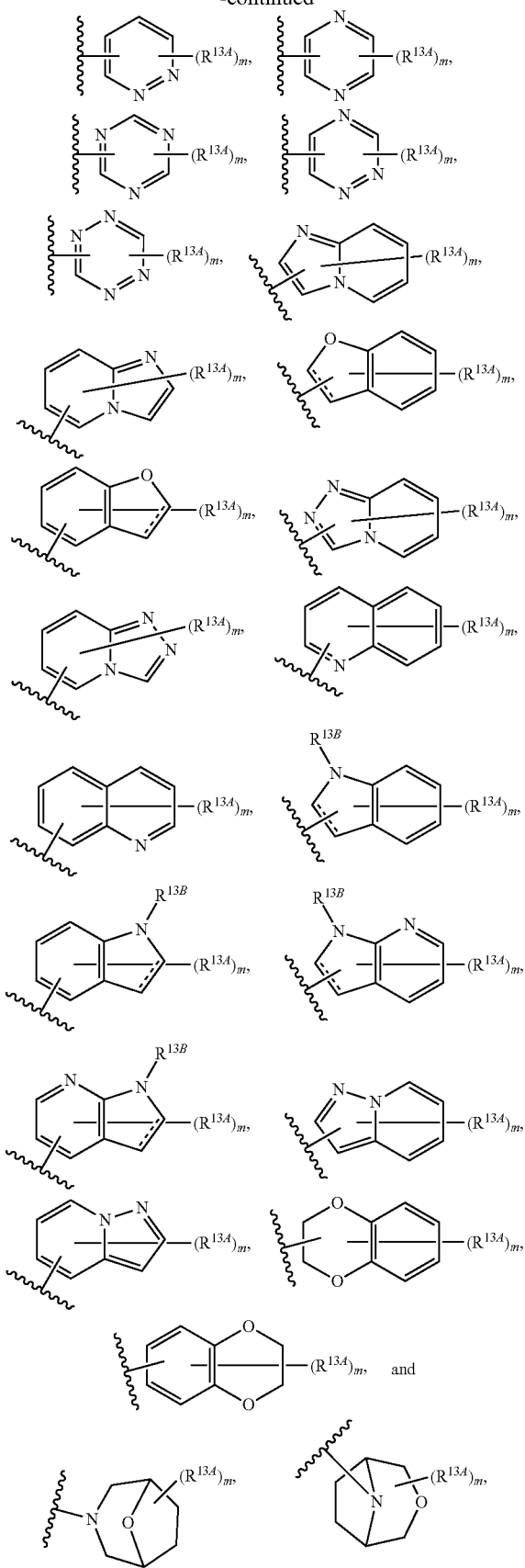

wherein:
each instance of ----- independently represents a single or double bond;

m is 0, 1, 2, or 3;

each instance of $R^{13A}$ is independently hydroxyl, substituted hydroxyl, thiol, substituted thiol, amino, substituted amino, carbonyl, sulfonyl, sulfinyl, —CN, —NO$_2$, halogen, optionally substituted alkyl, or two $R^{13A}$ groups are joined to form an optionally substituted carbocyclic, optionally substituted heterocyclic, optionally substituted aryl, or optionally substituted heteroaryl ring, or $R^{13A}$ and $R^{13B}$ group are joined to form an optionally substituted carbocyclic, optionally substituted heterocyclic, optionally substituted aryl, or optionally substituted heteroaryl ring; and $R^{13B}$ is hydrogen, optionally substituted alkyl, or a nitrogen protecting group.

In certain embodiments, m is 0. In certain embodiments, m is 1. In certain embodiments, m is 2. In certain embodiments, m is 3. In certain embodiments, each instance of $R^{13A}$ is independently hydroxyl, —OCH$_3$, optionally substituted C$_{1-4}$alkyl (e.g., methyl, trifluoromethyl, ethyl, propyl, isopropyl, butyl, isobutyl, secbutyl, tertbutyl), —CN, or sulfonyl (e.g., —S(O)$_2$CH$_3$).

As generally defined herein, each $R^L$ provided in $L^1$ and $L^2$ is independently hydrogen, optionally substituted alkyl, or a nitrogen protecting group, or $R^L$ and $R^3$ taken together form an optionally substituted heterocyclyl or optionally substituted heteroaryl ring, or $R^L$ and $R^{13}$ taken together form an optionally substituted heterocyclyl or optionally substituted heteroaryl ring. In certain embodiments, at least one instance of $R^L$ is hydrogen. In certain embodiments, each instance of $R^L$ is hydrogen. In certain embodiments, at least one instance of $R^L$ is optionally substituted alkyl, e.g., optionally substituted C$_{1-6}$ alkyl, optionally substituted C$_{1-5}$alkyl, optionally substituted C$_{1-4}$alkyl, optionally substituted C$_{1-2}$alkyl, optionally substituted C$_{2-3}$alkyl, optionally substituted C$_3$alkyl, optionally substituted C$_1$alkyl, optionally substituted C$_2$alkyl, optionally substituted C$_3$alkyl, optionally substituted C$_4$alkyl, optionally substituted C$_5$alkyl, or optionally substituted C$_6$alkyl. Exemplary $R^L$C$_{1-6}$alkyl groups include, but are not limited to, methyl (C$_1$), ethyl (C$_2$), n-propyl (C$_3$), isopropyl (C$_3$), n-butyl (C$_4$), tert-butyl (C$_4$), sec-butyl (C$_4$), iso-butyl (C$_4$), n-pentyl (C$_5$), 3-pentanyl (C$_5$), amyl (C$_5$), neopentyl (C$_5$), 3-methyl-2-butanyl (C$_5$), tertiary amyl (C$_5$), and n-hexyl (C$_6$). In certain embodiments, $R^L$ is alkyl substituted with —CN, e.g., —(CH$_2$)$_z$CN, wherein z is 1, 2, 3, 4, 5, or 6. In certain embodiments, $R^L$ is alkyl substituted with hydroxy or substituted hydroxy, e.g., —(CH$_2$)$_z$OCH$_3$, wherein z is 1, 2, 3, 4, 5, or 6. In certain embodiments, $R^L$ is alkyl substituted with amino or substituted amino, e.g., —(CH$_2$)$_z$NH$_2$, wherein z is 1, 2, 3, 4, 5, or 6. In certain embodiments, at least one instance of $R^L$ is a nitrogen protecting group. In certain embodiments, $R^L$ and $R^3$ taken together form an optionally substituted heterocyclyl ring, e.g., an optionally substituted 3- to 10-membered heterocyclyl, 3- to 8-membered heterocyclyl, 3- to 6-membered heterocyclyl, 3- to 5-membered heterocyclyl, 3- to 4-membered heterocyclyl, 3-membered heterocyclyl, 4-membered heterocyclyl, 5-membered heterocyclyl, 6-membered heterocyclyl, 7-membered heterocyclyl, 8-membered heterocyclyl, 9-membered heterocyclyl, or 10-membered heterocyclyl ring. In certain embodiments, $R^L$ and $R^3$ taken together form an optionally substituted heteroaryl ring, e.g., an optionally substituted 5- to 10-membered heteroaryl, optionally substituted 5- to 8-membered heteroaryl, optionally substituted 5- to 6-membered heteroaryl, optionally substituted 5-membered heteroaryl, or optionally substituted 6-membered heteroaryl. In certain embodiments, $R^L$ and $R^{13}$ taken together form an optionally substituted heterocyclyl ring, e.g., an optionally substituted 3- to 10-membered heterocyclyl, 3- to 8-membered heterocyclyl, 3- to 6-membered heterocyclyl, 3- to 5-membered heterocyclyl, 3- to 4-membered heterocyclyl, 3-membered heterocyclyl, 4-membered heterocyclyl, 5-membered heterocyclyl, 6-membered heterocyclyl, 7-membered heterocyclyl, 8-membered heterocyclyl, 9-membered heterocyclyl, or 10-membered heterocyclyl ring. In certain embodiments, $R^L$ and $R^{13}$ taken together form an optionally substituted heteroaryl ring, e.g., an optionally substituted 5- to 10-membered heteroaryl, optionally substituted 5- to 8-membered heteroaryl, optionally substituted 5-membered heteroaryl, or optionally substituted 6-membered heteroaryl.

Various combination of the above described embodiments are further contemplated herein. For example, in certain embodiments of Formula (I-h), wherein $G_8$ and $G_{12}$ are both N, provided is a compound of Formula (I-i):

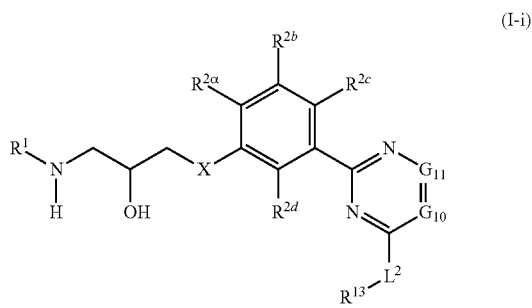

(I-i)

or a pharmaceutically acceptable salt thereof. In certain embodiments, X is —O—. In certain embodiments, $R^1$ is hydrogen, methyl, ethyl, n-propyl, isopropyl, or cyclopropyl. In certain embodiments, $R^{2a}$, $R^{2c}$, and $R^{2d}$ are hydrogen. In certain embodiments, $R^{2b}$ is halogen (e.g., chloro), —CN, —C(=O)$R^{A2}$, —O$R^{A2}$, —S$R^{A2}$, —N($R^{A2}$)$_2$, optionally substituted cyclopropyl, optionally substituted $C_{1-4}$alkyl, optionally substituted $C_{2-4}$alkenyl, optionally substituted $C_{2-4}$alkynyl, wherein $R^{A2}$ is optionally substituted alkyl. In certain embodiments, $L^2$ is a bond, —N($R^L$)—, —N$R^L$C(O)O—, —N$R^L$C(O)N($R^L$)—, —N($R^L$)—, —N($R^L$)SO$_2$N($R^L$)—, —N$R^L$—(CH$_2$)$_x$—C(O)O—, —N$R^L$—(CH$_2$)$_x$—O—, —N$R^L$C(O)N($R^L$)—, —N$R^L$—(CH$_2$)$_x$—, —(CH$_2$)$_x$—N$R^L$—, —N$R^L$C(O)O(CH$_2$)$_x$—, —N$R^L$C(O)N$R^L$(CH$_2$)$_x$—, or —N$R^L$(CH$_2$)$_x$N$R^L$C(O)—. In certain embodiments, $R^{13}$ is optionally substituted heterocylyl or optionally substituted heteroaryl.

In certain embodiments of Formula (I-h), wherein $G_8$ and $G_{12}$ are both N, and $G_{11}$ is a group of formula C—$R^{11}$, provided is a compound of Formula (I-j):

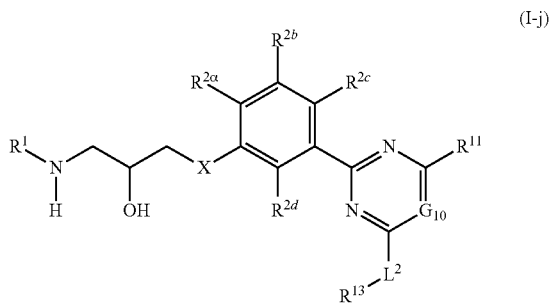

(I-j)

or a pharmaceutically acceptable salt thereof. In certain embodiments, X is —O—. In certain embodiments, $R^1$ is hydrogen, methyl, ethyl, n-propyl, isopropyl, or cyclopropyl. In certain embodiments, $R^{2a}$, $R^{2c}$, and $R^{2d}$ are hydrogen. In certain embodiments, $R^{2b}$ is halogen (e.g., chloro), —CN, —C(=O)$R^2$, —O$R^2$, —S$R^{A2}$, —N($R^{A2}$)$_2$, optionally substituted cyclopropyl, optionally substituted $C_{1-4}$alkyl, optionally substituted $C_{2-4}$alkenyl, optionally substituted $C_{2-4}$alkynyl, wherein $R^{A2}$ is optionally substituted alkyl. In certain embodiments, $L^2$ is a bond, —N($R^L$)—, —N$R^L$C(O)O—, —N$R^L$C(O)N($R^L$)—, —N($R^L$)—, —N($R^L$)SO$_2$N($R^L$)—, —N$R^L$—(CH$_2$)$_x$—C(O)O—, —N$R^L$—(CH$_2$)$_x$—O—, —N$R^L$C(O)N($R^L$)—, —N$R^L$—(CH$_2$)$_x$—, —(CH$_2$)$_x$—N$R^L$—, —N$R^L$C(O)O(CH$_2$)$_x$—, —N$R^L$C(O)N$R^L$(CH$_2$)$_x$—, or —N$R^L$(CH$_2$)$_x$N$R^L$C(O)—. In certain embodiments, $R^{13}$ is optionally substituted heterocylyl or optionally substituted heteroaryl. In certain embodiments, $R^{11}$ is hydrogen or a group -$L^1$-$R^3$.

In certain embodiments of Formula (I-h), wherein $G_8$ and $G_{12}$ are both N, $G_{11}$ is C—$R^{11}$, and $G_{10}$ is C—$R^{10}$, provided is a compound of Formula (I-k):

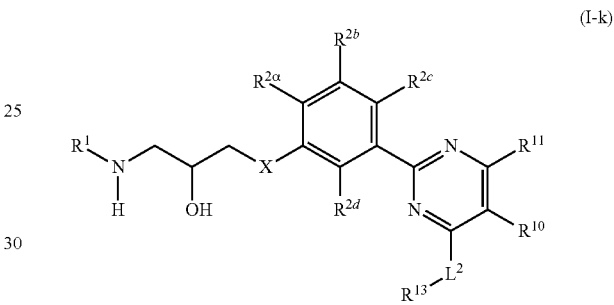

(I-k)

or a pharmaceutically acceptable salt thereof. In certain embodiments, X is —O—. In certain embodiments, $R^1$ is hydrogen, methyl, or ethyl. In certain embodiments, $R^{2a}$, $R^{2c}$, and $R^{2d}$ are hydrogen In certain embodiments, $R^{2b}$ is halogen (e.g., chloro), —CN, —C(=O)$R^2$, —O$R^2$, —S$R^{A2}$, —N($R^{A2}$)$_2$, optionally substituted cyclopropyl, optionally substituted $C_{1-4}$alkyl, optionally substituted $C_{2-4}$alkenyl, optionally substituted $C_{2-4}$alkynyl, wherein $R^{A2}$ is optionally substituted alkyl. In certain embodiments, $L^2$ is a bond, —N($R^L$)—, —N$R^L$C(O)O—, —N$R^L$C(O)N($R^L$)—, —N($R^L$)—, —N($R^L$)SO$_2$N($R^L$)—, —N$R^L$—(CH$_2$)$_x$—C(O)O—, —N$R^L$—(CH$_2$)$_x$—O—, —N$R^L$C(O)N($R^L$)—, —N$R^L$—(CH$_2$)$_x$—, —(CH$_2$)$_x$—N$R^L$—, —N$R^L$C(O)O(CH$_2$)$_x$—, —N$R^L$C(O)N$R^L$(CH$_2$)$_x$—, or —N$R^L$(CH$_2$)$_x$N$R^L$C(O)—. In certain embodiments, $R^{13}$ is optionally substituted heterocylyl or optionally substituted heteroaryl. In certain embodiments, $R^{11}$ is hydrogen or a group -$L^1$-$R^3$. In certain embodiments, $R^{10}$ is hydrogen or methyl.

In certain embodiments of Formula (I-h), wherein $G_8$ and $G_{12}$ are both N, $G_{11}$ is C—$R^{11}$, $R^{11}$ is -$L^1$-$R^3$, and $G_{10}$ is C—$R^{10}$, provided is a compound of Formula (I-l):

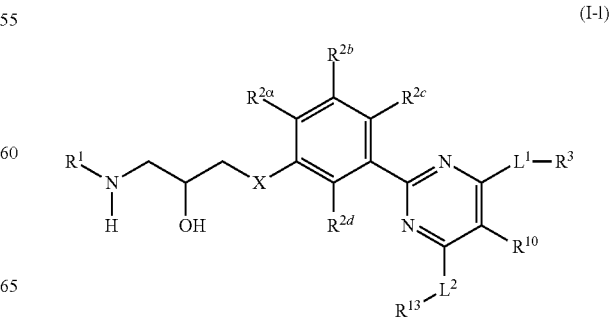

(I-l)

or a pharmaceutically acceptable salt thereof. In certain embodiments, X is —O—. In certain embodiments, $R^1$ is hydrogen, methyl, ethyl, n-propyl, isopropyl, or cyclopropyl. In certain embodiments, $R^{2a}$, $R^{2c}$, and $R^{2d}$ are hydrogen. In certain embodiments, $R^{2b}$ is halogen (e.g., chloro), —CN, —C(=O)$R^{A2}$, —OR$^{A2}$, —SR$^{A2}$, —N(R$^{A2}$)$_2$, optionally substituted cyclopropyl, optionally substituted $C_{1-4}$alkyl, optionally substituted $C_{2-4}$alkenyl, optionally substituted $C_{2-4}$alkynyl, wherein $R^{A2}$ is optionally substituted alkyl. In certain embodiments, $L^2$ is a bond, —N(R$^L$)—, —NR$^L$C(O)O—, —NR$^L$C(O)N(R$^L$)—, —N(R$^L$)—, —N(R$^L$)SO$_2$N(R$^L$)—, —NR$^L$—(CH$_2$)$_x$—C(O)O—, —NR$^L$—(CH$_2$)$_x$—O—, —NR$^L$C(O)N(R$^L$)—, —NR$^L$—(CH$_2$)$_x$—, —(CH$_2$)$_x$—NR$^L$—, —NR$^L$C(O)O(CH$_2$)$_x$, —NR$^L$C(O)NR$^L$(CH$_2$)$_x$—, or —NR$^L$(CH$_2$)$_x$NR$^L$C(O)—. In certain embodiments, $R^{13}$ is optionally substituted heterocylyl or optionally substituted heteroaryl. In certain embodiments, $L^1$ is a bond, —N(R$^L$)—, —NR$^L$C(O)O—, —NR$^L$C(O)N(R$^L$)—, —N(R$^L$)—, —N(R$^L$)SO$_2$N(R$^L$)—, —NR$^L$—(CH$_2$)$_x$—C(O)O—, —NR$^L$—(CH$_2$)$_x$—O—, —NR$^L$C(O)N(R$^L$)—, —NR$^L$—(CH$_2$)$_x$—, —(CH$_2$)$_x$—NR$^L$—, —NR$^L$C(O)O(CH$_2$)$_x$, —NR$^L$C(O)NR$^L$(CH$_2$)$_x$—, or —NR$^L$(CH$_2$)$_x$NR$^L$C(O)—. In certain embodiments, $R^3$ is an acyclic moiety. In certain embodiments, $R^3$ is a cyclic moiety. In certain embodiments, $R^{10}$ is hydrogen or methyl.

In other embodiments of Formula (I-h), wherein $G_8$ and $G_{10}$ are both N, provided is a compound of Formula (I-m):

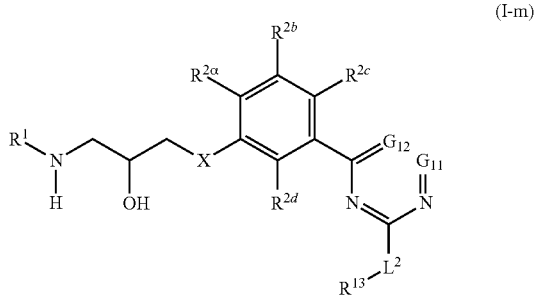

(I-m)

or a pharmaceutically acceptable salt thereof. In certain embodiments, X is —O—. In certain embodiments, $R^1$ is hydrogen, methyl, ethyl, n-propyl, isopropyl, or cyclopropyl. In certain embodiments, $R^{2a}$, $R^{2c}$, and $R^{2d}$ are hydrogen. In certain embodiments, $R^{2b}$ is halogen (e.g., chloro), —CN, —C(=O)$R^{A2}$, —OR$^{A2}$, —SR$^{A2}$, —N(R$^{A2}$)$_2$, optionally substituted cyclopropyl, optionally substituted $C_{1-4}$alkyl, optionally substituted $C_{2-4}$alkenyl, optionally substituted $C_{2-4}$alkynyl, wherein $R^{A2}$ is optionally substituted alkyl. In certain embodiments, $L^2$ is a bond, —N(R$^L$)—, —NR$^L$C(O)O—, —NR$^L$C(O)N(R$^L$)—, —N(R$^L$)—, —N(R$^L$)SO$_2$N(R$^L$)—, —NR$^L$—(CH$_2$)$_x$—C(O)O—, —NR$^L$—(CH$_2$)$_x$—O—, —NR$^L$C(O)N(R$^L$)—, —NR$^L$—(CH$_2$)$_x$—, —(CH$_2$)$_x$—NR$^L$—, —NR$^L$C(O)O(CH$_2$)$_x$, —NR$^L$C(O)NR$^L$(CH$_2$)$_x$—, or —NR$^L$(CH$_2$)$_x$NR$^L$C(O)—. In certain embodiments, $R^{13}$ is optionally substituted heterocylyl or optionally substituted heteroaryl.

In certain embodiments of Formula (I-h), wherein $G_8$ and $G_{12}$ are both N, and $G_{11}$ is C—R$^{11}$, provided is a compound of Formula (I-n):

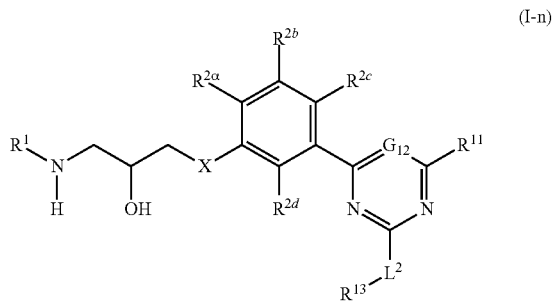

(I-n)

or a pharmaceutically acceptable salt thereof. In certain embodiments, X is —O—. In certain embodiments, $R^1$ is hydrogen, methyl, ethyl, n-propyl, isopropyl, or cyclopropyl. In certain embodiments, $R^{2a}$, $R^{2c}$, and $R^{2d}$ are hydrogen. In certain embodiments, $R^{2b}$ is halogen (e.g., chloro), —CN, —C(=O)$R^{A2}$, —OR$^{A2}$, —SR$^{A2}$, —N(R$^{A2}$)$_2$, optionally substituted cyclopropyl, optionally substituted $C_{1-4}$alkyl, optionally substituted $C_{2-4}$alkenyl, optionally substituted $C_{2-4}$alkynyl, wherein $R^{A2}$ is optionally substituted alkyl. In certain embodiments, $L^2$ is a bond, —N(R$^L$)—, —NR$^L$C(O)O—, —NR$^L$C(O)N(R$^L$)—, —N(R$^L$)—, —N(R$^L$)SO$_2$N(R$^L$)—, —NR$^L$—(CH$_2$)$_x$—C(O)O—, —NR$^L$—(CH$_2$)$_x$—O—, —NR$^L$C(O)N(R$^L$)—, —NR$^L$—(CH$_2$)$_x$—, —(CH$_2$)$_x$—NR$^L$—, —NR$^L$C(O)O(CH$_2$)$_x$, —NR$^L$C(O)NR$^L$(CH$_2$)$_x$—, or —NR$^L$(CH$_2$)$_x$NR$^L$C(O)—. In certain embodiments, $R^{13}$ is optionally substituted heterocylyl or optionally substituted heteroaryl. In certain embodiments, $R^{11}$ is hydrogen or a group -L$^1$-R$^3$.

In certain embodiments of Formula (I-h), wherein $G_8$ and $G_{12}$ are both N, $G_{11}$ is C—R$^{11}$, and $G_{12}$ is C—R$^{12}$, provided is a compound of Formula (I-o):

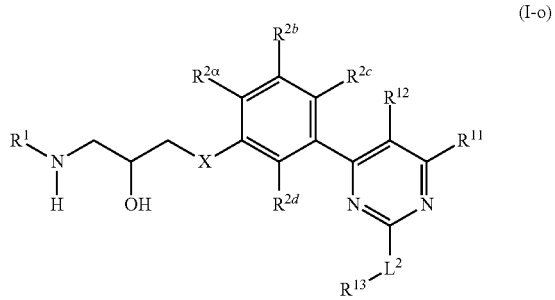

(I-o)

or a pharmaceutically acceptable salt thereof. In certain embodiments, X is —O—. In certain embodiments, $R^1$ is hydrogen, methyl, ethyl, n-propyl, isopropyl, or cyclopropyl. In certain embodiments, $R^{2a}$, $R^{2c}$, and $R^{2d}$ are hydrogen. In certain embodiments, $R^{2b}$ is halogen (e.g., chloro), —CN, —C(=O)$R^{A2}$, —OR$^{A2}$, —SR$^{A2}$, —N(R$^{A2}$)$_2$, optionally substituted cyclopropyl, optionally substituted $C_{1-4}$alkyl, optionally substituted $C_{2-4}$alkenyl, optionally substituted $C_{2-4}$alkynyl, wherein $R^{A2}$ is optionally substituted alkyl. In certain embodiments, $L^2$ is a bond, —N($R^L$)—, —$NR^LC(O)O$—, —$NR^LC(O)N(R^L)$—, —N($R^L$)—, —N($R^L$)$SO_2$N($R^L$)—, —$NR^L$—$(CH_2)_x$—C(O)O—, —$NR^L$—$(CH_2)_x$—O—, —$NR^LC(O)N(R^L)$—, —$NR^L$—$(CH_2)_x$—, —$(CH_2)_x$—$NR^L$—, —$NR^LC(O)O(CH_2)_x$, —$NR^LC(O)NR^L(CH_2)_x$—, or —$NR^L(CH_2)_xNR^LC(O)$—. In certain embodiments, $R^{13}$ is optionally substituted heterocylyl or optionally substituted heteroaryl. In certain embodiments, $R^{11}$ is hydrogen or a group -$L^1$-$R^3$. In certain embodiments, $R^{12}$ is hydrogen or methyl.

In certain embodiments of Formula (I-h), wherein $G_8$ and $G_{12}$ are both N, $G_{11}$ is C—$R^{11}$, $R^{11}$ is a group of formula -L-$R^3$, and $G_{12}$ is C—$R^{12}$, provided is a compound of Formula (I-p):

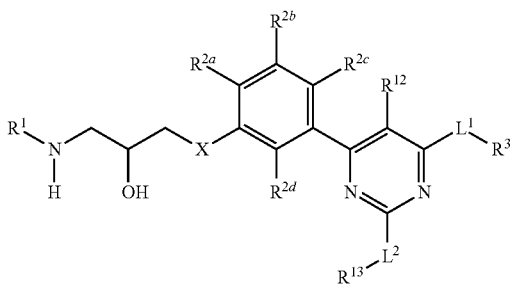

(I-p)

or a pharmaceutically acceptable salt thereof. In certain embodiments, X is —O—. In certain embodiments, $R^1$ is hydrogen, methyl, ethyl, n-propyl, isopropyl, or cyclopropyl. In certain embodiments, $R^{2a}$, $R^{2c}$, and $R^{2d}$ are hydrogen. In certain embodiments, $R^{2b}$ is halogen (e.g., chloro), —CN, —C(=O)$R^2$, —$OR^2$, —$SR^{42}$, —N($R^{42}$)$_2$, optionally substituted cyclopropyl, optionally substituted $C_{1-4}$alkyl, optionally substituted $C_{2-4}$alkenyl, optionally substituted $C_{2-4}$alkynyl, wherein $R^{42}$ is optionally substituted alkyl. In certain embodiments, $L^2$ is a bond, —N($R^L$)—, —$NR^LC(O)O$—, —$NR^LC(O)N(R^L)$—, —N($R^L$)—, —N($R^L$)$SO_2$N($R^L$)—, —$NR^L$—$(CH_2)_x$—C(O)O—, —$NR^L$—$(CH_2)_x$—O—, —$NR^LC(O)N(R^L)$—, —$NR^L$—$(CH_2)_x$—, —$(CH_2)_x$—$NR^L$—, —$NR^LC(O)O(CH_2)_x$, —$NR^LC(O)NR^L(CH_2)_x$—, or —$NR^L(CH_2)_xNR^LC(O)$—. In certain embodiments, $R^{13}$ is optionally substituted heterocylyl or optionally substituted heteroaryl. In certain embodiments, $L^1$ is a bond, —N($R^L$)—, —$NR^LC(O)O$—, —$NR^LC(O)N(R^L)$—, —N($R^L$)—, —N($R^L$)$SO_2$N($R^L$)—, —$NR^L$—$(CH_2)_x$—C(O)O—, —$NR^L$—$(CH_2)_x$—O—, —$NR^LC(O)N(R^L)$—, —$NR^L$—$(CH_2)_x$—, —$(CH_2)_x$—$NR^L$—, —$NR^LC(O)O(CH_2)_x$—, —$NR^LC(O)NR^L(CH_2)_x$—, or —$NR^L(CH_2)_xNR^LC(O)$—. In certain embodiments, $R^3$ is an acyclic moiety. In certain embodiments, $R^3$ is a cyclic moiety. In certain embodiments, $R^{12}$ is hydrogen or methyl.

In certain embodiments, a compound of Formula (I) is selected from any one of the compounds provided in Tables 1 and 2, or a pharmaceutically acceptable salt thereof.

TABLE 1

| | Exemplary Compounds | |
|---|---|---|
| # | Structure | LC-MS m/z (M + H) |
| 1-1 | | 450.3 |
| 2-1 | | 450.3 |

TABLE 1-continued
Exemplary Compounds
| # | Structure | LC-MS m/z (M + H) |
|---|---|---|
| 3-1 | 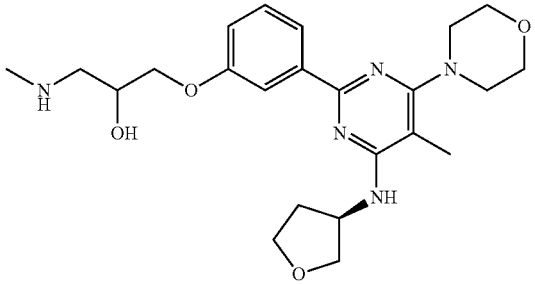 [SMILES: CNCC(O)COc1cccc(-c2nc(N[C@@H]3CCOC3)c(C)c(N3CCOCC3)n2)c1] | 444.3 |
| 4-1 | 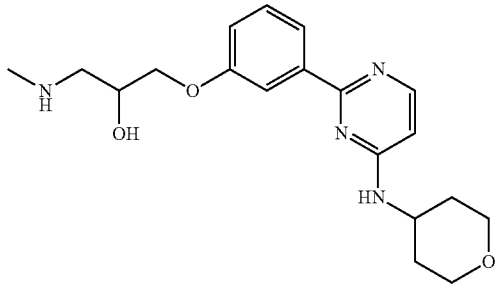 [SMILES: CNCC(O)COc1cccc(-c2nccc(NC3CCOCC3)n2)c1] | 359.2 |
| 5-1 | 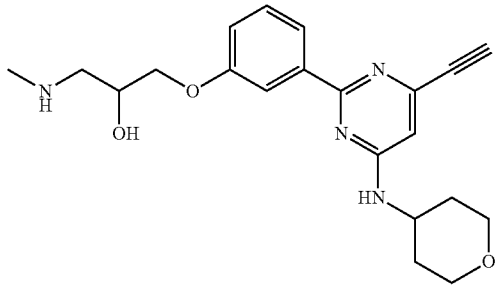 [SMILES: C#Cc1cc(NC2CCOCC2)nc(-c2cccc(OCC(O)CNC)c2)n1] | 383.2 |
| 6-1 | 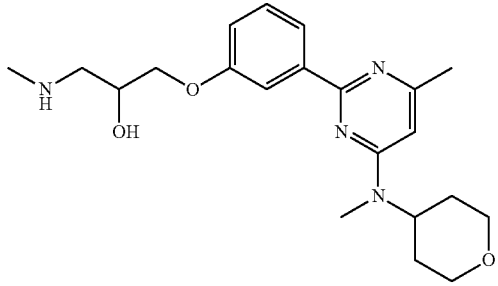 [SMILES: CNCC(O)COc1cccc(-c2nc(C)cc(N(C)C3CCOCC3)n2)c1] | 387.2 |
| 7-1 | 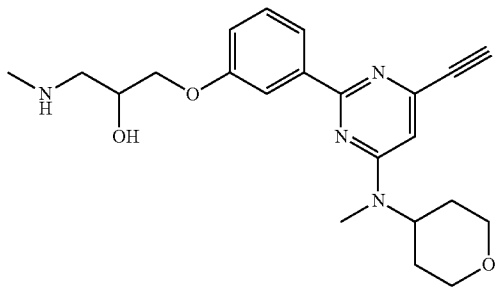 [SMILES: C#Cc1cc(N(C)C2CCOCC2)nc(-c2cccc(OCC(O)CNC)c2)n1] | 397.2 |

TABLE 1-continued

Exemplary Compounds

| # | Structure | LC-MS m/z (M + H) |
|---|---|---|
| 8-1 | 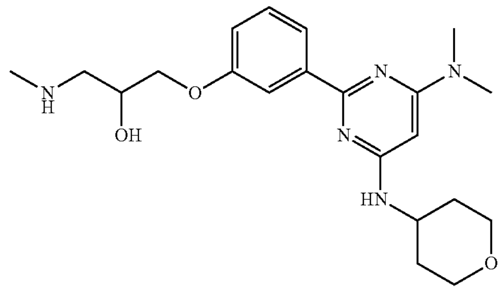 | 403.3 |
| 9-1 | 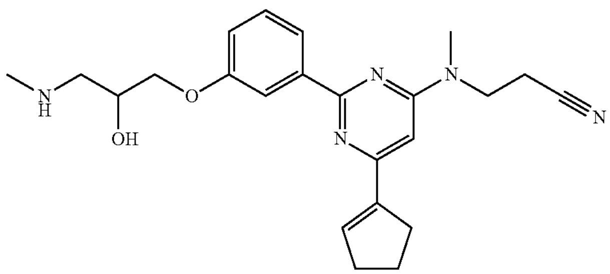 [SMILES: CNCC(O)COc1cccc(-c2nc(C3=CCCC3)cc(N(C)CCC#N)n2)c1] | 408.1 |
| 10-1 | 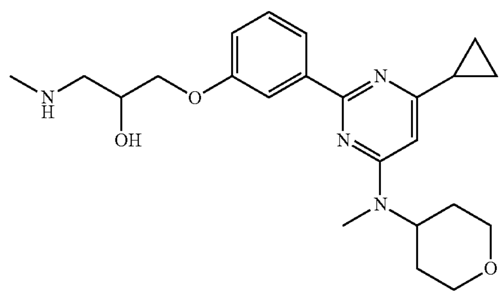 [SMILES: CNCC(O)COc1cccc(-c2nc(C3CC3)cc(N(C)C3CCOCC3)n2)c1] | 413.3 |
| 11-1 | 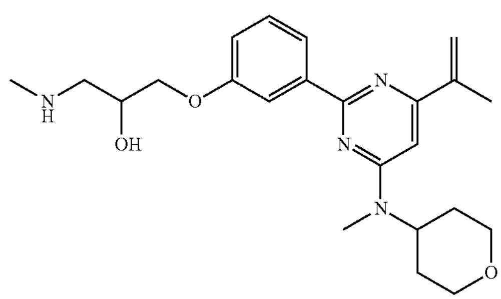 [SMILES: C=C(C)c1cc(N(C)C2CCOCC2)nc(-c2cccc(OCC(O)CNC)c2)n1] | 413.3 |
| 12-1 | 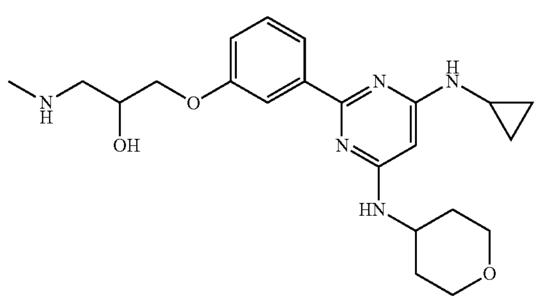 [SMILES: CNCC(O)COc1cccc(-c2nc(NC3CCOCC3)cc(NC3CC3)n2)c1] | 414.2 |

TABLE 1-continued

Exemplary Compounds

| # | Structure | LC-MS m/z (M + H) |
|---|---|---|
| 13-1 | 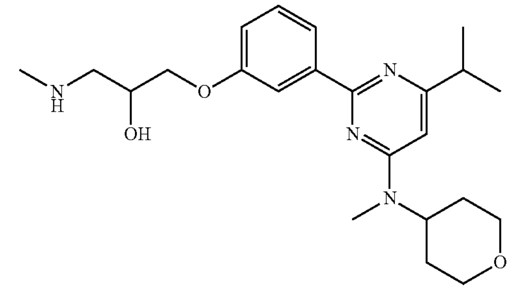 [SMILES: CNCC(O)COc1cccc(-c2nc(C(C)C)cc(N(C)C3CCOCC3)n2)c1] | 415.3 |
| 14-1 | 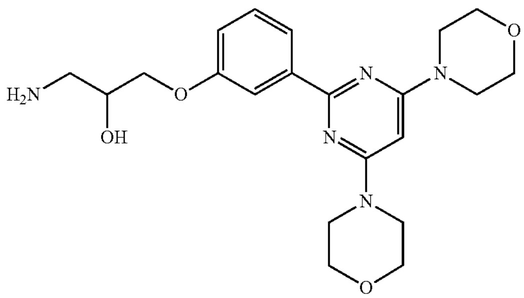 [SMILES: NCC(O)COc1cccc(-c2nc(N3CCOCC3)cc(N3CCOCC3)n2)c1] | 416.3 |
| 15-1 | 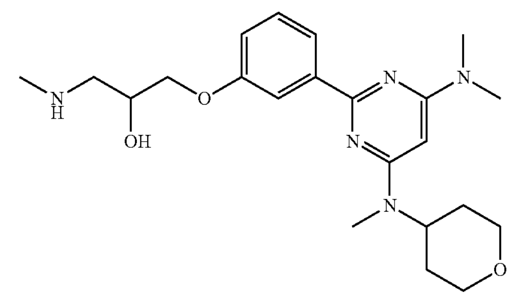 | 416.3 |
| 16-1 | 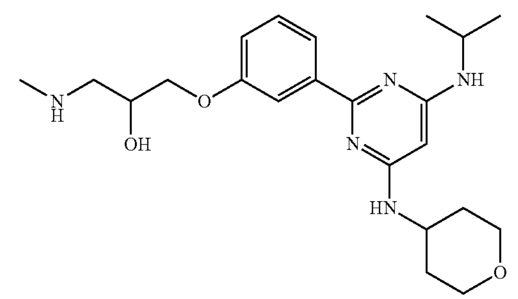 | 416.3 |
| 17-1 | 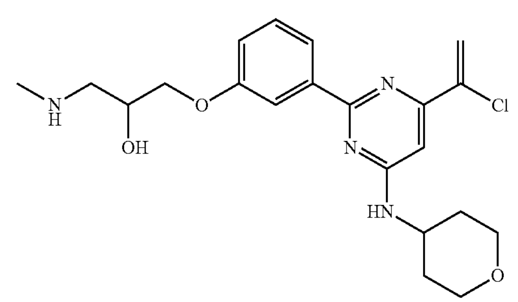 [SMILES: C=C(Cl)c1cc(NC2CCOCC2)nc(-c2cccc(OCC(O)CNC)c2)n1] | 419.2 |

TABLE 1-continued
Exemplary Compounds
| # | Structure | LC-MS m/z (M + H) |
|---|---|---|
| 18-1 | 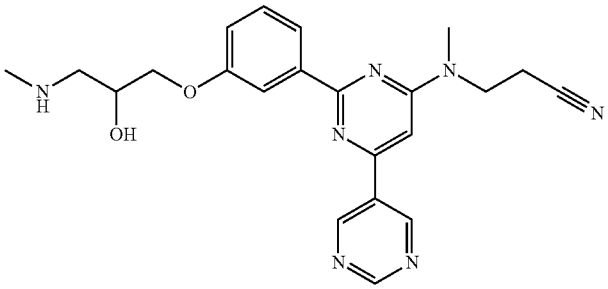 [SMILES: CNCC(O)COc1cccc(-c2nc(-c3cncnc3)cc(N(C)CCC#N)n2)c1] | 420.1 |
| 19-1 | 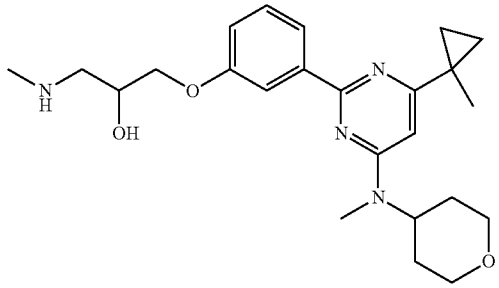 [SMILES: CNCC(O)COc1cccc(-c2nc(N(C)C3CCOCC3)cc(C3(C)CC3)n2)c1] | 427.2 |
| 20-1 | 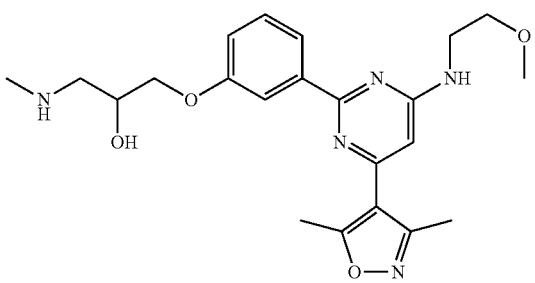 | 428.3 |
| 21-1 | 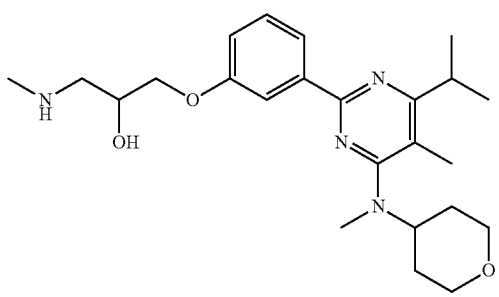 [SMILES: CNCC(O)COc1cccc(-c2nc(C(C)C)c(C)c(N(C)C3CCOCC3)n2)c1] | 429.3 |
| 22-1 | 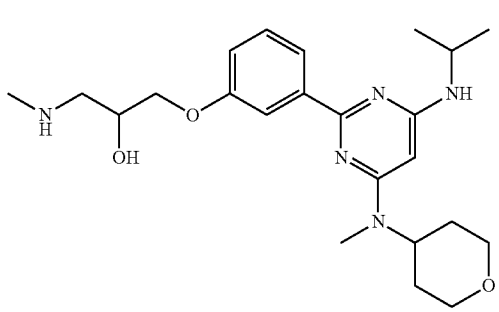 [SMILES: CNCC(O)COc1cccc(-c2nc(NC(C)C)cc(N(C)C3CCOCC3)n2)c1] | 430.3 |

TABLE 1-continued

Exemplary Compounds

| # | Structure | LC-MS m/z (M + H) |
|---|---|---|
| 23-1 | 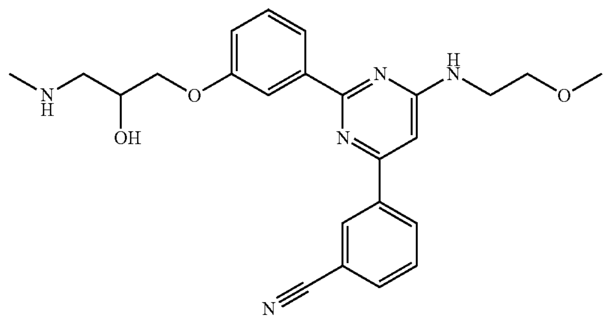 | 434.2 |
| 24-1 | 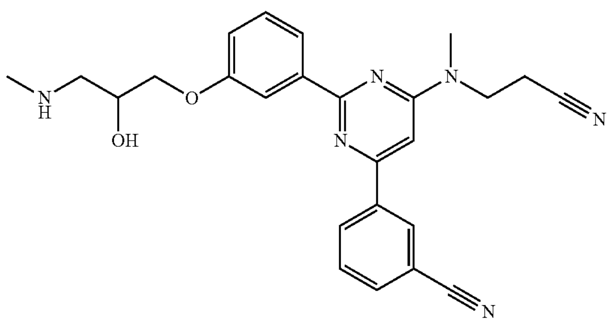 [SMILES: CNCC(O)COc1cccc(-c2nc(-c3cccc(C#N)c3)cc(N(C)CCC#N)n2)c1] | 443.2 |
| 25-1 | 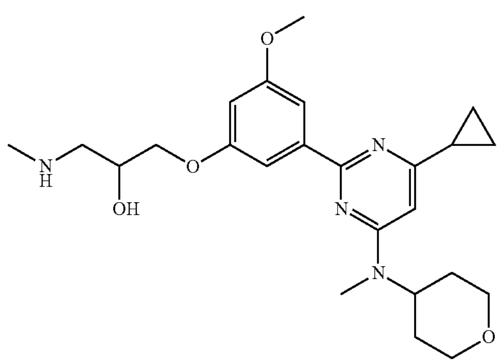 [SMILES: CNCC(O)COc1cc(OC)cc(-c2nc(C3CC3)cc(N(C)C3CCOCC3)n2)c1] | 443.3 |
| 26-1 | 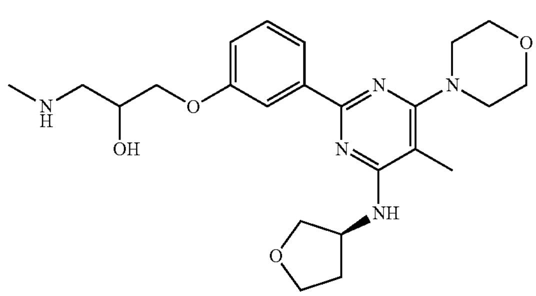 [SMILES: CNCC(O)COc1cccc(-c2nc(N[C@H]3CCOC3)c(C)c(N3CCOCC3)n2)c1] | 444.3 |

TABLE 1-continued

Exemplary Compounds

| # | Structure | LC-MS m/z (M + H) |
|---|-----------|-------------------|
| 27-1 | 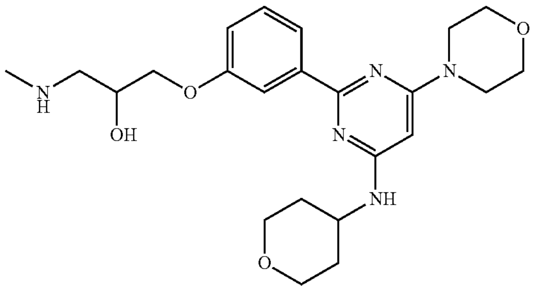 [SMILES: CNCC(O)COc1cccc(-c2nc(NC3CCOCC3)cc(N3CCOCC3)n2)c1] | 444.4 |
| 28-1 | 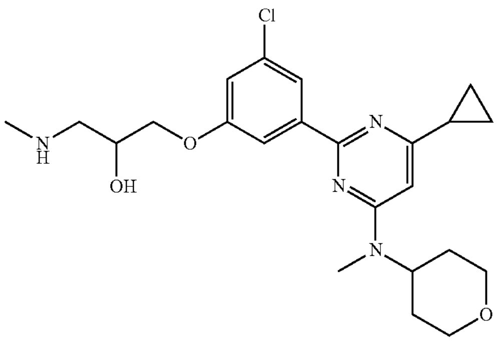 [SMILES: CNCC(O)COc1cc(Cl)cc(-c2nc(C3CC3)cc(N(C)C3CCOCC3)n2)c1] | 447.3 |
| 29-1 | 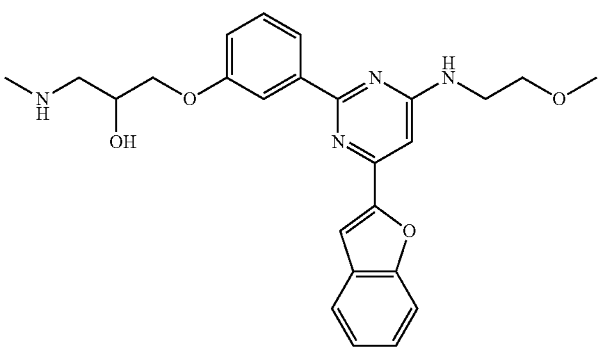 | 449.2 |
| 30-1 | 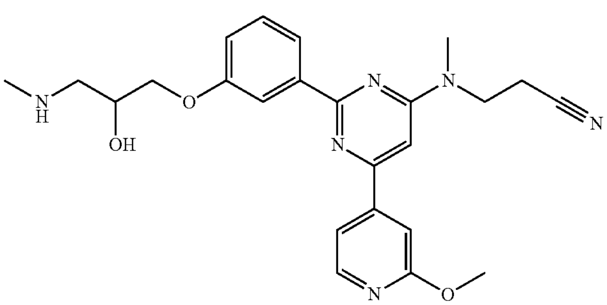 [SMILES: CNCC(O)COc1cccc(-c2nc(-c3ccnc(OC)c3)cc(N(C)CCC#N)n2)c1] | 449.2 |

TABLE 1-continued
Exemplary Compounds
| # | Structure | LC-MS m/z (M + H) |
|---|---|---|
| 31-1 | 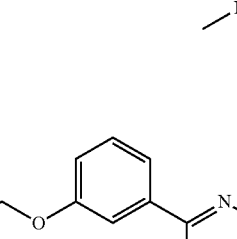 | 449.2 |
| 32-1 | 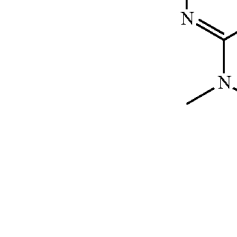 | 450.2 |
| 33-1 | 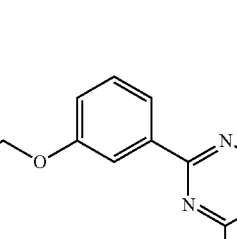 | 454.3 |
| 34-1 | 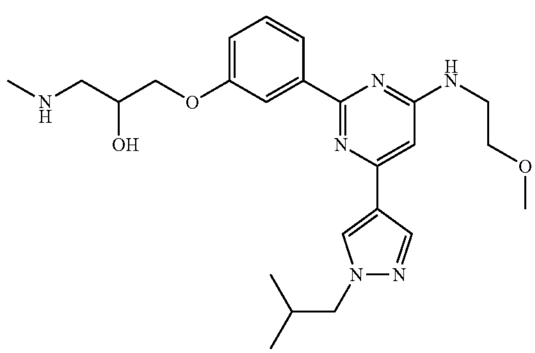 | 455.3 |

TABLE 1-continued

Exemplary Compounds

| # | Structure | LC-MS m/z (M + H) |
|---|---|---|
| 35-1 | 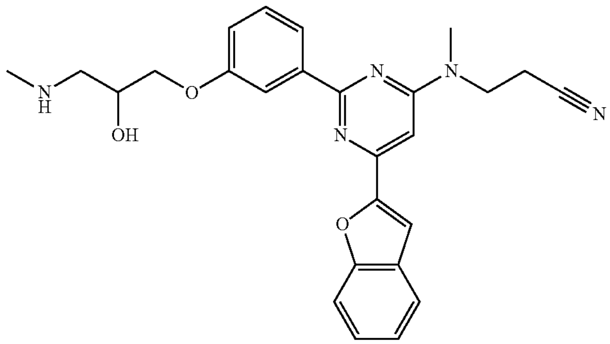 [SMILES: CNCC(O)COc1cccc(-c2nc(-c3cc4ccccc4o3)cc(N(C)CCC#N)n2)c1] | 458.2 |
| 36-1 | 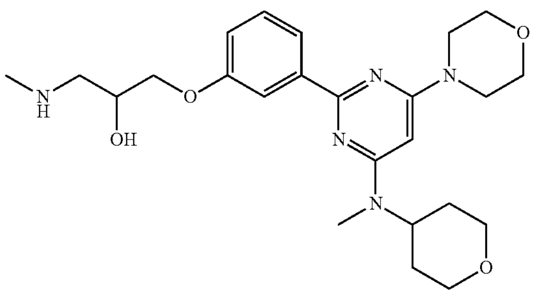 [SMILES: CNCC(O)COc1cccc(-c2nc(N3CCOCC3)cc(N(C)C3CCOCC3)n2)c1] | 458.4 |
| 37-1 | 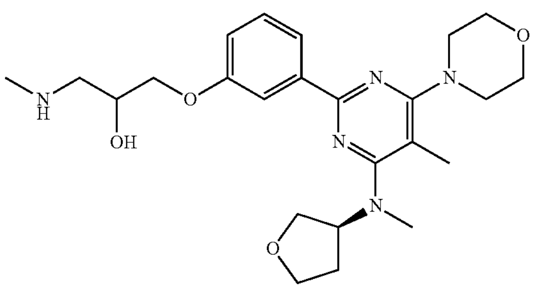 [SMILES: CNCC(O)COc1cccc(-c2nc(N3CCOCC3)c(C)c(N(C)[C@H]3CCOC3)n2)c1] | 458.3 |
| 38-1 | 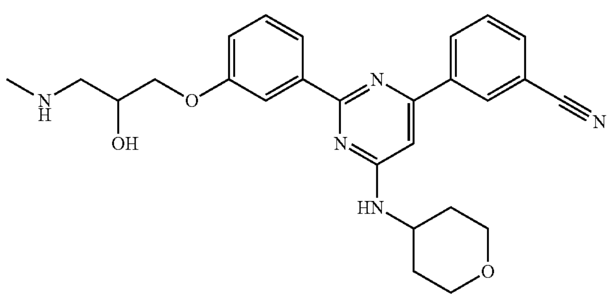 [SMILES: CNCC(O)COc1cccc(-c2nc(NC3CCOCC3)cc(-c3cccc(C#N)c3)n2)c1] | 460.2 |
| 39-1 | 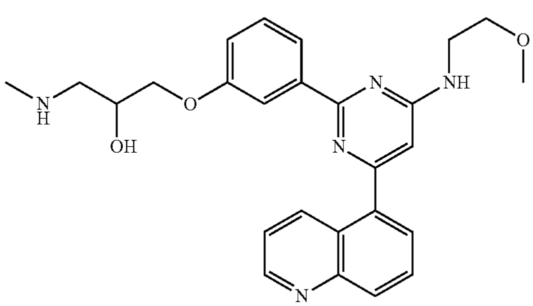 | 460.2 |

TABLE 1-continued

Exemplary Compounds

| # | Structure | LC-MS m/z (M + H) |
|---|---|---|
| 40-1 | 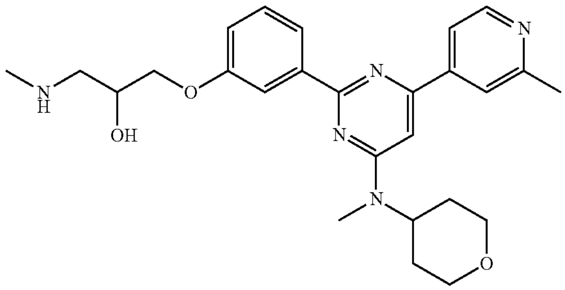 | 464.3 |
| 41-1 | 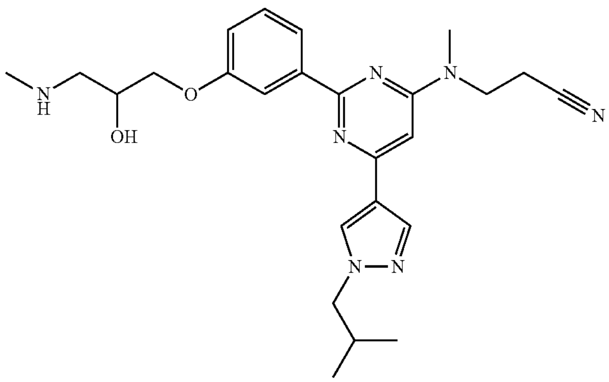 [SMILES: CNCC(O)COc1cccc(-c2nc(-c3cnn(CC(C)C)c3)cc(N(C)CCC#N)n2)c1] | 464.2 |
| 42-1 | 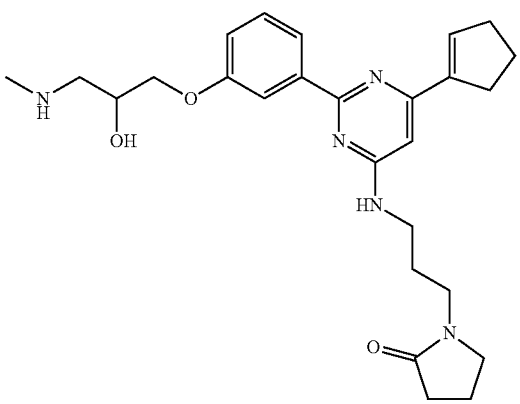 [SMILES: CNCC(O)COc1cccc(-c2nc(NCCCN3CCCC3=O)cc(C3=CCCC3)n2)c1] | 466.1 |
| 43-1 | 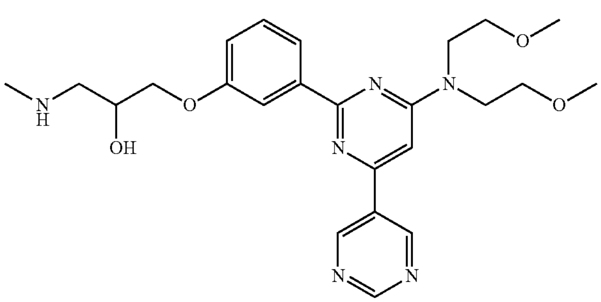 | 469.0 |

TABLE 1-continued

| # | Structure | LC-MS m/z (M + H) |
|---|---|---|
| 44-1 | 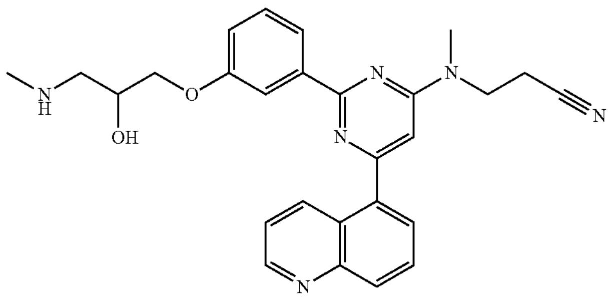 [SMILES: CNCC(O)COc1cccc(-c2nc(-c3cccc4ncccc34)cc(N(C)CCC#N)n2)c1] | 469.2 |
| 45-1 | 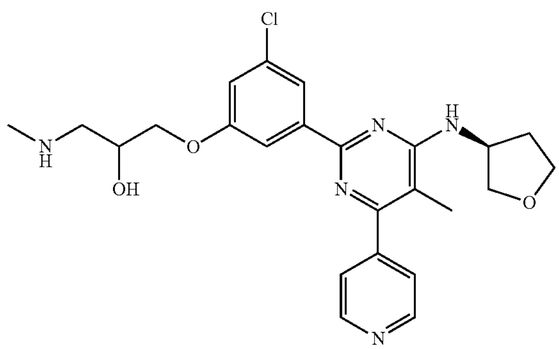 [SMILES: CNCC(O)COc1cc(Cl)cc(-c2nc(N[C@H]3CCOC3)c(C)c(-c3ccncc3)n2)c1] | 470.3 |
| 46-1 | 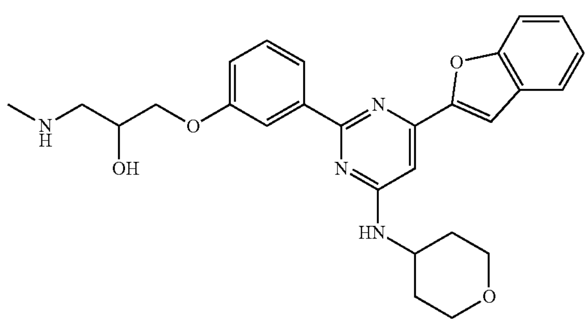 [SMILES: CNCC(O)COc1cccc(-c2nc(NC3CCOCC3)cc(-c3cc4ccccc4o3)n2)c1] | 475.2 |
| 47-1 | 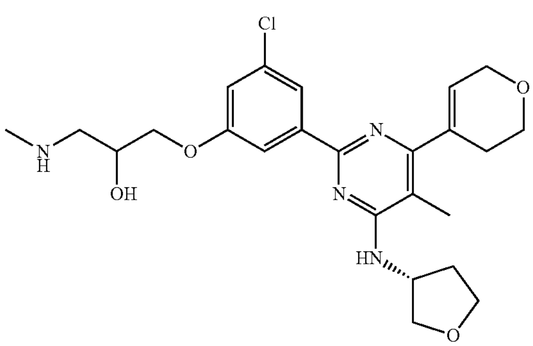 [SMILES: CNCC(O)COc1cc(Cl)cc(-c2nc(N[C@@H]3CCOC3)c(C)c(C3=CCOCC3)n2)c1] | 475.2 |

TABLE 1-continued

Exemplary Compounds

| # | Structure | LC-MS m/z (M + H) |
|---|---|---|
| 48-1 | 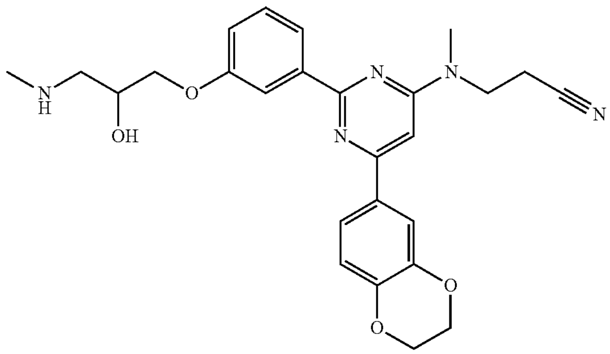 [SMILES: CNCC(O)COc1cccc(-c2nc(-c3ccc4c(c3)OCCO4)cc(N(C)CCC#N)n2)c1] | 476.0 |
| 49-1 | 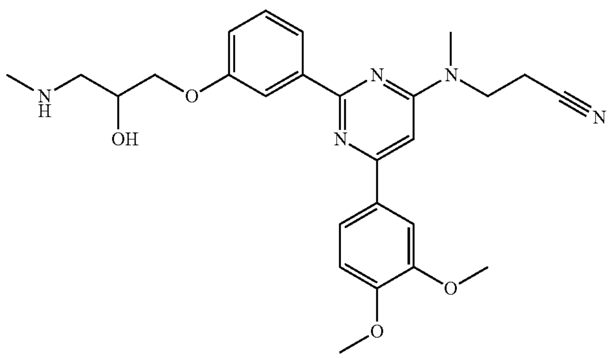 [SMILES: CNCC(O)COc1cccc(-c2nc(-c3ccc(OC)c(OC)c3)cc(N(C)CCC#N)n2)c1] | 478.2 |
| 50-1 | 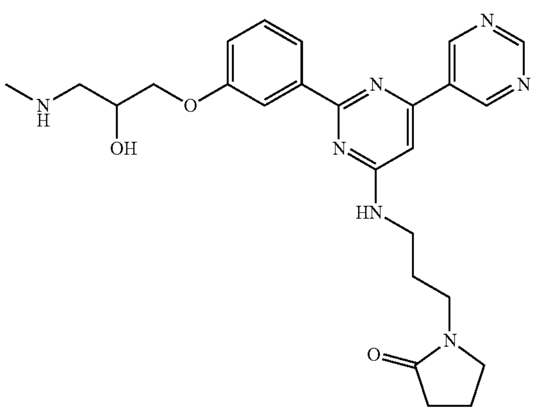 [SMILES: CNCC(O)COc1cccc(-c2nc(NCCCN3CCCC3=O)cc(-c3cncnc3)n2)c1] | 478.1 |
| 51-1 | 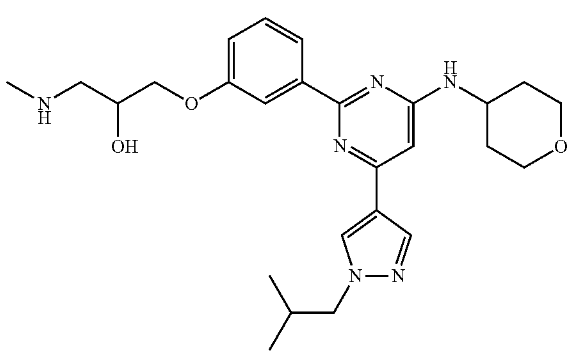 [SMILES: CNCC(O)COc1cccc(-c2nc(NC3CCOCC3)cc(-c3cnn(CC(C)C)c3)n2)c1] | 481.3 |

TABLE 1-continued

Exemplary Compounds

| # | Structure | LC-MS m/z (M + H) |
|---|---|---|
| 52-1 | 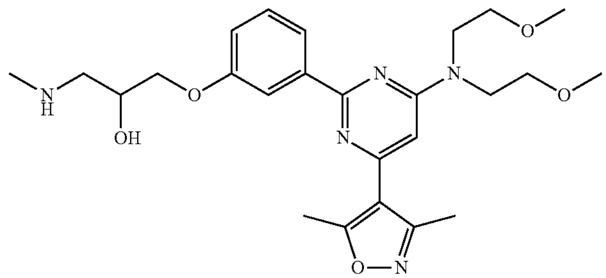 | 486.3 |
| 53-1 | 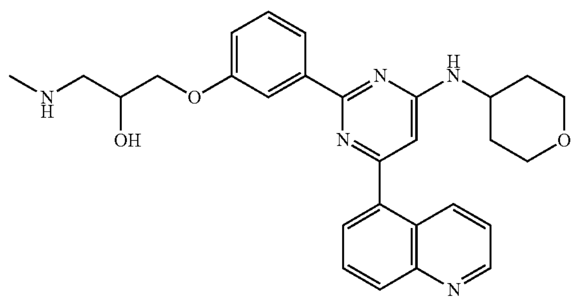 [SMILES: CNCC(O)COc1cccc(-c2nc(NC3CCOCC3)cc(-c3cccc4ncccc34)n2)c1] | 486.2 |
| 54-1 | 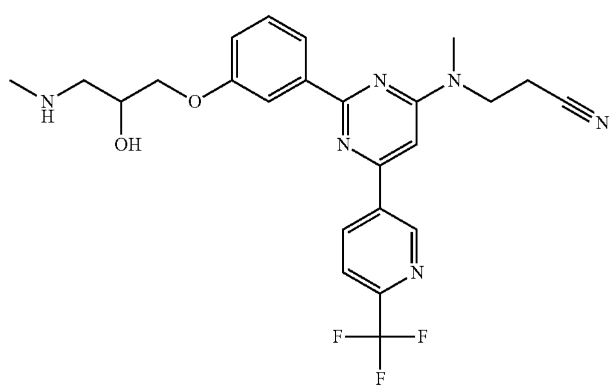 [SMILES: CNCC(O)COc1cccc(-c2nc(-c3ccc(C(F)(F)F)nc3)cc(N(C)CCC#N)n2)c1] | 487.1 |
| 55-1 | 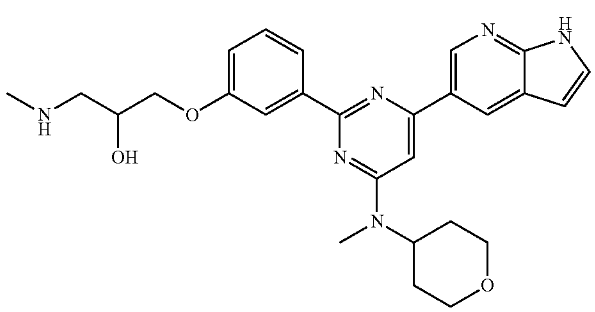 [SMILES: CNCC(O)COc1cccc(-c2nc(-c3cnc4[nH]ccc4c3)cc(N(C)C3CCOCC3)n2)c1] | 489.3 |

TABLE 1-continued

Exemplary Compounds

| # | Structure | LC-MS m/z (M + H) |
|---|---|---|
| 56-1 | 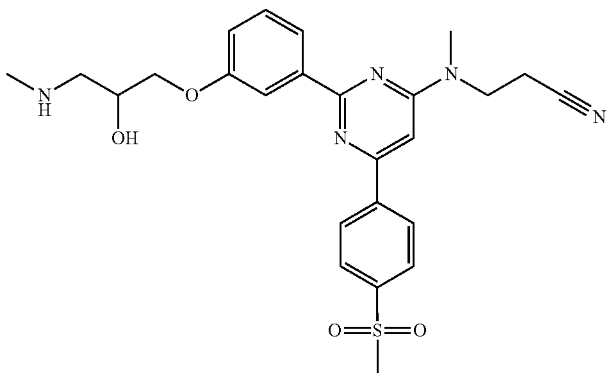 [SMILES: CNCC(O)COc1cccc(-c2nc(-c3ccc(S(C)(=O)=O)cc3)cc(N(C)CCC#N)n2)c1] | 496.3 |
| 57-1 | 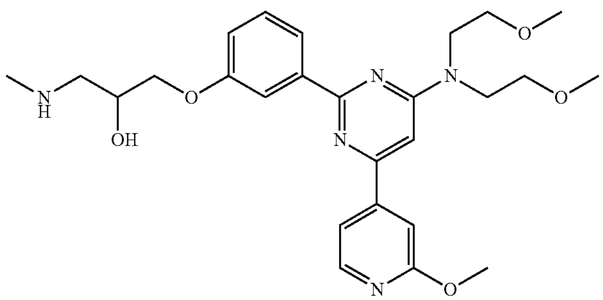 | 498.1 |
| 58-1 | 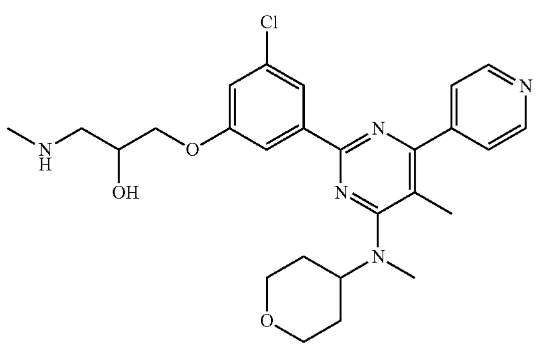 [SMILES: CNCC(O)COc1cc(Cl)cc(-c2nc(-c3ccncc3)c(C)c(N(C)C3CCOCC3)n2)c1] | 498.2 |
| 59-1 | 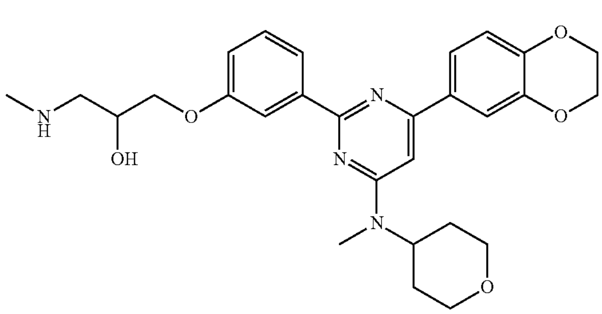 [SMILES: CNCC(O)COc1cccc(-c2nc(-c3ccc4c(c3)OCCO4)cc(N(C)C3CCOCC3)n2)c1] | 507.1 |

TABLE 1-continued
Exemplary Compounds
| # | Structure | LC-MS m/z (M + H) |
|---|---|---|
| 60-1 | 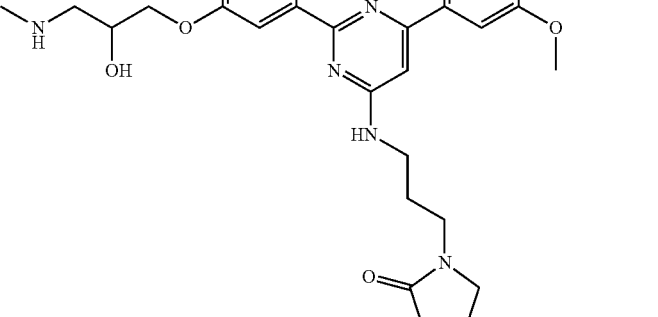 | 507.2 |
| 61-1 | 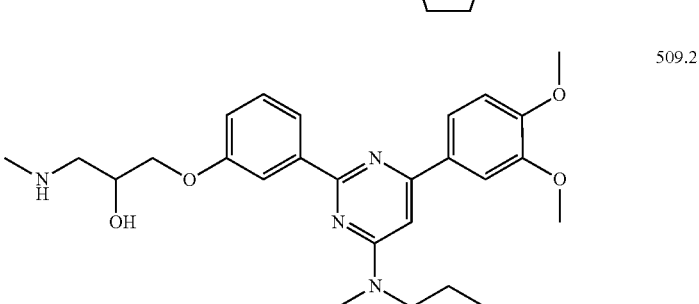 | 509.2 |
| 62-1 | 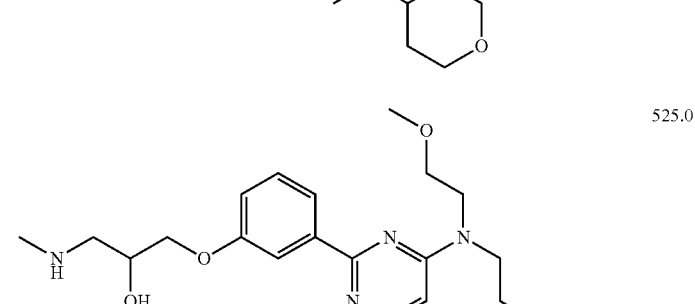 | 525.0 |
| 63-1 | 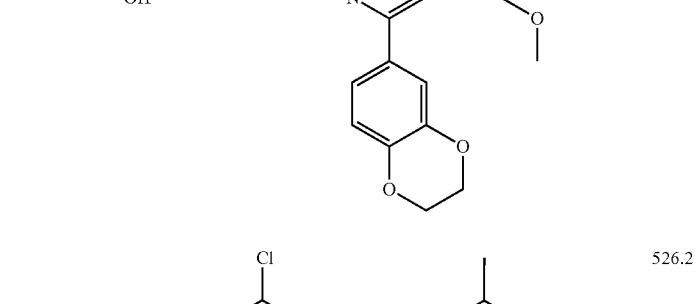 | 526.2 |

TABLE 1-continued

Exemplary Compounds

| # | Structure | LC-MS m/z (M + H) |
|---|---|---|
| 64-1 | 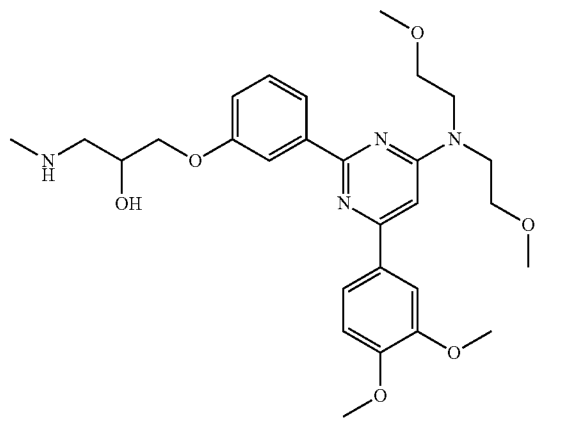 | 527.2 |
| 65-1 | 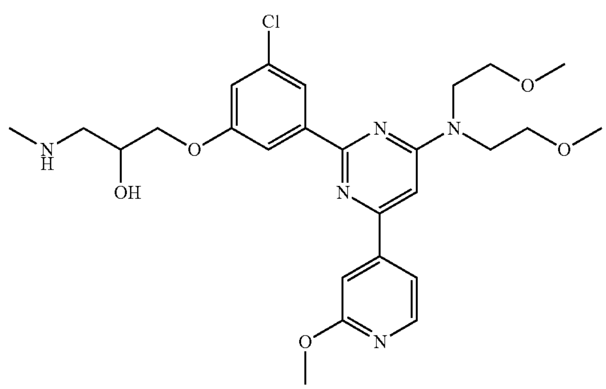 | 532.2 |
| 66-1 | 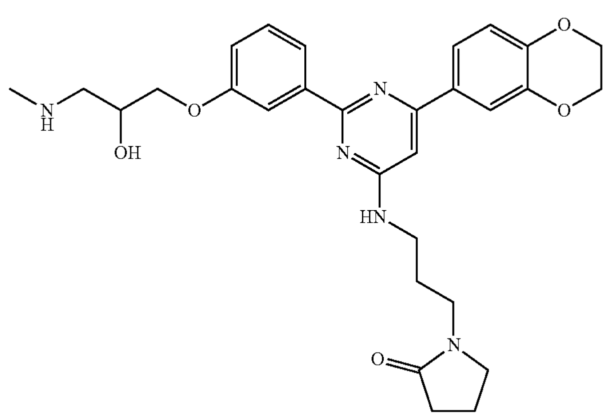 [SMILES: CNCC(O)COc1cccc(-c2nc(NCCCN3CCCC3=O)cc(-c3ccc4c(c3)OCCO4)n2)c1] | 534.2 |

TABLE 1-continued
Exemplary Compounds
| # | Structure | LC-MS m/z (M + H) |
|---|---|---|
| 67-1 | 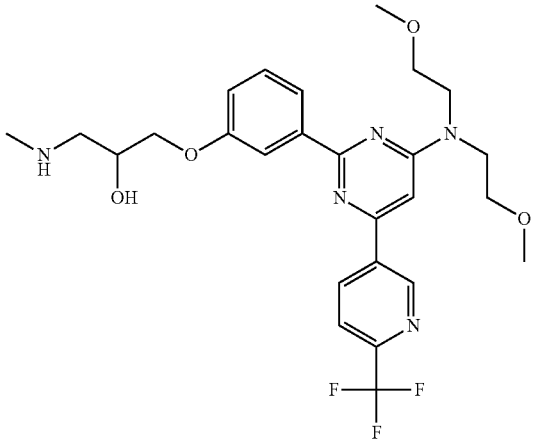 | 536.3 |
| 68-1 | 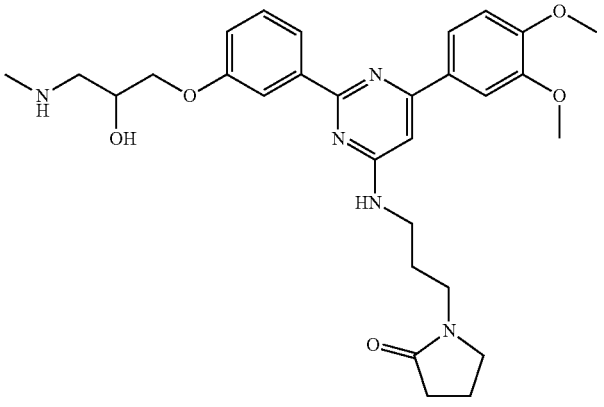 | 536.3 |
| 69-1 | 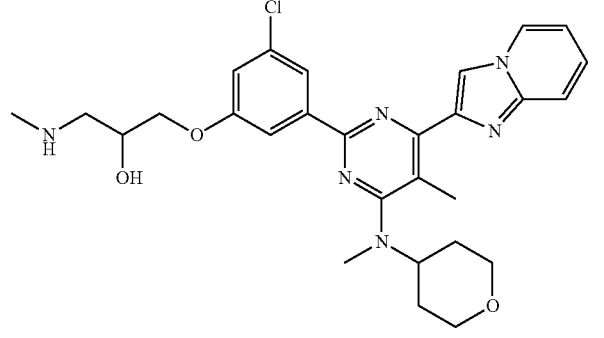 [SMILES: CNCC(O)COc1cc(Cl)cc(-c2nc(-c3cn4ccccc4n3)c(C)c(N(C)C3CCOCC3)n2)c1] | 537.3 |
| 70-1 | 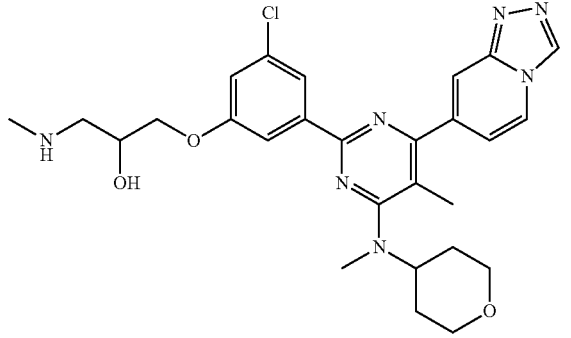 [SMILES: CNCC(O)COc1cc(Cl)cc(-c2nc(-c3ccn4cnnc4c3)c(C)c(N(C)C3CCOCC3)n2)c1] | 538.3 |

TABLE 1-continued
Exemplary Compounds
| # | Structure | LC-MS m/z (M + H) |
|---|---|---|
| 71-1 | 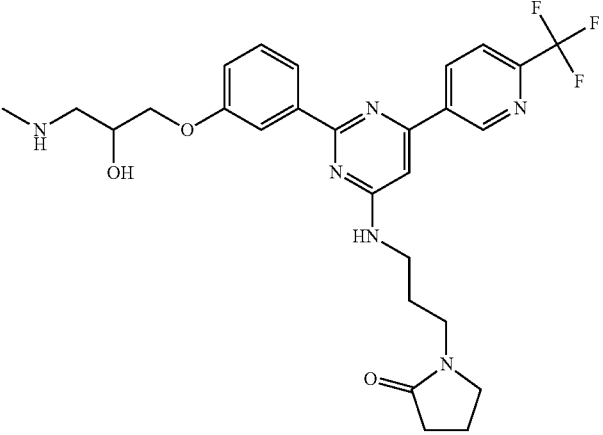 [SMILES: CNCC(O)COc1cccc(-c2nc(NCCCN3CCCC3=O)cc(-c3ccc(C(F)(F)F)nc3)n2)c1] | 545.2 |
| 72-1 | 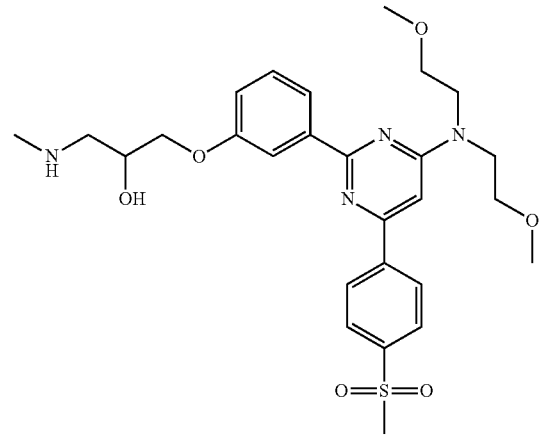 | 545.2 |
| 73-1 | 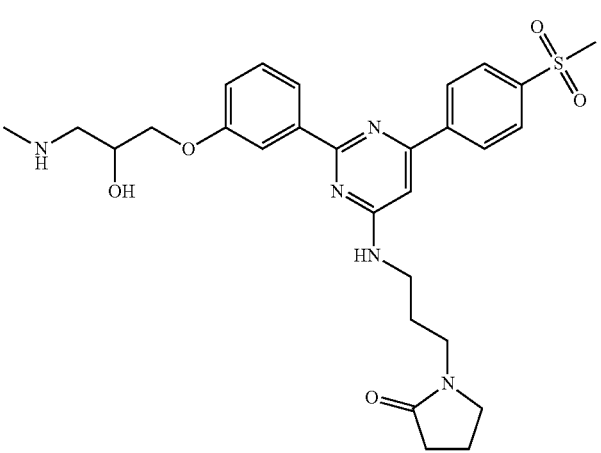 | 554.2 |

TABLE 1-continued
Exemplary Compounds
| # | Structure | LC-MS m/z (M + H) |
|---|---|---|
| 74-1 | 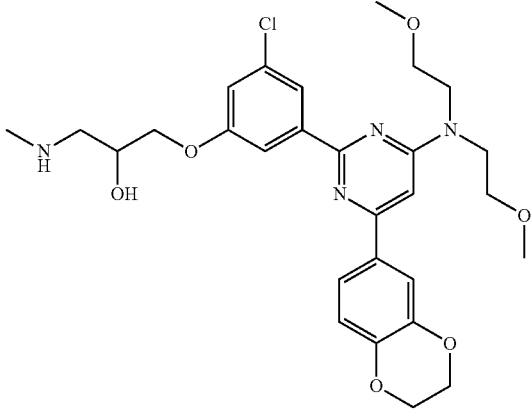 | 559.2 |
| 75-1 | 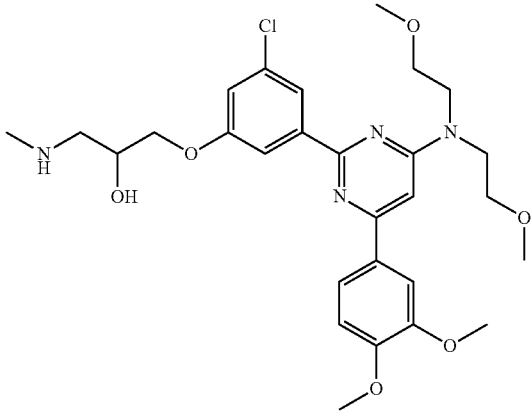 | 561.0 |
TABLE 2
Exemplary Conpounds
| # | Structure | LC-MS m/z (M + H) |
|---|---|---|
| 1-2 | 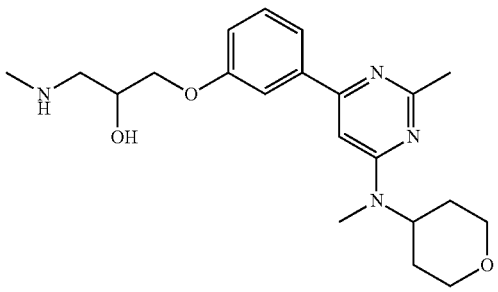 [SMILES: CNCC(O)COc1cccc(-c2cc(N(C)C3CCOCC3)nc(C)n2)c1] | 387.2 |

TABLE 2-continued

Exemplary Conpounds

| # | Structure | LC-MS m/z (M + H) |
|---|---|---|
| 2-2 | 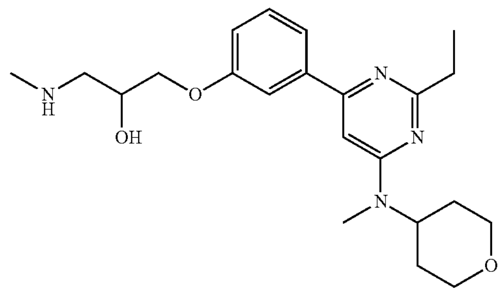 [SMILES: CCc1nc(-c2cccc(OCC(O)CNC)c2)cc(N(C)C2CCOCC2)n1] | 401.3 |
| 3-2 | 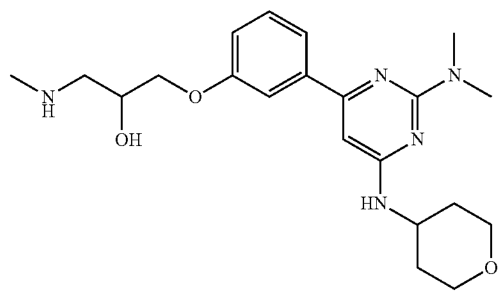 | 402.2 |
| 4-2 | 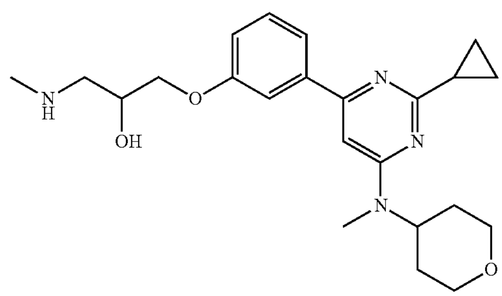 [SMILES: CNCC(O)COc1cccc(-c2cc(N(C)C3CCOCC3)nc(C3CC3)n2)c1] | 413.2 |
| 5-2 | 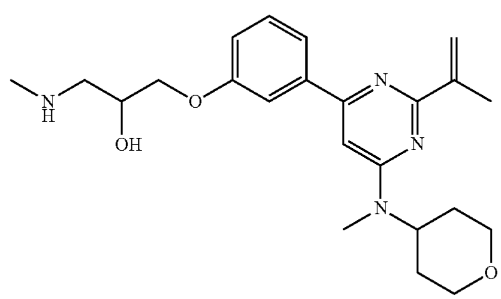 | 413.3 |
| 6-2 | 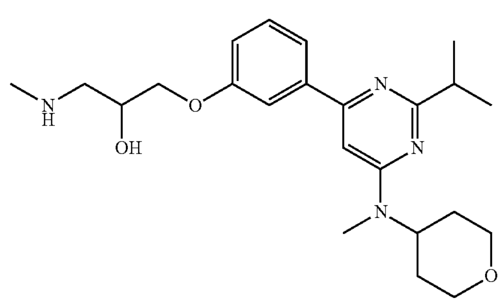 [SMILES: CNCC(O)COc1cccc(-c2cc(N(C)C3CCOCC3)nc(C(C)C)n2)c1] | 415.3 |

TABLE 2-continued

Exemplary Conpounds

| # | Structure | LC-MS m/z (M + H) |
|---|-----------|-------------------|
| 7-2 | 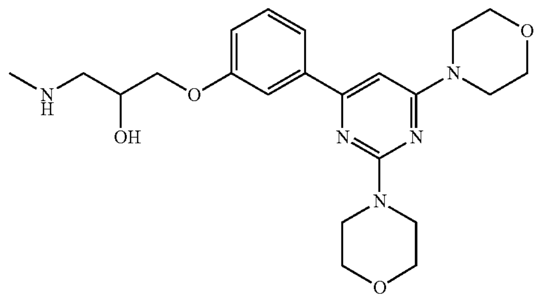 [SMILES: CNCC(O)COc1cccc(-c2cc(N3CCOCC3)nc(N3CCOCC3)n2)c1] | 416.3 |
| 8-2 | 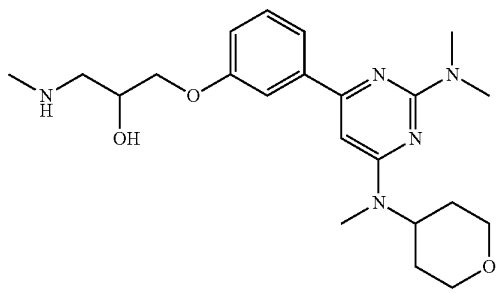 | 416.3 |
| 9-2 | 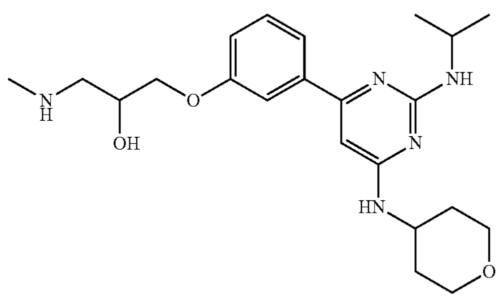 [SMILES: CNCC(O)COc1cccc(-c2cc(NC3CCOCC3)nc(NC(C)C)n2)c1] | 416.3 |
| 10-2 | 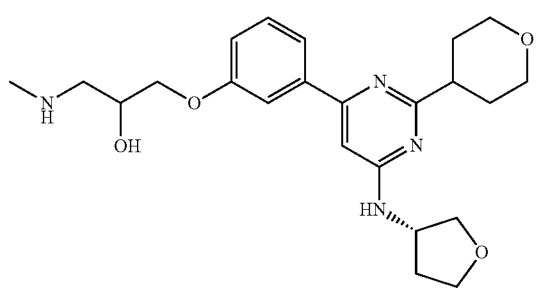 [SMILES: CNCC(O)COc1cccc(-c2cc(N[C@H]3CCOC3)nc(C3CCOCC3)n2)c1] | 429.3 |
| 11-2 | 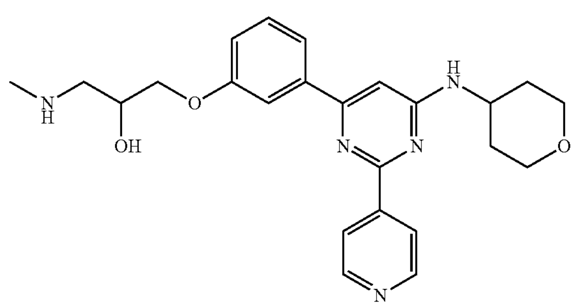 [SMILES: CNCC(O)COc1cccc(-c2cc(NC3CCOCC3)nc(-c3ccncc3)n2)c1] | 436.3 |

TABLE 2-continued

Exemplary Compounds

| # | Structure | LC-MS m/z (M + H) |
|---|-----------|-------------------|
| 12-2 | 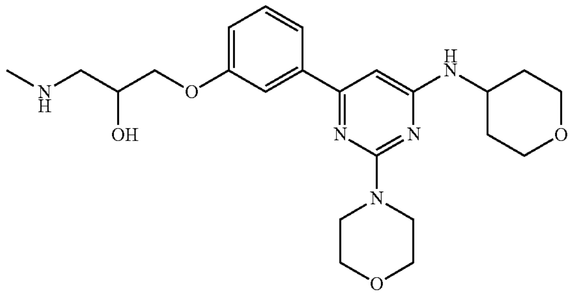 [SMILES: CNCC(O)COc1cccc(-c2cc(NC3CCOCC3)nc(N3CCOCC3)n2)c1] | 444.3 |
| 13-2 | 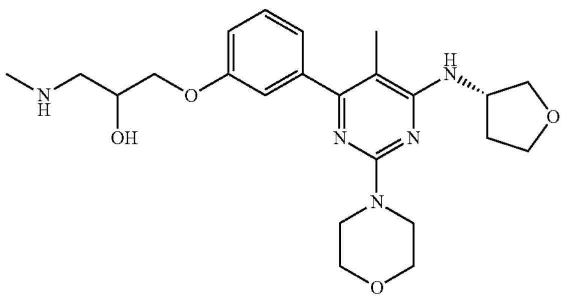 [SMILES: CNCC(O)COc1cccc(-c2nc(N3CCOCC3)nc(N[C@H]3CCOC3)c2C)c1] | 444.2 |
| 14-2 | 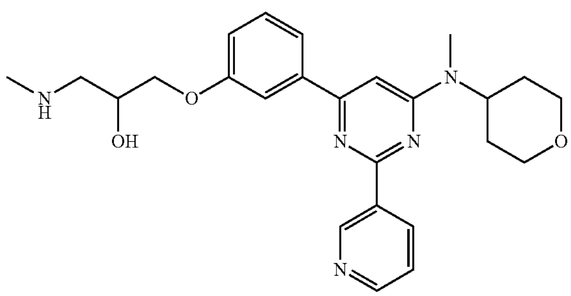 [SMILES: CNCC(O)COc1cccc(-c2cc(N(C)C3CCOCC3)nc(-c3cccnc3)n2)c1] | 450.2 |
| 15-2 | 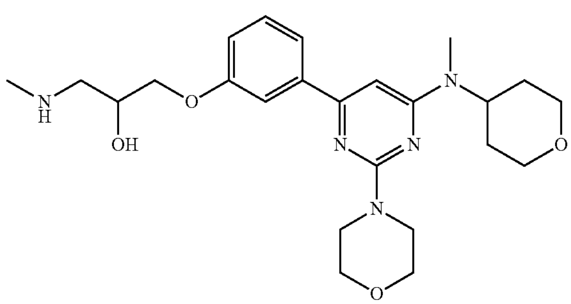 [SMILES: CNCC(O)COc1cccc(-c2cc(N(C)C3CCOCC3)nc(N3CCOCC3)n2)c1] | 458.2 |
| 16-2 | 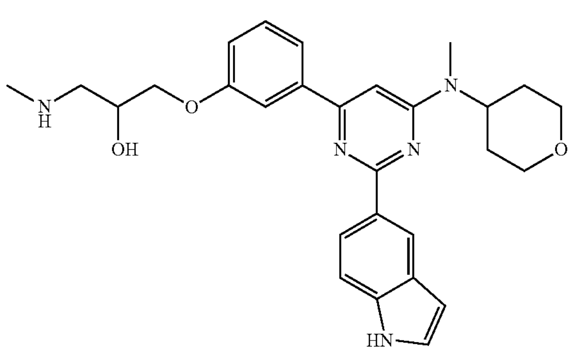 [SMILES: CNCC(O)COc1cccc(-c2cc(N(C)C3CCOCC3)nc(-c3ccc4[nH]ccc4c3)n2)c1] | 489.2 |

In certain embodiments, a provided compound inhibits CARM1. In certain embodiments, a provided compound inhibits wild-type CARM1. In certain embodiments, a provided compound inhibits a mutant CARM1. In certain embodiments, a provided compound inhibits CARM1, e.g., as measured in an assay described herein. In certain embodiments, the CARM1 is from a human. In certain embodiments, a provided compound inhibits CARM1 at an $IC_{50}$ less than or equal to 10 µM. In certain embodiments, a provided compound inhibits CARM1 at an $IC_{50}$ less than or equal to 1 µM. In certain embodiments, a provided compound inhibits CARM1 at an $IC_{50}$ less than or equal to 0.1 µM. In certain embodiments, a provided compound inhibits CARM1 in a cell at an $EC_{50}$ less than or equal to 10 µM. In certain embodiments, a provided compound inhibits CARM1 in a cell at an $EC_{50}$ less than or equal to 1 µM. In certain embodiments, a provided compound inhibits CARM1 in a cell at an $EC_{50}$ less than or equal to 0.1 µM. In certain embodiments, a provided compound inhibits cell proliferation at an $EC_{50}$ less than or equal to 10 µM. In certain embodiments, a provided compound inhibits cell proliferation at an $EC_{50}$ less than or equal to 1 µM. In certain embodiments, a provided compound inhibits cell proliferation at an $EC_{50}$ less than or equal to 0.1 µM. In some embodiments, a provided compound is selective for CARM1 over other methyltransferases. In certain embodiments, a provided compound is at least about 10-fold selective, at least about 20-fold selective, at least about 30-fold selective, at least about 40-fold selective, at least about 50-fold selective, at least about 60-fold selective, at least about 70-fold selective, at least about 80-fold selective, at least about 90-fold selective, or at least about 100-fold selective for PRMT1 relative to one or more other methyltransferases.

It will be understood by one of ordinary skill in the art that the CARM1 can be wild-type CARM1, or any mutant or variant of CARM1.

The present disclosure provides pharmaceutical compositions comprising a compound described herein, e.g., a compound of Formula (I), or a pharmaceutically acceptable salt thereof, as described herein, and optionally a pharmaceutically acceptable excipient. It will be understood by one of ordinary skill in the art that the compounds described herein, or salts thereof, may be present in various forms, such as amorphous, hydrates, solvates, or polymorphs. In certain embodiments, a provided composition comprises two or more compounds described herein. In certain embodiments, a compound described herein, or a pharmaceutically acceptable salt thereof, is provided in an effective amount in the pharmaceutical composition. In certain embodiments, the effective amount is a therapeutically effective amount. In certain embodiments, the effective amount is an amount effective for inhibiting CARM1. In certain embodiments, the effective amount is an amount effective for treating a CARM1-mediated disorder. In certain embodiments, the effective amount is a prophylactically effective amount. In certain embodiments, the effective amount is an amount effective to prevent a CARM1-mediated disorder.

Pharmaceutically acceptable excipients include any and all solvents, diluents, or other liquid vehicles, dispersions, suspension aids, surface active agents, isotonic agents, thickening or emulsifying agents, preservatives, solid binders, lubricants, and the like, as suited to the particular dosage form desired. General considerations in formulation and/or manufacture of pharmaceutical compositions agents can be found, for example, in *Remington's Pharmaceutical Sciences*, Sixteenth Edition, E. W. Martin (Mack Publishing Co., Easton, Pa., 1980), and *Remington: The Science and Practice of Pharmacy*, 21st Edition (Lippincott Williams & Wilkins, 2005).

Pharmaceutical compositions described herein can be prepared by any method known in the art of pharmacology. In general, such preparatory methods include the steps of bringing a compound described herein (the "active ingredient") into association with a carrier and/or one or more other accessory ingredients, and then, if necessary and/or desirable, shaping and/or packaging the product into a desired single- or multi-dose unit.

Pharmaceutical compositions can be prepared, packaged, and/or sold in bulk, as a single unit dose, and/or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

Relative amounts of the active ingredient, the pharmaceutically acceptable excipient, and/or any additional ingredients in a pharmaceutical composition of the present disclosure will vary, depending upon the identity, size, and/or condition of the subject treated and further depending upon the route by which the composition is to be administered. By way of example, the composition may comprise between 0.1% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

Exemplary granulating and/or dispersing agents include potato starch, corn starch, tapioca starch, sodium starch glycolate, clays, alginic acid, guar gum, citrus pulp, agar, bentonite, cellulose and wood products, natural sponge, cation-exchange resins, calcium carbonate, silicates, sodium carbonate, crosslinked poly(vinylpyrrolidone) (crospovidone), sodium carboxymethyl starch (sodium starch glycolate), carboxymethyl cellulose, crosslinked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and mixtures thereof.

Exemplary surface active agents and/or emulsifiers include natural emulsifiers (e.g., acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g., bentonite (aluminum silicate) and Veegum (magnesium aluminum silicate)), long chain amino acid derivatives, high molecular weight alcohols (e.g., stearyl alcohol, cetyl alcohol, oleyl alcohol, triacetin monostearate, ethylene glycol distearate, glyceryl monostearate, and propylene glycol monostearate, polyvinyl alcohol), carbomers (e.g., carboxy polymethylene, polyacrylic acid, acrylic acid polymer, and carboxyvinyl polymer), carrageenan, cellulosic derivatives (e.g., carboxymethylcellulose sodium, powdered cellulose, hydroxymethyl cellulose, hydroxypropyl cellulose, hydroxypropyl methylcellulose, methylcellulose), sorbitan fatty acid esters (e.g., polyoxyethylene sorbitan monolaurate (Tween 20), polyoxyethylene sorbitan (Tween 60), polyoxyethylene sorbitan monooleate (Tween 80), sorbitan monopalmitate (Span 40), sorbitan monostearate (Span 60], sorbitan tristearate (Span 65), glyceryl monooleate, sorbitan monooleate (Span 80)), polyoxyethylene esters (e.g., polyoxyethylene monostearate (Myrj 45), polyoxyethylene hydrogenated castor oil, polyethoxylated castor oil, polyoxymethylene stearate, and Solutol), sucrose fatty acid esters, polyethylene glycol fatty acid esters (e.g., Cremophor™) polyoxyethylene ethers, (e.g., polyoxyethylene lauryl ether (Brij 30)), poly(vinylpyrrolidone), diethylene glycol monolaurate, triethanolamine oleate, sodium oleate, potassium oleate, ethyl oleate, oleic acid, ethyl laurate, sodium lauryl sulfate, Pluronic F68, Poloxamer 188, cetrimonium bromide, cetylpyridinium chloride, benzalkonium chloride, docusate sodium, and/or mixtures thereof.

Exemplary binding agents include starch (e.g., cornstarch and starch paste), gelatin, sugars (e.g., sucrose, glucose, dextrose, dextrin, molasses, lactose, lactitol, mannitol, etc.), natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinylpyrrolidone), magnesium aluminum silicate (Veegum), and larch arabogalactan), alginates, polyethylene oxide, polyethylene glycol, inorganic calcium salts, silicic acid, polymethacrylates, waxes, water, alcohol, and/or mixtures thereof.

Exemplary preservatives include antioxidants, chelating agents, antimicrobial preservatives, antifungal preservatives, alcohol preservatives, acidic preservatives, and other preservatives.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol. Exemplary acidic preservatives include vitamin A, vitamin C, vitamin E, betacarotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus, Phenonip, methylparaben, Germall 115, Germaben II, Neolone, Kathon, and Euxyl. In certain embodiments, the preservative is an antioxidant. In other embodiments, the preservative is a chelating agent.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and mixtures thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macadamia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and mixtures thereof.

Liquid dosage forms for oral and parenteral administration include pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the compounds described herein are mixed with solubilizing agents such as Cremophor™, alcohols, oils, modified oils, glycols, polysorbates, cyclodextrins, polymers, and mixtures thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension or emulsion in a nontoxic parenterally acceptable diluent or solvent, for example, as a solution in 1,3-butanediol. Among the acceptable vehicles and solvents that can be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Compositions for rectal or vaginal administration are typically suppositories which can be prepared by mixing the compounds described herein with suitable nonirritating excipients or carriers such as cocoa butter, polyethylene glycol or a suppository wax which are solid at ambient temperature but liquid at body temperature and therefore melt in the rectum or vaginal cavity and release the active ingredient.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may comprise buffering agents.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes. Solid compositions of a similar type can be employed as fillers in soft and hard-filled gelatin capsules using such excipients as lactose or milk sugar as well as high molecular weight polyethylene glycols and the like.

The active ingredient can be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active ingredient can be admixed with at least one inert diluent such as sucrose, lactose, or starch. Such dosage forms may comprise, as is normal practice, additional substances other than inert diluents, e.g., tableting lubricants and other tableting aids such a magnesium stearate and microcrystalline cellulose. In the case of capsules, tablets, and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes.

Dosage forms for topical and/or transdermal administration of a provided compound may include ointments, pastes, creams, lotions, gels, powders, solutions, sprays, inhalants and/or patches. Generally, the active ingredient is admixed under sterile conditions with a pharmaceutically acceptable carrier and/or any desired preservatives and/or buffers as can be required. Additionally, the present disclosure encompasses the use of transdermal patches, which often have the added advantage of providing controlled delivery of an active ingredient to the body. Such dosage forms can be prepared, for example, by dissolving and/or dispensing the active ingredient in the proper medium. Alternatively or additionally, the rate can be controlled by either providing a rate controlling membrane and/or by dispersing the active ingredient in a polymer matrix and/or gel.

Formulations suitable for topical administration include, but are not limited to, liquid and/or semi liquid preparations such as liniments, lotions, oil in water and/or water in oil emulsions such as creams, ointments and/or pastes, and/or solutions and/or suspensions. Topically-administrable formulations may, for example, comprise from about 1% to about 10% (w/w) active ingredient, although the concentration of the active ingredient can be as high as the solubility limit of the active ingredient in the solvent. Formulations for topical administration may further comprise one or more of the additional ingredients described herein.

A provided pharmaceutical composition can be prepared, packaged, and/or sold in a formulation suitable for pulmonary administration via the buccal cavity. Such a formulation may comprise dry particles which comprise the active ingredient and which have a diameter in the range from about 0.5 to about 7 nanometers or from about 1 to about 6 nanometers. Such compositions are conveniently in the form of dry powders for administration using a device comprising a dry powder reservoir to which a stream of propellant can be directed to disperse the powder and/or using a self-propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nanometers and at least 95% of the particles by number have a diameter less than 7 nanometers. Alternatively, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic and/or solid anionic surfactant and/or a solid diluent (which may have a particle size of the same order as particles comprising the active ingredient).

Pharmaceutical compositions formulated for pulmonary delivery may provide the active ingredient in the form of droplets of a solution and/or suspension. Such formulations can be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. The droplets provided by this route of administration may have an average diameter in the range from about 0.1 to about 200 nanometers.

Formulations described herein as being useful for pulmonary delivery are useful for intranasal delivery of a pharmaceutical composition. Another formulation suitable for intranasal administration is a coarse powder comprising the active ingredient and having an average particle from about 0.2 to 500 micrometers. Such a formulation is administered by rapid inhalation through the nasal passage from a container of the powder held close to the nares.

Formulations for nasal administration may, for example, comprise from about as little as 0.1% (w/w) and as much as 100% (w/w) of the active ingredient, and may comprise one or more of the additional ingredients described herein. A provided pharmaceutical composition can be prepared, packaged, and/or sold in a formulation for buccal administration. Such formulations may, for example, be in the form of tablets and/or lozenges made using conventional methods, and may contain, for example, 0.1 to 20% (w/w) active ingredient, the balance comprising an orally dissolvable and/or degradable composition and, optionally, one or more of the additional ingredients described herein. Alternately, formulations for buccal administration may comprise a powder and/or an aerosolized and/or atomized solution and/or suspension comprising the active ingredient. Such powdered, aerosolized, and/or aerosolized formulations, when dispersed, may have an average particle and/or droplet size in the range from about 0.1 to about 200 nanometers, and may further comprise one or more of the additional ingredients described herein.

A provided pharmaceutical composition can be prepared, packaged, and/or sold in a formulation for ophthalmic administration. Such formulations may, for example, be in the form of eye drops including, for example, a 0.1/1.0% (w/w) solution and/or suspension of the active ingredient in an aqueous or oily liquid carrier. Such drops may further comprise buffering agents, salts, and/or one or more of the additional ingredients described herein. Other opthalmically-administrable formulations which are useful include those which comprise the active ingredient in microcrystalline form and/or in a liposomal preparation. Ear drops and/or eye drops are contemplated as being within the scope of this disclosure.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

Compounds provided herein are typically formulated in dosage unit form for ease of administration and uniformity of dosage. It will be understood, however, that the total daily usage of provided compositions will be decided by the attending physician within the scope of sound medical judgment. The specific therapeutically effective dose level for any particular subject or organism will depend upon a variety of factors including the disease, disorder, or condition being treated and the severity of the disorder; the activity of the specific active ingredient employed; the specific composition employed; the age, body weight, general health, sex and diet of the subject; the time of administration, route of administration, and rate of excretion of the specific active ingredient employed; the duration of the treatment; drugs used in combination or coincidental with the specific active ingredient employed; and like factors well known in the medical arts.

The compounds and compositions provided herein can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, sublingual; by intratracheal instillation, bronchial instillation, and/or inhalation; and/or as an oral spray, nasal spray, and/or aerosol. Specifically contemplated routes are oral administration, intravenous administration (e.g., systemic intravenous injection), regional administration via blood and/or lymph supply, and/or direct administration to an affected site. In general the most appropriate route of administration will depend upon a variety of factors including the nature of the agent (e.g., its stability in the environment of the gastrointestinal tract), and/or the condition of the subject (e.g., whether the subject is able to tolerate oral administration).

The exact amount of a compound required to achieve an effective amount will vary from subject to subject, depending, for example, on species, age, and general condition of a subject, severity of the side effects or disorder, identity of the particular compound(s), mode of administration, and the like. The desired dosage can be delivered three times a day, two times a day, once a day, every other day, every third day, every week, every two weeks, every three weeks, or every four weeks. In certain embodiments, the desired dosage can be delivered using multiple administrations (e.g., two, three, four, five, six, seven, eight, nine, ten, eleven, twelve, thirteen, fourteen, or more administrations).

In certain embodiments, an effective amount of a compound for administration one or more times a day to a 70 kg adult human may comprise about 0.0001 mg to about 3000 mg, about 0.0001 mg to about 2000 mg, about 0.0001 mg to about 1000 mg, about 0.001 mg to about 1000 mg, about 0.01 mg to about 1000 mg, about 0.1 mg to about 1000 mg, about 1 mg to about 1000 mg, about 1 mg to about 100 mg, about 10 mg to about 1000 mg, or about 100 mg to about 1000 mg, of a compound per unit dosage form.

In certain embodiments, a compound described herein may be administered at dosage levels sufficient to deliver from about 0.001 mg/kg to about 1000 mg/kg, from about 0.01 mg/kg to about mg/kg, from about 0.1 mg/kg to about 40 mg/kg, from about 0.5 mg/kg to about 30 mg/kg, from about 0.01 mg/kg to about 10 mg/kg, from about 0.1 mg/kg to about 10 mg/kg, or from about 1 mg/kg to about 25 mg/kg, of subject body weight per day, one or more times a day, to obtain the desired therapeutic effect.

In some embodiments, a compound described herein is administered one or more times per day, for multiple days. In some embodiments, the dosing regimen is continued for days, weeks, months, or years.

It will be appreciated that dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

It will be also appreciated that a compound or composition, as described herein, can be administered in combination with one or more additional therapeutically active agents. In certain embodiments, a compound or composition provided herein is administered in combination with one or more additional therapeutically active agents that improve its bioavailability, reduce and/or modify its metabolism, inhibit its excretion, and/or modify its distribution within the body. It will also be appreciated that the therapy employed may achieve a desired effect for the same disorder, and/or it may achieve different effects.

The compound or composition can be administered concurrently with, prior to, or subsequent to, one or more additional therapeutically active agents. In certain embodiments, the additional therapeutically active agent is a compound of Formula (I). In certain embodiments, the additional therapeutically active agent is not a compound of Formula (I). In general, each agent will be administered at a dose and/or on a time schedule determined for that agent. In will further be appreciated that the additional therapeutically active agent utilized in this combination can be administered together in a single composition or administered separately in different compositions. The particular combination to employ in a regimen will take into account compatibility of a provided compound with the additional therapeutically active agent and/or the desired therapeutic effect to be achieved. In general, it is expected that additional therapeutically active agents utilized in combination be utilized at levels that do not exceed the levels at which they are utilized individually. In some embodiments, the levels utilized in combination will be lower than those utilized individually.

Exemplary additional therapeutically active agents include, but are not limited to, small organic molecules such as drug compounds (e.g., compounds approved by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells.

Also encompassed by the present disclosure are kits (e.g., pharmaceutical packs). The kits provided may comprise a provided pharmaceutical composition or compound and a container (e.g., a vial, ampule, bottle, syringe, and/or dispenser package, or other suitable container). In some embodiments, provided kits may optionally further include a second container comprising a pharmaceutical excipient for dilution or suspension of a provided pharmaceutical composition or compound. In some embodiments, a provided pharmaceutical composition or compound provided in the container and the second container are combined to form one unit dosage form. In some embodiments, a provided kits further includes instructions for use.

Compounds and compositions described herein are generally useful for the inhibition of CARM1. In some embodiments, methods of treating CARM1-mediated disorder in a subject are provided which comprise administering an effective amount of a compound described herein (e.g., a compound of Formula (I), or a pharmaceutically acceptable salt thereof), to a subject in need of treatment. In certain embodiments, the effective amount is a therapeutically effective amount. In certain embodiments, the effective amount is a prophylactically effective amount. In certain embodiments, the subject is suffering from a CARM1-mediated disorder. In certain embodiments, the subject is susceptible to a CARM1-mediated disorder.

As used herein, the term "CARM1-mediated disorder" means any disease, disorder, or other pathological condition in which CARM1 is known to play a role. Accordingly, in some embodiments, the present disclosure relates to treating or lessening the severity of one or more diseases in which CARM1 is known to play a role.

In some embodiments, the present disclosure provides a method of inhibiting CARM1 comprising contacting CARM1 with an effective amount of a compound described herein, e.g., a compound of Formula (I), or a pharmaceutically acceptable salt thereof. The CARM1 may be purified or crude, and may be present in a cell, tissue, or subject. Thus, such methods encompass both inhibition of in vitro and in vivo CARM1 activity. In certain embodiments, the method is an in vitro method, e.g., such as an assay method. It will be understood by one of ordinary skill in the art that inhibition of CARM1 does not necessarily require that all of the CARM1 be occupied by an inhibitor at once. Exemplary levels of inhibition of CARM1 include at least 10% inhibition, about 10% to about 25% inhibition, about 25% to about 50% inhibition, about 50% to about 75% inhibition, at least 50% inhibition, at least 75% inhibition, about 80% inhibition, about 90% inhibition, and greater than 90% inhibition.

In some embodiments, provided is a method of inhibiting CARM1 activity in a subject in need thereof comprising administering to the subject an effective amount of a compound described herein (e.g., a compound of Formula (I), or a pharmaceutically acceptable salt thereof, or a pharmaceutical composition thereof.

In certain embodiments, provided is a method of modulating gene expression or activity in a cell which comprises contacting a cell with an effective amount of a compound of Formula (I), or a pharmaceutically acceptable salt thereof. In certain embodiments, the cell in culture in vitro. In certain embodiments, the cell is in an animal, e.g., a human. In certain embodiments, the cell is in a subject in need of treatment.

In certain embodiments, provided is a method of modulating transcription in a cell which comprises contacting a cell with an effective amount of a compound of Formula (I), or a pharmaceutically acceptable salt thereof. In certain embodiments, the cell in culture in vitro. In certain embodiments, the cell is in an animal, e.g., a human. In certain embodiments, the cell is in a subject in need of treatment.

In certain embodiments, a method is provided of selecting a therapy for a subject having a disease associated with CARM1-mediated disorder or mutation comprising the steps of determining the presence of CARM1-mediated disorder or gene mutation in the CARM1 gene or and selecting, based on the presence of CARM1-mediated disorder a gene mutation in the CARM1 gene a therapy that includes the administration of a provided compound. In certain embodiments, the disease is cancer.

In certain embodiments, a method of treatment is provided for a subject in need thereof comprising the steps of determining the presence of CARM1-mediated disorder or a gene mutation in the CARM1 gene and treating the subject in need thereof, based on the presence of a CARM1-mediated disorder or gene mutation in the CARM1 gene with a therapy that includes the administration of a provided compound. In certain embodiments, the subject is a cancer patient.

In some embodiments, a compound provided herein is useful in treating a proliferative disorder, such as cancer. For example, while not being bound to any particular mechanism, protein arginine methylation by CARM1 is a modification that has been implicated in signal transduction, gene transcription, DNA repair and mRNA splicing, among others; and overexpression of CARM1 within these pathways is often associated with various cancers. Thus, compounds which inhibit the action of PRMTs, and specifically CARM1, as provided herein, are effective in the treatment of cancer.

In some embodiments, compounds provided herein are effective in treating cancer through the inhibition of CARM1. For example, CARM1 levels have been shown to be elevated in castration-resistant prostate cancer (CRPC), as well as in aggressive breast tumors (Hong et al., Cancer 2004 101, 83-89; El Messaoudi et al., Proc. Natl. Acad. Sci. U.S.A. 2006, 103, 13351-13356; Majumder et al., Prostate 2006 66, 1292-1301). Thus, in some embodiments, inhibitors of CARM1, as described herein, are useful in treating cancers associated with aberrant CARM1 activity, e.g., CARM1 overexpression or aberrant protein methylation. CARM1 has also been shown to affect ERα-dependent breast cancer cell differentiation and proliferation (Al-Dhaheri et al., Cancer Res. 2011 71, 2118-2128), thus in some aspects CARM1 inhibitors, as described herein, are useful in treating ERα-dependent breast cancer by inhibiting cell differentiation and proliferation. In another example, CARM1 has been shown to be recruited to the promoter of E2F1 (which encodes a cell cycle regulator) as a transcriptional co-activator (Frietze et al., Cancer Res. 2008 68, 301-306). Thus, CARM1-mediated upregulation of E2F1 expression may contribute to cancer progression and chemoresistance as increased abundance of E2F1 triggers invasion and metastasis by activating growth receptor signaling pathways, which in turn promote an antiapoptotic tumor environment (Engelmann and Piitzer, Cancer Res 2012 72; 571). Accordingly, in some embodiments, the inhibition of CARM1, e.g., by compounds provided herein, is useful in treating cancers associated with E2F1 upregulation. Thus, without being bound by any particular mechanism, the inhibition of CARM1, e.g., by compounds described herein, is beneficial in the treatment of cancer. CARM1 overexpression has also been demonstrated to be elevated in 75% of colorectal cancers (Kim et al., BMC Cancer, 10, 197). It has been additionally been determined that depletion of CARM1 in WNT/β-catenin dysregulated colorectal cancer suppressed anchorage independent growth (Ou et al., Mol. Cancer. Res., 2011 9, 660-670). This, in some embodiments, the inhibition of CARM1, e.g. by compounds provided herein, is useful in colorectal cancer associated with elevated CARM1 expression or dysregulated WNT/β-catenin signaling.

In some embodiments, compounds described herein are useful for treating a cancer including, but not limited to, acoustic neuroma, adenocarcinoma, adrenal gland cancer, anal cancer, angiosarcoma (e.g., lymphangiosarcoma, lymphangioendotheliosarcoma, hemangiosarcoma), appendix cancer, benign monoclonal gammopathy, biliary cancer (e.g., cholangiocarcinoma), bladder cancer, breast cancer (e.g., adenocarcinoma of the breast, papillary carcinoma of the breast, mammary cancer, medullary carcinoma of the breast), brain cancer (e.g., meningioma; glioma, e.g., astrocytoma, oligodendroglioma; medulloblastoma), bronchus cancer, carcinoid tumor, cervical cancer (e.g., cervical adenocarcinoma), choriocarcinoma, chordoma, craniopharyngioma, colorectal cancer (e.g., colon cancer, rectal cancer, colorectal adenocarcinoma), epithelial carcinoma, ependymoma, endotheliosarcoma (e.g., Kaposi's sarcoma, multiple idiopathic hemorrhagic sarcoma), endometrial cancer (e.g., uterine cancer, uterine sarcoma), esophageal cancer (e.g., adenocarcinoma of the esophagus, Barrett's adenocarinoma), Ewing sarcoma, eye cancer (e.g., intraocular melanoma, retinoblastoma), familiar hypereosinophilia, gall bladder cancer, gastric cancer (e.g., stomach adenocarcinoma), gastrointestinal stromal tumor (GIST), head and neck cancer (e.g., head and neck squamous cell carcinoma, oral cancer (e.g., oral squamous cell carcinoma (OSCC), throat cancer (e.g., laryngeal cancer, pharyngeal cancer, nasopharyngeal cancer, oropharyngeal cancer)), hematopoietic cancers (e.g., leukemia such as acute lymphocytic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL); lymphoma such as Hodgkin lymphoma (HL) (e.g., B-cell HL, T-cell HL) and nonHodgkin lymphoma (NHL) (e.g., B-cell NHL such as diffuse large cell lymphoma (DLCL) (e.g., diffuse large B-cell lymphoma (DLBCL)), follicular lymphoma, chronic lymphocytic leukemia/small lymphocytic lymphoma (CLL/SLL), mantle cell lymphoma (MCL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt lymphoma, lymphoplasmacytic lymphoma (i.e., "Waldenström's macroglobulinemia"), hairy cell leukemia (HCL), immunoblastic large cell lymphoma, precursor B-lymphoblastic lymphoma and primary central nervous system (CNS) lymphoma; and T-cell NHL such as precursor T-lymphoblastic lymphoma/leukemia, peripheral T-cell lymphoma (PTCL) (e.g., cutaneous T-cell lymphoma (CTCL) (e.g., mycosis fungiodes, Sezary syndrome), angioimmunoblastic T-cell lymphoma, extranodal natural killer T-cell lymphoma, enteropathy type T-cell lymphoma, subcutaneous panniculitis-like T-cell lymphoma, anaplastic large cell lymphoma); a mixture of one or more leukemia/lymphoma as described above; and multiple myeloma (MM)), heavy chain disease (e.g., alpha chain disease, gamma chain disease, mu chain disease), hemangioblastoma, inflammatory myofibroblastic tumors, immunocytic amyloidosis, kidney cancer (e.g., nephroblastoma a.k.a. Wilms' tumor, renal cell carcinoma), liver cancer (e.g., hepatocellular cancer (HCC), malignant hepatoma), lung cancer (e.g., bronchogenic carcinoma, small cell lung cancer (SCLC), nonsmall cell lung cancer (NSCLC), adenocarcinoma of the lung), leiomyosarcoma (LMS), mastocytosis (e.g., systemic mastocytosis), myelodysplastic syndrome (MDS), mesothelioma, myeloproliferative disorder (MPD)

(e.g., polycythemia Vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)), neuroblastoma, neurofibroma (e.g., neurofibromatosis (NF) type 1 or type 2, schwannomatosis), neuroendocrine cancer (e.g., gastroenteropancreatic neuroendoctrine tumor (GEP-NET), carcinoid tumor), osteosarcoma, ovarian cancer (e.g., cystadenocarcinoma, ovarian embryonal carcinoma, ovarian adenocarcinoma), papillary adenocarcinoma, pancreatic cancer (e.g., pancreatic andenocarcinoma, intraductal papillary mucinous neoplasm (IPMN), Islet cell tumors), penile cancer (e.g., Paget's disease of the penis and scrotum), pinealoma, primitive neuroectodermal tumor (PNT), prostate cancer (e.g., prostate adenocarcinoma), rectal cancer, rhabdomyosarcoma, salivary gland cancer, skin cancer (e.g., squamous cell carcinoma (SCC), keratoacanthoma (KA), melanoma, basal cell carcinoma (BCC)), small bowel cancer (e.g., appendix cancer), soft tissue sarcoma (e.g., malignant fibrous histiocytoma (MFH), liposarcoma, malignant peripheral nerve sheath tumor (MPNST), chondrosarcoma, fibrosarcoma, myxosarcoma), sebaceous gland carcinoma, sweat gland carcinoma, synovioma, testicular cancer (e.g., seminoma, testicular embryonal carcinoma), thyroid cancer (e.g., papillary carcinoma of the thyroid, papillary thyroid carcinoma (PTC), medullary thyroid cancer), urethral cancer, vaginal cancer, and vulvar cancer (e.g., Paget's disease of the vulva).

CARM1 is also the most abundant PRMT expressed in skeletal muscle cells, and has been found to selectively control the pathways modulating glycogen metabolism, and associated AMPK (AMP-activated protein kinase) and p38 MAPK (mitogen-activated protein kinase) expression. See, e.g., Wang et al., Biochem (2012) 444:323-331. Thus, in some embodiments, inhibitors of CARM1, as described herein, are useful in treating metabolic disorders, e.g., for example skeletal muscle metabolic disorders, e.g., glycogen and glucose metabolic disorders. Exemplary skeletal muscle metabolic disorders include, but are not limited to, Acid Maltase Deficiency (Glycogenosis type 2; Pompe disease), Debrancher deficiency (Glycogenosis type 3), Phosphorylase deficiency (McArdle's; GSD 5), X-linked syndrome (GSD9D), Autosomal recessive syndrome (GSD9B), Tarui's disease (Glycogen storage disease VII; GSD 7), Phosphoglycerate Mutase deficiency (Glycogen storage disease X; GSDX; GSD 10), Lactate dehydrogenase A deficiency (GSD 11), Branching enzyme deficiency (GSD 4), Aldolase A (muscle) deficiency, β-Enolase deficiency, Triosephosphate isomerase (TIM) deficiency, Lafora's disease (Progressive myoclonic epilepsy 2), Glycogen storage disease (Muscle, Type 0, Phosphoglucomutase 1 Deficiency (GSD 14)), and Glycogenin Deficiency (GSD 15).

Scheme 1 shows a general synthesis route to compounds of Formula I-(ii) wherein $R^{3'}$ is the same as $R^3$ as defined above or is a suitable precursor that may be converted to $R^3$. This method is based on Suzuki coupling reactions of heteroaryl chloride intermediates of general Formula XI-(ii) with pinacol borane intermediates of general Formula X. In a first step, Suzuki coupling reaction of these intermediates is typically conducted in the presence of a palladium catalyst (e.g. $PdCl_2$ (dppf)) and a base (e.g. potassium carbonate) in an organic solvent (e.g. toluene) at elevated temperature. In a second optional set of steps the $R^{3'}$ group as well as other groups in the molecule may be converted to the defined final substituents in Formula I-(ii). In a final deprotection step the N-Boc protecting is removed by for example using an acid (e.g. HCl) in a suitable organic solvent (e.g. ethanol) to give certain corresponding embodiments of compounds of Formula I-(ii).

Scheme 1

Compounds of general Formula XI-(ii) can be prepared from heteroaryl dichlorides of general Formula XX-(ii) as depicted in Scheme 2. In certain embodiments when L is —N($R^L$)—, —C(O)N($R^L$), or —OC(O)N($R^L$)—, —N$R^L$C(O)N($R^L$)—, Buchwald coupling of XX-(ii) respectively with active amines $R^{3'}$N($R^L$)H, amides $R^{3'}$C(O)N($R^L$)H, carbamates OC(O)N($R^L$)H, or ureas —N$R^L$C(O)N($R^L$)H, may be implemented in the first step. In certain embodiments when $L^1$ is a bond, and the monocyclic heterocycle core structure is directly attached to $R^{3'}$ by a carbon-carbon bond, Suzuki coupling of XXI-(i) with boronic acids or ester intermediates $R^{3'}B(OH)_2$ may be implemented to yield the corresponding certain embodiments of XI-(ii). In certain embodiments the formation of compounds of Formula XI-(ii) using the methods described above can be accompanied by formation of the regioisomeric intermediate compounds of Formula XI-(ii)-a. In certain embodiments when a mixture of XI-(ii) and XI-(ii)-regioisomers is formed they may be separated by chromatography. Intermediates of Formula XI-(ii)-a may in turn be implemented to prepare compounds of the invention using the same general method described in Scheme 1.

-continued

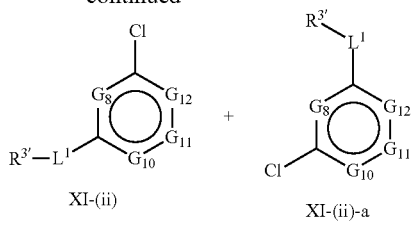

In certain embodiments wherein X in general Formulas I-(ii) is O, pinacol borane intermediates of general Formula X can be prepared using standard methods as depicted in Scheme 3. Thus, in a first step 3-bromophenols of general structure XXX are treated with epibromohydrin to give epoxides XXXI. Opening of the epoxide group of intermediates XXXI in with amines of Formula $R^1NH_2$ in an organic solvent with heating as necessary followed by protection of the resulting amine with Boc-anhydride gives intermediates XXXII. TBS protection of the alcohol group in the next step using t-butyldimethylsilyltriflate gives intermediate bromides XXXIII. In a final step the Br group is converted to the pinacol borane function to give intermediates XX under standard Suzuki-Miyura conditions.

Scheme 2

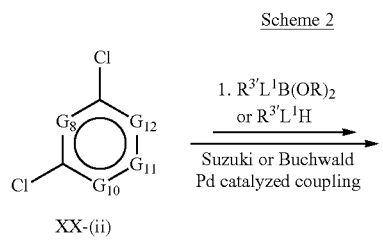

Scheme 3

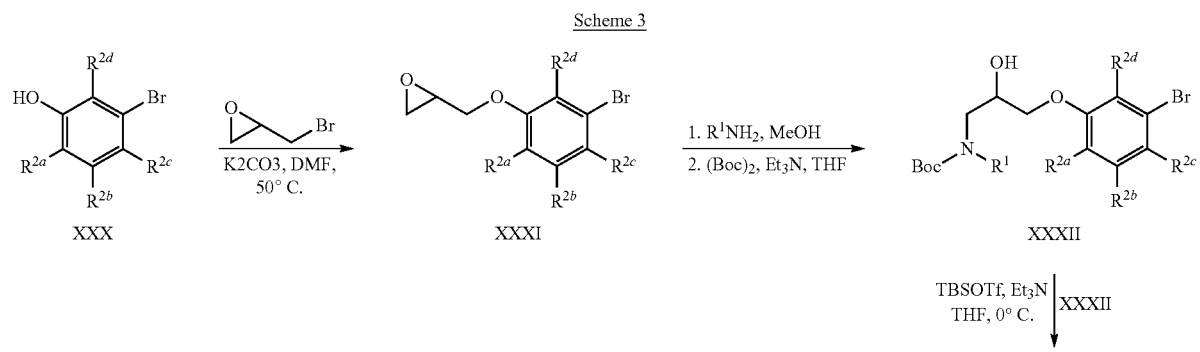

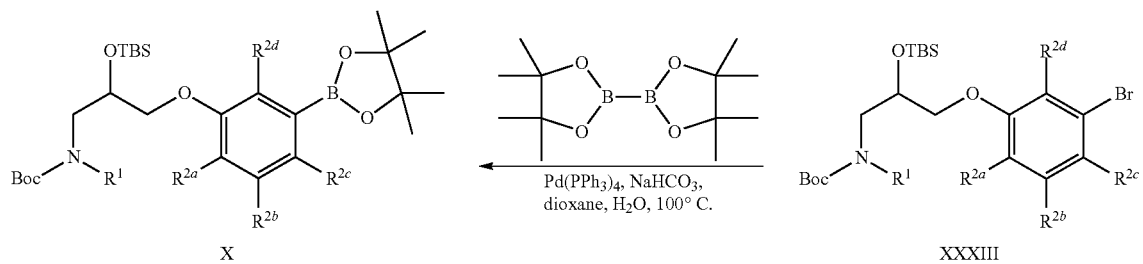

Certain heteroaryl dichlorides of general Formula XX-(ii) are commercially available. Certain embodiments of general structure XX-(ii) may be prepared by known methods. For example embodiments of intermediates of general structure XX-(ii)-x may be prepared from trichloropyrimidine intermediates L-(ii)-x as depicted in Scheme 4. In certain embodiments Suzuki coupling of L-(ii)-x with aryl or heteroaryl boronates gives intermediate compounds of Formula L-(ii)-x a wherein $R^{11}$ is aryl or heteroaryl. In certain embodiments Buchwald coupling of L-(ii)-x with primary or secondary cyclic (e.g. morpholine) or acyclic amines gives intermediate compounds of Formula L-(ii)-x a wherein $R^{11}$ is an acyclic or cyclic amino group.

Scheme 4

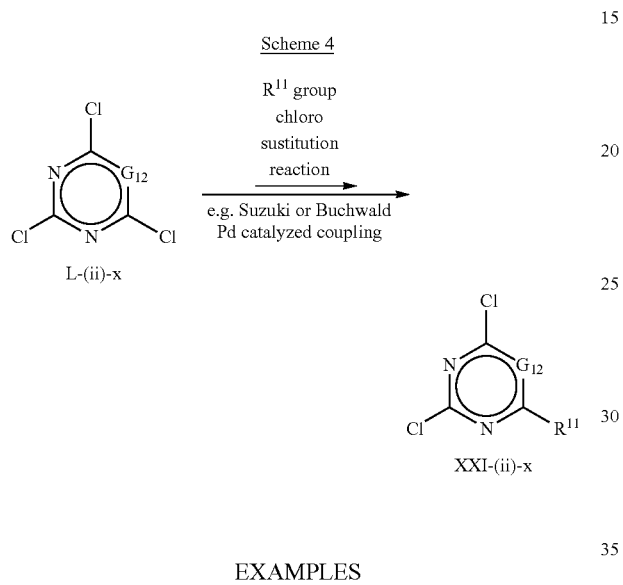

EXAMPLES

In order that the invention described herein may be more fully understood, the following examples are set forth. It should be understood that these examples are for illustrative purposes only and are not to be construed as limiting this invention in any manner.

Synthetic Methods

The synthesis of an exemplary set of compounds of Formula (I) is provided below. These compounds are also listed in Tables 1 and 2, infra. Compounds provided in Tables 1 and 2 have been prepared following Examples 1-3.

Example 1

Preparation of 1-(3-(4-(methyl(tetrahydro-2H-pyran-4-yl)amino)-6-(pyridine-4-yl)pyrimidin-2-yl)phenoxy)-3-(methylamino)propan-2-ol (a)

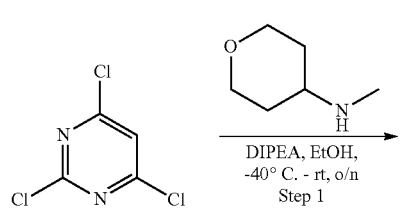

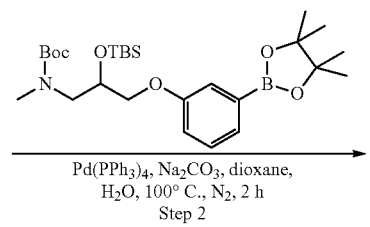

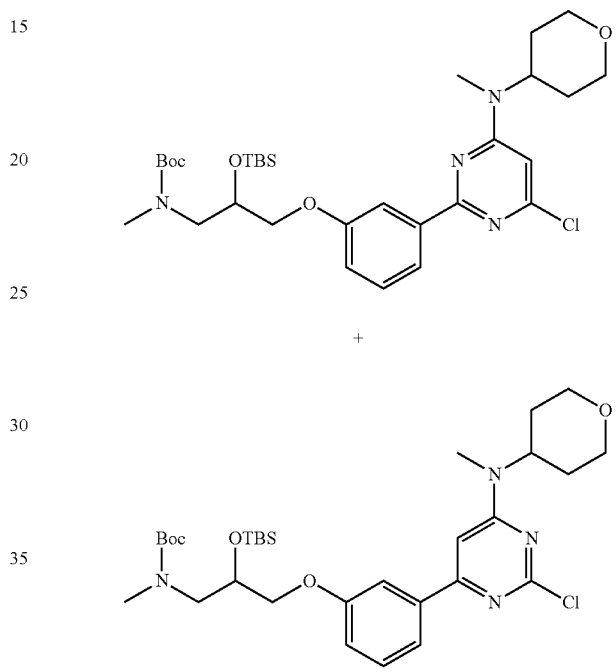

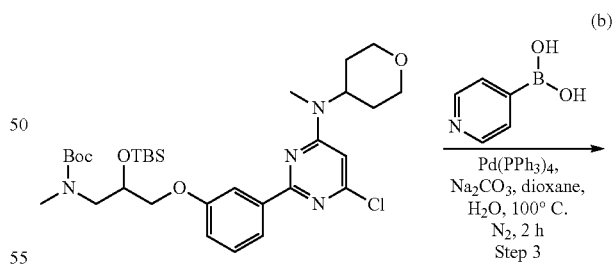

(b)

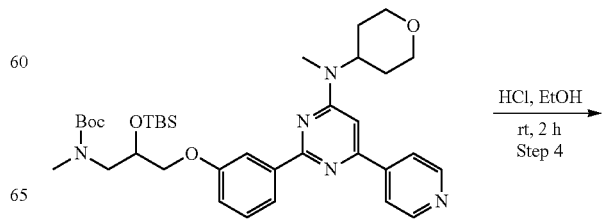

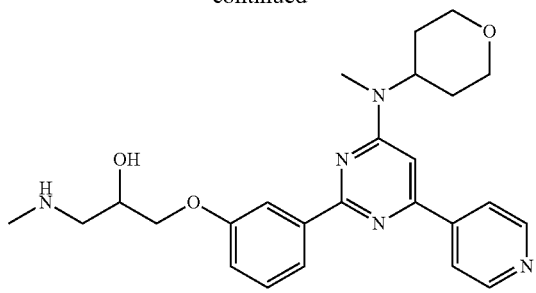

Step 1: Synthesis of (2,6-dichloro-pyrimidin-4-yl)-methyl-(tetrahydro-pyran-4-yl)amine To a solution of 2,4,6-trichloro-pyrimidine (9.2 g, 50 mmol) and triethylamine (10.1 g, 100 mmol) in EtOH (100 mL) was added N-methyltetrahydro-2H-pyran-4-amine (5.17 g, 45 mmol) dropwise at −40° C. The mixture was warmed up to room temperature then stirred for 14 h., quenched with H$_2$O (25 mL), concentrated and the residue was extracted with EtOAc (100 mL×3). The combined organic layers were dried over Na$_2$SO$_4$, filtered and concentrated. The residue was purified by chromatographic column on silica gel (petroleum ether/EtOAc=30/1 to 2/1) to give (2,6-dichloro-pyrimidin-4-yl)-methyl-(tetrahydro-pyran-4-yl)amine as white solid (7.8 g, 60% yield). ESI-LCMS (m/z): 263.14 [M+1]$^+$;

Step 2: Synthesis of [2-(tert-Butyl-dimethyl-silanyloxy)-3-(3-{4-chloro-6-[methyl-(tetrahydro-pyran-4-yl)-amino]-pyrimidin-2-yl}-phenoxy)-propyl]-methyl-carbamic acid tert-butyl ester and [2-(tert-Butyl-dimethyl-silanyloxy)-3-(3-{2-chloro-6-[methyl-(tetrahydro-pyran-4-yl)-amino]-pyrimidin-4-yl}-phenoxy)-propyl]-methyl-carbamic acid tert-butyl ester To a solution of (2,6-dichloro-pyrimidin-4-yl)-methyl-(tetrahydro-pyran-4-yl)amine (0.4 g, 1.5 mmol) in degassed dioxane and H$_2$O (4/1, 25 mL) was added Na$_2$CO$_3$ (315 mg, 3.0 mmol); Pd(PPh$_3$)$_4$ (86 mg, 0.075 mmol) and {2-(tert-Butyl-dimethyl-silanyloxy)-3-[3-(4,4,5,5-tetramethyl-[1,3,2]dioxaborolan-2-yl)-phenoxy]-propyl}-methyl-carbamic acid tert-butyl ester (703 mg, 1.35 mmol). The system was purged with N$_2$ stream and the mixture was stirred at 100° C. for 2 h., cooled to room temperature, diluted with water (50 mL) and extracted with EtOAc (50 mL×2). The organic layers were combined, dried over Na$_2$SO$_4$, filtered and concentrated. The residue was purified by preparative HPLC to give [2-(tert-Butyl-dimethyl-silanyloxy)-3-(3-{4-chloro-6-[methyl-(tetrahydro-pyran-4-yl)-amino]-pyrimidin-2-yl}-phenoxy)-propyl]-methyl-carbamic acid tert-butyl ester (373 mg, 40% yield) as major product. ESI-LCMS (m/z): 411.2 [M+1]$^+$along with the minor product [2-(tert-Butyl-dimethyl-silanyloxy)-3-(3-{2-chloro-6-[methyl-(tetrahydro-pyran-4-yl)-amino]-pyrimidin-4-yl}-phenoxy)-propyl]-methyl-carbamic acid tert-butyl ester (140 mg, 15% yield). ESI-LCMS (m/z): 411.2 [M+1]$^+$.

Step 3: Synthesis of [2-(tert-Butyl-dimethyl-silanyloxy)-3-(3-{4-[methyl-(tetrahydro-pyran-4-yl)-amino]-6-pyridin-4-yl-pyrimidin-2-yl}-phenoxy)-propyl]-methyl-carbamic acid tert-butyl ester To a solution of [2-(tert-Butyl-dimethyl-silanyloxy)-3-(3-{4-chloro-6-[methyl-(tetrahydro-pyran-4-yl)-amino]-pyrimidin-2-yl}-phenoxy)-propyl]-methyl-carbamic acid tert-butyl ester (160 mg, 0.26 mmol) in degassed dioxane and H$_2$O (4/1, 25 mL) was added Na$_2$CO$_3$ (83 mg, 0.78 mmol); Pd(PPh$_3$)$_4$ (30 mg, 0.026 mmol) and pyridin-4-ylboronic acid (64 mg, 0.52 mmol). The system was purged with N$_2$ stream and the mixture was stirred 100° C. for 2 h., cooled down to room temperature, diluted with water (25 mL) and extracted with EtOAc (25 mL×2). The organic layers were combined, dried over Na$_2$SO$_4$, filtered and concentrated. The residue was purified by chromatographic column on silica gel (petroleum ether/EtOAc=10/1 to 1/1) to give [2-(tert-Butyl-dimethyl-silanyloxy)-3-(3-{4-[methyl-(tetrahydro-pyran-4-yl)-amino]-6-pyridin-4-yl-pyrimidin-2-yl}-phenoxy)-propyl]-methyl-carbamic acid tert-butyl ester (128 mg, 75% yield). ESI-LCMS (m/z): 664.4 [M+1]$^+$.

Step 4: Synthesis of 1-methylamino-3-(3-{4-[methyl-(tetrahydro-pyran-4-yl)-amino]-6-pyridin-4-yl-pyrimidin-2-yl}-phenoxy)-propan-2-ol A solution of [2-(tert-Butyl-dimethyl-silanyloxy)-3-(3-{4-[methyl-(tetrahydro-pyran-4-yl)-amino]-6-pyridin-4-yl-pyrimidin-2-yl}-phenoxy)-propyl]-methyl-carbamic acid tert-butyl ester (135 mg, 0.20 mmol) was treated with a 2.5 N HCl solution in methanol (10 mL) and the mixture was stirred at room temperature for 4 h., concentrated under vacuum and the residue was purified by preparative HPLC to give 1-methylamino-3-(3-{4-[methyl-(tetrahydro-pyran-4-yl)-amino]-6-pyridin-4-yl-pyrimidin-2-yl}-phenoxy)-propan-2-ol as white solid (49 mg, 56% yield). $^1$HNMR (500 MHz, CD$_3$OD) δ ppm: 8.72-8.70 (m, 2H), 8.23 (brs, 2H), 8.14-8.10 (m, 2H), 7.43 (t, J=8.5 Hz, 1H), 7.16-7.10 (m, 2H), 4.24-4.18 (m, 1H), 4.15-4.08 (m, 4H), 3.72-3.65 (m, 2H), 3.14 (s, 3H), 3.00-2.85 (m, 2H), 2.56 (s, 3H), 2.09-1.98 (m, 2H), 1.79-1.72 (m, 2H). ESI-LCMS: 450.5 (M+1)$^+$.

Example 2

Preparation of 1-Methylamino-3-(3-{6-[methyl-(tetrahydro-pyran-4-yl)-amino]-2-pyridin-4-yl-pyrimidin-4-yl}-phenoxy)-propan-2-ol

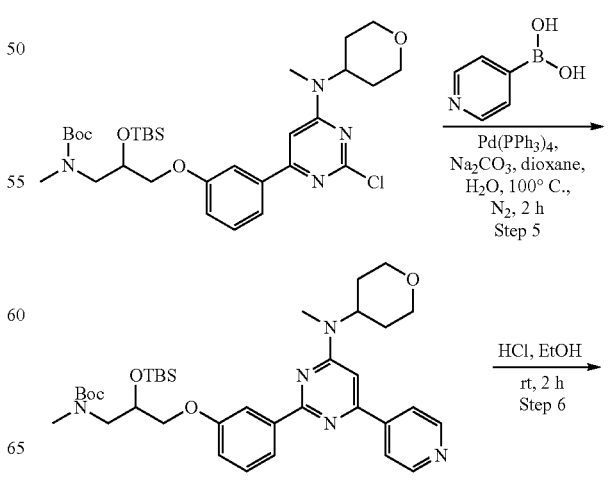

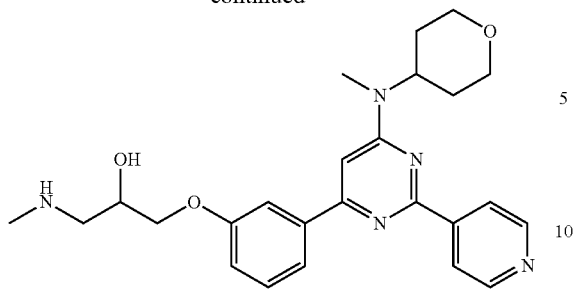

Step 5: Synthesis of [2-(tert-Butyl-dimethyl-silanyloxy)-3-(3-{4-[methyl-(tetrahydro-pyran-4-yl)-amino]-6-pyridin-4-yl-pyrimidin-2-yl}-phenoxy)-propyl]-methyl-carbamic acid tert-butyl ester To a solution of [2-(tert-Butyl-dimethyl-silanyloxy)-3-(3-{2-chloro-6-[methyl-(tetrahydro-pyran-4-yl)-amino]-pyrimidin-4-yl}-phenoxy)-propyl]-methyl-carbamic acid tert-butyl ester (160 mg, 0.26 mmol) in degassed dioxane and H$_2$O (4/1, 25 mL) was added Na$_2$CO$_3$ (83 mg, 0.78 mmol); Pd(PPh$_3$)$_4$ (30 mg, 0.026 mmol) and pyridin-4-ylboronic acid (64 mg, 0.52 mmol). The system purged with N$_2$ stream and the mixture was stirred to 100° C. for 2 h., cooled down to room temperature, diluted with water (25 mL) and extracted with EtOAc (25 mL×2). The organic layers were combined, dried over Na$_2$SO$_4$, filtered and concentrated. The residue was purified by chromatographic column on silica gel (petroleum ether/EtOAc=101 to 23) to give [2-(tert-Butyl-dimethyl-silanyloxy)-3-(3-{4-[methyl-(tetrahydro-pyran-4-yl)-amino]-6-pyridin-4-yl-pyrimidin-2-yl}-phenoxy)-propyl]-methyl-carbamic acid tert-butyl ester (135 mg, 79% yield). ESI-LCMS (m/z): 664.4 [M+1]$^+$.

Step 6: Synthesis of 1-Methylamino-3-(3-{6-[methyl-(tetrahydro-pyran-4-yl)-amino]-2-pyridin-4-yl-pyrimidin-4-yl}-phenoxy)-propan-2-ol A solution of [2-(tert-Butyl-dimethyl-silanyloxy)-3-(3-{4-[methyl-(tetrahydro-pyran-4-yl)-amino]-6-pyridin-4-yl-pyrimidin-2-yl}-phenoxy)-propyl]-methyl-carbamic acid tert-butyl ester (128 mg, 0.19 mmol) was treated with a 2.5 N HCl solution in methanol, (10 mL), and the mixture was stirred at room temperature for 4 h., concentrated under vacuum and the residue was purified by preparative HPLC to give 1-methylamino-3-(3-{6-[methyl-(tetrahydro-pyran-4-yl)-amino]-2-pyridin-4-yl-pyrimidin-4-yl}-phenoxy)-propan-2-ol as white solid (52 mg, 57% yield). $^1$HNMR (500 MHz, CD$_3$OD) δ ppm: 8.71 (d, J=5.5 Hz, 2H), 8.47 (d, J=5.0 Hz, 2H), 7.84 (s, 1H), 7.79 (d, J=8.0 Hz, 1H), 7.47-7.43 (m, 1H), 7.13 (d, J=8.0 Hz, 1H), 7.09 (s, 1H), 4.22-4.17 (m, 1H), 4.15-4.09 (m, 4H), 3.74-3.66 (m, 2H), 3.15 (s, 3H), 2.96-2.82 (m, 2H), 2.53 (s, 3H), 2.07-1.97 (m, 2H), 1.78-1.73 (m, 2H); LCMS: 450.3 (M+H)$^+$;

Example 3

Preparation of 1-(3-(5-methyl-4-morpholino-6-((R)-tetrahydrofuran-3-ylamino)pyrimidin-2-yl)phenoxy)-3-(methylamino)propan-2-ol

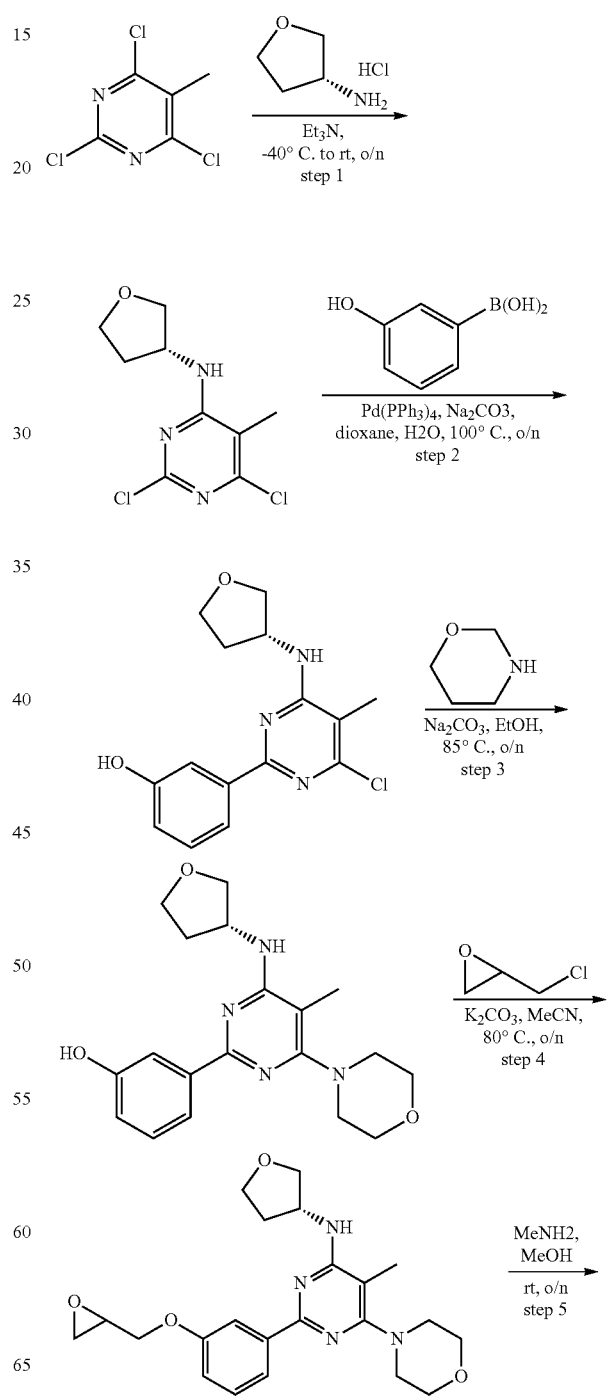

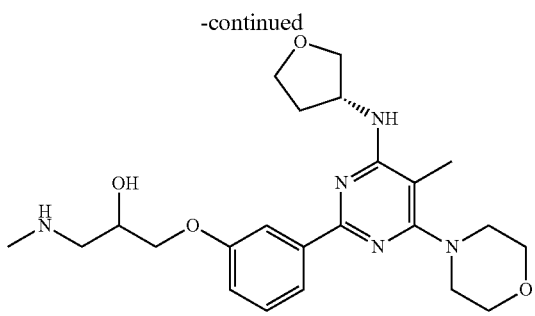

Step 1: Synthesis of (R)-2,6-dichloro-5-methyl-N-(tetrahydrofuran-3-yl)pyrimidin-4-amine A mixture of 2,4,6-trichloro-5-methylpyrimidine (2 g, 10.2 mmol), (R)-tetrahydrofuran-3-amine hydrochloride (1.12 g, 9.2 mmol) and Et₃N (2.1 g, 20.3 mmol) in EtOH (20 mL) was stirred at room temperature for 14 h., concentrated under vacuum and the residue was purified by chromatographic column on silica gel (EtOAc/petroleum ether, gradient elution, from 1/0 to 2/1) to give the (R)-2,6-dichloro-5-methyl-N-(tetrahydrofuran-3-yl)pyrimidin-4-amine (1.25 g, 53% yield) as a white solid. ESI-LCMS (m/z): 248.1 [M+1]⁺.

Step 2: Synthesis of (R)-3-(4-chloro-5-methyl-6-(tetrahydrofuran-3-ylamino)pyrimidin-2-yl)phenol To a solution of (R)-2,6-dichloro-5-methyl-N-(tetrahydrofuran-3-yl)pyrimidin-4-amine (1.8 g, 7.3 mmol) in degassed dioxane and H₂O (4/1, 21 mL) was added Na₂CO₃ (1.5 g, 14.5 mmol); Pd(PPh₃)₄ (296 mg, 0.36 mmol) and 3-hydroxy-phenylboronic acid (1.21 g, 8.8 mmol). The system was purged with nitrogen stream and then stirred at 100° C. for 14 h., cooled down to room temperature, diluted with water (30 mL) and the resulting mixture extracted with EtOAc (30 mL×2). The combined organic layer were dried over Na₂SO₄, filtered and concentrated. The residue was purified by chromatographic column on silica gel (EtOAc/petroleum ether, gradient elution, from 1/10 to 2:1) to give (R)-3-(4-chloro-5-methyl-6-(tetrahydrofuran-3-ylamino)pyrimidin-2-yl)phenol (2.4 g, 33%) as a white solid. ESI-LCMS (m/z): 306.1 [M+1]⁺.

Step 3: Synthesis of (R)-3-(5-methyl-4-morpholino-6-(tetrahydrofuran-3-ylamino)pyrimidin-2-yl)phenol A mixture of (R)-3-(4-chloro-5-methyl-6-(tetrahydrofuran-3-ylamino)pyrimidin-2-yl)phenol (800 mg, 2.6 mmol); neat morpholine (274 mg, 3.1 mmol) and Na₂CO₃ (556 mg, 5.2 mmol) in EtOH (12 mL) was stirred at 80° C. in a sealed vial for 14 h. The mixture was filtered and the filtrate was concentrated. The residue was purified by chromatographic column on silica gel (EtOAc/petroleum ether, gradient elution, from 1/2 to 2/1) to give the (R)-3-(5-methyl-4-morpholino-6-(tetrahydrofuran-3-ylamino)pyrimidin-2-yl)phenol (120 mg, 13% yield) as a light yellow solid. ESI-LCMS (m/z): 357.1 [M+1]⁺.

Step 4: Synthesis of 5-methyl-6-morpholino-2-(3-(oxiran-2-ylmethoxy)phenyl)-N—((R)-tetrahydrofuran-3-yl)pyrimidin-4-amine A mixture of (R)-3-(5-methyl-4-morpholino-6-(tetrahydrofuran-3-ylamino)pyrimidin-2-yl)phenol (50 mg, 0.14 mmol); 2-(chloromethyl)oxirane (16 mg, 0.17 mmol) and K₂CO₃ (39 mg, 0.28 mmol) in MeCN (10 mL) was heated at 80° C. in a sealed vial for 14 h. The mixture was filtered and the filtrate was concentrated. The residue was purified by chromatographic column on silica gel (EtOAc/petroleum ether, gradient elution, from 1/5 to 4:1) to give the 5-methyl-6-morpholino-2-(3-(oxiran-2-ylmethoxy)phenyl)-N—((R)-tetrahydrofuran-3-yl)pyrimidin-4-amine (20 mg, 34% yield) as a light yellow solid. ESI-LCMS (m/z): 413.2 [M+1]⁺.

Step 5: Synthesis of 1-(3-(5-methyl-4-morpholino-6-((R)-tetrahydrofuran-3-ylamino)pyrimidin-2-yl)phenoxy)-3-(methylamino)propan-2-ol 5-Methyl-6-morpholino-2-(3-(oxiran-2-ylmethoxy)phenyl)-N—((R)-tetra-hydrofuran-3-yl)pyrimidin-4-amine (20 mg, 0.05 mmol) was dissolved in a 2N MeNH₂ solution in methanol, (10 mL) and the mixture was stirred at room temperature for 14 h., concentrated under vacuum and the residue was purified by preparative HPLC to obtain the 1-(3-(5-methyl-4-morpholino-6-((R)-tetrahydrofuran-3-ylamino)pyrimidin-2-yl)phenoxy)-3-(methylamino)propan-2-ol (8 mg, 37% yield) as a white solid. ¹H NMR (500 MHz, CD₃OD) δ ppm: 8.02-7.96 (m, 2H), 7.34 (t, J=8.0 Hz, 1H), 7.05-7.00 (m, 1H), 4.85-4.80 (m, 1H), 4.20-4.14 (m, 2H), 4.07-4.01 (m, 3H), 3.93-3.84 (m, 5H), 3.78-3.74 (m, 1H), 2.96-2.92 (m, 1H), 2.88-2.82 (m, 1H), 2.53 (s, 3H), 2.42-2.35 (m, 1H), 2.11-2.04 (m, 4H); ESI-LCMS (m/z): 444.3 [M+1]⁺.

Biological Assays

General Materials

S-adenosylmethionine (SAM), S-adenosylhomocysteine (SAH), bicine, Tween20, dimethylsulfoxide (DMSO), bovine skin gelatin (BSG), sodium butyrate and Tris(2-carboxyethyl)phosphine hydrochloride solution (TCEP) were purchased from Sigma-Aldrich at the highest level of purity possible. ³H-SAM was purchase from American Radiolabeled Chemicals with a specific activity of 80 Ci/mmol. 384-well streptavidin Flashplates were purchased from PerkinElmer.

Substrates

Peptide representative of human histone H3 residues 16-30 was synthesized with an N-terminal linker-affinity tag motif and a C-terminal amide cap by 21$^{st}$ Century Biochemicals. The peptide was purified by high-performance liquid chromatography (HPLC) to greater than 95% purity and confirmed by liquid chromatography mass spectrometry (LC-MS). The sequence was Biot-Ahx-PRKQLATKAARKSAP-amide and contained a monomethylated arginine at position 26 (SEQ ID NO.:1).

Molecular Biology

Human CARM1 (PRMT4) (NM_199141.1) transcript clone was amplified from an HEK 293 cDNA library, incorporating a flanking 5' sequence encoding a FLAG tag (MDYKDDDDK) (SEQ ID NO.:2) fused directly to Ala 2 of CARM1 and 3' sequence encoding a hexa His sequence (EGHHHHHH) (SEQ ID NO.:3) fused directly to Ser 608. The gene sequence encoding isoform1 containing a deletion of amino acids 539-561 was amplified subsequently and subcloned into pFastBacMam (Viva Biotech).

Protein Expression

Recombinant baculovirus were generated according to Bac-to-Bac kit instructions (Life Technologies). Protein overexpression was accomplished by infecting exponentially growing HEK 293F cell culture at 1.3×10⁶ cell/ml with virus (MOI=10) in the presence of 8 mM sodium butyrate. Infections were carried out at 37° C. for 48 hours, harvested by centrifugation, and stored at −80° C. for purification.

Protein Purification

Expressed full-length human Flag- and His-tagged CARM1 protein was purified from cell paste by anti-flag M2 affinity chromatography with resin equilibrated with buffer containing 20 mM Tris, 150 mM NaCl, 5% glycerol, pH 7.8. Column was washed with 500 mM NaCl in buffer A and Flag-CARM1-His was eluted with 200 ug/ml FLAG peptide in buffer A. Pooled fractions were dialyzed in 20 mM Tris, 150 mM NaCl, 5% glycerol and 1 mM DTT, pH 7.8. The purity of recovered protein was 94.

Predicted Translations

```
Flag-CARM1-His
                                      (SEQ ID NO.: 4)
MDYKDDDDKAAAAAAVGPGAGGAGSAVPGGAGPCATVSVFPGARLLTI

GDANGEIQRHAEQQALRLEVRAGPDSAGIALYSHEDVCVFKCSVSRET

ECSRVGKQSFIITLGCNSVLIQFATPNDFCSFYNILKTCRGHTLERSV

FSERTEESSAVQYFQFYGYLSQQQNMMQDYVRTGTYQRAILQNHTDFK

DKIVLDVGCGSGILSFFAAQAGARKIYAVEASTMAQHAEVLVKSNNLT

DRIVVIPGKVEEVSLPEQVDIIISEPMGYMLFNERMLESYLHAKKYLK

PSGNMFPTIGDVHLAPFTDEQLYMEQFTKANFWYQPSFHGVDLSALRG

AAVDEYFRQPVVDTFDIRILMAKSVKYTVNFLEAKEGDLHRIEIPFK

FHMLHSGLVHGLAFWFDVAFIGSIMTVWLSTAPTEPLTHWYQVRCLFQ

SPLFAKAGDTLSGTCLLIANKRQSYDISIVAQVDQTGSKSSNLLDLKN

PFFRYTGTTPSPPPGSHYTSPSENMWNTGSTYNLSSGMAVAGMPTAYD

LSSVIASGSSVGHNNLIPLGSSGAQGSGGGSTSAHYAVNSQFTMGGPA

ISMASPMSIPTNTMHYGSEGHHHHHH
```

General Procedure for CARM1 Enzyme Assays on Peptide Substrates

The assays were all performed in a buffer consisting of 20 mM Bicine (pH=7.6), 1 mM TCEP, 0.005% BSG, and 0.002% Tween 20, prepared on the day of use. Compounds in 100% DMSO (1 ul) were spotted into a polypropylene 384-well V-bottom plates (Greiner) using a Platemate Plus outfitted with a 384-channel head (Thermo Scientific). DMSO (1 ul) was added to Columns 11, 12, 23, 24, rows A-H for the maximum signal control and 1 ul of SAH, a known product and inhibitor of CARM1, was added to columns 11, 12, 23, 24, rows I-P for the minimum signal control. A cocktail (40 ul) containing the CARM1 enzyme was added by Multidrop Combi (Thermo-Fisher). The compounds were allowed to incubate with CARM1 for 30 min at room temperature, then a cocktail (10 ul) containing $^3$H-SAM and peptide was added to initiate the reaction (final volume=51 ul). The final concentrations of the components were as follows: CARM1 was 0.25 nM, $^3$H-SAM was 30 nM, peptide was 250 nM, SAH in the minimum signal control wells was 1 mM, and the DMSO concentration was 2%. The assays were stopped by the addition of non-radiolabeled SAM (10 ul) to a final concentration of 300 uM, which dilutes the $^3$H-SAM to a level where its incorporation into the peptide substrate is no longer detectable. 50 ul of the reaction in the 384-well polypropylene plate was then transferred to a 384-well Flashplate and the biotinylated peptides were allowed to bind to the streptavidin surface for at least 1 hour before being washed once with 0.1% Tween20 in a Biotek ELx405 plate washer. The plates were then read in a PerkinElmer TopCount plate reader to measure the quantity of $^3$H-labeled peptide bound to the Flashplate surface, measured as disintegrations per minute (dpm) or alternatively, referred to as counts per minute (cpm).

$$\% \text{ inhibition calculation } \% \text{ inh} = 100 - \left(\frac{dpm_{cmpd} - dpm_{min}}{dpm_{max} - dpm_{min}}\right) \times 100$$

where dpm=disintegrations per minute, cmpd=signal in assay well, and min and max are the respective minimum and maximum signal controls.

$$\text{parameter } IC_{50} \text{ fit } Y = \text{Bottom} + \frac{(\text{Top} - \text{Bottom})}{\left(1 + \left(\frac{X}{IC_{50}}\right)^{Hill\ Coefficient}\right)}$$

where top and bottom are the normally allowed to float, but may be fixed at 100 or 0 respectively in a 3-parameter fit. The Hill Coefficient normally allowed to float but may also be fixed at 1 in a 3-parameter fit. Y is the % inhibition and X is the compound concentration.

RKO methylation assay

RKO adherent cells were purchased from ATCC (American Type Culture Collection), Manassas, Va., USA. DMEM/Glutamax medium, penicillin-streptomycin, heat inactivated fetal bovine serum, 0.05% trypsin and D-PBS were purchased from Life Technologies, Grand Island, N.Y., USA. Odyssey blocking buffer, 800CW goat anti-rabbit IgG (H+L) antibody, and Licor Odyssey infrared scanner were purchased from Licor Biosciences, Lincoln, Nebr., USA. Asymmetric di-methyl PABP1 antibody was purchased from Cell Signaling Technology, Danvers, Mass., USA. Methanol was purchased from VWR, Franklin, Mass., USA. 10% Tween 20 was purchased from KPL, Inc., Gaithersburg, Md., USA. Paraformaldehyde (PFA) was purchased from EM Sciences. DRAQ5 was purchased from Biostatus Limited, Leicestershire, UK.

RKO adherent cells were maintained in growth medium (DMEM/Glutamax medium supplemented with 10% v/v heat inactivated fetal bovine serum and 100 units/mL penicillin-streptomycin) and cultured at 37° C. under 5% $CO_2$ Cell treatment, In Cell Western (ICW) for detection of asymmetric di-methyl PABP1 and DNA content: RKO cells were seeded in assay medium at a concentration of 30,000 cells per mL to a poly-D-lysine coated 384 well culture plate (BD Biosciences 356697) with 50 μL per well. Compound (100 nL) from a 96-well source plate was added directly to 384 well cell plate. Plates were incubated at 37° C., 5% $CO_2$ for 48 hours. After two days of incubation, plates were brought to room temperature outside of the incubator for ten minutes and blotted on paper towels to remove cell media. Cells were fixed for 20 minutes at room temperature by adding 50 ul of 8% PFA followed by aspiration of supernatant with the Biotek EL406 plate washer. Cells were then permeabilized by addition of 50 μL of ice cold 100% methanol directly to each well and incubated for 30 min at room temperature. After 30 min, plates were transferred to a Biotek EL406 plate washer and washed 2 times with 100 μL per well of wash buffer (1×PBS). Next 60 μL per well of Odyssey blocking buffer (Odyssey Buffer with 0.1% Tween 20 (v/v)) were added to each plate and incubated 1 hour at room temperature. Blocking buffer was removed and 20 μL per well of primary antibody was added (asymmetric-methyl PABP1) diluted 1:400 in Odyssey buffer with 0.1% Tween 20 (v/v)) and plates were incubated overnight (16 hours) at 4° C. Plates were washed 5 times with 100 μL per well of wash buffer.

Next 20 µL per well of secondary antibody was added (1:800 800CW goat anti-rabbit IgG (H+L) antibody, 1:2000 DRAQ5 in Odyssey buffer with 0.1% Tween 20 (v/v)) and incubated for 1 hour at room temperature. The plates were washed 5 times with 100 µL per well wash buffer then 2 times with 100 µL per well of water. Plates were allowed to dry at room temperature then imaged on the Licor Odyssey machine which measures integrated intensity at 700 nm and 800 nm wavelengths. Both 700 and 800 channels were scanned.

Calculations.

First, the ratio for each well was determined by:

$$\left(\frac{\text{asymmetric di-methyl } PABP1\,800 \text{ nm value}}{DRAQ5\,700 \text{ nm value}}\right)$$

Each plate included fourteen control wells of DMSO only treatment (minimum inhibition) as well as fourteen control wells for maximum inhibition treated with 20 µM of a reference compound. The average of the ratio values for each control type was calculated and used to determine the percent activation for each test well in the plate. Reference compound was serially diluted three-fold in DMSO for a total of nine test concentrations, beginning at 20 µM.

Percent inhibition was determined and IC$_{50}$ curves were generated using triplicate wells per concentration of compound.

$$\text{Percent Inhibition} = 100 - \left(\left(\frac{(\text{Minimum Inhibition Ratio}) - (\text{Individual Test Sample Ratio})}{(\text{Minimum Inhibition Ratio}) - (\text{Maximum Inhibition Ratio})}\right) * 100\right)$$

TABLE 3

Biochemical potencies

| Compound | Biochem IC$_{50}$ |
| --- | --- |
| 1-1 | A |
| 2-1 | A |
| 3-1 | A |
| 4-1 | E |
| 5-1 | D |
| 6-1 | B |
| 7-1 | B |
| 8-1 | B |
| 9-1 | A |
| 10-1 | A |
| 11-1 | A |
| 12-1 | B |
| 13-1 | A |
| 14-1 | A |
| 15-1 | A |
| 16-1 | B |
| 17-1 | C |
| 18-1 | A |
| 19-1 | A |
| 20-1 | A |
| 21-1 | B |
| 22-1 | A |
| 23-1 | B |
| 24-1 | A |
| 25-1 | A |
| 26-1 | A |
| 27-1 | B |
| 28-1 | B |
| 29-1 | A |

TABLE 3-continued

Biochemical potencies

| Compound | Biochem IC$_{50}$ |
| --- | --- |
| 30-1 | B |
| 31-1 | B |
| 32-1 | A |
| 33-1 | A |
| 34-1 | A |
| 35-1 | B |
| 36-1 | A |
| 37-1 | A |
| 38-1 | B |
| 39-1 | B |
| 40-1 | B |
| 41-1 | A |
| 42-1 | A |
| 43-1 | B |
| 44-1 | B |
| 45-1 | A |
| 46-1 | A |
| 47-1 | B |
| 48-1 | A |
| 49-1 | A |
| 50-1 | A |
| 51-1 | B |
| 52-1 | B |
| 53-1 | A |
| 54-1 | B |
| 55-1 | A |
| 56-1 | A |
| 57-1 | A |
| 58-1 | B |
| 59-1 | A |
| 60-1 | A |
| 61-1 | C |
| 62-1 | A |
| 63-1 | B |
| 64-1 | A |
| 65-1 | B |
| 66-1 | B |
| 67-1 | B |
| 68-1 | B |
| 69-1 | B |
| 70-1 | A |
| 71-1 | A |
| 72-1 | B |
| 73-1 | B |
| 74-1 | B |
| 75-1 | B |
| 1-2 | B |
| 2-2 | A |
| 3-2 | B |
| 4-2 | A |
| 5-2 | A |
| 6-2 | A |
| 7-2 | B |
| 8-2 | A |
| 9-2 | B |
| 10-2 | B |
| 11-2 | B |
| 12-2 | B |
| 13-2 | B |

TABLE 3-continued

Biochemical potencies

| Compound | Biochem IC$_{50}$ |
|---|---|
| 14-2 | A |
| 15-2 | A |
| 16-2 | A |

Classification codes for biochemical potencies:
A: IC$_{50}$ < 0.1 uM
B: 0.1 uM ≤ IC$_{50}$ < 1 uM
C: 1 uM ≤ IC$_{50}$ < 3 uM
D: 3 uM ≤ IC$_{50}$ < 10 uM
E: 10 uM < IC$_{50}$

TABLE 4

Cellular potencies

| Compound | Cellular IC$_{50}$ |
|---|---|
| 3-1 | B |
| 26-1 | C |
| 33-1 | A |
| 40-1 | B |
| 41-1 | C |
| 51-1 | C |
| 52-1 | C |
| 70-1 | C |

Classification codes for cellular potencies:
A: IC$_{50}$ < 5 uM
B: 5 uM ≤ IC$_{50}$ < 10 uM
C: 10 uM ≤ IC$_{50}$ < 20 uM Other Embodiments The foregoing has been a description of certain nonlimiting embodiments of the invention. Those of ordinary skill in the art will appreciate that various changes and modifications to this description may be made without departing from the spirit or scope of the present invention, as defined in the following claims.

What is claimed is:
1. A compound of Formula (I):

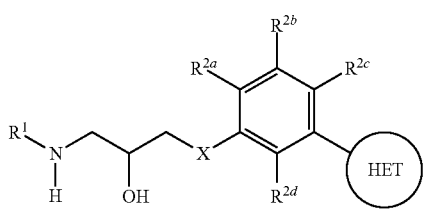

or a pharmaceutically acceptable salt thereof;
wherein:
X is —O—, —S—, or —CH$_2$—;
R$^1$ is hydrogen or optionally substituted C$_{1-4}$ aliphatic;
each of R$^{2a}$, R$^{2b}$, R$^{2c}$, and R$^{2d}$ is independently hydrogen, halogen, —CN, —NO$_2$, —C(=O)R$^{A2}$, —C(=O)OR$^{A2}$, —C(=O)N(R$^{A2}$)$_2$, —OR$^{A2}$, —SR$^A$, —N(R$^{A2}$)$_2$, —S(=O)R$^{A2}$, —S(=O)$_2$R$^{A2}$, optionally substituted alkyl, optionally substituted alkenyl, optionally substituted alkynyl, optionally substituted carbocyclyl, or optionally substituted heterocyclyl, wherein each instance of R$^{A2}$ is independently hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl, or two R$^{A2}$ groups attached to the same nitrogen atom are joined to form an optionally substituted heterocyclyl or optionally substituted heteroaryl ring;

Ring HET is a 6-membered monocyclic heteroaryl ring system of the formula:

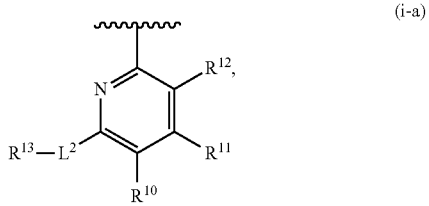

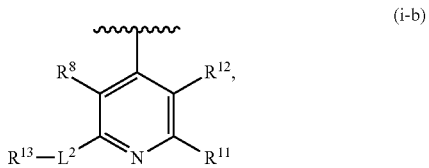

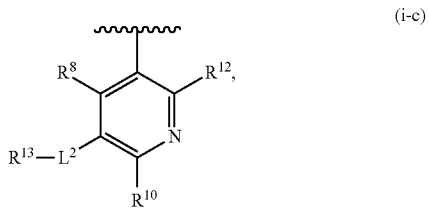

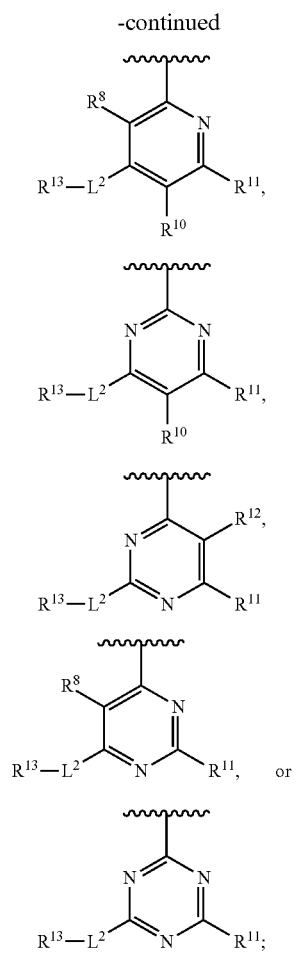

each instance of $R^8$, $R^{10}$, $R^{11}$, and $R^{12}$ is independently selected from the group consisting of hydrogen, halo, —CN, —NO$_2$, —C(=O)R', —C(=O)OR', —C(=O)N(R')$_2$, optionally substituted alkyl, and -L$^1$-R$^3$;

each instance of R' is independently hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl, or two R' groups attached to the same nitrogen are joined to form an optionally substituted heterocyclyl ring or optionally substituted heteroaryl ring;

each instance of L$^1$ and L$^2$ is independently a bond, —O—, —N(R$^L$)—, —S—, —C(O)—, —C(O)O—, —C(O)S—, —C(O)N(R$^L$)—, —C(O)N(R$^L$)N(R$^L$)—, —OC(O)—, —OC(O)N(R$^L$)—, —NR$^L$C(O)—, —NR$^L$C(O)N(R$^L$)—, —NR$^L$C(O)N(R$^L$)N(R$^L$)—, —NR$^L$C(O)O—, —SC(O)—, —C(=NR$^L$)—, —C(=NNR$^L$)—, —C(=NOR$^L$)—, —C(=NR$^L$)N(R$^L$)—, —NR$^L$C(=NR$^L$)—, —C(S)—, —C(S)N(R$^L$)—, —NR$^L$C(S)—, —S(O)—, —OS(O)$_2$—, —S(O)$_2$O—, —SO$_2$—, —N(R$^L$)SO$_2$—, —SO$_2$N(R$^L$)—, —N(R$^L$)SO$_2$N(R$^L$)—, or an optionally substituted C$_{1-10}$ saturated or unsaturated hydrocarbon chain, wherein one or more moieties selected from the group consisting of —O—, —N(R$^L$)—, —S—, —C(O)—, —C(O)O—, —C(O)S—, —C(O)N(R$^L$)—, —C(O)N(R$^L$)N(R$^L$)—, —OC(O)—, —OC(O)N(R$^L$)—, —NR$^L$C(O)—, —NR$^L$C(O)N(R$^L$)—, —NR$^L$C(O)N(R$^L$)N(R$^L$)—, —NR$^L$C(O)O—, —SC(O)—, —C(=NR$^L$)—, —C(=NNR$^L$)—, —C(=NOR$^L$)—, —C(=NR$^L$)N(R$^L$)—, —NR$^L$C(=NR$^L$)—, —C(S)—, —C(S)N(R$^L$)—, —NR$^L$C(S)—, —S(O)—, —OS(O)$_2$—, —S(O)$_2$O—, —SO$_2$—, —N(R$^L$)SO$_2$—, —SO$_2$N(R$^L$)—, and —N(R$^L$)SO$_2$N(R$^L$)— is optionally and independently present between two carbon atoms of the hydrocarbon chain, and is optionally and independently present at one or both ends of the hydrocarbon chain;

each R$^L$ is independently hydrogen, optionally substituted alkyl, or a nitrogen protecting group, or R$^L$ and R$^3$ taken together form an optionally substituted heterocyclyl or optionally substituted heteroaryl ring, or R$^L$ and R$^{13}$ taken together form an optionally substituted heterocyclyl or optionally substituted heteroaryl ring;

R$^3$ is hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl, provided when R$^3$ is hydrogen, then L$^1$ is not a bond; and R$^{13}$ is optionally substituted carbocyclyl, optionally substituted heterocyclyl, optionally substituted aryl, or optionally substituted heteroaryl.

2. The compound of claim 1, wherein X is —O—.

3. The compound of claim 1, wherein X is —S— or —CH$_2$—.

4. The compound of claim 1, wherein Ring HET is:

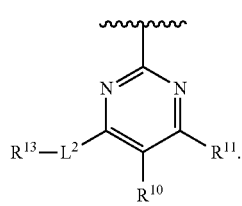

5. The compound of claim 1, wherein Ring HET is:

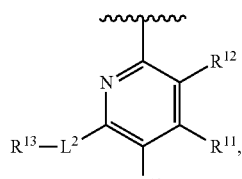

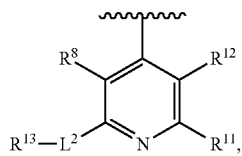

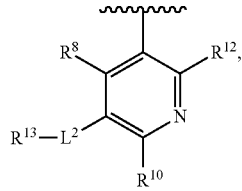

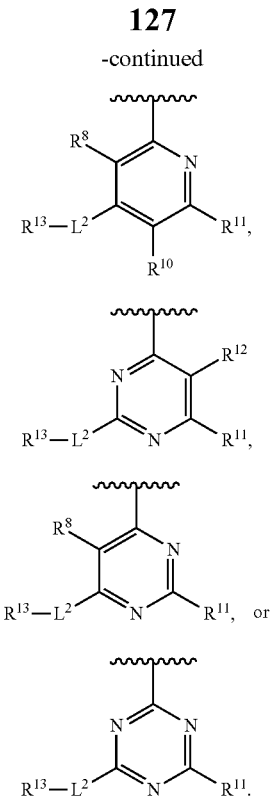

6. The compound of claim 1, wherein $R^1$ is hydrogen, methyl, ethyl, n-propyl, isopropyl, or cyclopropyl.

7. The compound of claim 1, wherein $R^{2a}$, $R^{2b}$, and $R^{2d}$ are hydrogen.

8. The compound of claim 1, wherein at least one of $R^{2a}$, $R^{2b}$, $R^{2c}$, and $R^{2d}$ is halo.

9. The compound of claim 1, wherein $L^2$ is a bond, —N($R^L$)—, —N$R^L$C(O)O—, —N$R^L$C(O)N($R^L$)—, —N($R^L$)—, —N($R^L$)SO$_2$N($R^L$)—, —N$R^L$—(CH$_2$)$_x$—C(O)O—, —N$R^L$—(CH$_2$)$_x$—O—, —N$R^L$C(O)N($R^L$)—, —N$R^L$—(CH$_2$)$_x$—, —(CH$_2$)$_x$—N$R^L$—, —N$R^L$C(O)O(CH$_2$)$_x$—, —N$R^L$C(O)N$R^L$(CH$_2$)$_x$—, or —N$R^L$(CH$_2$)$_x$N-$R^L$C(O)—, wherein x is 1, 2, 3, 4, 5, 6, 7, 8, 9, or 10.

10. The compound of claim 1, wherein $R^{13}$ is selected from the group consisting of:

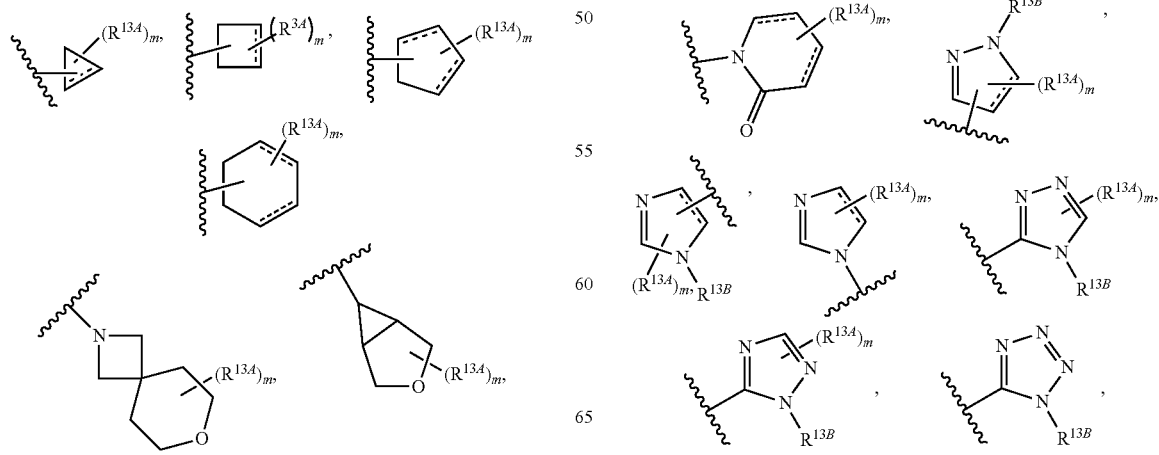

-continued

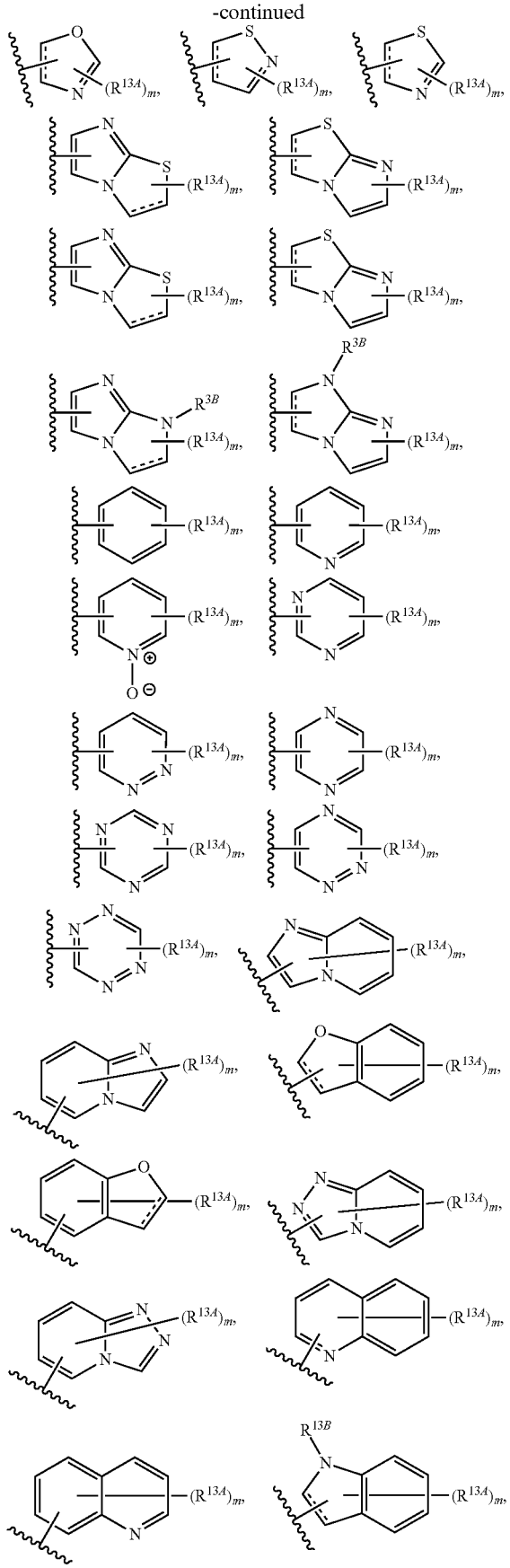

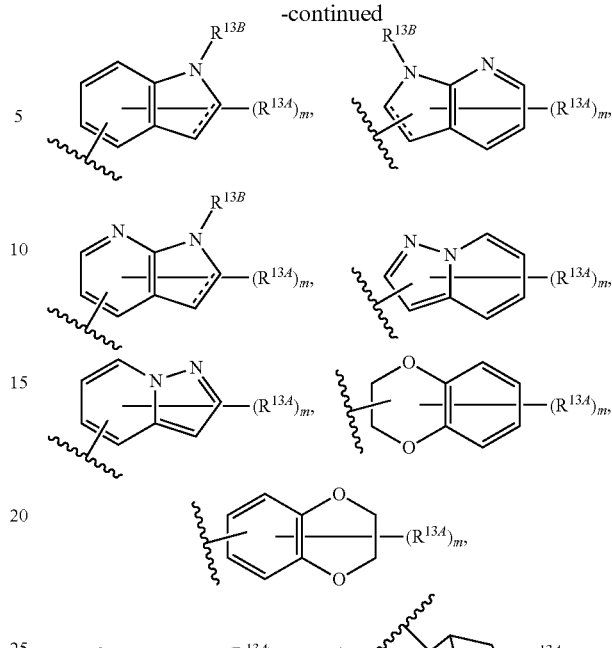

wherein:
each instance of ≈ independently represents a single or double bond;
m is 0, 1, 2, or 3;
each instance of $R^{13A}$ is independently hydroxyl, substituted hydroxyl, thiol, substituted thiol, amino, substituted amino, carbonyl, sulfonyl, sulfinyl, —CN, —NO$_2$, halogen, or optionally substituted alkyl, or two $R^{13A}$ groups are joined to form an optionally substituted carbocyclic, optionally substituted heterocyclic, optionally substituted aryl, or optionally substituted heteroaryl ring, or $R^{13A}$ and $R^{13B}$ group are joined to form an optionally substituted carbocyclic, optionally substituted heterocyclic, optionally substituted aryl, or optionally substituted heteroaryl ring; and
$R^{3B}$ and $R^{13B}$ are independently hydrogen, optionally substituted alkyl, or a nitrogen protecting group.

11. The compound of claim 1, wherein Ring HET comprises a group -L$^1$-R$^3$ is attached thereto.

12. The compound of claim 11, wherein L$^1$ is a bond, —N(R$^L$)—, —NR$^L$C(O)O—, —NR$^L$C(O)N(R$^L$)—, —N(R$^L$)—, —N(R$^L$)SO$_2$N(R$^L$)—, —NR$^L$—(CH$_2$)$_x$—C(O) O—, —NR$^L$—(CH$_2$)$_x$—O—, —NR$^L$C(O)N(R$^L$)—, —NR$^L$—(CH$_2$)$_x$—, —(CH$_2$)$_x$—NR$^L$—, —NR$^L$C(O)O (CH$_2$)$_x$—, —NR$^L$C(O)NR$^L$(CH$_2$)$_x$—, or —NR$^L$(CH$_2$)$_x$N-R$^L$C(O)—, wherein x is 1, 2, 3, 4, 5, 6, 7, 8, 9, or 10.

13. The compound of claim 11, wherein R$^3$ is selected from the group consisting of:

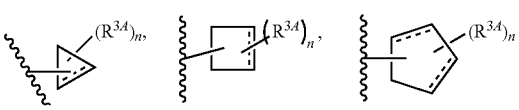

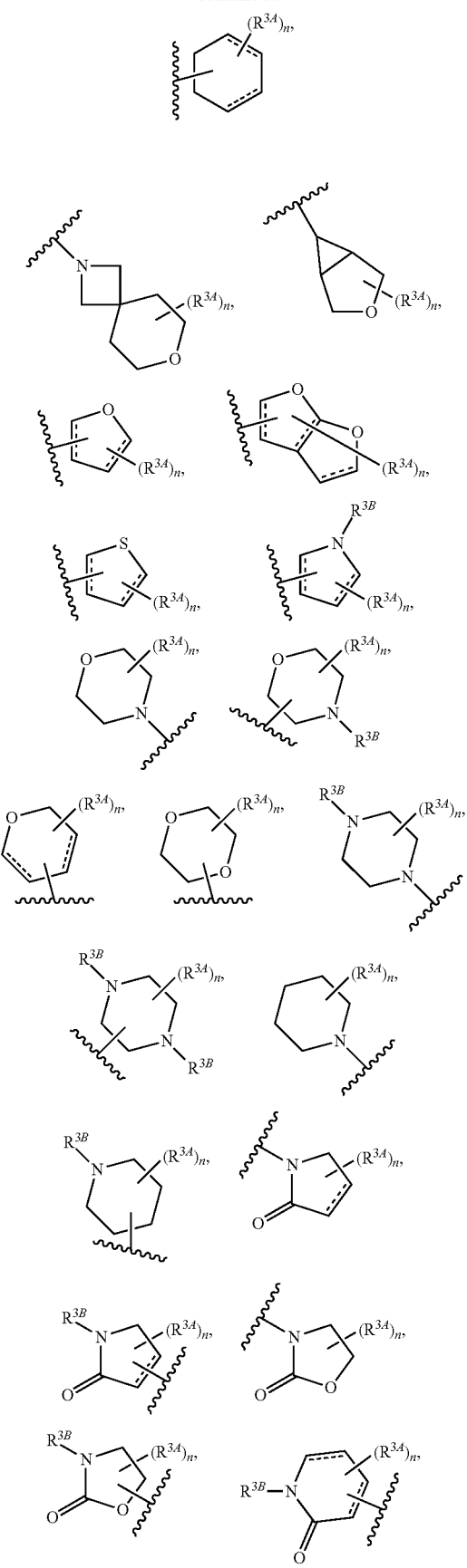
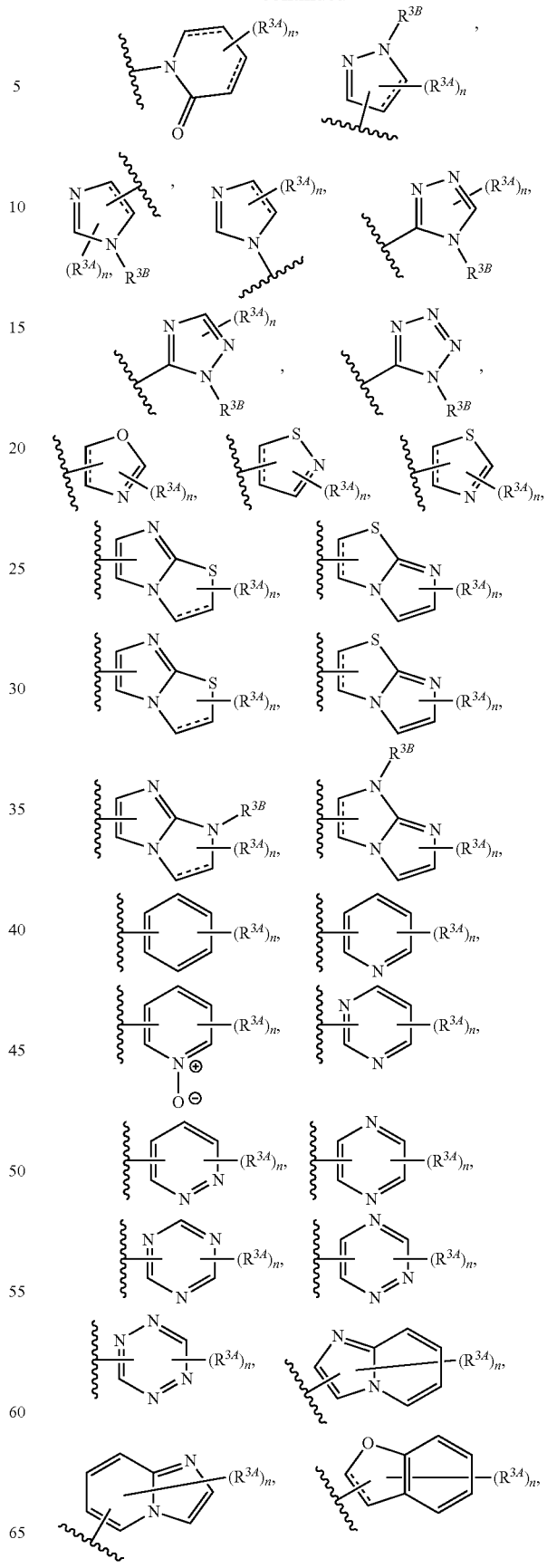

-continued

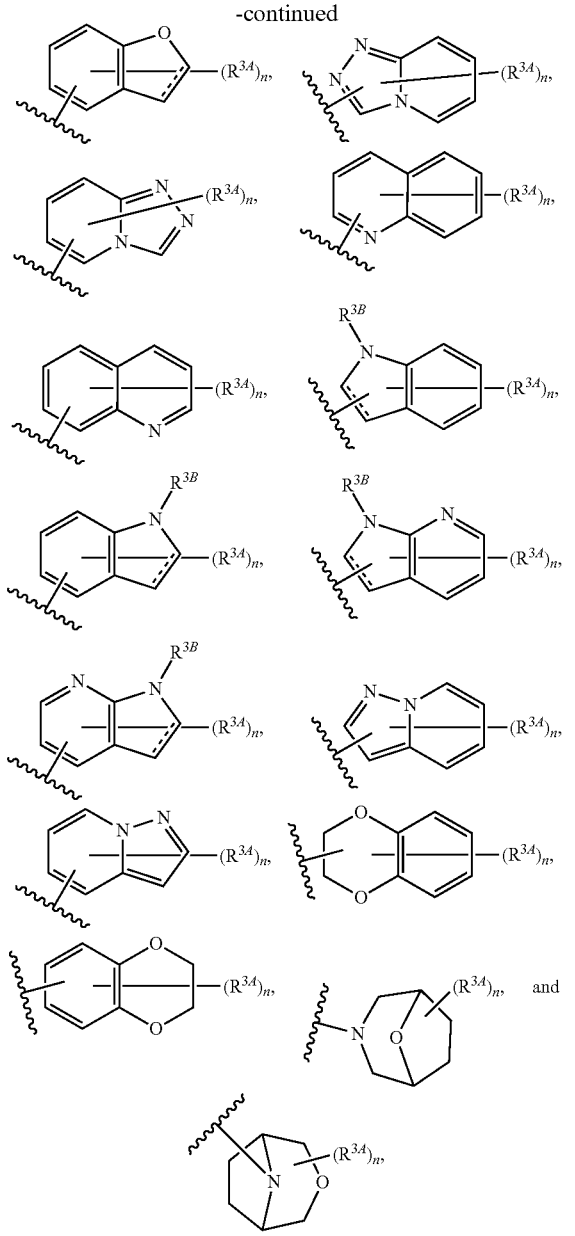

wherein:

each instance of ----- independently represents a single or double bond;

n is 0, 1, 2, or 3;

each instance of $R^{3A}$ is independently hydroxyl, substituted hydroxyl, thiol, substituted thiol, amino, substituted amino, carbonyl, sulfonyl, sulfinyl, —CN, —NO$_2$, halogen, or optionally substituted alkyl, or two $R^{3A}$ groups are joined to form an optionally substituted carbocyclic, optionally substituted heterocyclic, optionally substituted aryl, or optionally substituted heteroaryl ring, or $R^{3A}$ and $R^{3B}$ groups are joined to form an optionally substituted carbocyclic, optionally substituted heterocyclic, optionally substituted aryl, or optionally substituted heteroaryl ring; and $R^{3B}$ is hydrogen, optionally substituted alkyl, or a nitrogen protecting group.

14. The compound of claim 1, wherein the compound is selected from the group consisting of:

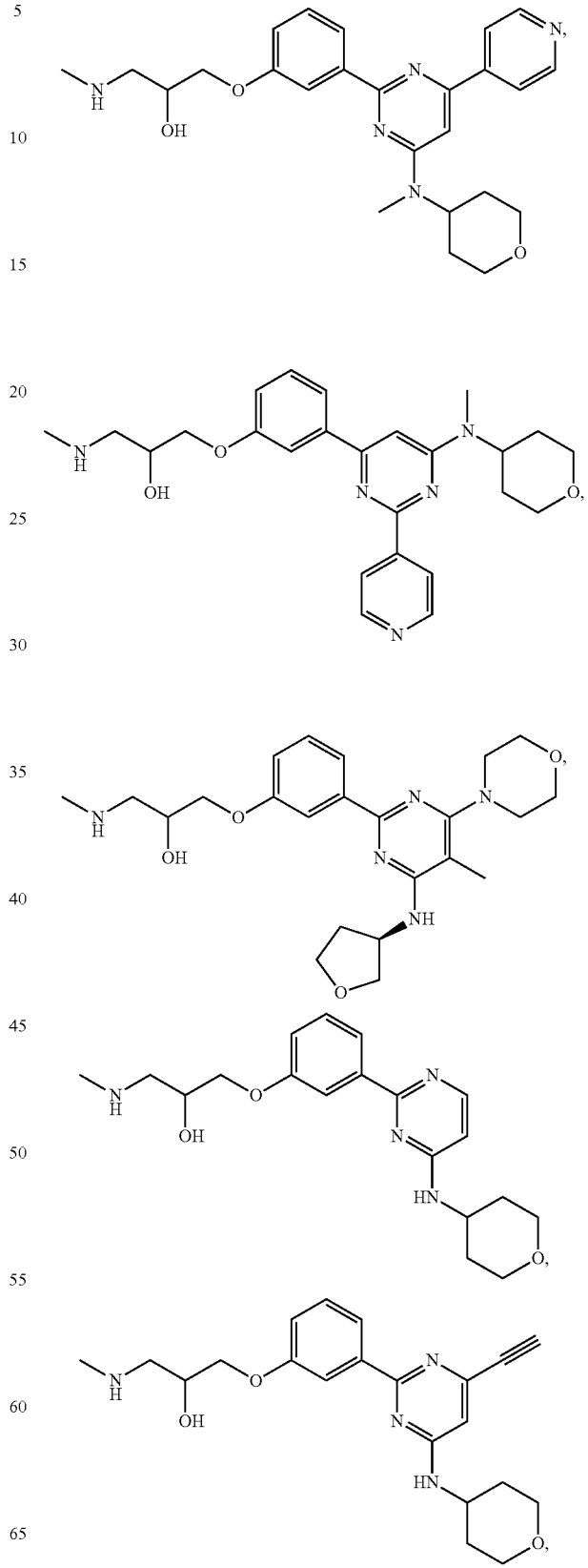

135
-continued
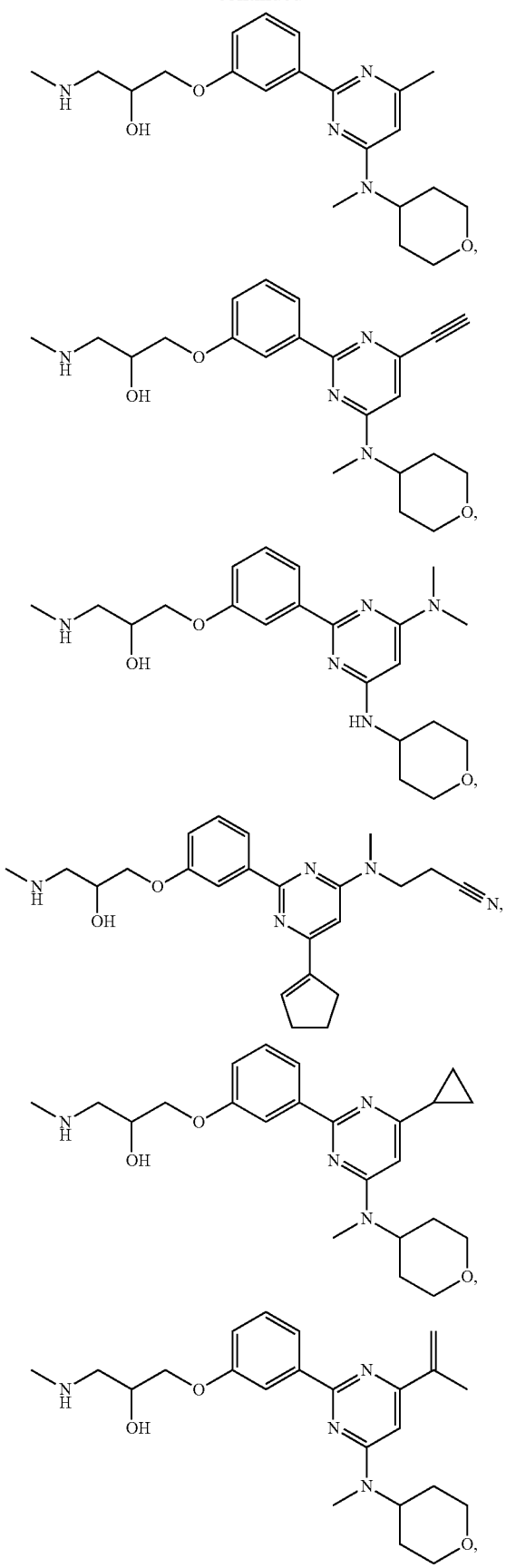
136
-continued
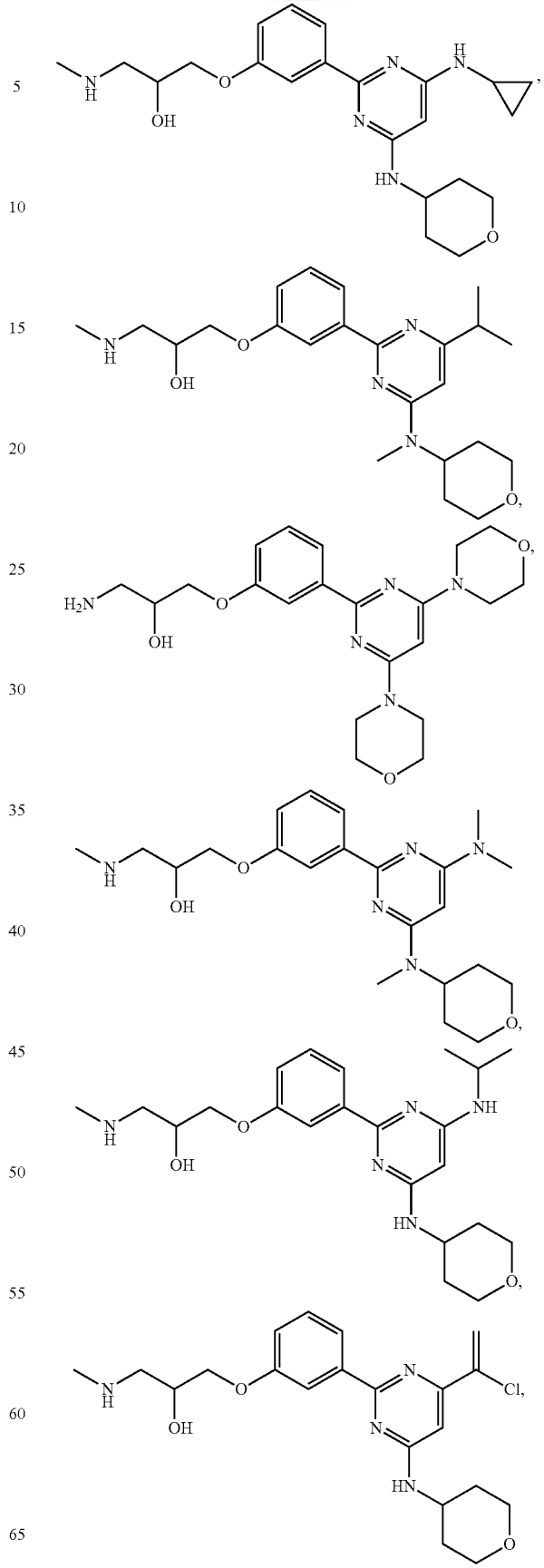

137
-continued
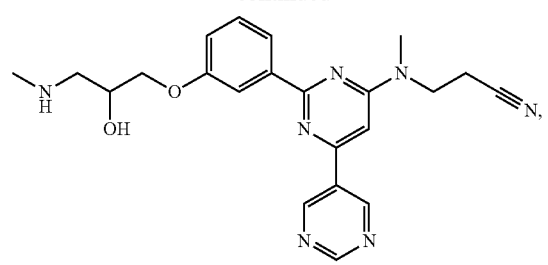
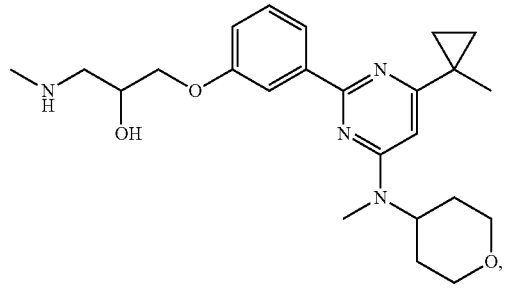
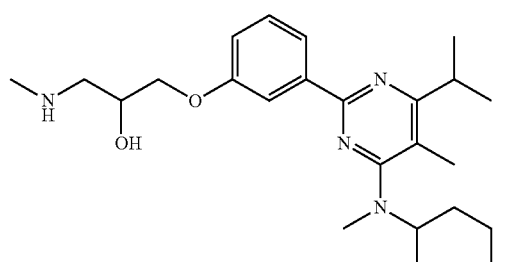
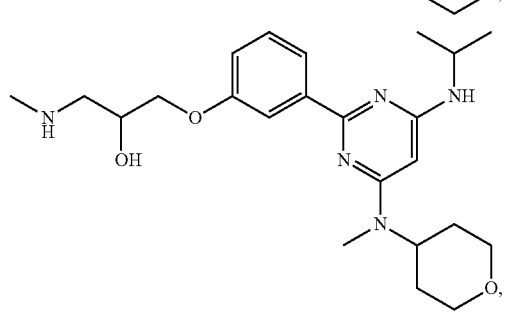
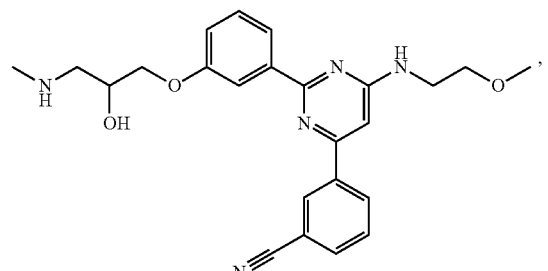
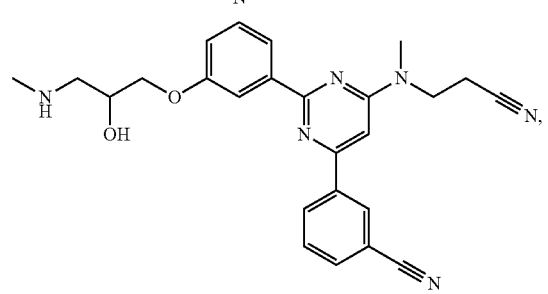
138
-continued
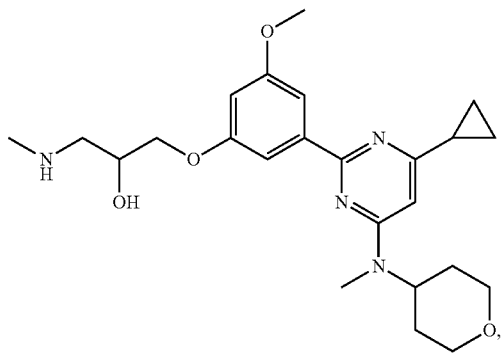
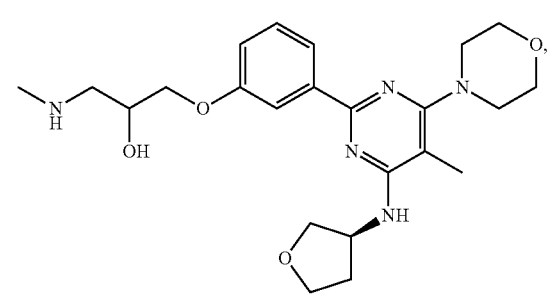
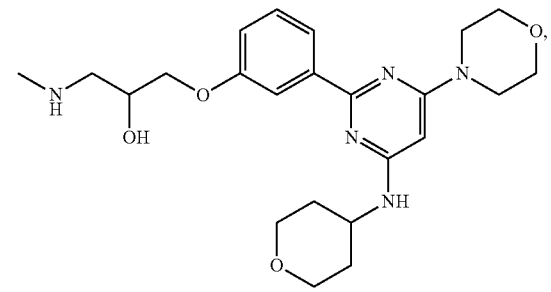
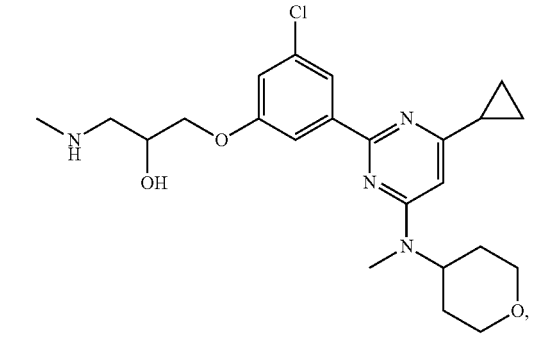
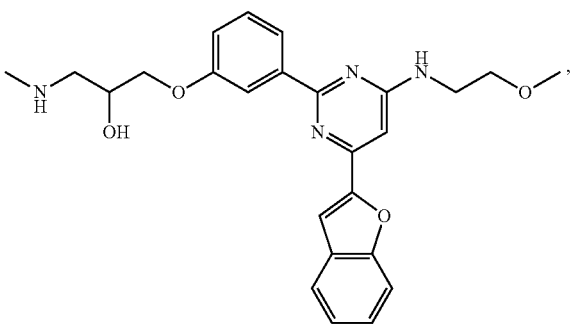

139
-continued
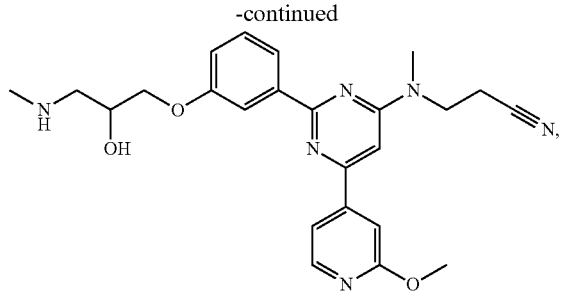
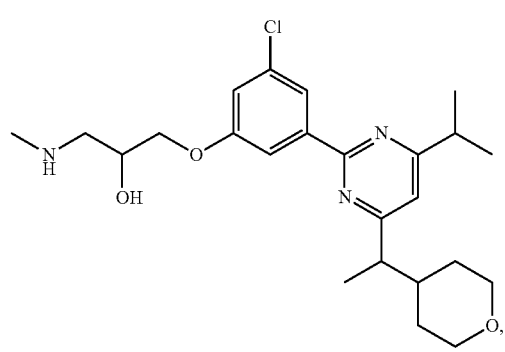
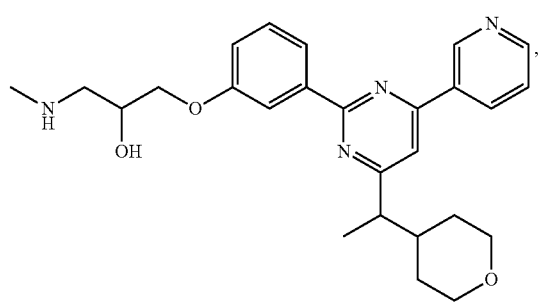
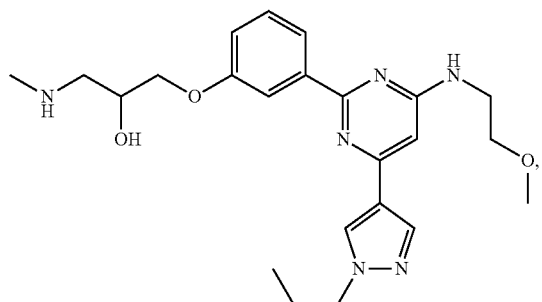
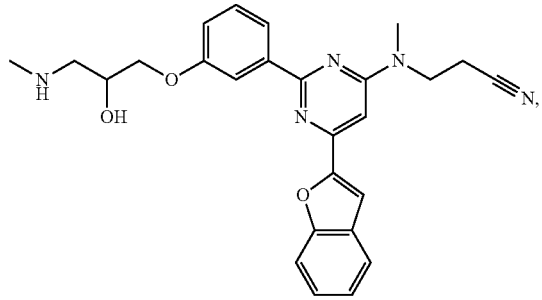
140
-continued
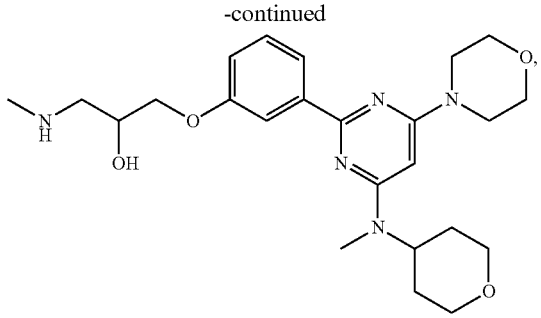
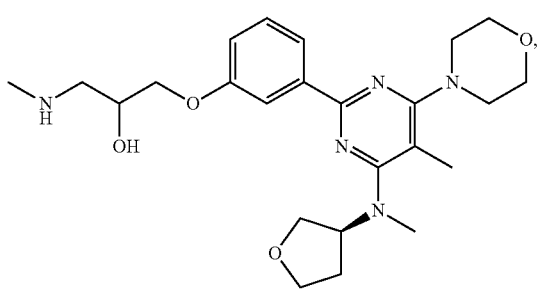
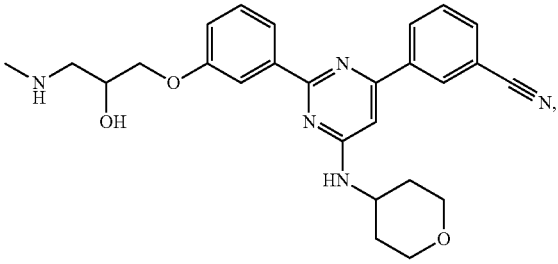
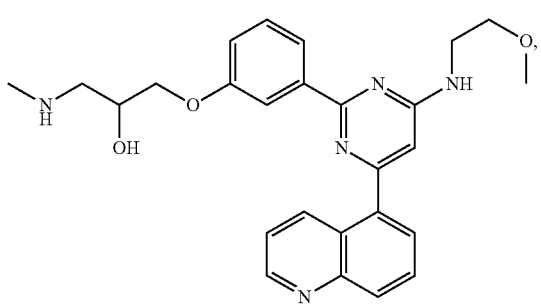
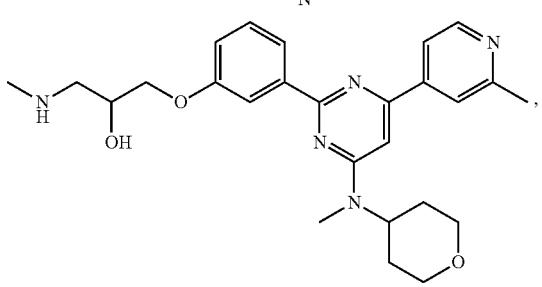

141
-continued
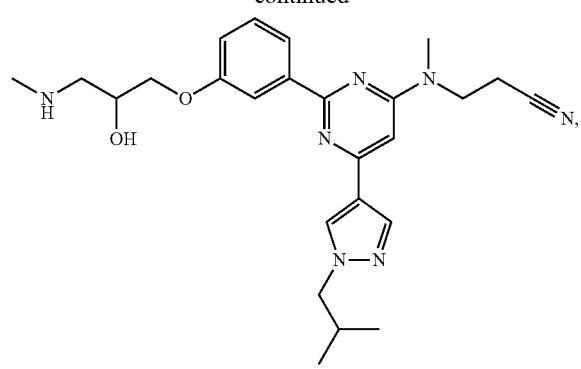
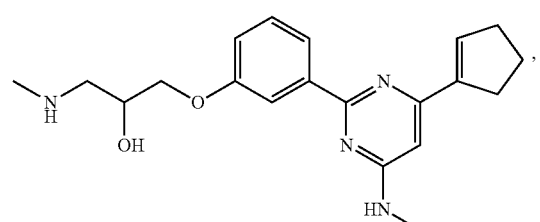
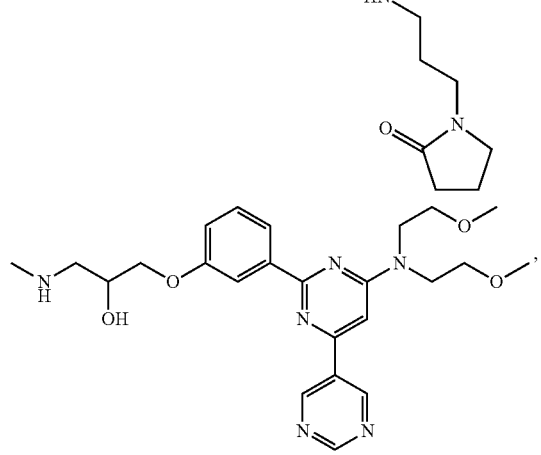
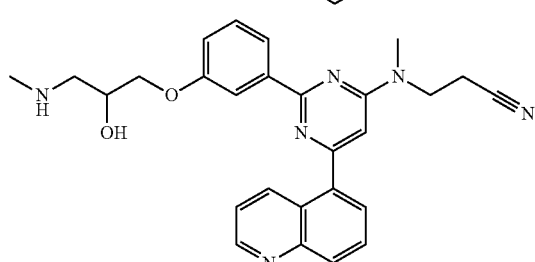
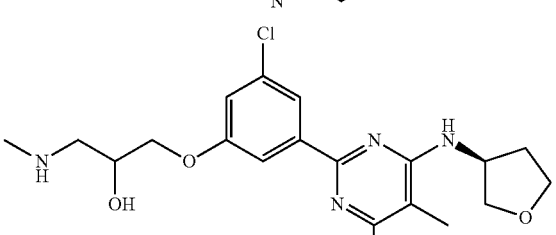
142
-continued
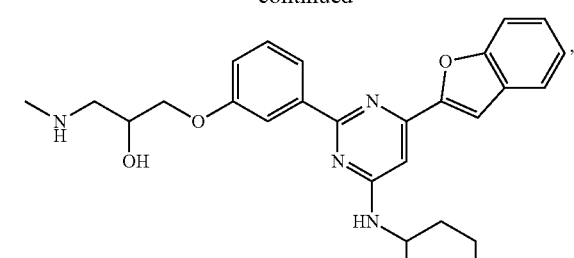
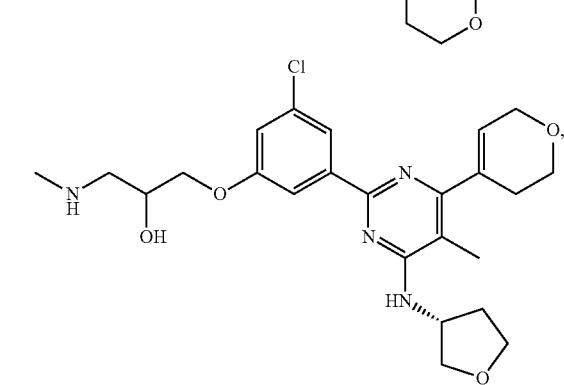
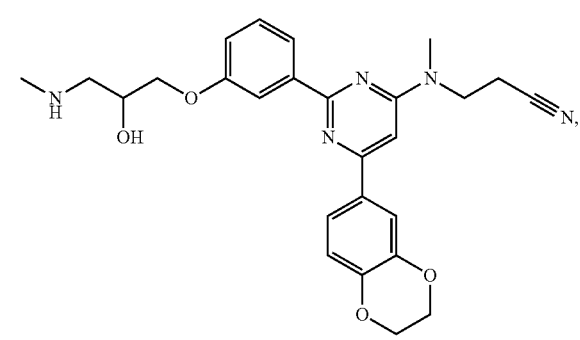
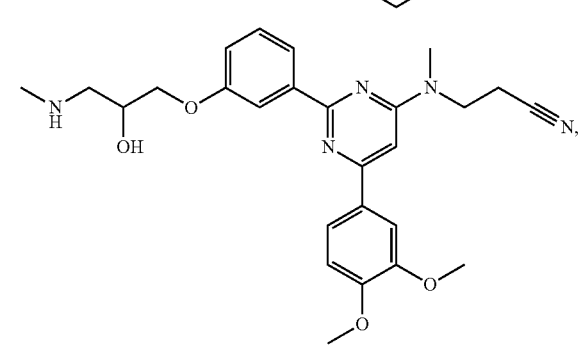
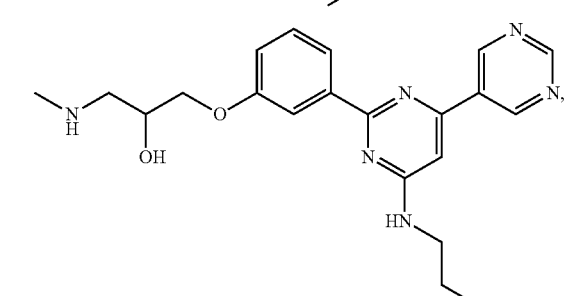

143
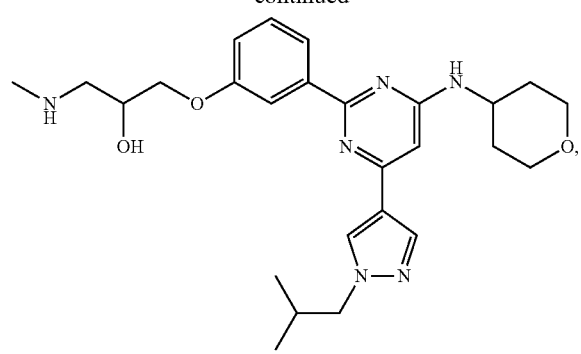
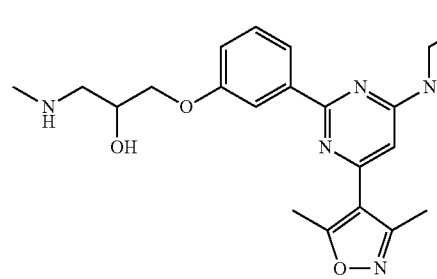
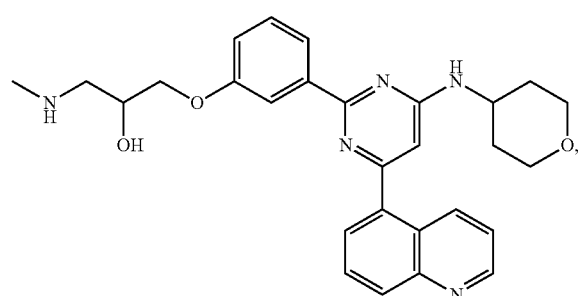
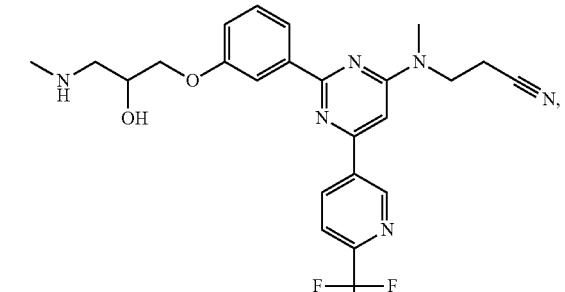
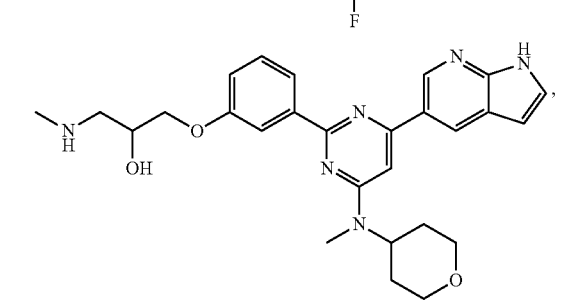
144
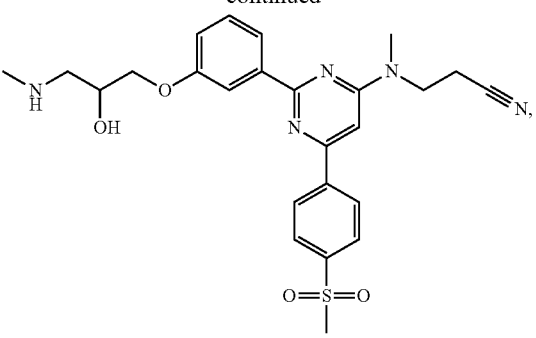
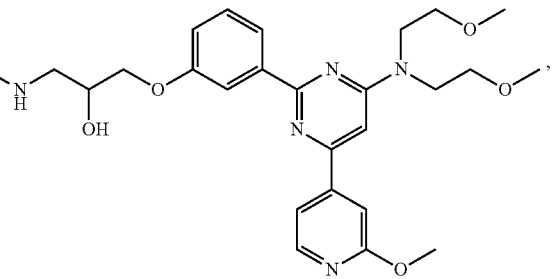
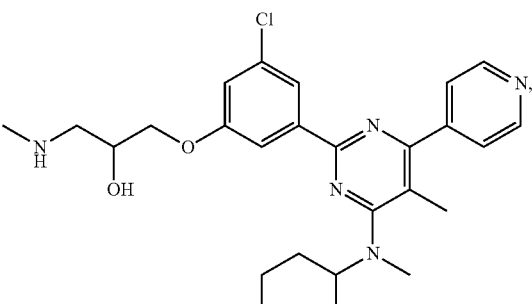
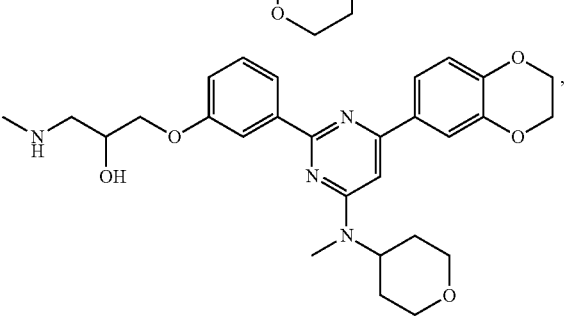
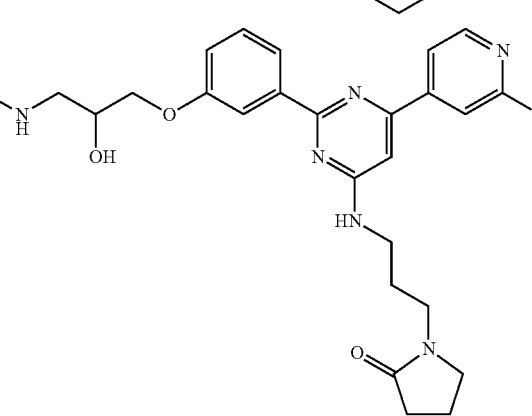

145
-continued
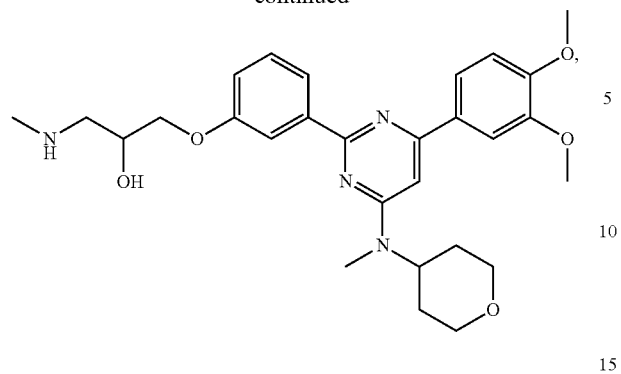
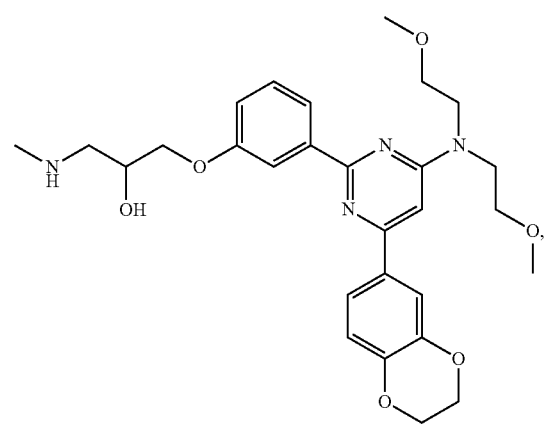
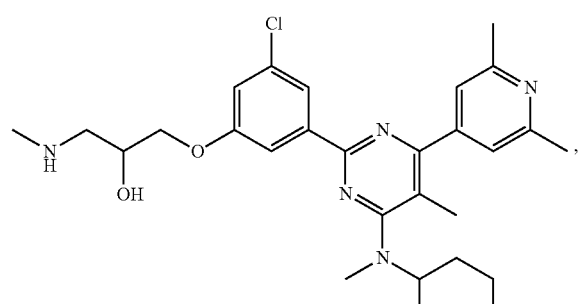
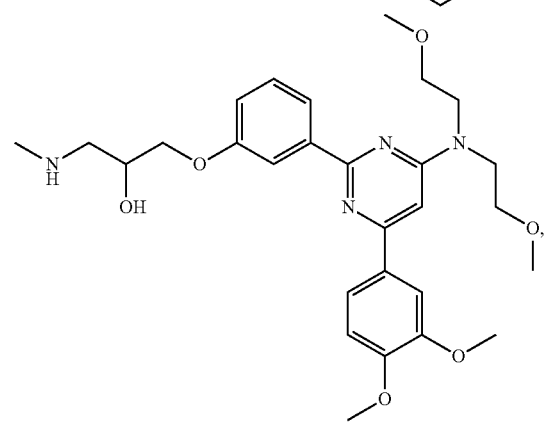
146
-continued
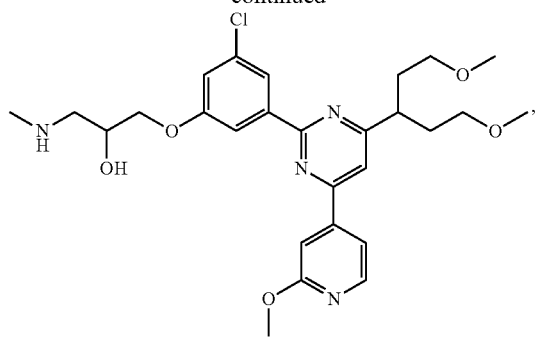
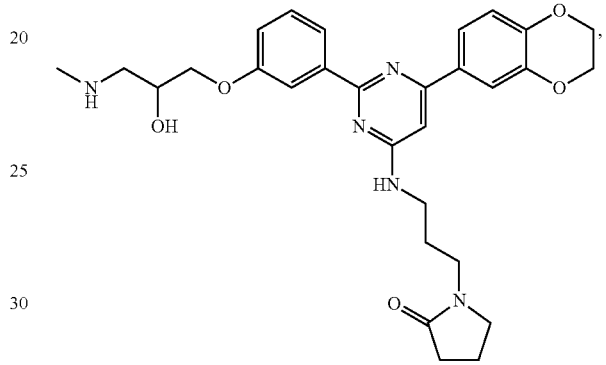
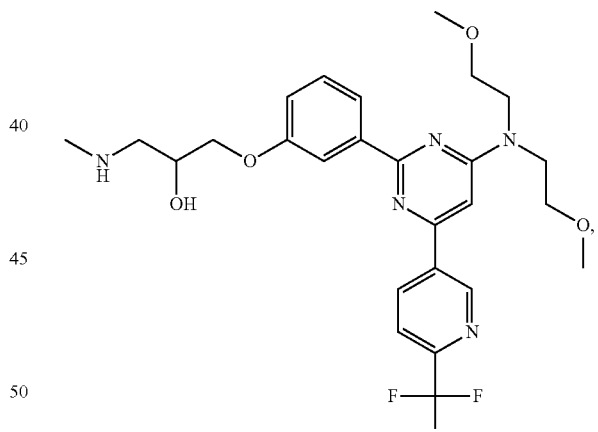
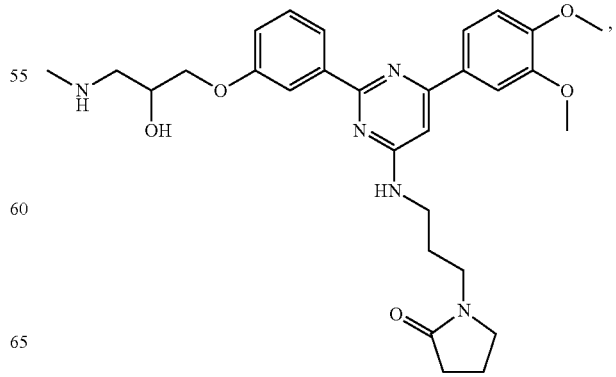

147
-continued
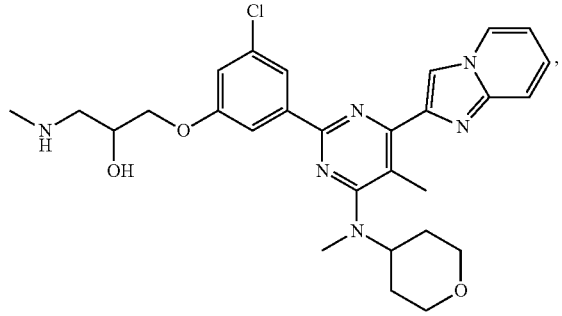
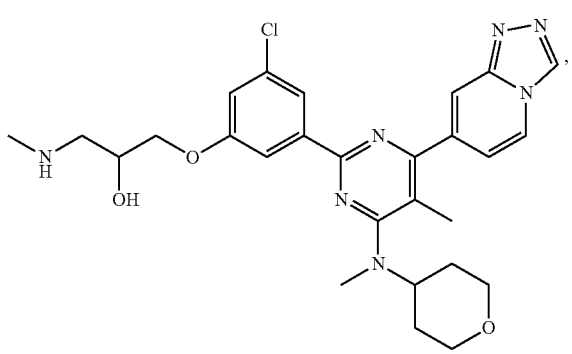
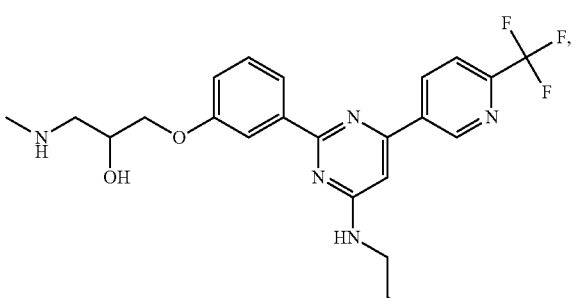
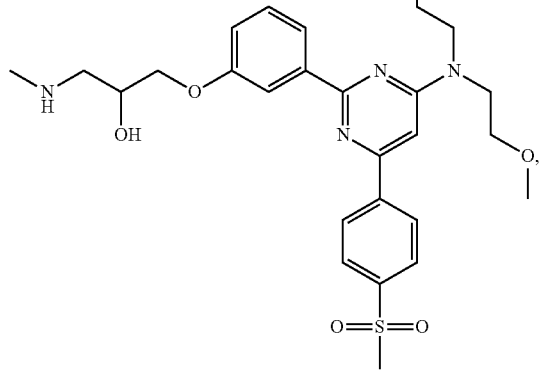
148
-continued
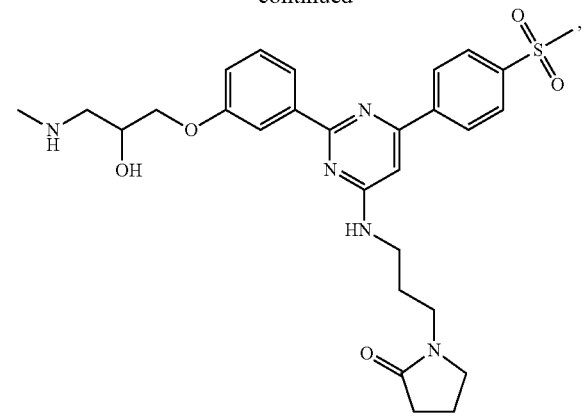
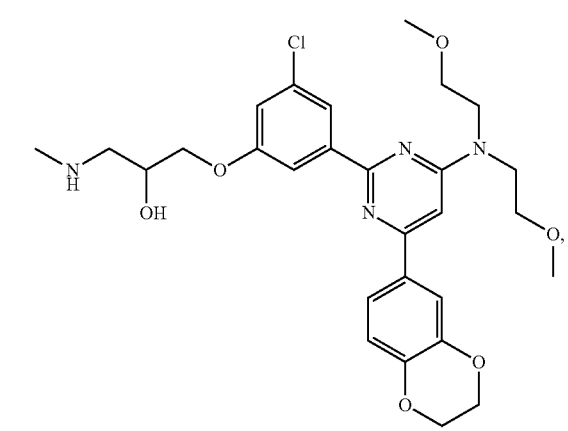
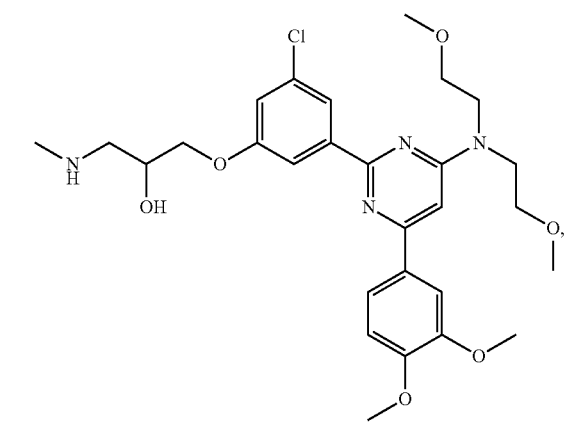
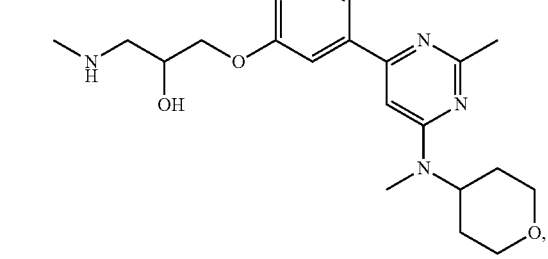

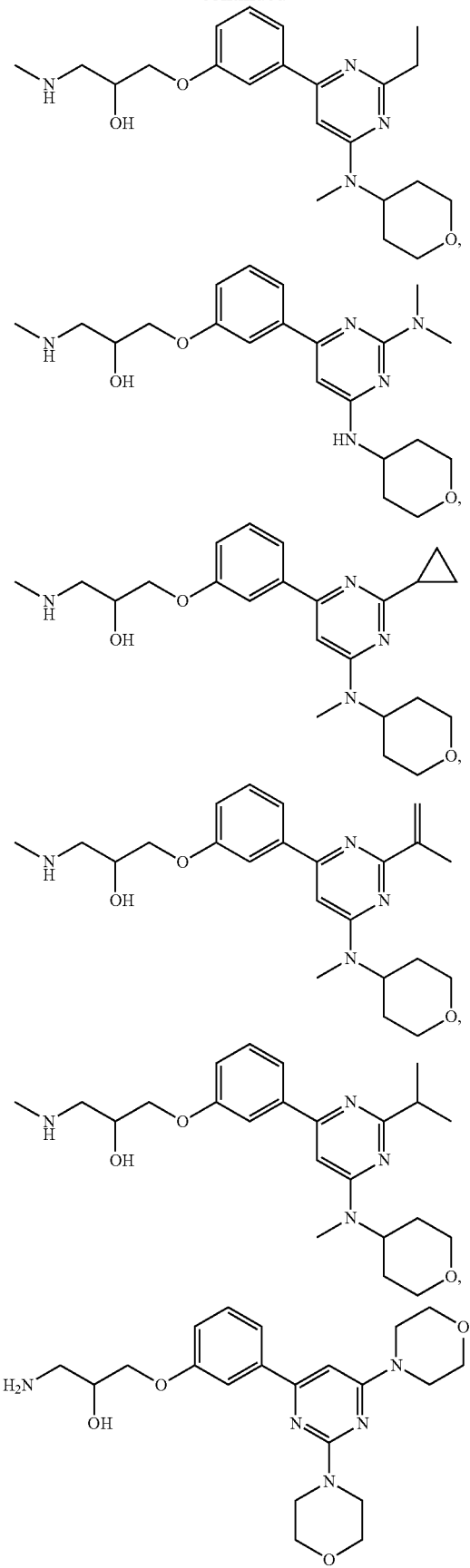
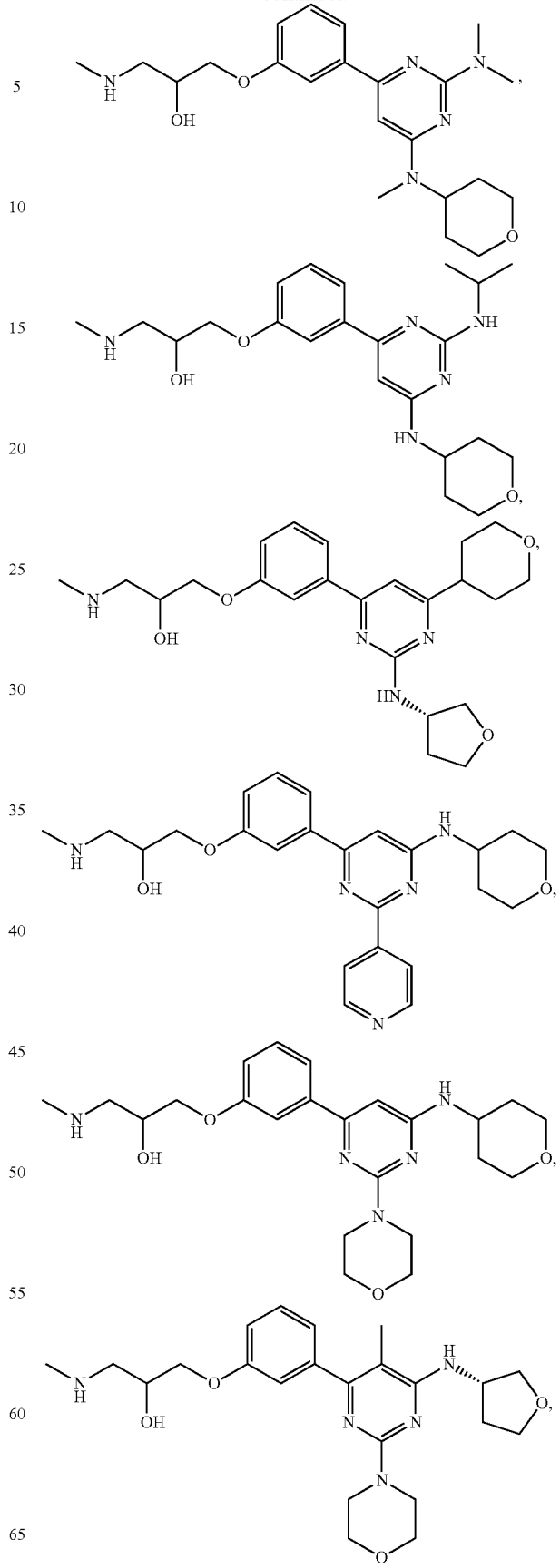

-continued

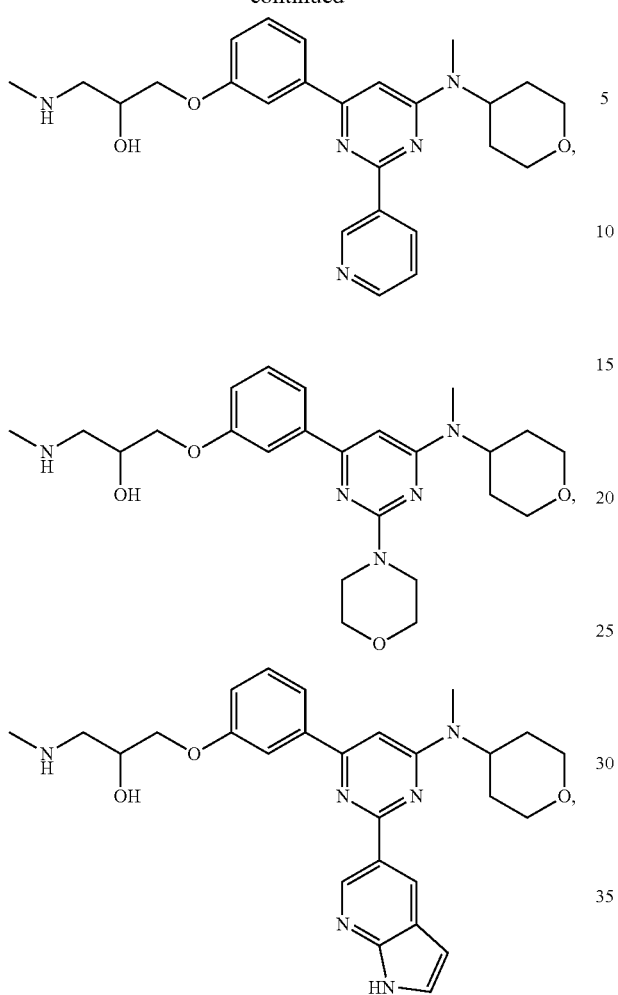

and pharmaceutically acceptable salts thereof.

15. A pharmaceutical composition comprising a compound of claim 1 or a pharmaceutically acceptable salt thereof, and a pharmaceutically acceptable excipient.

16. The compound of claim 1, wherein Ring HET is a 6-membered monocyclic heteroaryl ring system of the formula:

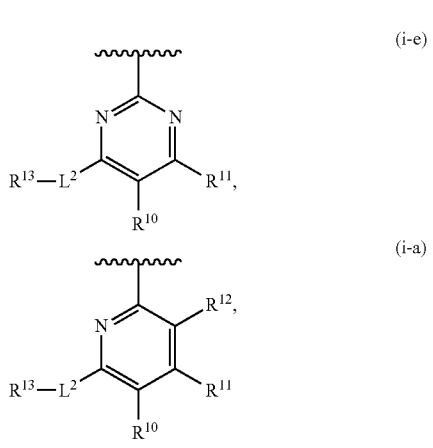

-continued

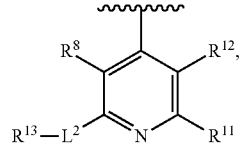

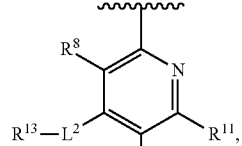

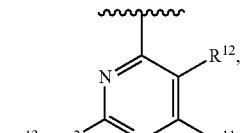

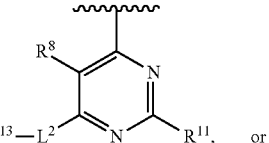

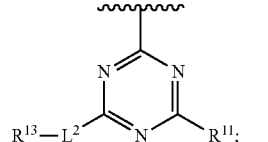

each instance of $R^8$, $R^{10}$, and $R^{12}$ is independently selected from the group consisting of hydrogen, halo, —CN, —NO$_2$, —C(=O)R', —C(=O)OR', —C(=O)N(R')$_2$, and optionally substituted alkyl;

$R^{11}$ is -$L^1$-$R^3$; and $R^3$ is optionally substituted alkyl, optionally substituted alkenyl, optionally substituted alkynyl, optionally substituted carbocyclyl, optionally substituted heterocyclyl, optionally substituted aryl, or optionally substituted heteroaryl.

17. A compound of Formula (I):

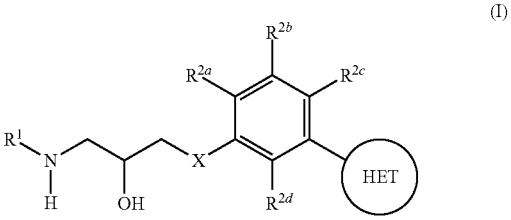

or a pharmaceutically acceptable salt thereof;
wherein:
X is —O—, —S—, or —CH$_2$—;
$R^1$ is hydrogen or optionally substituted C$_{1-4}$ aliphatic;
each of $R^{2a}$, $R^{2b}$, $R^{2c}$, and $R^{2d}$ is independently hydrogen, halogen, —CN, —NO$_2$, —C(=O)R$^{A2}$, —C(=O)OR$^{A2}$, —C(=O)N(R$^{A2}$)$_2$, —OR$^{A2}$, —SR$^{A2}$, —N(R$^{A2}$)$_2$, —S(=O)R$^{A2}$, —S(=O)$_2$R$^{A2}$, optionally substituted alkyl, optionally substituted alkenyl, optionally substituted alkynyl, optionally substituted carbocyclyl, or optionally substituted heterocyclyl, wherein each instance of $R^{A2}$ is independently hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl, or two $R^{A2}$ groups attached to the same nitrogen atom are joined to form an optionally substituted heterocyclyl or optionally substituted heteroaryl ring;

Ring HET is a 6-membered monocyclic heteroaryl ring system of the formula:

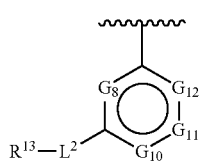

wherein:
$G_8$ is C—$R^8$ or N;
$G_{10}$ is C—$R^{10}$ or N;
$G_{11}$ is C—$R^{11}$ or N;
$G_{12}$ is C—$R^{12}$ or N;
provided at least one instance of $G_8$, $G_{10}$, $G_{11}$, or $G_{12}$ is N;
each instance of $R^8$, $R^{10}$, $R^{11}$, and $R^{12}$ is independently selected from the group consisting of hydrogen, halo, —CN, —NO$_2$, —C(=O)R', —C(=O)OR', —C(=O)N(R')$_2$, optionally substituted alkyl, and -L$^1$-R$^3$;
each instance of R' is independently hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl, or two R' groups attached to the same nitrogen are joined to form an optionally substituted heterocyclyl ring or optionally substituted heteroaryl ring;
each instance of $L^1$ and $L^2$ is independently a bond, —O—, —N(R$^L$)—, —S—, —C(O)—, —C(O)O—, —C(O)S—, —C(O)N(R$^L$)—, —C(O)N(R$^L$)N(R$^L$)—, —OC(O)—, —OC(O)N(R$^L$)—, —NR$^L$C(O)—, —NR$^L$C(O)N(R$^L$)—, —NR$^L$C(O)N(R$^L$)N(R$^L$)—, —NR$^L$C(O)O—, —SC(O)—, —C(=NR$^L$)—, —C(=NNR$^L$)—, —C(=NOR$^L$)—, —C(=NR$^L$)N(R$^L$)—, —NR$^L$C(=NR$^L$)—, —C(S)—, —C(S)N(R$^L$)—, —NR$^L$C(S)—, —S(O)—, —OS(O)$_2$—, —S(O)$_2$O—, —SO$_2$—, —N(R$^L$)SO$_2$—, —SO$_2$N(R$^1$)—, —N(R$^L$)SO$_2$N(R$^1$)—, or an optionally substituted C$_{1-10}$ saturated or unsaturated hydrocarbon chain, wherein one or more moieties selected from the group consisting of —O—, —N(R$^L$)—, —S—, —C(O)—, —C(O)O—, —C(O)S—, —C(O)N(R$^L$)—, —C(O)N(R$^L$)N(R$^L$)—, —OC(O)—, —OC(O)N(R$^L$)—, —NR$^L$C(O)—, —NR$^L$C(O)N(R$^L$)—, —NR$^L$C(O)N(R$^L$)N(R$^L$)—, —NR$^L$C(O)O—, —SC(O)—, —C(=NR$^L$)—, —C(=NNR$^L$)—, —C(=NOR$^L$)—, —C(=NR$^L$)N(R$^L$)—, —NR$^L$C(=NR$^L$)—, —C(S)—, —C(S)N(R$^L$)—, —NR$^L$C(S)—, —S(O)—, —OS(O)$_2$—, —S(O)$_2$O—, —SO$_2$—, —N(R$^L$)SO$_2$—, —SO$_2$N(R$^L$)—, and —N(R$^L$)SO$_2$N(R$^L$)— is optionally and independently present between two carbon atoms of the hydrocarbon chain, and is optionally and independently present at one or both ends of the hydrocarbon chain;

each $R^L$ is independently hydrogen, optionally substituted alkyl, or a nitrogen protecting group, or $R^L$ and $R^3$ taken together form an optionally substituted heterocyclyl or optionally substituted heteroaryl ring, or $R^L$ and $R^{13}$ taken together form an optionally substituted heterocyclyl or optionally substituted heteroaryl ring;

$R^3$ is hydrogen, optionally substituted alkyl, optionally substituted alkenyl, optionally substituted alkynyl, optionally substituted carbocyclyl, optionally substituted heterocyclyl, optionally substituted heteroaryl, or aryl unsubstituted or substituted with one or more substituents independently selected from the group consisting of halogen, —CN, —NO$_2$, —N$_3$, —SO$_2$H, —SO$_3$H, —OH, —OR$^{aa}$, —N(R$^{bb}$)$_2$, —SH, —SR$^{aa}$, —C(=O)R$^{aa}$, —CO$_2$H, —CHO, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, C$_1$ alkyl, C$_1$ perhaloalkyl, C$_{2-4}$ alkenyl, and C$_{2-4}$ alkynyl, provided when $R^3$ is hydrogen, then $L^1$ is not a bond; and $R^{13}$ is optionally substituted carbocyclyl, optionally substituted heterocyclyl, optionally substituted heteroaryl, or aryl unsubstituted or substituted with one or more substituents independently selected from the group consisting of halogen, —CN, —NO$_2$, —N$_3$, —SO$_2$H, —SO$_3$H, —OH, —OR$^{aa}$, —N(R$^{bb}$)$_2$, —SH, —SR$^{aa}$, —C(=O)R$^{aa}$, —CO$_2$H, —CHO, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, C$_1$ alkyl, C$_1$ perhaloalkyl, C$_{2-4}$ alkenyl, and C$_{2-4}$ alkynyl;

wherein:
each instance of $R^{aa}$ is, independently, C$_1$ alkyl; and
each instance of $R^{bb}$ is, independently, hydrogen or C$_1$ alkyl, or two $R^{bb}$ groups are joined to form a 3-6 membered heterocyclyl or 5-6 membered heteroaryl ring.

18. The compound of claim 17, wherein X is —O—.

19. The compound of claim 17, wherein X is —S— or —CH$_2$—.

20. The compound of claim 17, wherein Ring HET is:

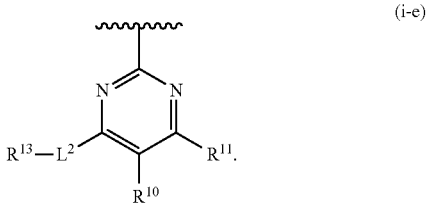

(i-e)

21. The compound of claim 17, wherein Ring HET is:

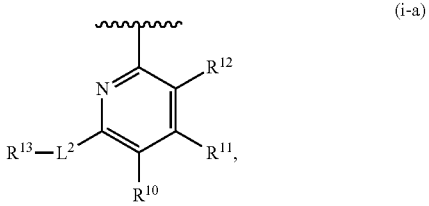

(i-a)

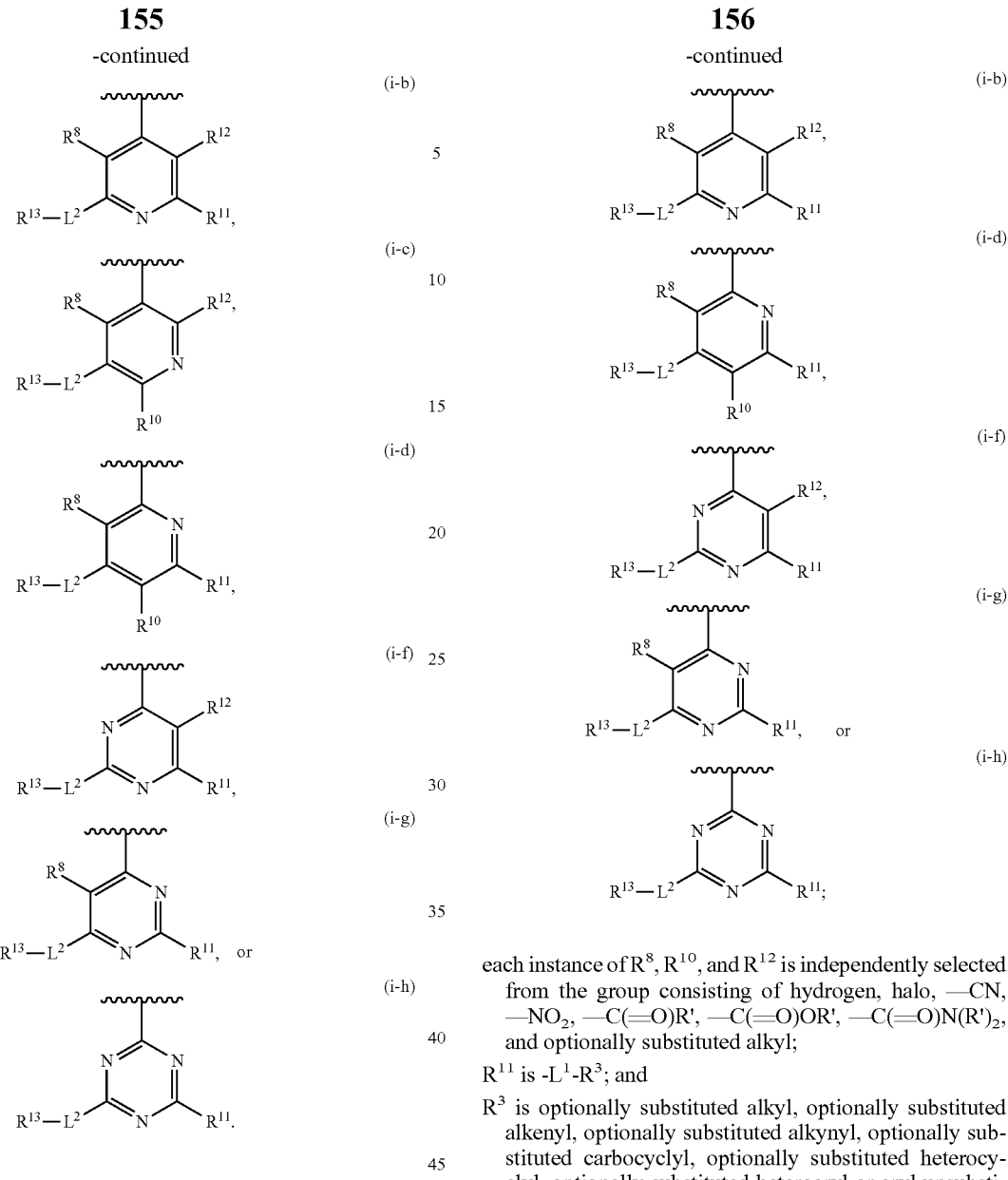

22. The compound of claim 17, wherein Ring HET is a 6-membered monocyclic heteroaryl ring system of the formula:

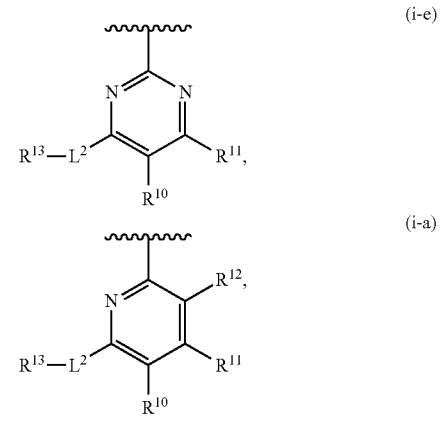

each instance of $R^8$, $R^{10}$, and $R^{12}$ is independently selected from the group consisting of hydrogen, halo, —CN, —NO$_2$, —C(=O)R', —C(=O)OR', —C(=O)N(R')$_2$, and optionally substituted alkyl;

$R^{11}$ is -L$^1$-R$^3$; and $R^3$ is optionally substituted alkyl, optionally substituted alkenyl, optionally substituted alkynyl, optionally substituted carbocyclyl, optionally substituted heterocyclyl, optionally substituted heteroaryl or aryl unsubstituted or substituted with one or more substituents independently selected from the group consisting of halogen, —CN, —NO$_2$, —N$_3$, —SO$_2$H, —SO$_3$H, —OH, —OR$^{aa}$, —N(R$^{bb}$)$_2$, —SH, —SR$^{aa}$, —C(=O) R$^{aa}$, —CO$_2$H, —CHO, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, C$_1$ alkyl, C$_1$ perhaloalkyl, C$_2$ alkenyl, and C$_2$ alkynyl.

23. The compound of claim 17, wherein $R^1$ is hydrogen, methyl, ethyl, n-propyl, isopropyl, or cyclopropyl.

24. The compound of claim 17, wherein $R^{2a}$, $R^{2b}$, and $R^{2d}$ are hydrogen.

25. The compound of claim 17, wherein at least one of $R^{2a}$, $R^{2b}$, $R^{2c}$, and $R^{2d}$ is halo.

26. The compound of claim 17, wherein L$^2$ is a bond, —N(R$^L$)—, —NR$^L$C(O)O—, —NR$^L$C(O)N(R$^L$)—, —N(R$^L$)—, —N(R$^L$)SO$_2$N(R$^L$)—, —NR$^L$—(CH$_2$)$_x$—C(O) O—, —NR$^L$—(CH$_2$)$_x$—O—, —NR$^L$C(O)N(R$^L$)—, —NR$^L$—(CH$_2$)$_x$—, —(CH$_2$)$_x$—NR$^L$—, —NR$^L$C(O)O (CH$_2$)$_x$—, —NR$^L$C(O)NR$^L$(CH$_2$)$_x$—, or —NR$^L$(CH$_2$)$_x$N-R$^L$C(O)—, wherein x is 1, 2, 3, 4, 5, 6, 7, 8, 9, or 10.

27. The compound of claim 17, wherein $R^{13}$ is selected from the group consisting of:
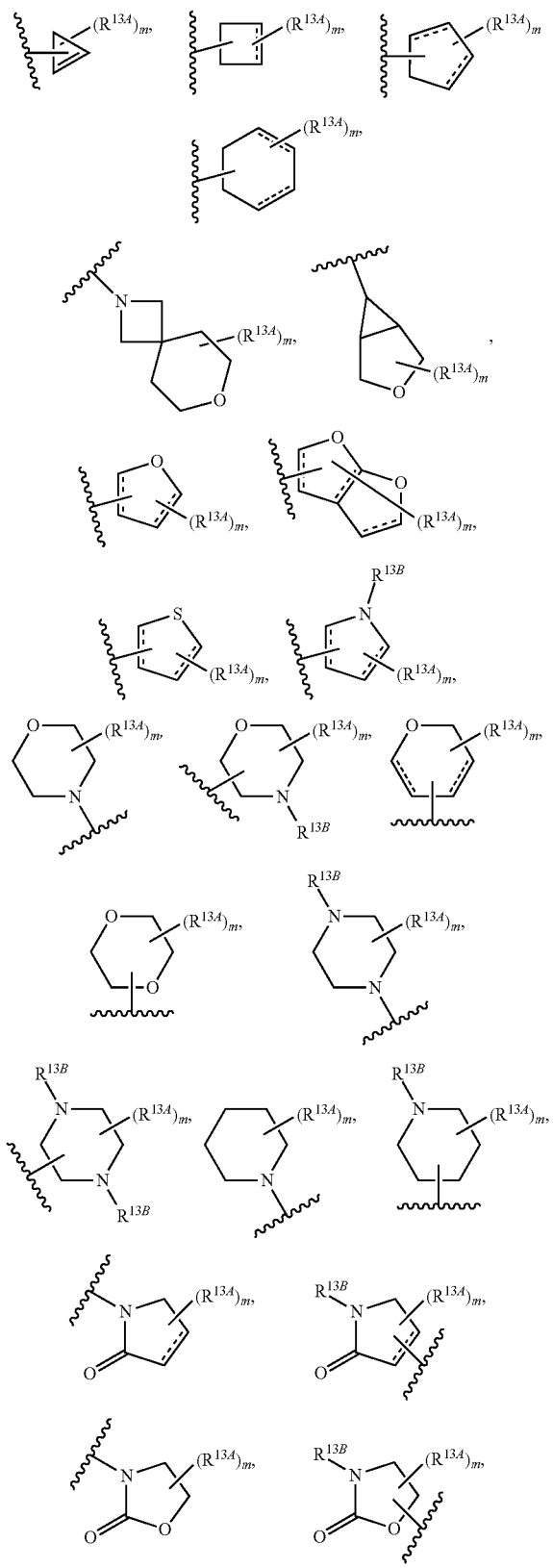
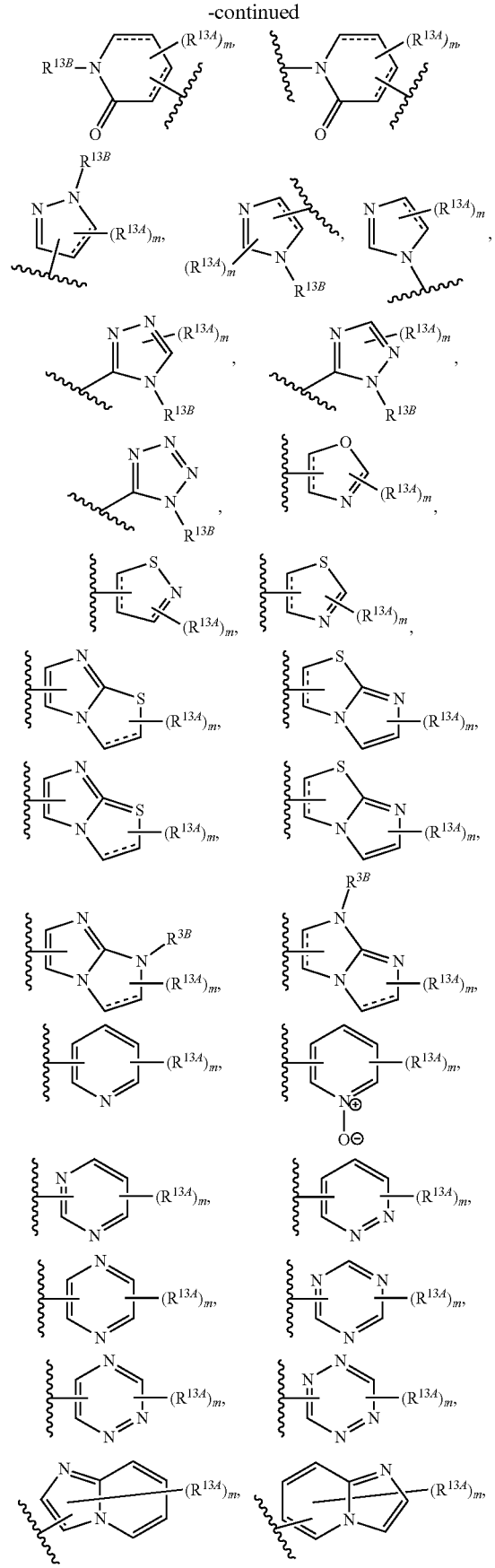

-continued

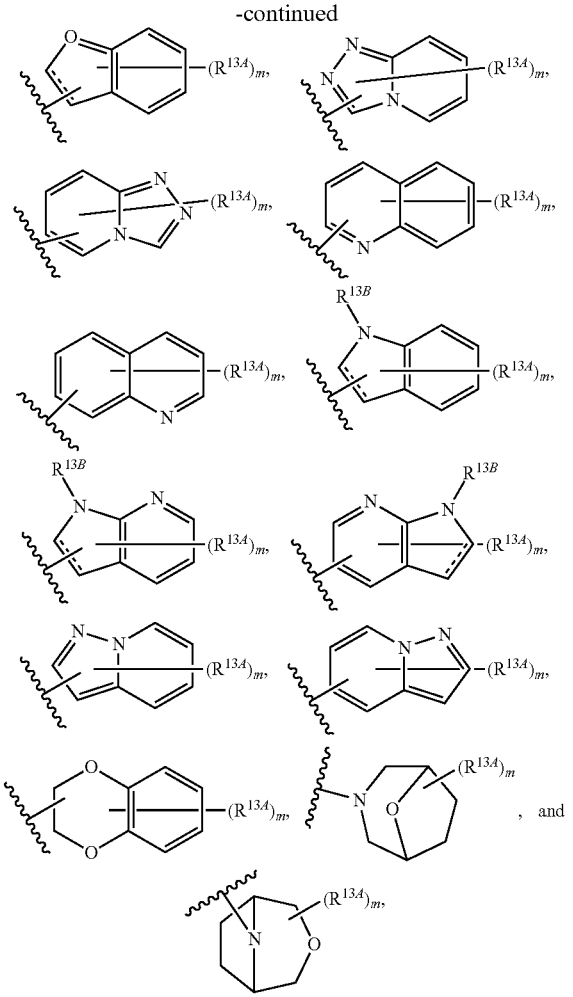

wherein:
- each instance of ≈≈≈ independently represents a single or double bond;
- m is 0, 1, 2, or 3;
- each instance of $R^{13A}$ is independently hydroxyl, substituted hydroxyl, thiol, substituted thiol, amino, substituted amino, carbonyl, sulfonyl, sulfinyl, —CN, —NO$_2$, halogen, or optionally substituted alkyl, or two $R^{13A}$ groups are joined to form an optionally substituted carbocyclic, optionally substituted heterocyclic, optionally substituted aryl, or optionally substituted heteroaryl ring, or $R^{13A}$ and $R^{13B}$ group are joined to form an optionally substituted carbocyclic, optionally substituted heterocyclic, optionally substituted aryl, or optionally substituted heteroaryl ring; and
- $R^{3b}$ and $R^{13B}$ are independently hydrogen, optionally substituted alkyl, or a nitrogen protecting group.

28. The compound of claim 17, wherein Ring HET comprises a group -L$^1$-R$^3$ is attached thereto.

29. The compound of claim 28, wherein L$^1$ is a bond, —N(R$^L$)—, —NR$^L$C(O)O—, —NR$^L$C(O)N(R$^L$)—, —N(R$^L$)—, —N(R$^L$)SO$_2$N(R$^L$)—, —NR$^L$—(CH$_2$)$_x$—C(O)O—, —NR$^L$—(CH$_2$)$_x$—O—, —NR$^L$C(O)N(R$^L$)—, —NR$^L$—(CH$_2$)$_x$—, —(CH$_2$)$_x$—NR$^L$—, —NR$^L$C(O)O (CH$_2$)$_x$—, —NR$^L$C(O)NR$^L$(CH$_2$)$_x$—, or —NR$^L$(CH$_2$)—NR$^L$C(O)—, wherein x is 1, 2, 3, 4, 5, 6, 7, 8, 9, or 10.

30. The compound of claim 28, wherein R$^3$ is selected from the group consisting of:

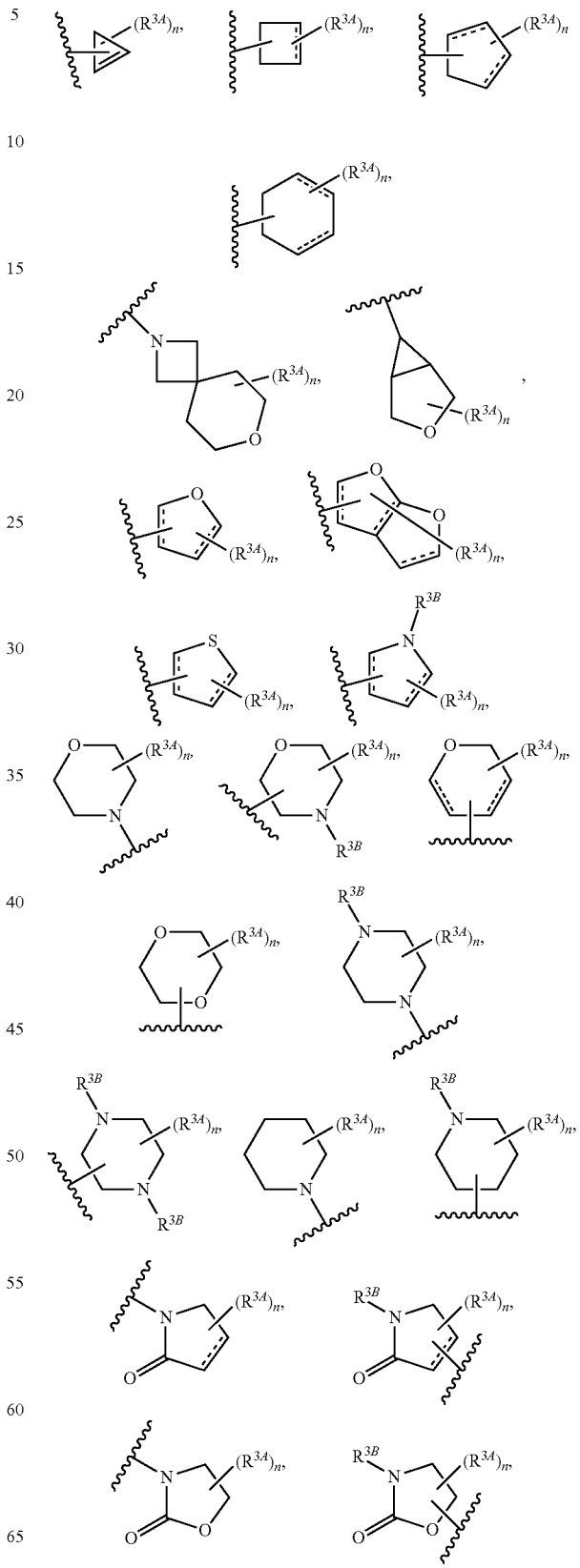

-continued

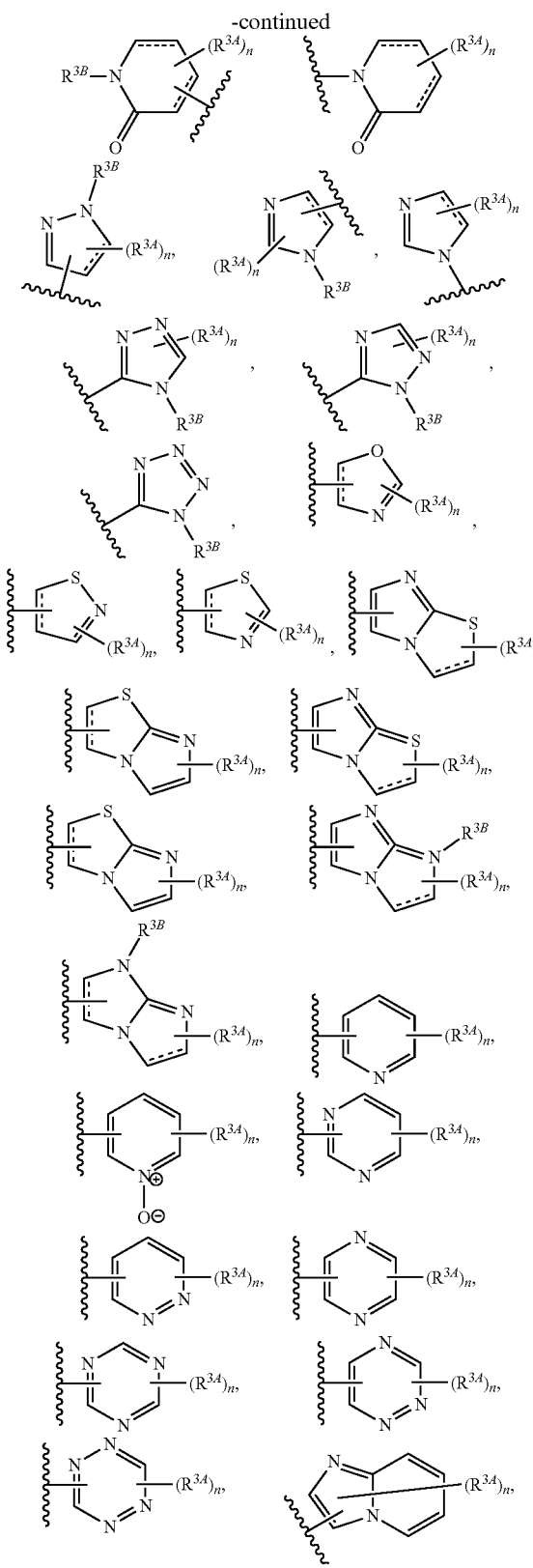
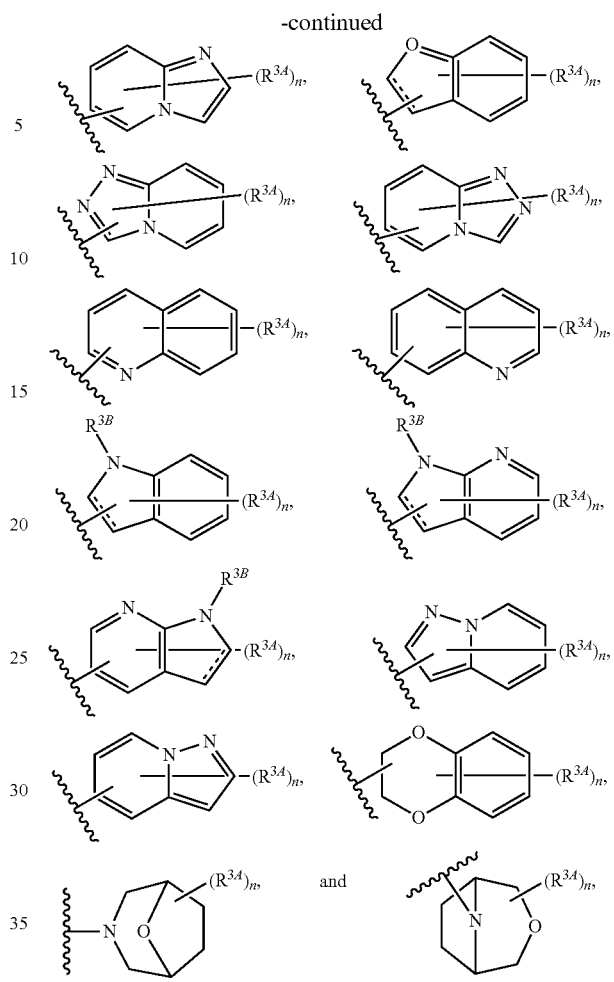

wherein:
each instance of ╌╌╌ independently represents a single or double bond;
n is 0, 1, 2, or 3;
each instance of $R^{3A}$ is independently hydroxyl, substituted hydroxyl, thiol, substituted thiol, amino, substituted amino, carbonyl, sulfonyl, sulfinyl, —CN, —NO$_2$, halogen, or optionally substituted alkyl, or two $R^{3A}$ groups are joined to form an optionally substituted carbocyclic, optionally substituted heterocyclic, optionally substituted aryl, or optionally substituted heteroaryl ring, or $R^{3A}$ and $R^{3B}$ groups are joined to form an optionally substituted carbocyclic, optionally substituted heterocyclic, optionally substituted aryl, or optionally substituted heteroaryl ring; and
$R^{3B}$ is hydrogen, optionally substituted alkyl, or a nitrogen protecting group.

31. A pharmaceutical composition comprising a compound of claim 17 or a pharmaceutically acceptable salt thereof, and a pharmaceutically acceptable excipient.

32. A pharmaceutical composition comprising a compound of claim 14 or a pharmaceutically acceptable salt thereof, and a pharmaceutically acceptable excipient.

* * * * *

SEQUENCE LISTING

```
<160> NUMBER OF SEQ ID NOS: 4

<210> SEQ ID NO 1
<211> LENGTH: 16
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (1)..(1)
<223> OTHER INFORMATION: Xaa is Acp

<400> SEQUENCE: 1

Xaa Pro Arg Lys Gln Leu Ala Thr Lys Ala Ala Arg Lys Ser Ala Pro
1               5                   10                  15

<210> SEQ ID NO 2
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 2

Met Asp Tyr Lys Asp Asp Asp Asp Lys
1               5

<210> SEQ ID NO 3
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 3

Glu Gly His His His His His His
1               5

<210> SEQ ID NO 4
<211> LENGTH: 601
<212> TYPE: PRT
<213> ORGANISM: Artificial Sequence
```

```
<220> FEATURE:
<223> OTHER INFORMATION: Synthetic Polypeptide

<400> SEQUENCE: 4

Met Asp Tyr Lys Asp Asp Asp Lys Ala Ala Ala Ala Ala Ala Val
1               5                   10                  15

Gly Pro Gly Ala Gly Ala Gly Ser Ala Val Pro Gly Gly Ala Gly
                20                  25                  30

Pro Cys Ala Thr Val Ser Val Phe Pro Gly Ala Arg Leu Leu Thr Ile
            35                  40                  45

Gly Asp Ala Asn Gly Glu Ile Gln Arg His Ala Glu Gln Gln Ala Leu
        50                  55                  60

Arg Leu Glu Val Arg Ala Gly Pro Asp Ser Ala Gly Ile Ala Leu Tyr
65                  70                  75                  80

Ser His Glu Asp Val Cys Val Phe Lys Cys Ser Val Ser Arg Glu Thr
                85                  90                  95

Glu Cys Ser Arg Val Gly Lys Gln Ser Phe Ile Ile Thr Leu Gly Cys
            100                 105                 110

Asn Ser Val Leu Ile Gln Phe Ala Thr Pro Asn Asp Phe Cys Ser Phe
        115                 120                 125

Tyr Asn Ile Leu Lys Thr Cys Arg Gly His Thr Leu Glu Arg Ser Val
    130                 135                 140

Phe Ser Glu Arg Thr Glu Glu Ser Ser Ala Val Gln Tyr Phe Gln Phe
145                 150                 155                 160

Tyr Gly Tyr Leu Ser Gln Gln Gln Asn Met Met Gln Asp Tyr Val Arg
                165                 170                 175

Thr Gly Thr Tyr Gln Arg Ala Ile Leu Gln Asn His Thr Asp Phe Lys
            180                 185                 190

Asp Lys Ile Val Leu Asp Val Gly Cys Gly Ser Gly Ile Leu Ser Phe
        195                 200                 205

Phe Ala Ala Gln Ala Gly Ala Arg Lys Ile Tyr Ala Val Glu Ala Ser
    210                 215                 220

Thr Met Ala Gln His Ala Glu Val Leu Val Lys Ser Asn Asn Leu Thr
225                 230                 235                 240

Asp Arg Ile Val Val Ile Pro Gly Lys Val Glu Val Ser Leu Pro
                245                 250                 255

Glu Gln Val Asp Ile Ile Ser Glu Pro Met Gly Tyr Met Leu Phe
            260                 265                 270

Asn Glu Arg Met Leu Glu Ser Tyr Leu His Ala Lys Lys Tyr Leu Lys
    275                 280                 285

Pro Ser Gly Asn Met Phe Pro Thr Ile Gly Asp Val His Leu Ala Pro
290                 295                 300

Phe Thr Asp Glu Gln Leu Tyr Met Glu Gln Phe Thr Lys Ala Asn Phe
305                 310                 315                 320

Trp Tyr Gln Pro Ser Phe His Gly Val Asp Leu Ser Ala Leu Arg Gly
                325                 330                 335

Ala Ala Val Asp Glu Tyr Phe Arg Gln Pro Val Val Asp Thr Phe Asp
            340                 345                 350

Ile Arg Ile Leu Met Ala Lys Ser Val Lys Tyr Thr Val Asn Phe Leu
        355                 360                 365

Glu Ala Lys Glu Gly Asp Leu His Arg Ile Glu Ile Pro Phe Lys Phe
    370                 375                 380

His Met Leu His Ser Gly Leu Val His Gly Leu Ala Phe Trp Phe Asp
385                 390                 395                 400
```

```
Val Ala Phe Ile Gly Ser Ile Met Thr Val Trp Leu Ser Thr Ala Pro
                405             410                 415

Thr Glu Pro Leu Thr His Trp Tyr Gln Val Arg Cys Leu Phe Gln Ser
            420                 425                 430

Pro Leu Phe Ala Lys Ala Gly Asp Thr Leu Ser Gly Thr Cys Leu Leu
        435             440                 445

Ile Ala Asn Lys Arg Gln Ser Tyr Asp Ile Ser Ile Val Ala Gln Val
    450                 455                 460

Asp Gln Thr Gly Ser Lys Ser Ser Asn Leu Leu Asp Leu Lys Asn Pro
465                 470                 475                 480

Phe Phe Arg Tyr Thr Gly Thr Thr Pro Ser Pro Pro Pro Gly Ser His
                485                 490                 495

Tyr Thr Ser Pro Ser Glu Asn Met Trp Asn Thr Gly Ser Thr Tyr Asn
            500                 505                 510

Leu Ser Ser Gly Met Ala Val Ala Gly Met Pro Thr Ala Tyr Asp Leu
        515                 520                 525

Ser Ser Val Ile Ala Ser Gly Ser Ser Val Gly His Asn Asn Leu Ile
    530                 535                 540

Pro Leu Gly Ser Ser Gly Ala Gln Gly Ser Gly Gly Gly Ser Thr Ser
545             550                 555                 560

Ala His Tyr Ala Val Asn Ser Gln Phe Thr Met Gly Gly Pro Ala Ile
                565                 570                 575

Ser Met Ala Ser Pro Met Ser Ile Pro Thr Asn Thr Met His Tyr Gly
            580                 585                 590

Ser Glu Gly His His His His His His
        595             600
```